US010208055B2

(12) United States Patent
Yu et al.

(10) Patent No.: US 10,208,055 B2
(45) Date of Patent: Feb. 19, 2019

(54) PYRAZOLE COMPOUNDS AS MODULATORS OF FSHR AND USES THEREOF

(71) Applicant: TOCOPHERX, INC., Burlington, MA (US)

(72) Inventors: Henry Yu, Wellesley, MA (US); Changhe Qi, Shanghai (CN); Paul Tempest, Shanghai (CN); Selvaraj G. Nataraja, Wellesley, MA (US); Stephen S. Palmer, Groton, MA (US)

(73) Assignee: TOCOPHERX, INC., Burlington, MA (US)

(*) Notice: Subject to any disclaimer, the term of this patent is extended or adjusted under 35 U.S.C. 154(b) by 0 days.

(21) Appl. No.: 15/321,249

(22) PCT Filed: Dec. 22, 2014

(86) PCT No.: PCT/CN2014/094459
§ 371 (c)(1),
(2) Date: Dec. 22, 2016

(87) PCT Pub. No.: WO2015/196759
PCT Pub. Date: Dec. 30, 2015

(65) Prior Publication Data
US 2017/0253605 A1    Sep. 7, 2017

(30) Foreign Application Priority Data
Jun. 23, 2014  (WO) ................ PCT/CN2014/080519

(51) Int. Cl.
*C07D 491/052* (2006.01)
(52) U.S. Cl.
CPC ................ *C07D 491/052* (2013.01)
(58) Field of Classification Search
None
See application file for complete search history.

(56) References Cited

U.S. PATENT DOCUMENTS

| | | |
|---|---|---|
| 8,791,114 B2 | 7/2014 | Yu et al. |
| 9,181,226 B2 | 11/2015 | Yu et al. |
| 9,409,897 B2 | 8/2016 | Yu et al. |
| 9,498,475 B2 | 11/2016 | Yu et al. |
| 9,517,227 B2 | 12/2016 | Yu et al. |
| 9,775,830 B2 | 10/2017 | Yu et al. |
| 9,938,262 B2 | 4/2018 | Yu et al. |
| 2010/0215741 A1 | 8/2010 | Lazzari et al. |
| 2010/0216785 A1 | 8/2010 | Lazzari et al. |

FOREIGN PATENT DOCUMENTS

| | | |
|---|---|---|
| CN | 1039026 A | 1/1990 |
| CN | 102695710 A | 9/2012 |
| CN | 105473596 A | 4/2016 |
| JP | H03505204 A | 11/1991 |
| JP | 2005-510466 A | 4/2005 |
| JP | 2013-510825 A | 3/2013 |
| RU | 2332412 C2 | 8/2008 |
| RU | 2016101958 A | 7/2017 |
| WO | 89/12638 A1 | 12/1989 |
| WO | 03024936 A1 | 3/2003 |
| WO | 2006124581 A2 | 11/2006 |
| WO | 2008035356 A2 | 3/2008 |
| WO | 2010136438 A1 | 12/2010 |
| WO | 2011058149 A1 | 5/2011 |
| WO | 2013/006308 A2 | 1/2013 |
| WO | 2013/012848 A1 | 1/2013 |
| WO | 2013/106409 A1 | 7/2013 |
| WO | 2013/117299 A1 | 8/2013 |
| WO | 2014/209978 A1 | 12/2014 |
| WO | 2014/209980 A1 | 12/2014 |
| WO | 2014209980 A1 | 12/2014 |
| WO | 2015196335 A1 | 12/2015 |
| WO | 2015196759 A1 | 12/2015 |

OTHER PUBLICATIONS

STN Registry database entry for CAS RN 1015696-56-6; Entered STN Apr. 18, 2008; Accessed Sep. 6, 2017.*
Ito et al. in Cancer Science 94(1), 3-8 (2003).*
STN Registry database entry for CAS RN 1015695-23-4, Entry Date Sep. 27, 2004, Accessed Mar. 23, 2018.*
NPL International Search Report and Written Opinion for International Application No. PCTCN2014080519, dated Dec. 11, 2014.
NPL International Search Report and Written Opinion for International Application No. PCTCN2014094459, dated Feb. 25, 2015.
Registry (STN) [online], Dec. 4, 2011 [retrieved on Jun. 15, 2018] CAS registration No. 1348894-85-8.
Registry (STN) [online], Dec. 5, 2011 [retrieved on Jun. 15, 2018] CAS registration No. 1348795-91-4.
Registry (STN) [online], Dec. 4, 2011 [retrieved on Jun. 15, 2018] CAS registration No. 1347828-02-7.
Registry (STN) [online], Dec. 2, 2011 [retrieved on Jun. 15, 2018] CAS registration No. 1347357-34-9.

* cited by examiner

*Primary Examiner* — Alicia L Otton
(74) *Attorney, Agent, or Firm* — Lando & Anastasi, LLP

(57) ABSTRACT

Disclosed are pyrazole compounds, and pharmaceutically acceptable compositions thereof. The compounds and the compositions can be used for positive allosteric modulators of follicle stimulating hormone receptor (FSHR).

13 Claims, No Drawings

PYRAZOLE COMPOUNDS AS MODULATORS OF FSHR AND USES THEREOF

CROSS-REFERENCE TO RELATED APPLICATIONS

This application is a U.S. National Stage Application under 35 U.S.C. § 371 of International Application No. PCT/CN2014/094459, filed Dec. 22, 2014, which claims priority to PCT/CN2014/080519, filed Jun. 23, 2014, the entire contents of each of which are incorporated herein by reference in their entirety.

TECHNICAL FIELD OF THE INVENTION

The present invention relates to pyrazole compounds useful as agonists of follicle stimulating hormone receptor (FSHR). The invention also provides pharmaceutically acceptable compositions comprising compounds of the present invention and methods of using said compositions in the treatment of various disorders.

BACKGROUND OF THE INVENTION

Gonadotropins serve important functions in a variety of bodily functions including metabolism, temperature regulation and the reproductive process. Gonadotropins act on specific gonadal cell types to initiate ovarian and testicular differentiation and steroidogenesis. The gonadotropin FSH (follicle stimulating hormone) is released from the anterior pituitary under the influence of gonadotropin-releasing hormone and estrogens, and from the placenta during pregnancy. FSH is a heterodimeric glycoprotein hormone that shares structural similarities with luteinizing hormone (LH) and thyroid stimulating hormone (TSH), both of which are also produced in the pituitary gland, and chorionic gonadotropin (CG), which is produced in the placenta. In the female, FSH plays a pivotal role in the stimulation of follicle development and maturation and in addition, it is the major hormone regulating secretion of estrogens, whereas LH induces ovulation. In the male, FSH is responsible for the integrity of the seminiferous tubules and acts on Sertoli cells to support gametogenesis.

The hormones are relatively large (28-38 kDa) and are composed of a common α-subunit non-covalently bound to a distinct β-subunit that confers receptor binding specificity. The cellular receptor for these hormones is expressed on testicular Sertoli cells and ovarian granulosa cells. The FSH receptor is known to be members of the G protein-coupled class of membrane-bound receptors, which when activated stimulate an increase in the activity of adenylyl cyclase. This results in an increase in the level of the intracellular second messenger adenosine 3', 5'-monophosphate (cAMP), which in turn causes increased steroid synthesis and secretion. Hydropathicity plots of the amino acid sequences of these receptors reveal three general domains: a hydrophilic amino-terminal region, considered to be the amino-terminal extracellular domain; seven hydrophobic segments of membrane-spanning length, considered to be the transmembrane domain; and a carboxy-terminal region that contains potential phosphorylation sites (serine, threonine, and tyrosine residues), considered to be the carboxy-terminal intracellular or cytoplasmic domain. The glycoprotein hormone receptor family is distinguished from other G protein-coupled receptors, such as the β-2-adrenergic, rhodopsin, and substance K receptors, by the large size of the hydrophilic amino-terminal domain, which is involved in hormone binding.

Annually in the U.S. there are 2.4 million couples experiencing infertility that are potential candidates for treatment. FSH, either extracted from urine or produced by recombinant DNA technology, is a parenterally-administered protein product used by specialists for ovulation induction and for controlled ovarial hyperstimulation. Whereas ovulation induction is directed at achieving a single follicle to ovulate, controlled ovarial hyperstimulation is directed at harvesting multiple oocytes for use in various in-vitro assisted reproductive technologies, e.g. in-vitro fertilization (IVF). FSH is also used clinically to treat male hypogonadism and male infertility, e.g. some types of failure of spermatogenesis.

FSHR is a highly specific target in the ovarian follicle growth process and is exclusively expressed in the ovary. However, the use of FSH is limited by its high cost, lack of oral dosing, and need of extensive monitoring by specialist physicians. Hence, identification of a non-peptidic small molecule substitute for FSH that could potentially be developed for oral administration is desirable. Low molecular weight FSH mimetics with agonistic properties are disclosed in the international applications WO 2002/09706 and WO 2010/136438 as well as the U.S. Pat. No. 6,653,338. There is still a need for low molecular weight hormone mimetics that selectively activate FSHR.

SUMMARY OF THE INVENTION

It has now been found that compounds of this invention, and pharmaceutically acceptable compositions thereof, are effective as modulators of FSHR. Such compounds have general formula I or formula II:

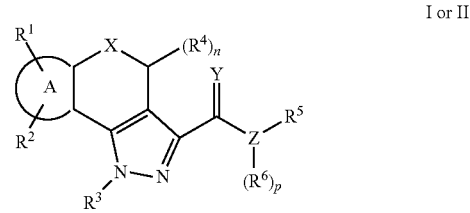

or a pharmaceutically acceptable salt thereof, wherein each of Ring A, X, Y, Z, $R^1$, $R^2$, $R^3$, $R^4$, $R^5$, $R^6$, n, and p, is as defined and described in embodiments herein.

Compounds of the present invention, and pharmaceutically acceptable compositions thereof, are useful for treating a variety of diseases, disorders or conditions, associated with abnormal cellular responses triggered by follicle stimulating hormone events. Such diseases, disorders, or conditions include those described herein.

DETAILED DESCRIPTION OF CERTAIN EMBODIMENTS

1. General Description of Compounds of the Invention

In certain embodiments, the present invention provides modulators of follicle stimulating hormone receptor (FSHR). In certain embodiments, the present invention provides positive allosteric modulators of FSHR. In some embodiments, such compounds include those of the formulae described herein, or a pharmaceutically acceptable salt thereof, wherein each variable is as defined and described herein.

2. Compounds and Definitions

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Exemplary aliphatic groups are linear or branched, substituted or unsubstituted $C_1$-$C_8$ alkyl, $C_2$-$C_8$ alkenyl, $C_2$-$C_8$ alkynyl groups and hybrids thereof such as (cycloalkyl)alkyl, (cycloalkenyl)alkyl or (cycloalkyl)alkenyl.

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, or phosphorus (including, any oxidized form of nitrogen, sulfur, or phosphorus; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated", as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., —(CH$_2$)$_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "halogen" means F, Cl, Br, or I.

The term "aryl" used alone or as part of a larger moiety as in "aralkyl", "aralkoxy", or "aryloxyalkyl", refers to monocyclic and bicyclic ring systems having a total of five to fourteen ring members, wherein at least one ring in the system is aromatic and wherein each ring in the system contains three to seven ring members. The term "aryl" is used interchangeably with the term "aryl ring". In certain embodiments of the present invention, "aryl" refers to an aromatic ring system. Exemplary aryl groups are phenyl, biphenyl, naphthyl, anthracyl and the like, which optionally includes one or more substituents. Also included within the scope of the term "aryl", as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-", used alone or as part of a larger moiety, e.g., "heteroaralkyl", or "heteroaralkoxy", refer to groups having 5 to 10 ring atoms, preferably 5, 6, or 9 ring atoms; having 6, 10, or 14 n electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thiophenyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group is optionally mono- or bicyclic. The term "heteroaryl" is used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "thienyl" and "thiophenyl" are used interchangeably and refer to a 5-membered monocyclic heteroaryl ring containing a single sulfur heteroatom.

As used herein, the terms "heterocycle", "heterocyclyl", "heterocyclic radical", and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen is N (as in 3,4-dihydro-2H-pyrrolyl), NH (as in pyrrolidinyl), or +NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group is optionally mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, certain compounds of the invention contain "optionally substituted" moieties. In general, the term "substituted", whether preceded by the term "optionally" or not, means that one or more hydrogens of the designated moiety are replaced with a suitable substituent. "Substituted" applies to one or more hydrogens that are either explicit or implicit from the structure

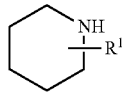
(e.g., refers to at least

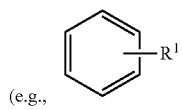
;

and

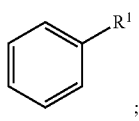

refers to at least

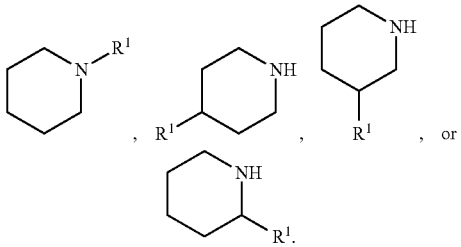
, or $R^1$.

Unless otherwise indicated, an "optionally substituted" group has a suitable substituent at each substitutable position of the group, and when more than one position in any given structure is substituted with more than one substituent selected from a specified group, the substituent is either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently deuterium; halogen; —$(CH_2)_{0-4}R°$; —$(CH_2)_{0-4}OR°$; —$O(CH_2)_{0-4}R°$, —$O$—$(CH_2)_{0-4}C(O)OR°$; —$(CH_2)_{0-4}CH(OR°)_2$; —$(CH_2)_{0-4}SR°$; —$(CH_2)_{0-4}Ph$, which are optionally substituted with R°; —$(CH_2)_{0-4}O(CH_2)_{0-1}Ph$ which is optionally substituted with R°; —CH=CHPh, which is optionally substituted with R°; —$(CH_2)_{0-4}O(CH_2)_{0-1}$-pyridyl which is optionally substituted with R°; —$NO_2$; —CN; —$N_3$; —$(CH_2)_{0-4}N(R°)_2$; —$(CH_2)_{0-4}N(R°)C(O)R°$; —$N(R°)C(S)R°$; —$(CH_2)_{0-4}N(R°)C(O)NR°_2$; —$N(R°)C(S)NR°_2$; —$(CH_2)_{0-4}N(R°)C(O)OR°$; —$N(R°)N(R°)C(O)R°$; —$N(R°)N(R°)C(O)NR°_2$; —$N(R°)N(R°)C(O)OR°$; —$(CH_2)_{0-4}C(O)R°$; —$C(S)R°$; —$(CH_2)_{0-4}C(O)OR°$; —$(CH_2)_{0-4}C(O)SR°$; —$(CH_2)_{0-4}C(O)OSiR°_3$; —$(CH_2)_{0-4}OC(O)R°$; —$OC(O)(CH_2)_{0-4}SR°$, $SC(S)SR°$; —$(CH_2)_{0-4}SC(O)R°$; —$(CH_2)_{0-4}C(O)NR°_2$; —$C(S)NR°_2$; —$C(S)SR°$; —$SC(S)SR°$, —$(CH_2)_{0-4}OC(O)NR°_2$; —$C(O)N(OR°)R°$; —$C(O)C(O)R°$; —$C(O)CH_2C(O)R°$; —$C(NOR°)R°$; —$(CH_2)_{0-4}SSR°$; —$(CH_2)_{0-4}S(O)_2R°$; —$(CH_2)_{0-4}S(O)_2OR°$; —$(CH_2)_{0-4}OS(O)_2R°$; —$S(O)_2NR°_2$; —$(CH_2)_{0-4}S(O)R°$; —$N(R°)S(O)_2NR°_2$; —$N(R°)S(O)_2R°$; —$N(OR°)R°$; —$C(NH)NR°_2$; —$P(O)_2R°$; —$P(O)R°_2$; —$OP(O)R°_2$; —$OP(O)(OR°)_2$; $SiR°_3$; —$(C_{1-4}$ straight or branched alkylene)O—$N(R°)_2$; or —$(C_{1-4}$ straight or branched alkylene)C(O)O—$N(R°)_2$, wherein each R° is optionally substituted as defined below and is independently hydrogen, $C_{1-6}$ aliphatic, —$CH_2Ph$, —$O(CH_2)_{0-1}Ph$, —$CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which is optionally substituted as defined below.

Suitable monovalent substituents on R° (or the ring formed by taking two independent occurrences of R° together with their intervening atoms), are independently deuterium, halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet{}_2$, —NO$_2$, —SiR$^\bullet{}_3$, —OSiR$^\bullet{}_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which is substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which is optionally substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet{}_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger{}_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger{}_2$, —C(S)NR$^\dagger{}_2$, —C(NH)NR$^\dagger{}_2$, or —N(R$^\dagger$)S(O)$_2$R$^\dagger$; wherein each R$^\dagger$ is independently hydrogen, C$_{1-6}$ aliphatic which is optionally substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on a substitutable sulfur of an "optionally substituted" group include =O, (=O)$_2$, —R$^\dagger$, —NR$^\dagger{}_2$, —(=O)NR$^\dagger{}_2$, —(=O)$_2$NR$^\dagger{}_2$, —C(O)R$^\dagger$, —C(O)OR$^\dagger$, —C(O)C(O)R$^\dagger$, —C(O)CH$_2$C(O)R$^\dagger$, —C(S)NR$_2$, —C(NH)NR$^\dagger{}_2$, or —N(R$^\dagger$)S(O)$_2$R$^\dagger$; wherein each R$^\dagger$ is independently hydrogen, C$_{1-6}$ aliphatic which is optionally substituted as defined below, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet{}_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

In certain embodiments, the terms "optionally substituted", "optionally substituted alkyl," "optionally substituted "optionally substituted alkenyl," "optionally substituted alkynyl", "optionally substituted carbocyclic," "optionally substituted aryl", "optionally substituted heteroaryl," "optionally substituted heterocyclic," and any other optionally substituted group as used herein, refer to groups that are substituted or unsubstituted by independent replacement of one, two, or three or more of the hydrogen atoms thereon with typical substituents including, but not limited to:

—F, —Cl, —Br, —I, deuterium,

—OH, protected hydroxy, alkoxy, oxo, thiooxo,

—NO$_2$, —CN, CF$_3$, N$_3$,

—NH$_2$, protected amino, —NH alkyl, —NH alkenyl, —NH alkynyl, —NH cycloalkyl, —NH-aryl, —NH-heteroaryl, —NH-heterocyclic, -dialkylamino, -diarylamino, -diheteroarylamino, —O-alkyl, —O-alkenyl, —O-alkynyl, —O-cycloalkyl, —O-aryl, —O-heteroaryl, —O-heterocyclic, —C(O)-alkyl, —C(O)-alkenyl, —C(O)-alkynyl, —C(O)-carbocyclyl, —C(O)-aryl, —C(O)-heteroaryl, —C(O)-heterocyclyl, —CONH$_2$, —CONH-alkyl, —CONH-alkenyl, —CONH-alkynyl, —CONH-carbocyclyl, —CONH-aryl, —CONH-heteroaryl, —CONH-heterocyclyl, —OCO$_2$-alkyl, —OCO$_2$-alkenyl, —OCO$_2$-alkynyl, —OCO$_2$-carbocyclyl, —OCO$_2$-aryl, —OCO$_2$-heteroaryl, —OCO$_2$-heterocyclyl, —OCONH$_2$, —OCONH-alkyl, —OCONH-alkenyl, —OCONH-alkynyl, —OCONH-carbocyclyl, —OCONH-aryl, —OCONH-heteroaryl, —OCONH-heterocyclyl, —NHC(O)-alkyl, —NHC(O)-alkenyl, —NHC(O)-alkynyl, —NHC(O)-carbocyclyl, —NHC(O)-aryl, —NHC(O)-heteroaryl, —NHC(O)-heterocyclyl, —NHCO$_2$-alkyl, —NHCO$_2$-alkenyl, —NHCO$_2$-alkynyl, —NHCO$_2$-carbocyclyl, —NHCO$_2$-aryl, —NHCO$_2$-heteroaryl, —NHCO$_2$-heterocyclyl, —NHC(O)NH$_2$, —NHC(O)NH-alkyl, —NHC(O)NH-alkenyl, —NHC(O)NH-alkenyl, —NHC(O)NH-carbocyclyl, —NHC(O)NH-aryl, —NHC(O)NH-heteroaryl, —NHC(O)NH-heterocyclyl, NHC(S)NH$_2$, —NHC(S)NH-alkyl, —NHC(S)NH-alkenyl, —NHC(S)NH-alkynyl, —NHC(S)NH-carbocyclyl, —NHC(S)NH-aryl, —NHC(S)NH-heteroaryl, —NHC(S)NH-heterocyclyl, —NHC(NH)NH$_2$, —NHC(NH)NH-alkyl, —NHC(NH)NH-alkenyl, —NHC(NH)NH-alkenyl, —NHC(NH)NH-carbocyclyl, —NHC(NH)NH-aryl, —NHC(NH)NH-heteroaryl, —NHC(NH)NH-heterocyclyl, —NHC(NH)-alkyl, —NHC (NH)-alkenyl, —NHC(NH)-alkenyl, —NHC(NH)-carbocyclyl, —NHC(NH)-aryl, —NHC(NH)-heteroaryl, —NHC(NH)-heterocyclyl, —C(NH)NH-alkyl, —C(NH)NH-alkenyl, —C(NH)NH-alkynyl, —C(NH)NH-carbocyclyl, —C(NH)NH-aryl, —C(NH)NH-heteroaryl, —C(NH)NH-heterocyclyl, —S(O)-alkyl, —S(O)-alkenyl, —S(O)-alkynyl, —S(O)-carbocyclyl, —S(O)-aryl, —S(O)-heteroaryl, —S(O)-heterocyclyl —$SO_2NH_2$, —$SO_2$NH-alkyl, —$SO_2$NH-alkenyl, —$SO_2$NH-alkynyl, —$SO_2$NH-carbocyclyl, —$SO_2$NH-aryl, —$SO_2$NH-heteroaryl, —$SO_2$NH-heterocyclyl, —$NHSO_2$-alkyl, —$NHSO_2$-alkenyl, —$NHSO_2$-alkynyl, —$NHSO_2$-carbocyclyl, —$NHSO_2$-aryl, —$NHSO_2$-heteroaryl, —$NHSO_2$-heterocyclyl,

—$CH_2NH_2$, —$CH_2SO_2CH_3$,

-mono-, di-, or tri-alkyl silyl,

-alkyl, -alkenyl, -alkynyl, -aryl, -arylalkyl, -heteroaryl, -heteroarylalkyl, -heterocycloalkyl, -cycloalkyl, -carbocyclic, -heterocyclic, polyalkoxyalkyl, polyalkoxy, -methoxymethoxy, -methoxyethoxy, —SH, —S-alkyl, —S-alkenyl, —S-alkynyl, —S— carbocyclyl, —S-aryl, —S-heteroaryl, —S-heterocyclyl, or methylthiomethyl.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+$ ($C_{1-4}$alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention.

Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. In some embodiments, the group comprises one or more deuterium atoms.

There is furthermore intended that a compound of formula (I) or formula (II) includes isotope-labeled forms thereof. An isotope-labeled form of a compound of formula (I) or formula (II) is identical to this compound apart from the fact that one or more atoms of the compound have been replaced by an atom or atoms having an atomic mass or mass number which differs from the atomic mass or mass number of the atom which usually occurs naturally. Examples of isotopes which are readily commercially available and which can be incorporated into a compound of formula (I) or formula (II) by well-known methods include isotopes of hydrogen, carbon, nitrogen, oxygen, phosphorus, fluorine and chlorine, for example $^2$H, $^3$H, $^{13}$C, $^{14}$C, $^{15}$N, $^{18}$O, $^{17}$O, $^{31}$P, $^{32}$P, $^{35}$S, $^{18}$F and $^{36}$Cl, respectively. A compound of formula (I) or formula (II), a prodrug, thereof or a pharmaceutically acceptable salt of either which contains one or more of the above-mentioned isotopes and/or other isotopes of other atoms is intended to be part of the present invention. An isotope-labeled compound of formula (I) or formula (II) can be used in a number of beneficial ways. For example, an isotope-labeled compound of the formula (I) or formula (II) into which, for example, a radioisotope, such as $^3$H or $^{14}$C, has been incorporated, is suitable for medicament and/or substrate tissue distribution assays. These radioisotopes, i.e. tritium ($^3$H) and carbon-14 ($^{14}$C), are particularly preferred owing to simple preparation and excellent detectability. Incorporation of heavier isotopes, for example deuterium ($^2$H), into a compound of formula (I) or formula (II) has therapeutic advantages owing to the higher metabolic stability of this isotope-labeled compound. Higher metabolic stability translates directly into an increased in vivo half-life or lower dosages, which under most circumstances would represent a preferred embodiment of the present invention. An isotope-labeled compound of formula (I) or formula (II) can usually be prepared by carrying out the procedures disclosed in the synthesis schemes and the related description, in the example part and in the preparation part in the present text, replacing a non-isotope-labeled reactant by a readily available isotope-labeled reactant.

Deuterium ($^2$H) can also be incorporated into a compound of formula (I) or formula (II) for the purpose in order to manipulate the oxidative metabolism of the compound by way of the primary kinetic isotope effect. The primary kinetic isotope effect is a change of the rate for a chemical reaction that results from exchange of isotopic nuclei, which in turn is caused by the change in ground state energies necessary for covalent bond formation after this isotopic exchange. Exchange of a heavier isotope usually results in a lowering of the ground state energy for a chemical bond and thus causes a reduction in the rate in rate-limiting bond breakage. If the bond breakage occurs in or in the vicinity of a saddle-point region along the coordinate of a multi-product reaction, the product distribution ratios can be altered substantially. For explanation: if deuterium is bonded to a carbon atom at a non-exchangeable position, rate differences of $k_M/k_D$=2-7 are typical. If this rate difference is successfully applied to a com-pound of formula (I) or formula (II) that is susceptible to oxidation, the profile of this compound in vivo can be drastically modified and result in improved pharmacokinetic properties.

When discovering and developing therapeutic agents, the person skilled in the art is able to optimize pharmacokinetic parameters while retaining desirable in vitro properties. It is reasonable to assume that many compounds with poor pharmacokinetic profiles are susceptible to oxidative metabolism. In vitro liver microsomal assays currently available provide valuable information on the course of oxidative metabolism of this type, which in turn permits the rational design of deuterated compounds of formula (I) or formula (II) with improved stability through resistance to such oxidative metabolism. Significant improvements in the pharmacokinetic profiles of compounds of formula (I) or formula (II) are thereby obtained, and can be expressed quantitatively in terms of increases in the in vivo half-life (t/2), concentration at maximum therapeutic effect ($C_{max}$), area under the dose response curve (AUC), and F; and in terms of reduced clearance, dose and materials costs.

The following is intended to illustrate the above: a compound of formula (I) or formula (II) which has multiple potential sites of attack for oxidative metabolism, for example benzylic hydrogen atoms and hydrogen atoms bonded to a nitrogen atom, is prepared as a series of analogues in which various combinations of hydrogen atoms are replaced by deuterium atoms, so that some, most or all of these hydrogen atoms have been replaced by deuterium atoms. Half-life determinations enable favorable and accurate determination of the extent of the extent to which the improvement in resistance to oxidative metabolism has improved. In this way, it is determined that the half-life of the parent compound can be extended by up to 100% as the result of deuterium-hydrogen exchange of this type.

Deuterium-hydrogen exchange in a compound of formula (I) or formula (II) can also be used to achieve a favorable modification of the metabolite spectrum of the starting compound in order to diminish or eliminate undesired toxic metabolites. For example, if a toxic metabolite arises through oxidative carbon-hydrogen (C—H) bond cleavage, it can reasonably be assumed that the deuterated analogue will greatly diminish or eliminate production of the unwanted metabolite, even if the particular oxidation is not a rate-determining step. Further information on the state of the art with respect to deuterium-hydrogen exchange may be found, for example in Hanzlik et al., J. Org. Chem. 55, 3992-3997, 1990, Reider et al., J. Org. Chem. 52, 3326-3334, 1987, Foster, Adv. Drug Res. 14, 1-40, 1985, Gillette et al, Biochemistry 33(10) 2927-2937, 1994, and Jarman et al. Carcinogenesis 16(4), 683-688, 1993.

As used herein, the term "modulator" is defined as a compound that binds to and/or inhibits the target with measurable affinity. In certain embodiments, a modulator has an $IC_{50}$ and/or binding constant of less about 50 μM, less than about 1 μM, less than about 500 nM, less than about 100 nM, or less than about 10 nM.

The terms "measurable affinity" and "measurably inhibit," as used herein, means a measurable change in FSHR activity between a sample comprising a compound of the present invention, or composition thereof, and FSHR, and an equivalent sample comprising FSHR, in the absence of said compound, or composition thereof.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

3. Description of Exemplary Compounds

According to one aspect, the present invention provides a compound of formula I,

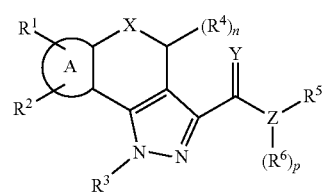

or a pharmaceutically acceptable salt thereof, wherein:

X is O, S, SO, $SO_2$, or NR;

Y is O, S, or NR;

Z is O, S, SO, $SO_2$, or N; wherein when Z is O, S, SO, or $SO_2$, then p is 0;

each R is independently hydrogen, $C_{1-6}$ aliphatic, aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted; or two R groups on the same atom are taken together with the atom to which they are attached to form an aryl ring, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted;

Ring A is a fused aryl, a fused 3-8 membered saturated or partially unsaturated carbocyclic ring, a fused 3-7 membered heterocylic ring having 1-4 heteroatoms independently selected from nitrogen, oxygen, or sulfur, or a fused 5-6 membered monocyclic heteroaryl ring having 1-4 heteroatoms independently selected from nitrogen, oxygen, or sulfur;

$R^1$ is —OR, —SR, —CN, —$NO_2$, —$SO_2R$, —SOR, —C(O)R, —$CO_2R$, —C(O)N(R)$_2$, —NRC(O)R, —NRC(O)N(R)$_2$, —$NRSO_2R$, or —N(R)$_2$;

$R^2$ is —R, halogen, -haloalkyl, —OR, —SR, —CN, —$NO_2$, —$SO_2R$, —SOR, —C(O)R, —$CO_2R$, —C(O)N(R)$_2$, —NRC(O)R, —NRC(O)N(R)$_2$, —$NRSO_2R$, or —N(R)$_2$;

$R^3$ is an optionally substituted aryl;

each $R^4$ is independently —R, halogen, -haloalkyl, —OR, —SR, —CN, —NO$_2$, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$;

$R^5$ is C$_{1-6}$ aliphatic, —SO$_2$R, —SOR, aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted;

$R^6$ is hydrogen, C$_{1-6}$ aliphatic, —SO$_2$R, —SOR, aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted;

or $R^5$ and $R^6$, together with the atom to which each is attached, form a 3-8 membered heterocylic ring having 1-4 heteroatoms independently selected from nitrogen, oxygen, or sulfur, or a 3-8 membered heteroaryl ring having 1-4 heteroatoms independently selected from nitrogen, oxygen, or sulfur; each of which is optionally substituted;

n is 0, 1, or 2; and p is 0 or 1.

In certain embodiments, X is O. In certain embodiments, X is S. In certain embodiments, X is SO or SO$_2$. In certain embodiments, X is NR.

In certain embodiments, Y is O. In certain embodiments, Y is S. In certain embodiments, Y is NR.

In certain embodiments, Z is O. In certain embodiments, Z is S. In certain embodiments, Z is SO or SO$_2$. In certain embodiments, Z is N.

In certain embodiments, Ring A is a fused aryl. In certain embodiments, Ring A is a fused 3-8 membered saturated or partially unsaturated carbocyclic ring. In certain embodiments, Ring A is a fused 3-7 membered heterocylic ring having 1-4 heteroatoms independently selected from nitrogen, oxygen, or sulfur. In certain embodiments, Ring A is a fused 5-6 membered monocyclic heteroaryl ring having 1-4 heteroatoms independently selected from nitrogen, oxygen, or sulfur.

In certain embodiments, Ring A is phenyl, cyclopropyl, cyclobutyl, cyclopentyl, cyclohexyl, cycloheptyl, furanyl, furazanyl, imidazolidinyl, imidazolinyl, imidazolyl, 1H-indazolyl, indolenyl, isoxazolyl, morpholinyl, oxadiazolyl, 1,2,3-oxadiazolyl, 1,2,4-oxadiazolyl; 1,2,5-oxadiazolyl, 1,3,4-oxadiazolyl, oxazolidinyl, oxazolyl, oxazolidinyl, pyrimidinyl, piperazinyl, piperidinyl, purinyl, pyranyl, pyrazinyl, pyrazolidinyl, pyrazolinyl, pyrazolyl, pyridazinyl, pyridinyl, pyridyl, pyrimidinyl, pyrrolidinyl, pyrrolinyl, 2H-pyrrolyl, pyrrolyl, tetrahydrofuranyl, thiazolyl, thiophenyl, oxetanyl, or azetidinyl.

In certain embodiments, Ring A is phenyl.

In certain embodiments, $R^1$ is —OR, —SR, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$. In certain embodiments, $R^1$ is —OR, —SR, —SO$_2$R, or —SOR. In certain embodiments, $R^1$ is —C(O)R, —CO$_2$R, or —C(O)N(R)$_2$. In certain embodiments, $R^1$ is —NRC(O)R, —NRC(O)N(R)$_2$, —NRSO$_2$R, or —N(R)$_2$.

In certain embodiments, $R^1$ is —OR, and R is hydrogen.

In certain embodiments, $R^1$ is —OR, and R is C$_{1-6}$ aliphatic, aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted.

In certain embodiments, $R^1$ is —OR, and R is C$_{1-6}$ aliphatic. In certain embodiments, R is methyl, ethyl, propyl, i-propyl, butyl, s-butyl, t-butyl, straight or branched pentyl, or straight or branched hexyl; each of which is optionally substituted. In certain embodiments, R is methyl or or deuterated methyl. In certain embodiments, R is methyl.

In certain embodiments, $R^1$ is —OR, and R is aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur. In certain embodiments, R is phenyl, naphthyl, cyclopropyl, cyclobutyl, cyclopentyl, cyclohexyl, cycloheptyl, adamantyl, cyclooctyl, [3.3.0]bicyclooctanyl, [4.3.0]bicyclononanyl, [4.4.0]bicyclodecanyl, [2.2.2]bicyclooctanyl, fluorenyl, indanyl, tetrahydronaphthyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro [2,3-b] tetrahydrofuran, furanyl, furazanyl, imidazolidinyl, imidazolinyl, imidazolyl, 1H-indazolyl, indolenyl, indolinyl, indolizinyl, indolyl, 3H-indolyl, isoindolinyl, isoindolenyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, oxetanyl, azetidinyl, or xanthenyl; each of which is optionally substituted.

In certain embodiments, $R^1$ is —OR, and $R^2$ is aryl, a 3-8 membered saturated or partially unsaturated carbocyclic ring, or a 5-6 membered monocyclic heteroaryl ring having 1-4 heteroatoms independently selected from nitrogen, oxygen, or sulfur; each of which is optionally substituted.

In certain embodiments, $R^1$ is —OR, and $R^2$ is a 6-membered aryl ring, a 3-membered carbocyclic ring, or a 5-6 membered monocyclic heteroaryl ring having 1-4 nitrogen atoms; each of which is optionally substituted.

In certain embodiments, $R^2$ is hydrogen.

In certain embodiments, $R^2$ is C$_{1-6}$ aliphatic. In certain embodiments, $R^2$ is C$_{1-6}$ aliphatic wherein the aliphatic group is a C$_{1-6}$ alkyl. In certain embodiments, $R^2$ is methyl, ethyl, propyl, i-propyl, butyl, s-butyl, t-butyl, straight or branched pentyl, or straight or branched hexyl; each of which is optionally substituted. In certain embodiments, $R^2$ is $C_{1-6}$ aliphatic wherein the aliphatic group is a $C_{1-6}$ alkenyl.

In certain embodiments, $R^2$ is aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted.

In certain embodiments, $R^2$ is phenyl, naphthyl, cyclopropyl, cyclobutyl, cyclopentyl, cyclohexyl, cycloheptyl, adamantyl, cyclooctyl, [3.3.0]bicyclooctanyl, [4.3.0]bicyclononanyl, [4.4.0]bicyclodecanyl, [2.2.2]bicyclooctanyl, fluorenyl, indanyl, tetrahydronaphthyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro [2,3-b] tetrahydrofuran, furanyl, furazanyl, imidazolidinyl, imidazolinyl, imidazolyl, 1H-indazolyl, indolenyl, indolinyl, indolizinyl, indolyl, 3H-indolyl, isoindolinyl, isoindolenyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, oxetanyl, azetidinyl, or xanthenyl; each of which is optionally substituted.

In certain embodiments, $R^2$ is halogen, -haloalkyl, —OR, —SR, —CN, —NO$_2$, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$.

In certain embodiments, $R^2$ is F, Cl, Br, I, or haloalkyl.

In certain embodiments, $R^2$ is —OR, —SR, —CN, —NO$_2$, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$. In certain embodiments, R is $C_{1-6}$ aliphatic, aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted. In certain embodiments, R is methyl, ethyl, propyl, i-propyl, butyl, s-butyl, t-butyl, straight or branched pentyl, or straight or branched hexyl; each of which is optionally substituted. In certain embodiments, R is methyl, ethyl, or propyl; each of which is optionally substituted. In other embodiments, R is phenyl, naphthyl, cyclopropyl, cyclobutyl, cyclopentyl, cyclohexyl, cycloheptyl, adamantyl, cyclooctyl, [3.3.0]bicyclooctanyl, [4.3.0]bicyclononanyl, [4.4.0]bicyclodecanyl, [2.2.2]bicyclooctanyl, fluorenyl, indanyl, tetrahydronaphthyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro [2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isoindolinyl, isoindolenyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, oxetanyl, azetidinyl, or xanthenyl; each of which is optionally substituted.

In certain embodiments, $R^2$ is

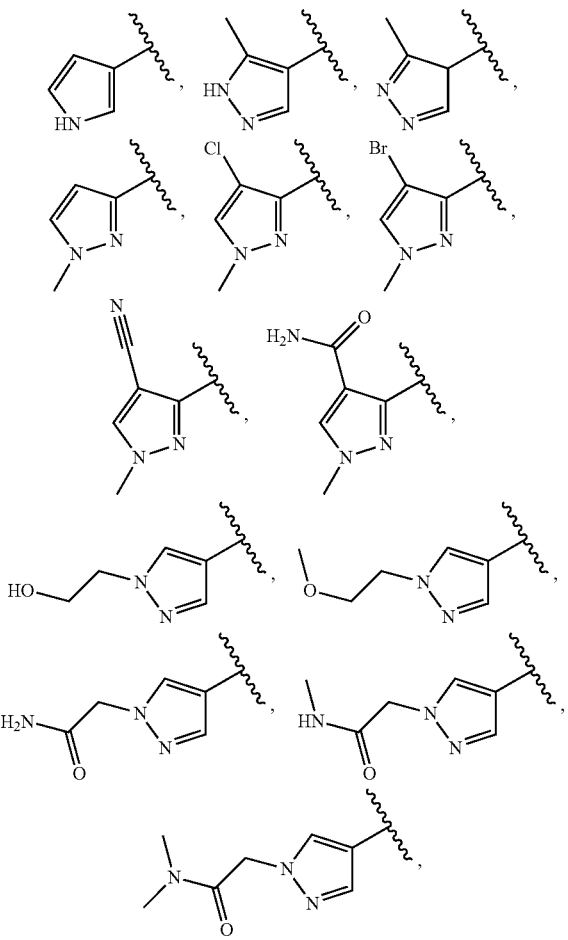

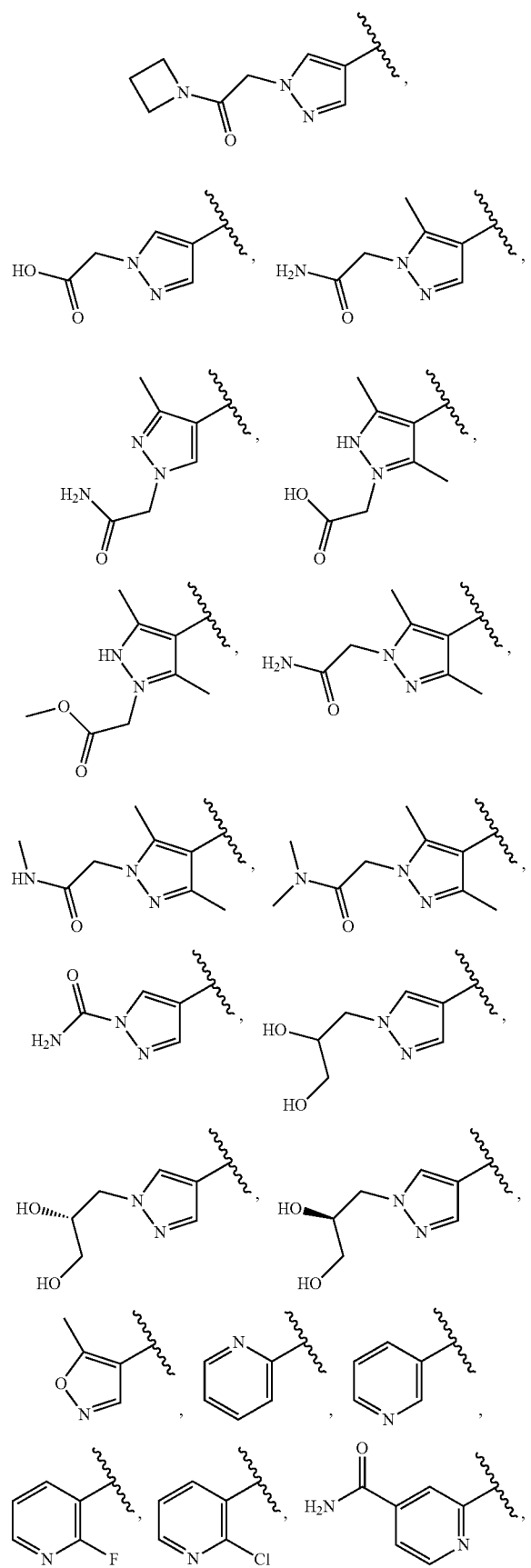
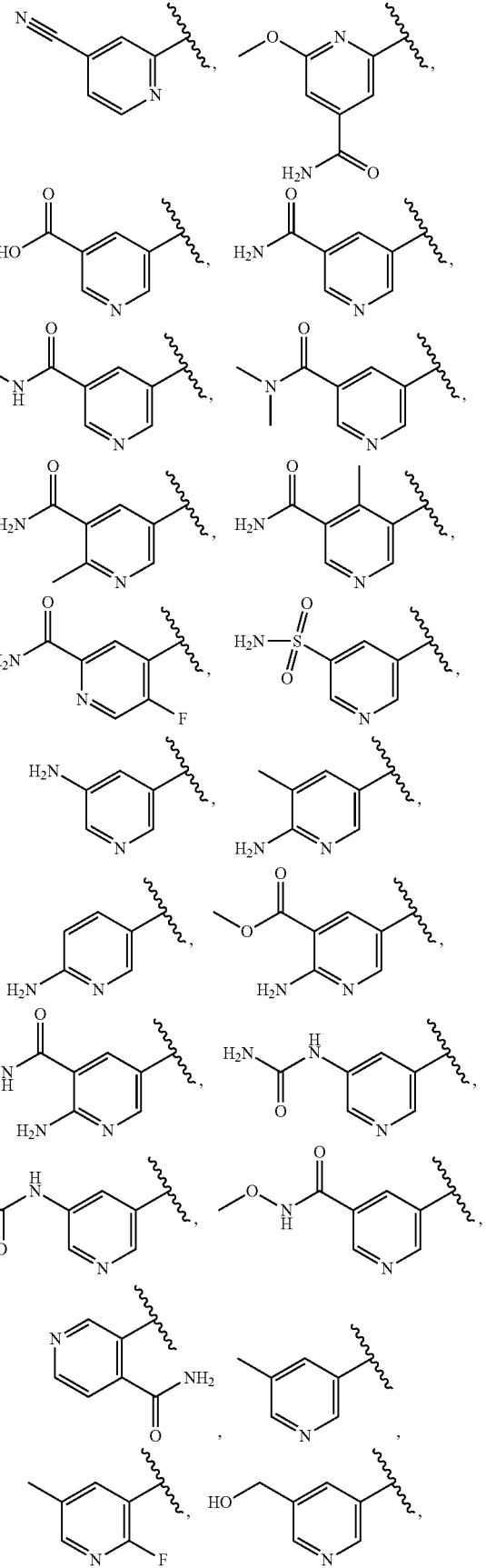

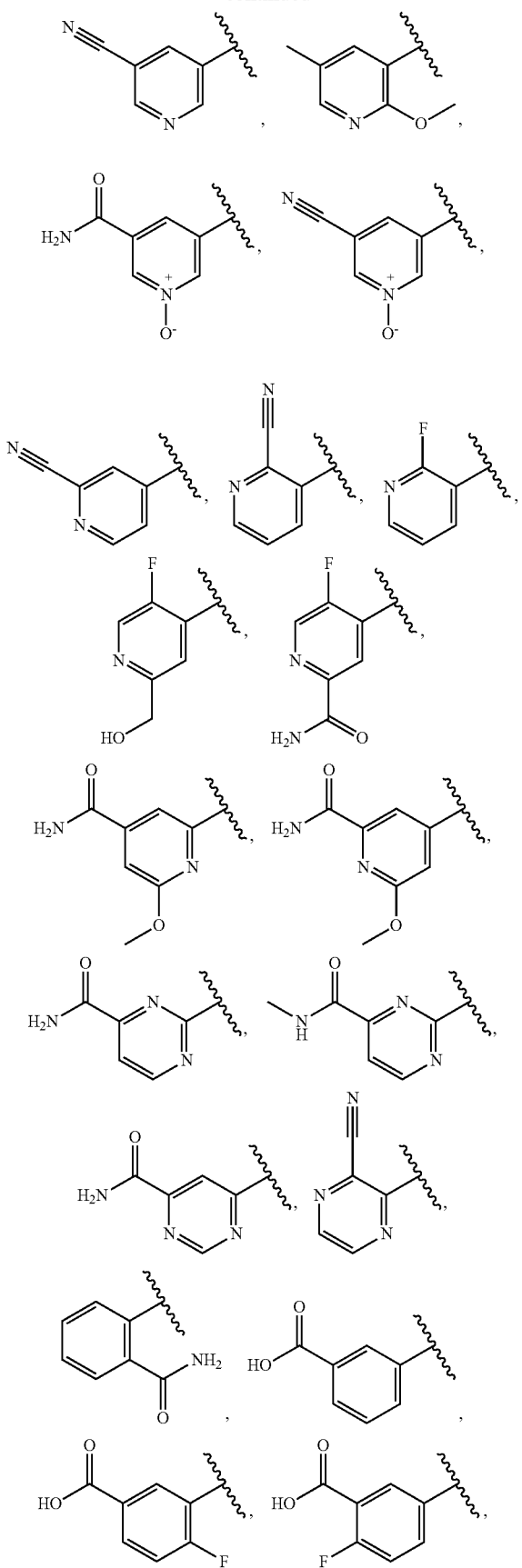
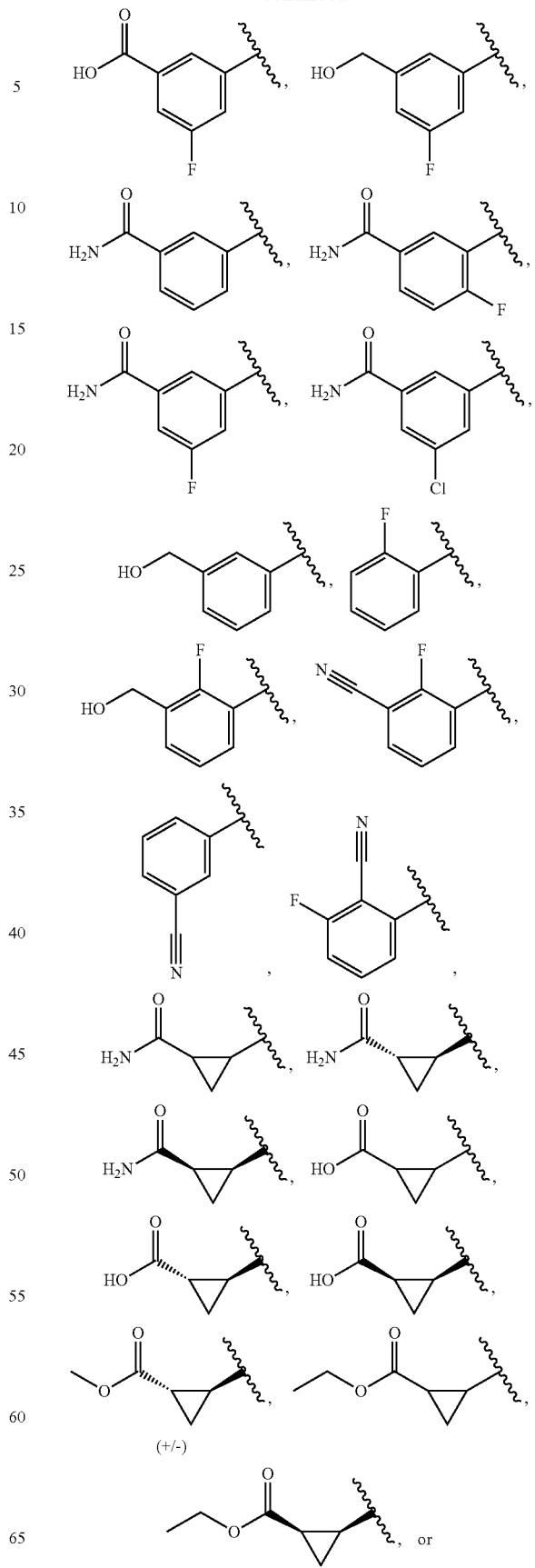

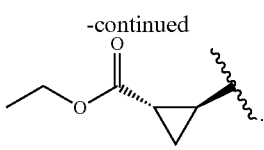

In certain embodiments, $R^3$ is phenyl or naphthyl; each of which is optionally substituted.

In certain embodiments, $R^3$ is an optionally substituted phenyl. In certain embodiments, $R^3$ is phenyl substituted by —R, halogen, -haloalkyl, —OR, —SR, —CN, —NO$_2$, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$.

In certain embodiments, $R^3$ is

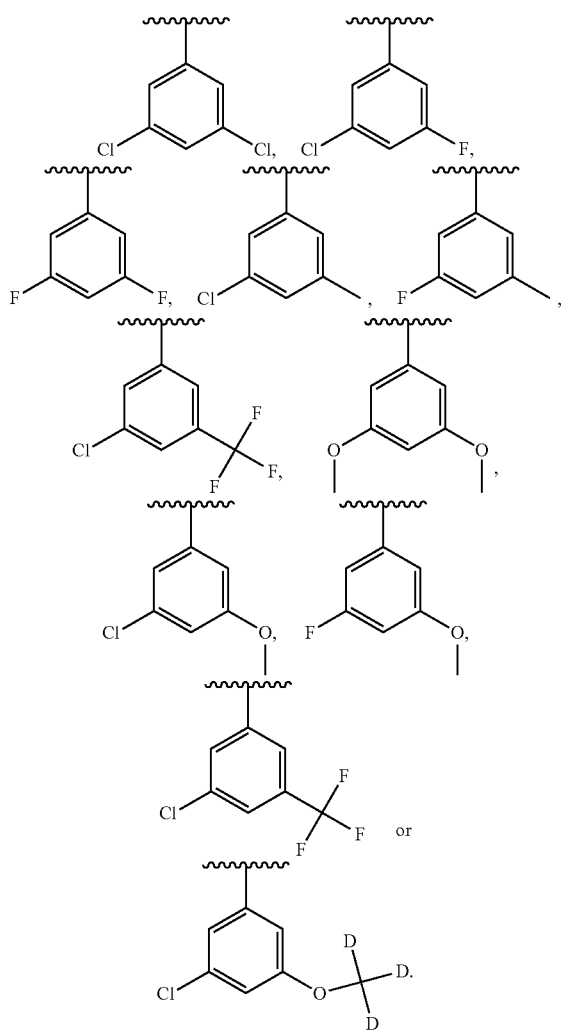

In certain embodiments, each $R^4$ is independently hydrogen.

In certain embodiments, each $R^4$ is independently $C_{1-6}$ aliphatic, aryl, a 3-8 membered saturated or partially unsaturated carbocyclic ring, a 3-7 membered heterocyclic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted.

In certain embodiments, each $R^4$ is independently an optionally substituted $C_{1-6}$ aliphatic. In certain embodiments, each $R^4$ is independently an optionally substituted aryl. In certain embodiments, each $R^4$ is independently an optionally substituted 3-8 membered saturated or partially unsaturated carbocyclic ring. In certain embodiments, each $R^4$ is independently an optionally substituted 3-7 membered heterocylic ring having 1-4 heteroatoms independently selected from nitrogen, oxygen, or sulfur. In certain embodiments, each $R^4$ is independently an optionally substituted 5-6 membered monocyclic heteroaryl ring having 1-4 heteroatoms independently selected from nitrogen, oxygen, or sulfur.

In certain embodiments, each $R^4$ is independently halogen, -haloalkyl, —OR, —SR, —CN, —NO$_2$, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$.

In certain embodiments, $R^5$ is $C_{1-6}$ aliphatic, SO$_2$R, —SOR, aryl, a 3-8 membered saturated or partially unsaturated carbocyclic ring, a 3-7 membered heterocyclic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted.

In certain embodiments, $R^5$ is an optionally substituted $C_{1-6}$ aliphatic. In certain embodiments, $R^5$ is an optionally substituted aryl. In certain embodiments, $R^5$ is an optionally substituted 3-8 membered saturated or partially unsaturated carbocyclic ring. In certain embodiments, $R^5$ is an optionally substituted 3-7 membered heterocylic ring having 1-4 heteroatoms independently selected from nitrogen, oxygen, or sulfur. In certain embodiments, $R^5$ is an optionally substituted 5-6 membered monocyclic heteroaryl ring having 1-4 heteroatoms independently selected from nitrogen, oxygen, or sulfur.

In certain embodiments, $R^5$ is $C_{1-6}$ aliphatic. In certain embodiments, $R^5$ is methyl, ethyl, propyl, i-propyl, butyl, s-butyl, t-butyl, straight or branched pentyl, or straight or branched hexyl; each of which is optionally substituted.

In certain embodiments, $R^5$ is phenyl, naphthyl, cyclopropyl, cyclobutyl, cyclopentyl, cyclohexyl, cycloheptyl, adamantyl, cyclooctyl, [3.3.0]bicyclooctanyl, [4.3.0]bicyclononanyl, [4.4.0]bicyclodecanyl, [2.2.2]bicyclooctanyl, fluorenyl, indanyl, tetrahydronaphthyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro [2,3-b] tetrahydrofuran, furanyl, furazanyl, imidazolidinyl, imidazolinyl, imidazolyl, 1H-indazolyl, indolenyl, indolinyl, indolizinyl, indolyl, 3H-indolyl, isoindolinyl, isoindolenyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, oxetanyl, azetidinyl, or xanthenyl; each of which is optionally substituted.

In certain embodiments, $R^5$ and $R^6$, together with the atom to which each is attached, form a 3-8 membered heterocylic 1 ring having 1-4 heteroatoms independently selected from nitrogen, oxygen, or sulfur, or a 5-6 membered heteroaryl ring having 1-4 heteroatoms independently selected from nitrogen, oxygen, or sulfur; each of which is optionally substituted.

In certain embodiments, $R^5$ is methyl, t-butyl,

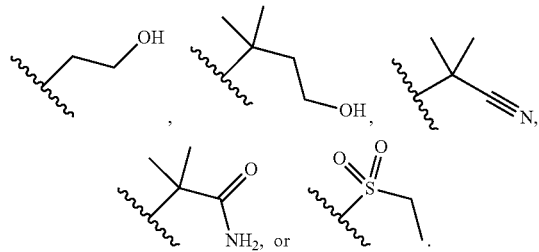

In certain embodiments, Z is N. In certain embodiments, Z is N and $R^5$, $R^6$, and Z together with the atoms to which each is attached form an optionally substituted 3-8 membered heterocylic ring having 1-4 heteroatoms independently selected from nitrogen, oxygen, or sulfur. In certain embodiments, Z is N and the ring formed by Z, $R^5$ and $R^6$ is

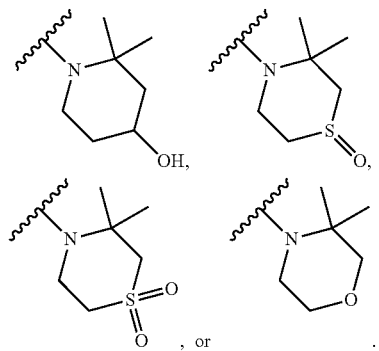

In certain embodiments, $R^6$ is hydrogen.

In certain embodiments, $R^6$ is $C_{1-6}$ aliphatic, $SO_2R$, —SOR, aryl, a 3-8 membered saturated or partially unsaturated carbocyclic ring, a 3-7 membered heterocyclic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted.

In certain embodiments, $R^6$ is an optionally substituted $C_{1-6}$ aliphatic. In certain embodiments, $R^6$ is an optionally substituted aryl. In certain embodiments, $R^6$ is an optionally substituted 3-8 membered saturated or partially unsaturated carbocyclic ring. In certain embodiments, $R^6$ is an optionally substituted 3-7 membered heterocylic ring having 1-4 heteroatoms independently selected from nitrogen, oxygen, or sulfur. In certain embodiments, $R^6$ is an optionally substituted 5-6 membered monocyclic heteroaryl ring having 1-4 heteroatoms independently selected from nitrogen, oxygen, or sulfur.

In certain embodiments, $R^6$ is $C_{1-6}$ aliphatic. In certain embodiments, $R^6$ is methyl, ethyl, propyl, i-propyl, butyl, s-butyl, t-butyl, straight or branched pentyl, or straight or branched hexyl; each of which is optionally substituted.

In certain embodiments, $R^6$ is phenyl, naphthyl, cyclopropyl, cyclobutyl, cyclopentyl, cyclohexyl, cycloheptyl, adamantyl, cyclooctyl, [3.3.0]bicyclooctanyl, [4.3.0]bicyclononanyl, [4.4.0]bicyclodecanyl, [2.2.2]bicyclooctanyl, fluorenyl, indanyl, tetrahydronaphthyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro [2,3-b] tetrahydrofuran, furanyl, furazanyl, imidazolidinyl, imidazolinyl, imidazolyl, 1H-indazolyl, indolenyl, indolinyl, indolizinyl, indolyl, 3H-indolyl, isoindolinyl, isoindolenyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, oxetanyl, azetidinyl, or xanthenyl; each of which is optionally substituted.

In certain embodiments, $R^6$ is hydrogen.

In certain embodiments, $R^6$ is $SO_2R$ or —SOR.

In certain embodiments, $R^6$ is optionally substituted $C_{1-6}$ aliphatic or —$SO_2R$.

In certain embodiments, $R^6$ is methyl, ethyl, t-butyl, or

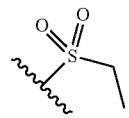

In certain embodiments, n is 0. In certain embodiments, n is 1. In certain embodiments, n is 2.

In certain embodiments, p is 0. In certain embodiments, p is 1.

In certain embodiments, each of $R^1$, $R^2$, $R^3$, $R^4$, $R^5$, $R^6$, X, Y, Z, n, and p is as defined above and described in embodiments, classes and subclasses above and herein, singly or in combination.

In certain embodiments, the present invention provides a compound of formula I-a,

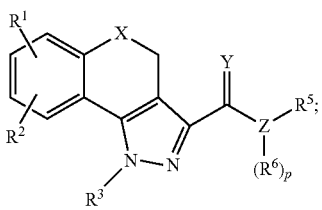

or a pharmaceutically acceptable salt thereof, wherein each of $R^1$, $R^2$, $R^3$, $R^5$, $R^6$, X, Y, Z, and p is as defined above and described in embodiments, classes and subclasses above and herein, singly or in combination.

In certain embodiments, the present invention provides a compound of formula I-b,

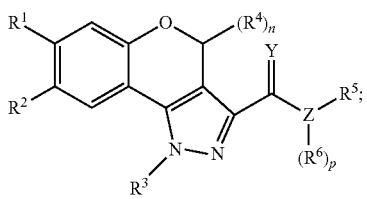

or a pharmaceutically acceptable salt thereof, wherein each of $R^1$, $R^2$, $R^3$, $R^4$, $R^5$, $R^6$, Y, Z, n, and p is as defined above and described in embodiments, classes and subclasses above and herein, singly or in combination.

In certain embodiments, the compound is of formula I-c:

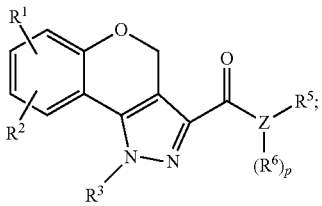

or a pharmaceutically acceptable salt thereof, wherein each of $R^1$, $R^2$, $R^3$, $R^5$, $R^6$, Z, and p is as defined above and described in embodiments, classes and subclasses above and herein, singly or in combination.

In certain embodiments, the invention provides a compound of formula I-d:

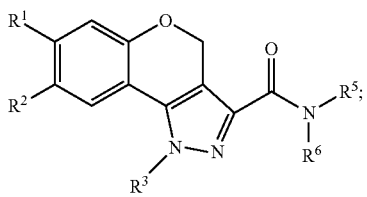

or a pharmaceutically acceptable salt thereof, wherein each of $R^1$, $R^2$, $R^3$, $R^5$, and $R^6$ is as defined above and described in embodiments, classes and subclasses above and herein, singly or in combination.

In other embodiments, the invention provides a compound of formula I-e:

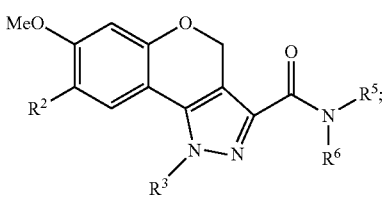

or a pharmaceutically acceptable salt thereof, wherein each of $R^2$, $R^3$, $R^5$, and $R^6$ is as defined above and described in embodiments, classes and subclasses above and herein, singly or in combination.

In other embodiments, the invention provides a compound of formula I-f:

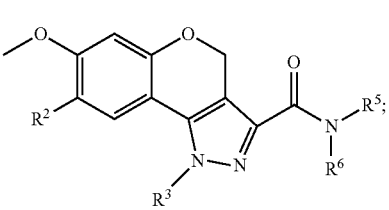

or a pharmaceutically acceptable salt thereof, wherein $R^2$ is aryl, a 3-8 membered saturated or partially unsaturated carbocyclic ring, or a 5-6 membered monocyclic heteroaryl ring having 1-4 heteroatoms independently selected from nitrogen, oxygen, or sulfur; each of which is optionally substituted; $R^3$ is an optionally substituted phenyl; $R^5$ is an optionally substituted $C_{1-6}$ aliphatic; $R^6$ is an optionally substituted $C_{1-6}$ aliphatic; or $R^5$ and $R^6$, together with the atom to which each is attached, form an optionally substituted 3-8 membered heterocylic ring having 1-4 heteroatoms independently selected from nitrogen, oxygen, or sulfur.

In a second aspect, the present invention provides a compound of formula II,

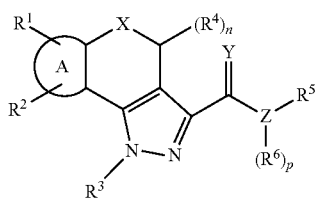

or a pharmaceutically acceptable salt thereof, wherein:

X is O, S, SO, $SO_2$, or NR;

Y is O, S, or NR;

Z is O, S, SO, $SO_2$, or N; wherein when Z is O, S, SO, or $SO_2$, then p is 0;

each R is independently hydrogen, $C_{1-6}$ aliphatic, aryl, a 3-8 membered saturated or partially unsaturated carbocyclic ring, a 3-7 membered heterocyclic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted; or two R groups on the same atom are taken together with the atom to which they are attached to form an aryl ring, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted;

Ring A is a fused aryl, a fused 3-8 membered saturated or partially unsaturated carbocyclic ring, a fused 3-7 membered heterocyclic ring having 1-4 heteroatoms independently selected from nitrogen, oxygen, or sulfur, or a fused 5-6 membered monocyclic heteroaryl ring having 1-4 heteroatoms independently selected from nitrogen, oxygen, or sulfur;

$R^1$ is —OR, —SR, —CN, —NO$_2$, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$;

$R^2$ is —R, halogen, -haloalkyl, —OR, —SR, —CN, —NO$_2$, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$;

$R^3$ is an optionally substituted 5-6 membered monocyclic heteroaryl ring;

each $R^4$ is independently —R, halogen, -haloalkyl, —OR, —SR, —CN, —NO$_2$, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$;

$R^5$ is $C_{1-6}$ aliphatic, —SO$_2$R, —SOR, aryl, a 3-8 membered saturated or partially unsaturated carbocyclic ring, a 3-7 membered heterocyclic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted;

$R^6$ is hydrogen, $C_{1-6}$ aliphatic, —SO$_2$R, —SOR, aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted;

or $R^5$ and $R^6$, together with the atom to which each is attached, form a 3-8 membered heterocylic ring having 1-4 heteroatoms independently selected from nitrogen, oxygen, or sulfur, or a 3-8 membered heteroaryl ring having 1-4 heteroatoms independently selected from nitrogen, oxygen, or sulfur; each of which is optionally substituted;

n is 0, 1, or 2; and
p is 0 or 1.

In certain embodiments, X is O. In certain embodiments, X is S. In certain embodiments, X is SO or SO$_2$. In certain embodiments, X is NR.

In certain embodiments, Y is O. In certain embodiments, Y is S. In certain embodiments, Y is NR.

In certain embodiments, Z is O. In certain embodiments, Z is S. In certain embodiments, Z is SO or SO$_2$. In certain embodiments, Z is N.

In certain embodiments, Ring A is a fused aryl. In certain embodiments, Ring A is a fused 3-8 membered saturated or partially unsaturated carbocyclic ring. In certain embodiments, Ring A is a fused 3-7 membered heterocyclic ring having 1-4 heteroatoms independently selected from nitrogen, oxygen, or sulfur. In certain embodiments, Ring A is a fused 5-6 membered monocyclic heteroaryl ring having 1-4 heteroatoms independently selected from nitrogen, oxygen, or sulfur.

In certain embodiments, Ring A is phenyl, cyclopropyl, cyclobutyl, cyclopentyl, cyclohexyl, cycloheptyl, furanyl, furazanyl, imidazolidinyl, imidazolinyl, imidazolyl, 1H-indazolyl, indolenyl, isoxazolyl, morpholinyl, oxadiazolyl, 1,2,3-oxadiazolyl, 1,2,4-oxadiazolyl; 1,2,5-oxadiazolyl, 1,3,4-oxadiazolyl, oxazolidinyl, oxazolyl, oxazolidinyl, pyrimidinyl, piperazinyl, piperidinyl, purinyl, pyranyl, pyrazinyl, pyrazolidinyl, pyrazolinyl, pyrazolyl, pyridazinyl, pyridinyl, pyridyl, pyrimidinyl, pyrrolidinyl, pyrrolinyl, 2H-pyrrolyl, pyrrolyl, tetrahydrofuranyl, thiazolyl, thiophenyl, oxetanyl, or azetidinyl.

In certain embodiments, Ring A is phenyl.

In certain embodiments, $R^1$ is —OR, —SR, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$. In certain embodiments, $R^1$ is —OR, —SR, —SO$_2$R, or —SOR. In certain embodiments, $R^1$ is —C(O)R, —CO$_2$R, or —C(O)N(R)$_2$. In certain embodiments, $R^1$ is —NRC(O)R, —NRC(O)N(R)$_2$, —NRSO$_2$R, or —N(R)$_2$.

In certain embodiments, $R^1$ is —OR, and R is hydrogen.

In certain embodiments, $R^1$ is —OR, and R is $C_{1-6}$ aliphatic, aryl, a 3-8 membered saturated or partially unsaturated carbocyclic ring, a 3-7 membered heterocyclic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted.

In certain embodiments, $R^1$ is —OR, and R is $C_{1-6}$ aliphatic. In certain embodiments, R is methyl, ethyl, propyl, i-propyl, butyl, s-butyl, t-butyl, straight or branched pentyl, or straight or branched hexyl; each of which is optionally substituted. In certain embodiments, R is methyl.

In certain embodiments, $R^1$ is —OR, and R is aryl, a 3-8 membered saturated or partially unsaturated carbocyclic ring, a 3-7 membered heterocyclic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur. In certain embodiments, R is phenyl, naphthyl, cyclopropyl, cyclobutyl, cyclopentyl, cyclohexyl, cycloheptyl, adamantyl, cyclooctyl, [3.3.0]bicyclooctanyl, [4.3.0]bicyclononanyl, [4.4.0]bicyclodecanyl, [2.2.2]bicyclooctanyl, fluorenyl, indanyl, tetrahydronaphthyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro [2,3-b] tetrahydrofuran, furanyl, furazanyl, imidazolidinyl, imidazolinyl, imidazolyl, 1H-indazolyl, indolenyl, indolinyl, indolizinyl, indolyl, 3H-indolyl, isoindolinyl, isoindolenyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, oxetanyl, azetidinyl, or xanthenyl; each of which is optionally substituted.

In certain embodiments, $R^1$ is —OR, and $R^2$ is OR, $C_{1-6}$ aliphatic, Aryl, a 3-8 membered saturated or partially unsaturated carbocyclic ring, or a 5-6 membered monocyclic heteroaryl ring having 1-4 heteroatoms independently selected from nitrogen, oxygen, or sulfur; each of which is optionally substituted.

In certain embodiments, $R^1$ is —OR, and $R^2$ is —OR, $C_{1-6}$ aliphatic, a 6-membered aryl ring, or a 5-6 membered monocyclic heteroaryl ring having 1-4 nitrogen atoms; each of which is optionally substituted.

In certain embodiments, $R^2$ is hydrogen.

In certain embodiments, $R^2$ is $C_{1-6}$ aliphatic. In certain embodiments, $R^2$ is $C_{1-6}$ aliphatic wherein the aliphatic group is a $C_{1-6}$ alkyl. In certain embodiments, $R^2$ is methyl, ethyl, propyl, i-propyl, butyl, s-butyl, t-butyl, straight or branched pentyl, or straight or branched hexyl; each of which is optionally substituted. In certain embodiments, $R^2$ is methyl, ethyl, propyl, or i-propyl. In certain embodiments, $R^2$ is i-propyl. In certain embodiments, $R^2$ is $C_{1-6}$ aliphatic wherein the aliphatic group is a $C_{1-6}$ alkenyl.

In certain embodiments, $R^2$ is aryl, a 3-8 membered saturated or partially unsaturated carbocyclic ring, a 3-7 membered heterocyclic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted.

In certain embodiments, $R^2$ is phenyl, naphthyl, cyclopropyl, cyclobutyl, cyclopentyl, cyclohexyl, cycloheptyl, adamantyl, cyclooctyl, [3.3.0]bicyclooctanyl, [4.3.0]bicyclononanyl, [4.4.0]bicyclodecanyl, [2.2.2]bicyclooctanyl, fluorenyl, indanyl, tetrahydronaphthyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro [2,3-b] tetrahydrofuran, furanyl, furazanyl, imidazolidinyl, imidazolinyl, imidazolyl, 1H-indazolyl, indolenyl, indolinyl, indolizinyl, indolyl, 3H-indolyl, isoindolinyl, isoindolenyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, oxetanyl, azetidinyl, or xanthenyl; each of which is optionally substituted.

In certain embodiments, $R^2$ is halogen, -haloalkyl, —OR, —SR, —CN, —NO$_2$, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$.

In certain embodiments, $R^2$ is F, Cl, Br, I, or haloalkyl.

In certain embodiments, $R^2$ is —OR, —SR, —CN, —NO$_2$, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$. In certain embodiments, R is $C_{1-6}$ aliphatic, aryl, a 3-8 membered saturated or partially unsaturated carbocyclic ring, a 3-7 membered heterocyclic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted. In certain embodiments, R is methyl, ethyl, propyl, i-propyl, butyl, s-butyl, t-butyl, straight or branched pentyl, or straight or branched hexyl; each of which is optionally substituted. In other embodiments, R is phenyl, naphthyl, cyclopropyl, cyclobutyl, cyclopentyl, cyclohexyl, cycloheptyl, adamantyl, cyclooctyl, [3.3.0]bicyclooctanyl, [4.3.0]bicyclononanyl, [4.4.0]bicyclodecanyl, [2.2.2]bicyclooctanyl, fluorenyl, indanyl, tetrahydronaphthyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro [2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isoindolinyl, isoindolenyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, oxetanyl, azetidinyl, or xanthenyl; each of which is optionally substituted.

In certain embodiments, $R^2$ is

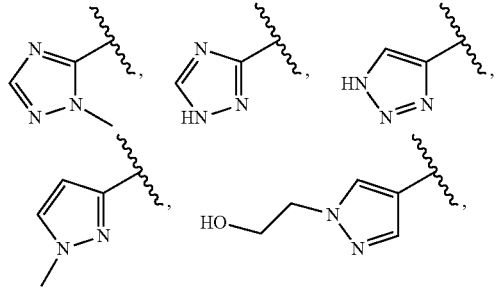

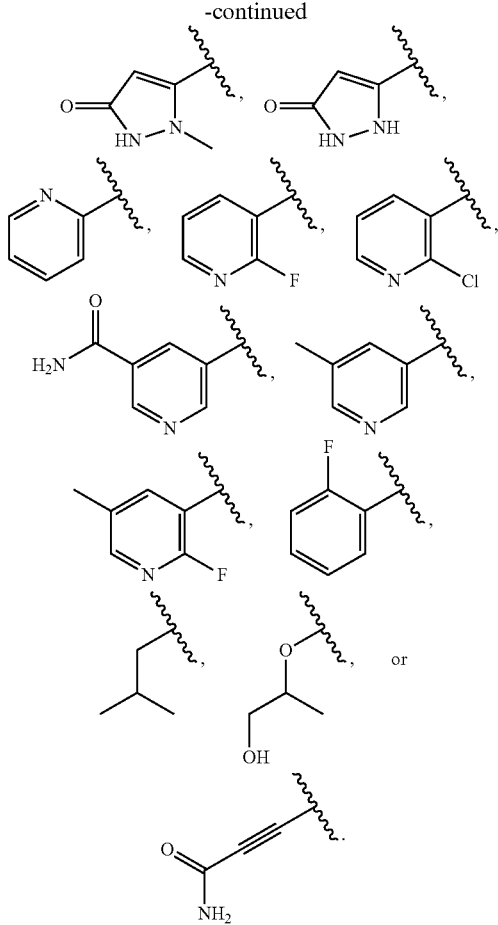

In certain embodiments, $R^3$ is thiophenyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, and pyrazinyl.

In certain embodiments, $R^3$ is thiophenyl or pyridyl; each of which is optionally substituted.

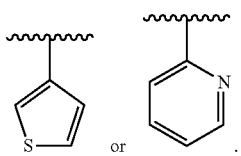 [SMILES: *c1ccsc1 ; *c1ccccn1]

In certain embodiments, $R^3$ is or

In certain embodiments, each $R^4$ is independently hydrogen.

In certain embodiments, each $R^4$ is independently $C_{1-6}$ aliphatic, $C_{3-10}$ aryl, a 3-8 membered saturated or partially unsaturated carbocyclic ring, a 3-7 membered heterocyclic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted.

In certain embodiments, each $R^4$ is independently an optionally substituted $C_{1-6}$ aliphatic. In certain embodiments, each $R^4$ is independently an optionally substituted aryl. In certain embodiments, each $R^4$ is independently an optionally substituted 3-8 membered saturated or partially unsaturated carbocyclic ring. In certain embodiments, each $R^4$ is independently an optionally substituted 3-7 membered heterocylic ring having 1-4 heteroatoms independently selected from nitrogen, oxygen, or sulfur. In certain embodiments, each $R^4$ is independently an optionally substituted 5-6 membered monocyclic heteroaryl ring having 1-4 heteroatoms independently selected from nitrogen, oxygen, or sulfur.

In certain embodiments, each $R^4$ is independently halogen, -haloalkyl, —OR, —SR, —CN, —NO$_2$, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$.

In certain embodiments, $R^5$ is $C_{1-6}$ aliphatic, aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted.

In certain embodiments, $R^5$ is an optionally substituted $C_{1-6}$ aliphatic. In certain embodiments, $R^5$ is an optionally substituted aryl. In certain embodiments, $R^5$ is an optionally substituted 3-8 membered saturated or partially unsaturated carbocyclic ring. In certain embodiments, $R^5$ is an optionally substituted 3-7 membered heterocylic ring having 1-4 heteroatoms independently selected from nitrogen, oxygen, or sulfur. In certain embodiments, $R^5$ is an optionally substituted 5-6 membered monocyclic heteroaryl ring having 1-4 heteroatoms independently selected from nitrogen, oxygen, or sulfur.

In certain embodiments, $R^5$ is $C_{1-6}$ aliphatic. In certain embodiments, $R^5$ is methyl, ethyl, propyl, i-propyl, butyl, s-butyl, t-butyl, straight or branched pentyl, or straight or branched hexyl; each of which is optionally substituted.

In certain embodiments, $R^5$ is phenyl, naphthyl, cyclopropyl, cyclobutyl, cyclopentyl, cyclohexyl, cycloheptyl, adamantyl, cyclooctyl, [3.3.0]bicyclooctanyl, [4.3.0]bicyclononanyl, [4.4.0]bicyclodecanyl, [2.2.2]bicyclooctanyl, fluorenyl, indanyl, tetrahydronaphthyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro [2,3-b] tetrahydrofuran, furanyl, furazanyl, imidazolidinyl, imidazolinyl, imidazolyl, 1H-indazolyl, indolenyl, indolinyl, indolizinyl, indolyl, 3H-indolyl, isoindolinyl, isoindolenyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienothiazolyl, thienooxazolyl, thienoimidazolyl, thiophenyl, triazinyl, 1,2,3-triazolyl, 1,2,4-triazolyl, 1,2,5- triazolyl, 1,3,4-triazolyl, oxetanyl, azetidinyl, or xanthenyl; each of which is optionally substituted.

In certain embodiments, $R^5$ and $R^6$, together with the atom to which each is attached, form a 3-8 membered heterocylic 1 ring having 1-4 heteroatoms independently selected from nitrogen, oxygen, or sulfur, or a 5-6 membered heteroaryl ring having 1-4 heteroatoms independently selected from nitrogen, oxygen, or sulfur; each of which is optionally substituted.

In certain embodiments, $R^5$ is methyl, t-butyl,

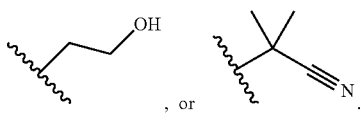

, or .

In certain embodiments, Z is N. In certain embodiments, Z is N and $R^5$, $R^6$, and Z together with the atoms to which each is attached form an optionally substituted 3-8 membered heterocyclic ring having 1-4 heteroatoms independently selected from nitrogen, oxygen, or sulfur. In certain embodiments, Z is N and the ring formed by Z, $R^5$ and $R^6$ is

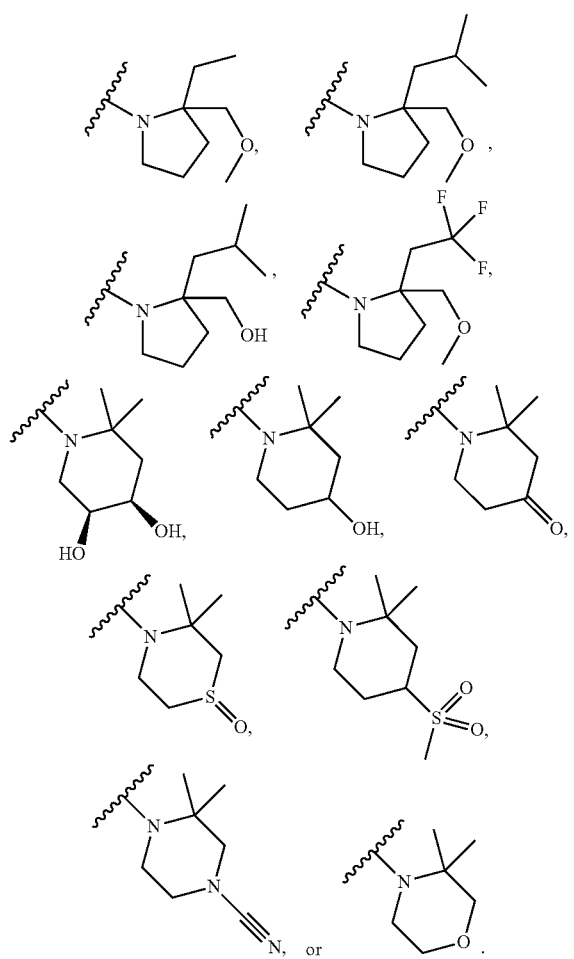

In certain embodiments, $R^6$ is hydrogen.

In certain embodiments, $R^6$ is $C_{1-6}$ aliphatic, aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted.

In certain embodiments, $R^6$ is an optionally substituted $C_{1-6}$ aliphatic. In certain embodiments, $R^6$ is an optionally substituted aryl. In certain embodiments, $R^6$ is an optionally substituted 3-8 membered saturated or partially unsaturated carbocyclic ring. In certain embodiments, $R^6$ is an optionally substituted 3-7 membered heterocylic ring having 1-4 heteroatoms independently selected from nitrogen, oxygen, or sulfur. In certain embodiments, $R^6$ is an optionally substituted 5-6 membered monocyclic heteroaryl ring having 1-4 heteroatoms independently selected from nitrogen, oxygen, or sulfur.

In certain embodiments, $R^6$ is $C_{1-6}$ aliphatic. In certain embodiments, $R^6$ is methyl, ethyl, propyl, i-propyl, butyl, s-butyl, t-butyl, straight or branched pentyl, or straight or branched hexyl; each of which is optionally substituted.

In certain embodiments, $R^6$ is phenyl, naphthyl, cyclopropyl, cyclobutyl, cyclopentyl, cyclohexyl, cycloheptyl, adamantyl, cyclooctyl, [3.3.0]bicyclooctanyl, [4.3.0]bicyclononanyl, [4.4.0]bicyclodecanyl, [2.2.2]bicyclooctanyl, fluorenyl, indanyl, tetrahydronaphthyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro [2,3-b] tetrahydrofuran, furanyl, furazanyl, imidazolidinyl, imidazolinyl, imidazolyl, 1H-indazolyl, indolenyl, indolinyl, indolizinyl, indolyl, 3H-indolyl, isoindolinyl, isoindolenyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, oxetanyl, azetidinyl, or xanthenyl; each of which is optionally substituted.

In certain embodiments, $R^6$ is hydrogen.

In certain embodiments, $R^6$ is methyl or t-butyl.

In certain embodiments, n is 0. In certain embodiments, n is 1. In certain embodiments, n is 2.

In certain embodiments, p is 0. In certain embodiments, p is 1.

In certain embodiments, each of $R^1$, $R^2$, $R^3$, $R^4$, $R^5$, $R^6$, X, Y, Z, n, and p is as defined above and described in embodiments, classes and subclasses above and herein, singly or in combination.

In certain embodiments, the present invention provides a compound of formula II-a,

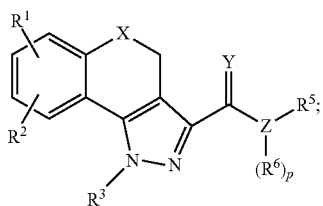

II-a or a pharmaceutically acceptable salt thereof, wherein each of $R^1$, $R^2$, $R^3$, $R^5$, $R^6$, X, Y, Z, and p is as defined above and described in embodiments, classes and subclasses above and herein, singly or in combination.

In certain embodiments, the present invention provides a compound of formula II-b,

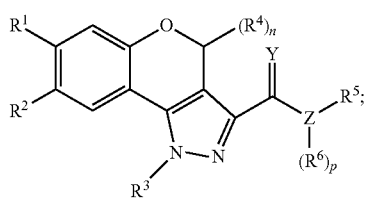

II-b or a pharmaceutically acceptable salt thereof, wherein each of $R^1$, $R^2$, $R^3$, $R^4$, $R^5$, $R^6$, Y, Z, n, and p is as defined above and described in embodiments, classes and subclasses above and herein, singly or in combination.

In certain embodiments, the compound is of formula II-c:

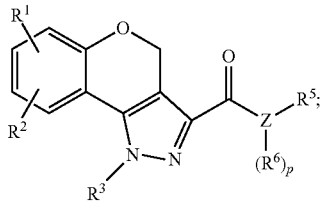

II-c or a pharmaceutically acceptable salt thereof, wherein each of $R^1$, $R^2$, $R^3$, $R^5$, $R^6$, Z, and p is as defined above and described in embodiments, classes and subclasses above and herein, singly or in combination.

In certain embodiments, the invention provides a compound of formula II-d:

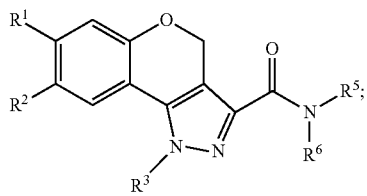

II-d or a pharmaceutically acceptable salt thereof, wherein each of $R^1$, $R^2$, $R^3$, $R^5$, and $R^6$ is as defined above and described in embodiments, classes and subclasses above and herein, singly or in combination.

In other embodiments, the invention provides a compound of formula II-e:

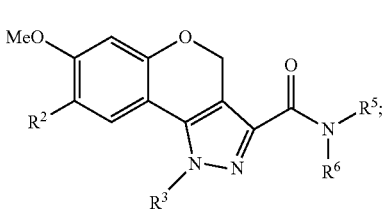

II-e or a pharmaceutically acceptable salt thereof, wherein each of $R^2$, $R^3$, $R^5$, and $R^6$ is as defined above and described in embodiments, classes and subclasses above and herein, singly or in combination.

In other embodiments, the invention provides a compound of formula II-f:

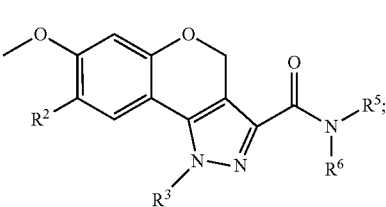

II-f or a pharmaceutically acceptable salt thereof, wherein $R^2$ is $C_{1-6}$ aliphatic, —OR, aryl, a 3-8 membered saturated or partially unsaturated carbocyclic ring, or a 5-6 membered monocyclic heteroaryl ring having 1-4 heteroatoms independently selected from nitrogen, oxygen, or sulfur; each of which is optionally substituted; $R^3$ is an optionally substituted thiophenyl or pyridyl; $R^5$ is an optionally substituted $C_{1-6}$ aliphatic; $R^6$ is an optionally substituted $C_{1-6}$ aliphatic or —$SO_2R$; or $R^5$ and $R^6$, together with the atom to which each is attached, form an optionally substituted 3-8 membered heterocyclic ring having 1-4 heteroatoms independently selected from nitrogen, oxygen, or sulfur.

In certain embodiments, the invention provides a compound selected from Table 1.

TABLE 1
Exemplary compounds of the invention.
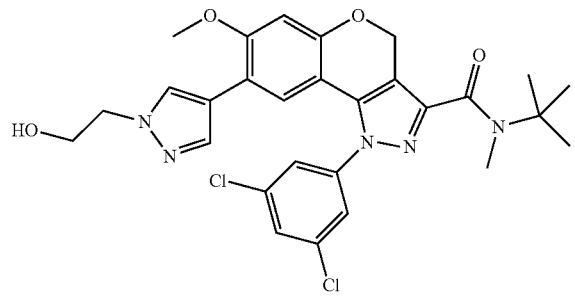 [SMILES: COc1cc2c(cc1-c1cnn(CCO)c1)-c1c(c(C(=O)N(C)C(C)(C)C)nn1-c1cc(Cl)cc(Cl)c1)CO2]
1
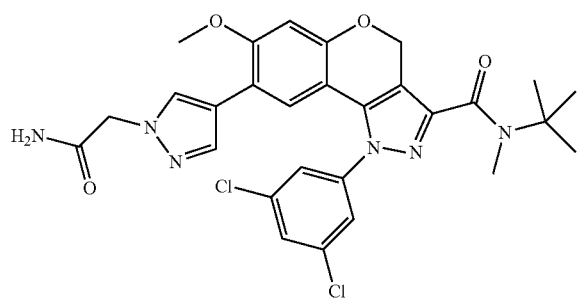 [SMILES: COc1cc2c(cc1-c1cnn(CC(N)=O)c1)-c1c(c(C(=O)N(C)C(C)(C)C)nn1-c1cc(Cl)cc(Cl)c1)CO2]
2
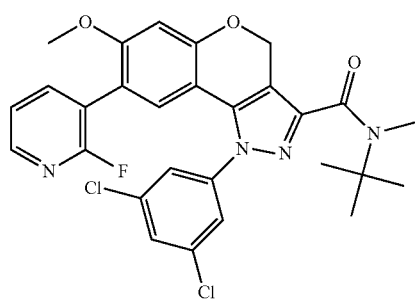 [SMILES: COc1cc2c(cc1-c1cccnc1F)-c1c(c(C(=O)N(C)C(C)(C)C)nn1-c1cc(Cl)cc(Cl)c1)CO2]
3
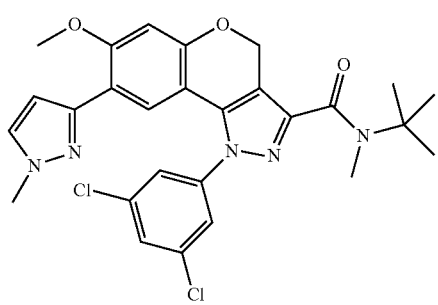 [SMILES: COc1cc2c(cc1-c1ccn(C)n1)-c1c(c(C(=O)N(C)C(C)(C)C)nn1-c1cc(Cl)cc(Cl)c1)CO2]
4
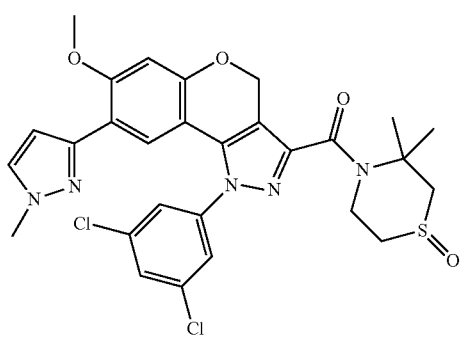 [SMILES: COc1cc2c(cc1-c1ccn(C)n1)-c1c(c(C(=O)N3CCS(=O)CC3(C)C)nn1-c1cc(Cl)cc(Cl)c1)CO2]
5

TABLE 1-continued
Exemplary compounds of the invention.
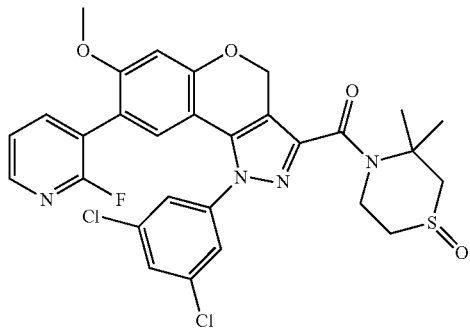 [SMILES: COc1cc2c(cc1-c1cccnc1F)-c1c(c(C(=O)N3CCS(=O)CC3(C)C)nn1-c1cc(Cl)cc(Cl)c1)CO2]
6
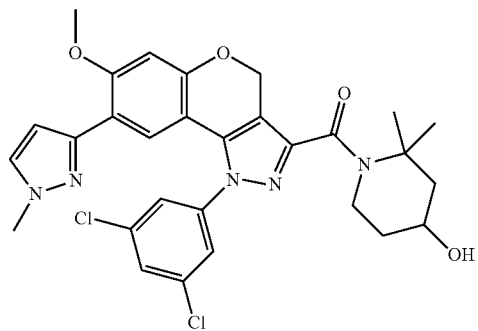 [SMILES: COc1cc2c(cc1-c1ccn(C)n1)-c1c(c(C(=O)N3CCC(O)CC3(C)C)nn1-c1cc(Cl)cc(Cl)c1)CO2]
7
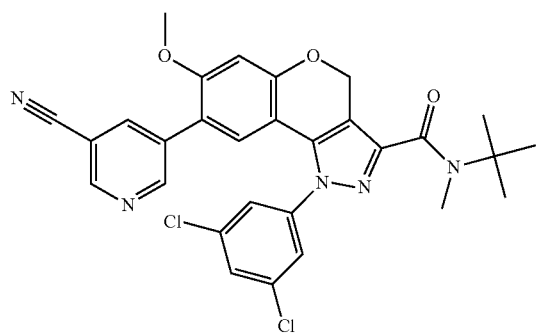
8
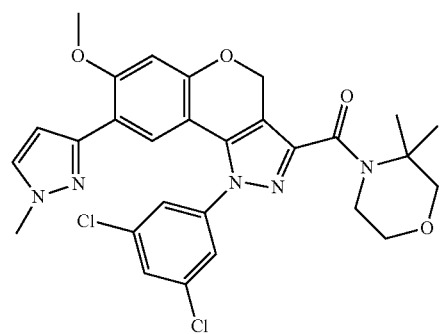 [SMILES: COc1cc2c(cc1-c1ccn(C)n1)-c1c(c(C(=O)N3CCOCC3(C)C)nn1-c1cc(Cl)cc(Cl)c1)CO2]
9

TABLE 1-continued
Exemplary compounds of the invention.
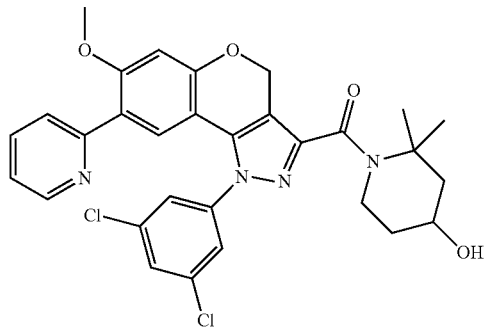 [SMILES: COc1cc2c(cc1-c1ccccn1)-c1c(c(C(=O)N3CCC(O)CC3(C)C)nn1-c1cc(Cl)cc(Cl)c1)CO2]
10
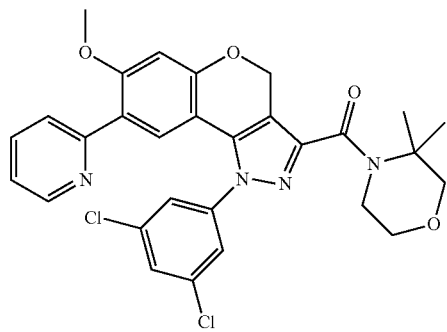 [SMILES: COc1cc2c(cc1-c1ccccn1)-c1c(c(C(=O)N3CCOCC3(C)C)nn1-c1cc(Cl)cc(Cl)c1)CO2]
11
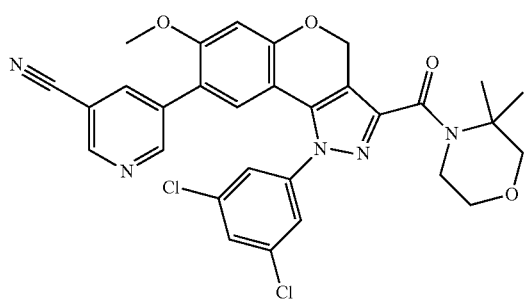 [SMILES: COc1cc2c(cc1-c1cncc(C#N)c1)-c1c(c(C(=O)N3CCOCC3(C)C)nn1-c1cc(Cl)cc(Cl)c1)CO2]
12
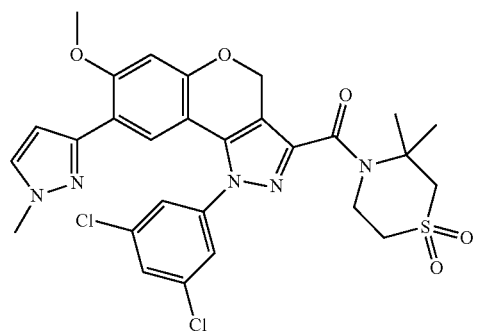 [SMILES: COc1cc2c(cc1-c1ccn(C)n1)-c1c(c(C(=O)N3CCS(=O)(=O)CC3(C)C)nn1-c1cc(Cl)cc(Cl)c1)CO2]
13

TABLE 1-continued
Exemplary compounds of the invention.
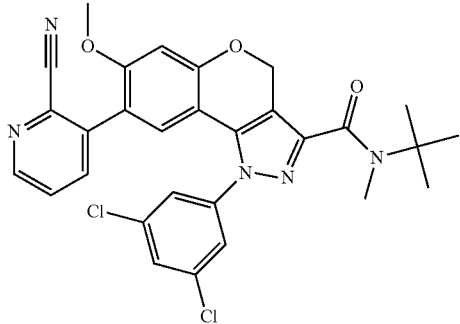 [SMILES: COc1cc2c(cc1-c1cccnc1C#N)-c1c(c(C(=O)N(C)C(C)(C)C)nn1-c1cc(Cl)cc(Cl)c1)CO2] 14
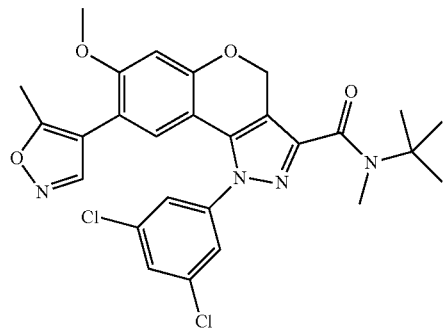 [SMILES: COc1cc2c(cc1-c1cnoc1C)-c1c(c(C(=O)N(C)C(C)(C)C)nn1-c1cc(Cl)cc(Cl)c1)CO2] 15
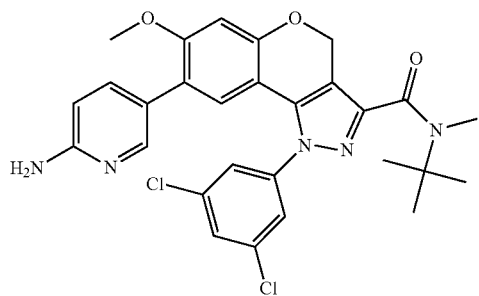 [SMILES: COc1cc2c(cc1-c1ccc(N)nc1)-c1c(c(C(=O)N(C)C(C)(C)C)nn1-c1cc(Cl)cc(Cl)c1)CO2] 16
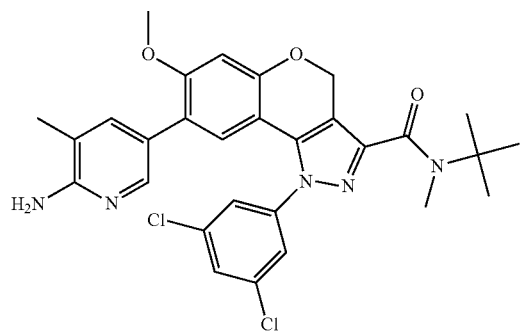 [SMILES: COc1cc2c(cc1-c1cnc(N)c(C)c1)-c1c(c(C(=O)N(C)C(C)(C)C)nn1-c1cc(Cl)cc(Cl)c1)CO2] 17

TABLE 1-continued
Exemplary compounds of the invention.
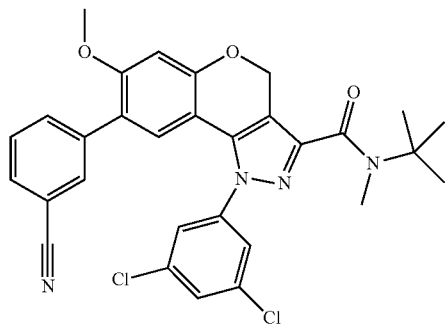 [SMILES: COc1cc2c(cc1-c1cccc(C#N)c1)-c1c(c(C(=O)N(C)C(C)(C)C)nn1-c1cc(Cl)cc(Cl)c1)CO2]
18
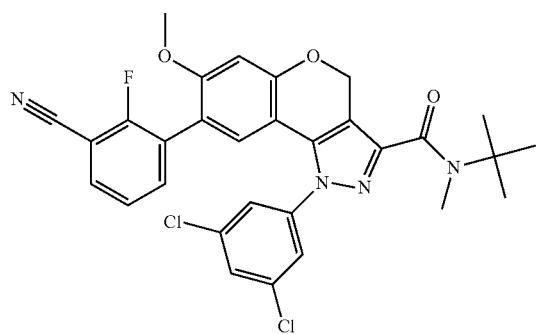 [SMILES: COc1cc2c(cc1-c1cccc(C#N)c1F)-c1c(c(C(=O)N(C)C(C)(C)C)nn1-c1cc(Cl)cc(Cl)c1)CO2]
19
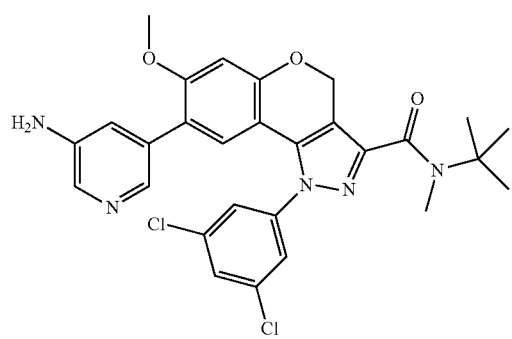 [SMILES: COc1cc2c(cc1-c1cncc(N)c1)-c1c(c(C(=O)N(C)C(C)(C)C)nn1-c1cc(Cl)cc(Cl)c1)CO2]
20
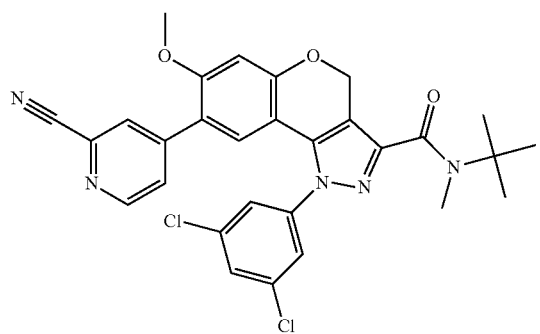 [SMILES: COc1cc2c(cc1-c1ccnc(C#N)c1)-c1c(c(C(=O)N(C)C(C)(C)C)nn1-c1cc(Cl)cc(Cl)c1)CO2]
21

TABLE 1-continued
Exemplary compounds of the invention.
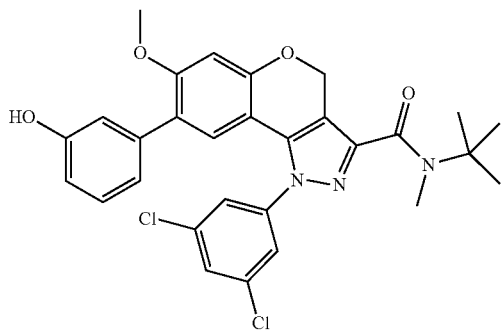 [SMILES: COc1cc2c(cc1-c1cccc(O)c1)-c1c(c(C(=O)N(C)C(C)(C)C)nn1-c1cc(Cl)cc(Cl)c1)CO2]
22
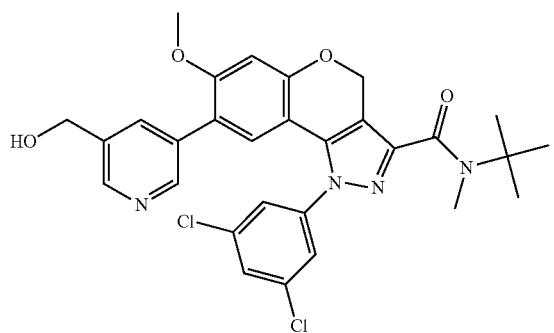 [SMILES: COc1cc2c(cc1-c1cncc(CO)c1)-c1c(c(C(=O)N(C)C(C)(C)C)nn1-c1cc(Cl)cc(Cl)c1)CO2]
23
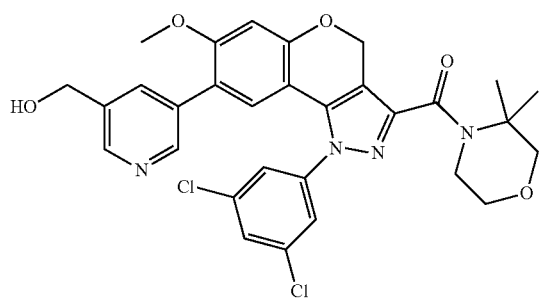 [SMILES: COc1cc2c(cc1-c1cncc(CO)c1)-c1c(c(C(=O)N3CCOCC3(C)C)nn1-c1cc(Cl)cc(Cl)c1)CO2]
24
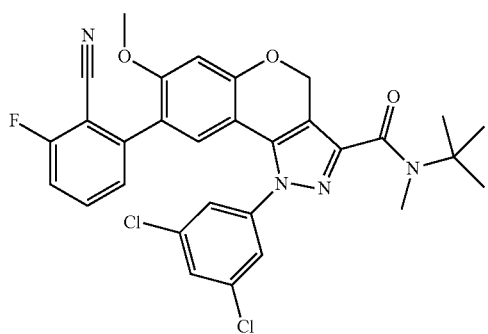 [SMILES: COc1cc2c(cc1-c1cccc(F)c1C#N)-c1c(c(C(=O)N(C)C(C)(C)C)nn1-c1cc(Cl)cc(Cl)c1)CO2]
25

TABLE 1-continued
Exemplary compounds of the invention.
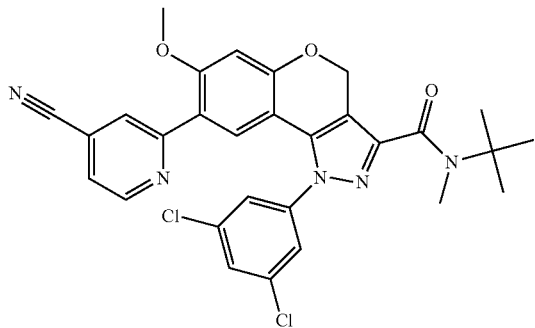 [SMILES: COc1cc2c(cc1-c1cc(C#N)ccn1)-c1c(c(C(=O)N(C)C(C)(C)C)nn1-c1cc(Cl)cc(Cl)c1)CO2]
26
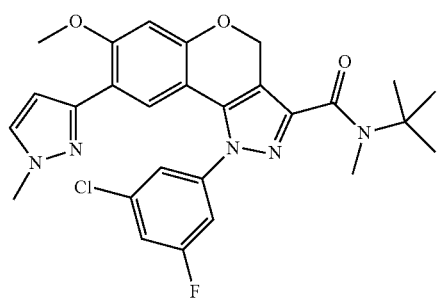 [SMILES: COc1cc2c(cc1-c1ccn(C)n1)-c1c(c(C(=O)N(C)C(C)(C)C)nn1-c1cc(F)cc(Cl)c1)CO2]
27
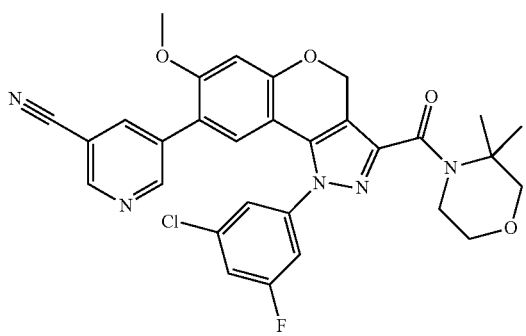 [SMILES: COc1cc2c(cc1-c1cncc(C#N)c1)-c1c(c(C(=O)N3CCOCC3(C)C)nn1-c1cc(F)cc(Cl)c1)CO2]
28
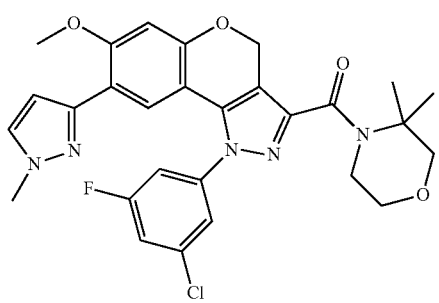 [SMILES: COc1cc2c(cc1-c1ccn(C)n1)-c1c(c(C(=O)N3CCOCC3(C)C)nn1-c1cc(F)cc(Cl)c1)CO2]
29
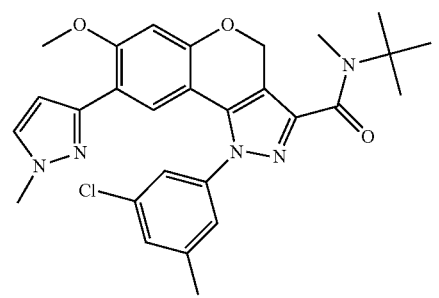 [SMILES: COc1cc2c(cc1-c1ccn(C)n1)-c1c(c(C(=O)N(C)C(C)(C)C)nn1-c1cc(C)cc(Cl)c1)CO2]
30

TABLE 1-continued
Exemplary compounds of the invention.
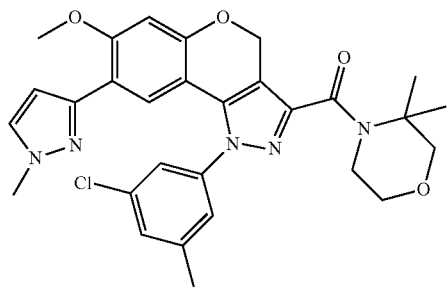 [SMILES: COc1cc2c(cc1-c1ccn(C)n1)-c1c(c(C(=O)N3CCOCC3(C)C)nn1-c1cc(C)cc(Cl)c1)CO2]
31
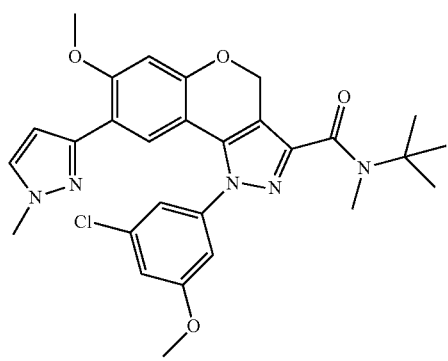 [SMILES: COc1cc(Cl)cc(-n2nc(C(=O)N(C)C(C)(C)C)c3c2-c2cc(-c4ccn(C)n4)c(OC)cc2OC3)c1]
32
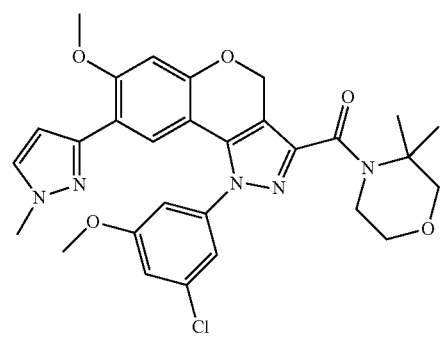
33
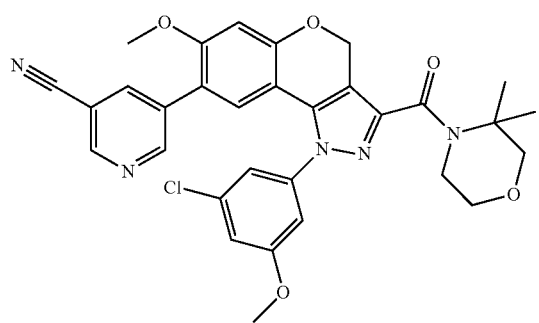 [SMILES: COc1cc(Cl)cc(-n2nc(C(=O)N3CCOCC3(C)C)c3c2-c2cc(-c4cncc(C#N)c4)c(OC)cc2OC3)c1]
34

TABLE 1-continued
Exemplary compounds of the invention.
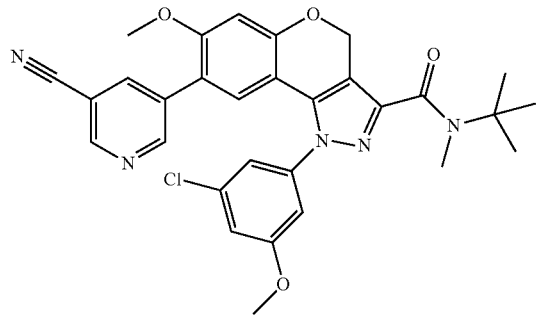 [SMILES: COc1cc(Cl)cc(-n2nc(C(=O)N(C)C(C)(C)C)c3c2-c2cc(-c4cncc(C#N)c4)c(OC)cc2OC3)c1]
35
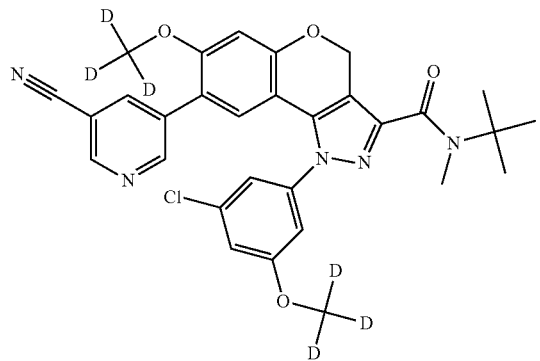 [SMILES: [2H]C([2H])([2H])Oc1cc(Cl)cc(-n2nc(C(=O)N(C)C(C)(C)C)c3c2-c2cc(-c4cncc(C#N)c4)c(OC([2H])([2H])[2H])cc2OC3)c1]
36
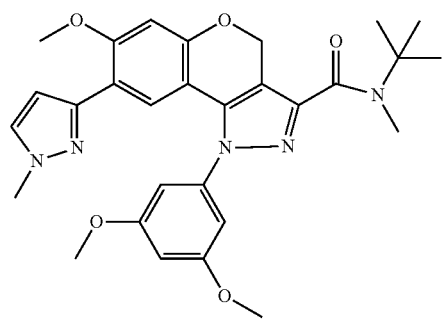 [SMILES: COc1cc(OC)cc(-n2nc(C(=O)N(C)C(C)(C)C)c3c2-c2cc(-c4ccn(C)n4)c(OC)cc2OC3)c1]
37
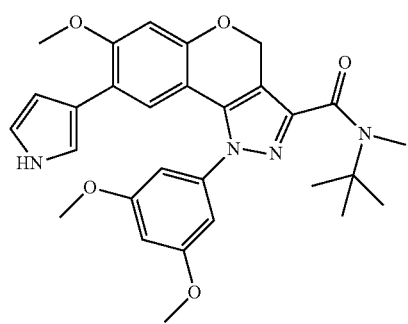 [SMILES: COc1cc(OC)cc(-n2nc(C(=O)N(C)C(C)(C)C)c3c2-c2cc(-c4cc[nH]c4)c(OC)cc2OC3)c1]
38

TABLE 1-continued
Exemplary compounds of the invention.
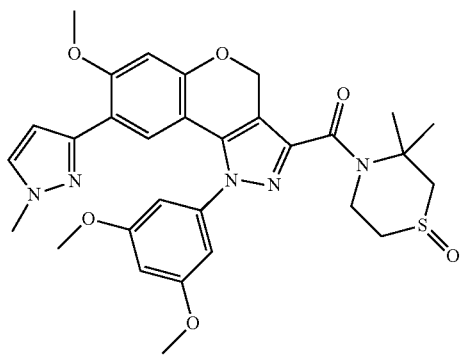 [SMILES: COc1cc(OC)cc(-n2nc(C(=O)N3CCS(=O)CC3(C)C)c3c2-c2cc(-c4ccn(C)n4)c(OC)cc2OC3)c1]
39
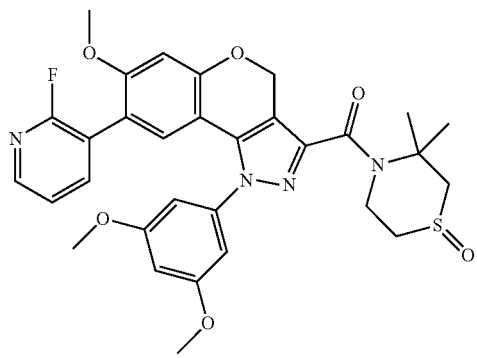 [SMILES: COc1cc(OC)cc(-n2nc(C(=O)N3CCS(=O)CC3(C)C)c3c2-c2cc(-c4cccnc4F)c(OC)cc2OC3)c1]
40
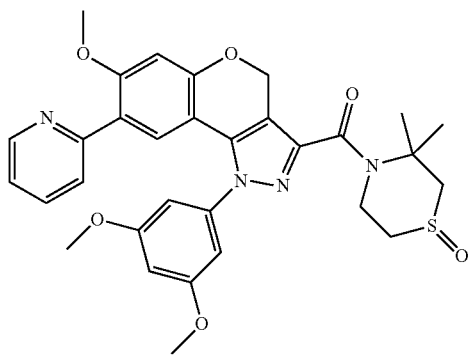 [SMILES: COc1cc(OC)cc(-n2nc(C(=O)N3CCS(=O)CC3(C)C)c3c2-c2cc(-c4ccccn4)c(OC)cc2OC3)c1]
41
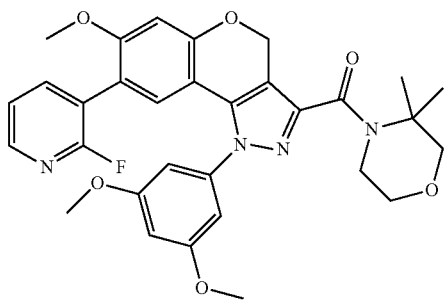 [SMILES: COc1cc(OC)cc(-n2nc(C(=O)N3CCOCC3(C)C)c3c2-c2cc(-c4cccnc4F)c(OC)cc2OC3)c1]
42

TABLE 1-continued
Exemplary compounds of the invention.
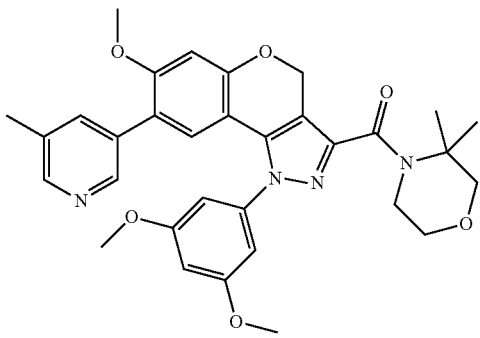
43
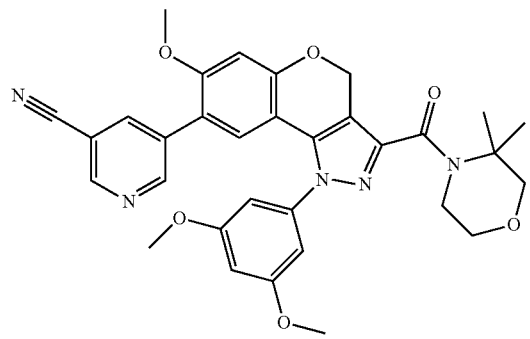 [SMILES: COc1cc(OC)cc(-n2nc(C(=O)N3CCOCC3(C)C)c3c2-c2cc(-c4cncc(C#N)c4)c(OC)cc2OC3)c1]
44
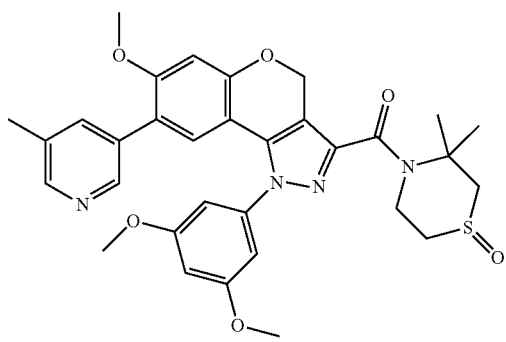 [SMILES: COc1cc(OC)cc(-n2nc(C(=O)N3CCS(=O)CC3(C)C)c3c2-c2cc(-c4cncc(C)c4)c(OC)cc2OC3)c1]
45
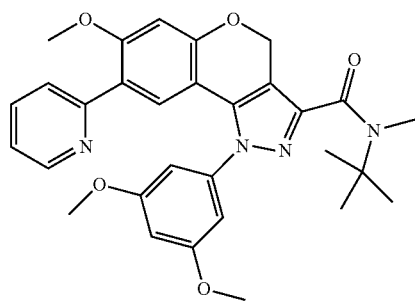 [SMILES: COc1cc(OC)cc(-n2nc(C(=O)N(C)C(C)(C)C)c3c2-c2cc(-c4ccccn4)c(OC)cc2OC3)c1]
46

TABLE 1-continued
Exemplary compounds of the invention.
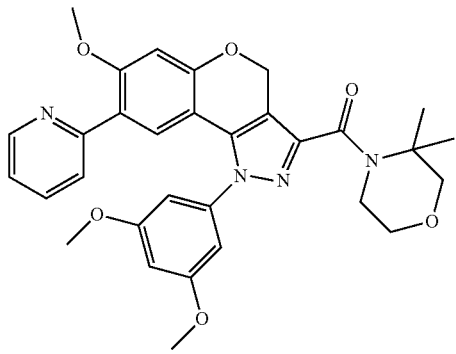 [SMILES: COc1cc(OC)cc(-n2nc(C(=O)N3CCOCC3(C)C)c3c2-c2cc(-c4ccccn4)c(OC)cc2OC3)c1]
47
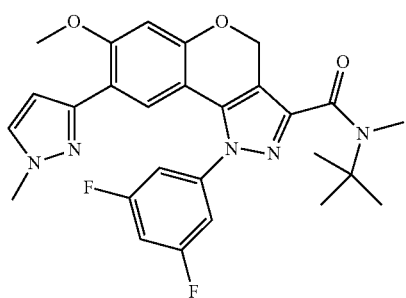 [SMILES: COc1cc2c(cc1-c1ccn(C)n1)-c1c(c(C(=O)N(C)C(C)(C)C)nn1-c1cc(F)cc(F)c1)CO2]
48
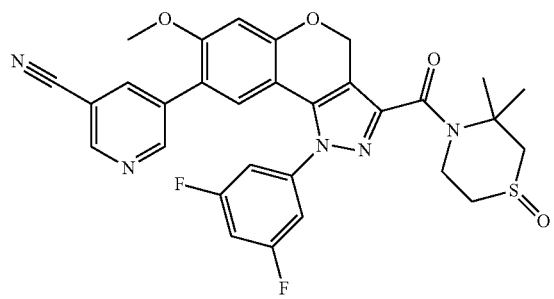 [SMILES: COc1cc2c(cc1-c1cncc(C#N)c1)-c1c(c(C(=O)N3CCS(=O)CC3(C)C)nn1-c1cc(F)cc(F)c1)CO2]
49
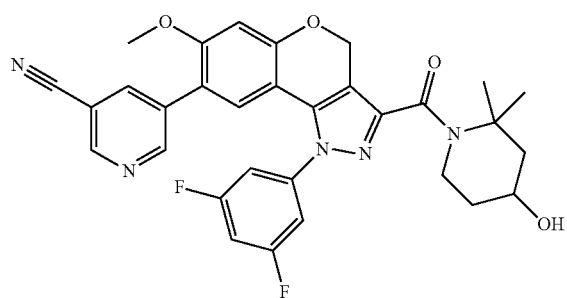 [SMILES: COc1cc2c(cc1-c1cncc(C#N)c1)-c1c(c(C(=O)N3CCC(O)CC3(C)C)nn1-c1cc(F)cc(F)c1)CO2]
50
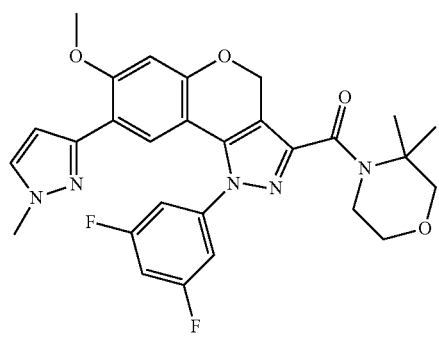 [SMILES: COc1cc2c(cc1-c1ccn(C)n1)-c1c(c(C(=O)N3CCOCC3(C)C)nn1-c1cc(F)cc(F)c1)CO2]
51

TABLE 1-continued
Exemplary compounds of the invention.
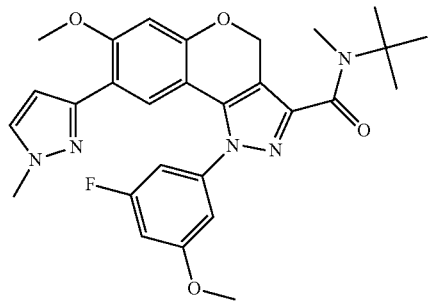 [SMILES: COc1cc(F)cc(-n2nc(C(=O)N(C)C(C)(C)C)c3c2-c2cc(-c4ccn(C)n4)c(OC)cc2OC3)c1] 52
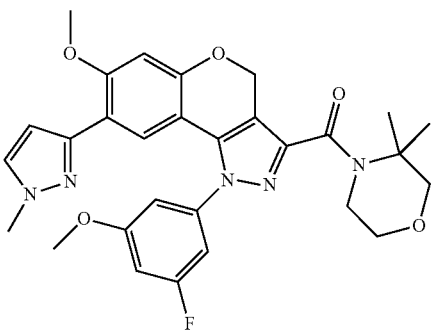 [SMILES: COc1cc(F)cc(-n2nc(C(=O)N3CCOCC3(C)C)c3c2-c2cc(-c4ccn(C)n4)c(OC)cc2OC3)c1] 53
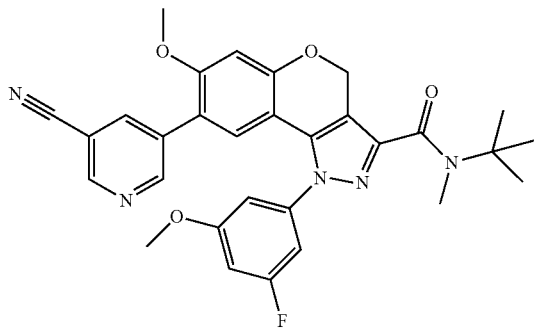 [SMILES: COc1cc(F)cc(-n2nc(C(=O)N(C)C(C)(C)C)c3c2-c2cc(-c4cncc(C#N)c4)c(OC)cc2OC3)c1] 54
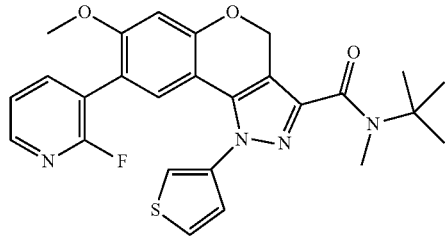 [SMILES: COc1cc2c(cc1-c1cccnc1F)-c1c(c(C(=O)N(C)C(C)(C)C)nn1-c1ccsc1)CO2] 55
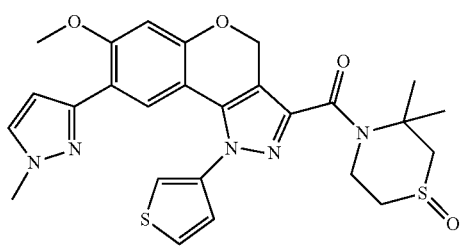 [SMILES: COc1cc2c(cc1-c1ccn(C)n1)-c1c(c(C(=O)N3CCS(=O)CC3(C)C)nn1-c1ccsc1)CO2] 56

TABLE 1-continued
Exemplary compounds of the invention.
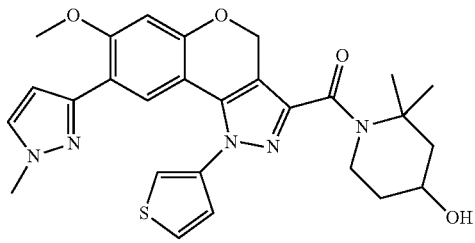
57
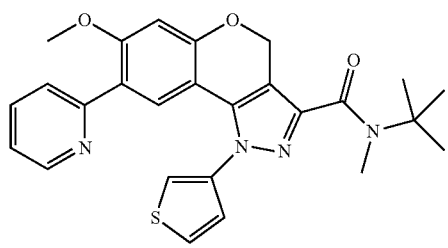 [SMILES: COc1cc2c(cc1-c1ccccn1)-c1c(c(C(=O)N(C)C(C)(C)C)nn1-c1ccsc1)CO2]
58
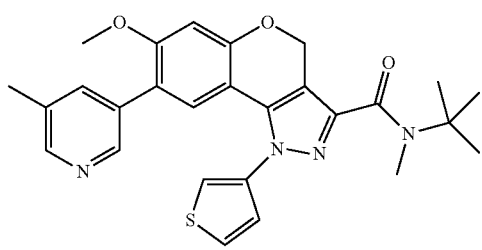 [SMILES: COc1cc2c(cc1-c1cncc(C)c1)-c1c(c(C(=O)N(C)C(C)(C)C)nn1-c1ccsc1)CO2]
59
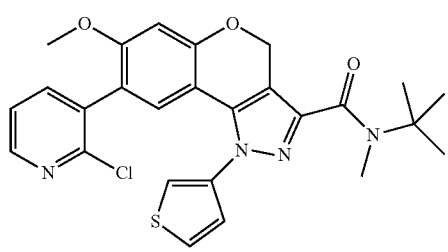 [SMILES: COc1cc2c(cc1-c1cccnc1Cl)-c1c(c(C(=O)N(C)C(C)(C)C)nn1-c1ccsc1)CO2]
60
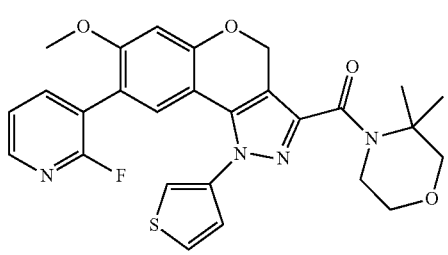 [SMILES: COc1cc2c(cc1-c1cccnc1F)-c1c(c(C(=O)N3CCOCC3(C)C)nn1-c1ccsc1)CO2]
61
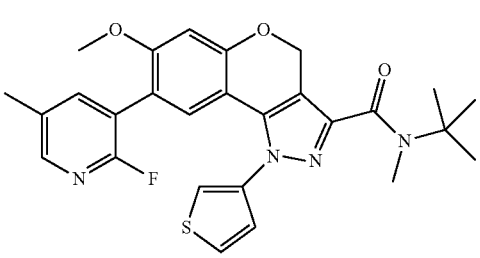 [SMILES: COc1cc2c(cc1-c1cc(C)cnc1F)-c1c(c(C(=O)N(C)C(C)(C)C)nn1-c1ccsc1)CO2]
62

TABLE 1-continued
Exemplary compounds of the invention.
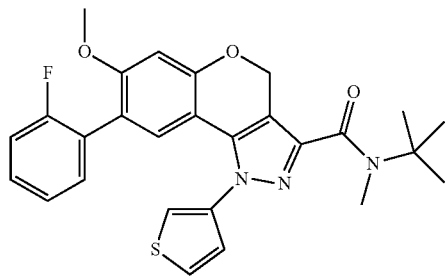 [SMILES: COc1cc2c(cc1-c1ccccc1F)-c1c(c(C(=O)N(C)C(C)(C)C)nn1-c1ccsc1)CO2]
63
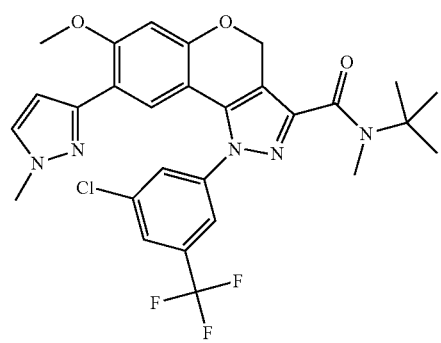 [SMILES: COc1cc2c(cc1-c1ccn(C)n1)-c1c(c(C(=O)N(C)C(C)(C)C)nn1-c1cc(Cl)cc(C(F)(F)F)c1)CO2]
64
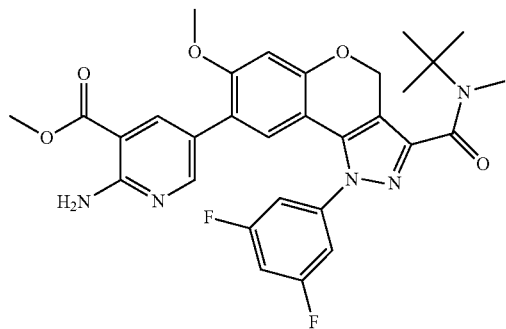
65
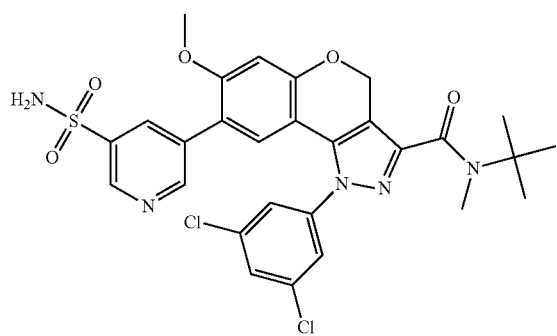 [SMILES: COc1cc2c(cc1-c1cncc(S(N)(=O)=O)c1)-c1c(c(C(=O)N(C)C(C)(C)C)nn1-c1cc(Cl)cc(Cl)c1)CO2]
66

TABLE 1-continued
Exemplary compounds of the invention.
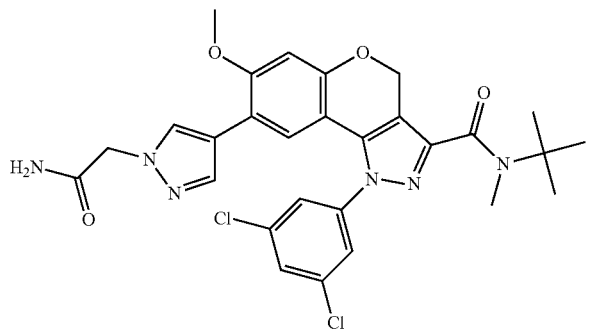 [SMILES: COc1cc2c(cc1-c1cnn(CC(N)=O)c1)-c1c(c(C(=O)N(C)C(C)(C)C)nn1-c1cc(Cl)cc(Cl)c1)CO2]
67
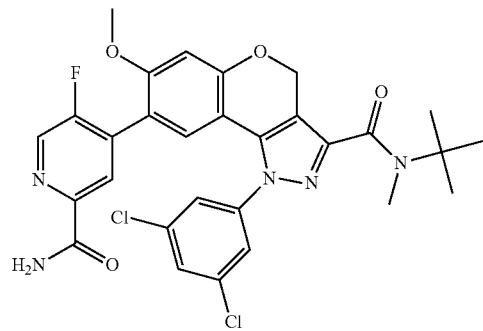 [SMILES: COc1cc2c(cc1-c1cc(C(N)=O)ncc1F)-c1c(c(C(=O)N(C)C(C)(C)C)nn1-c1cc(Cl)cc(Cl)c1)CO2]
68
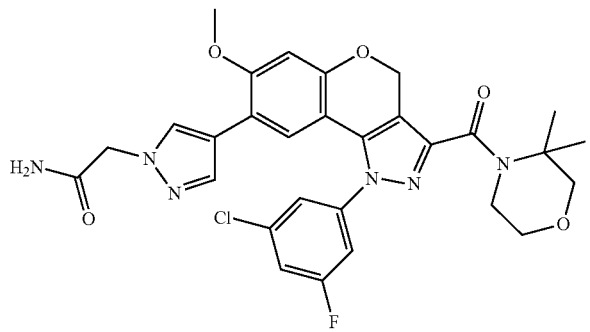 [SMILES: COc1cc2c(cc1-c1cnn(CC(N)=O)c1)-c1c(c(C(=O)N3CCOCC3(C)C)nn1-c1cc(F)cc(Cl)c1)CO2]
69
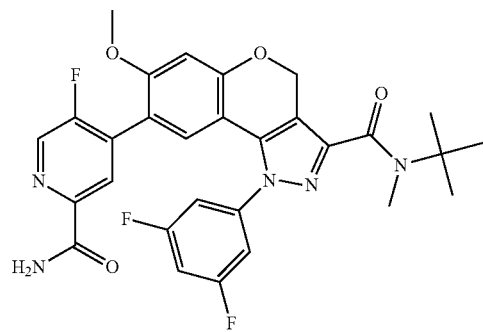 [SMILES: COc1cc2c(cc1-c1cc(C(N)=O)ncc1F)-c1c(c(C(=O)N(C)C(C)(C)C)nn1-c1cc(F)cc(F)c1)CO2]
70

TABLE 1-continued
Exemplary compounds of the invention.
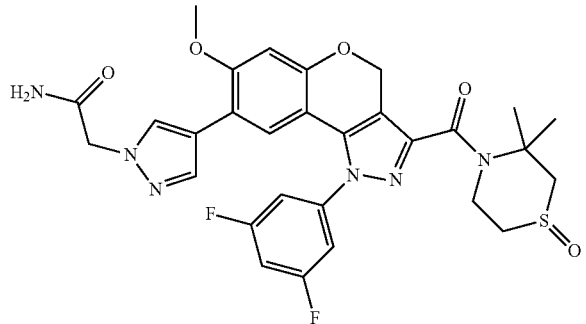 [SMILES: COc1cc2c(cc1-c1cnn(CC(N)=O)c1)-c1c(c(C(=O)N3CCS(=O)CC3(C)C)nn1-c1cc(F)cc(F)c1)CO2]
71
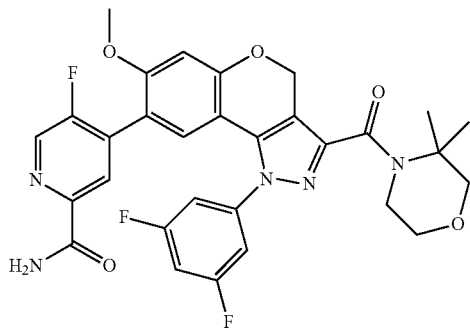 [SMILES: COc1cc2c(cc1-c1cc(C(N)=O)ncc1F)-c1c(c(C(=O)N3CCOCC3(C)C)nn1-c1cc(F)cc(F)c1)CO2]
72
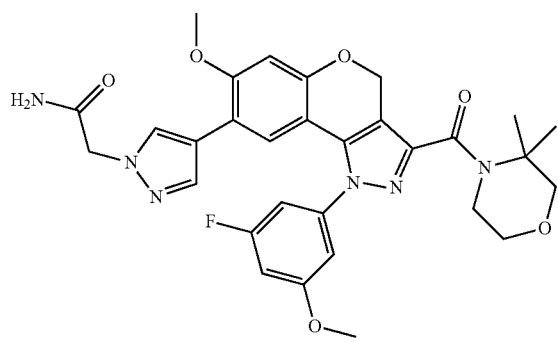 [SMILES: COc1cc(F)cc(-n2nc(C(=O)N3CCOCC3(C)C)c3c2-c2cc(-c4cnn(CC(N)=O)c4)c(OC)cc2OC3)c1]
73
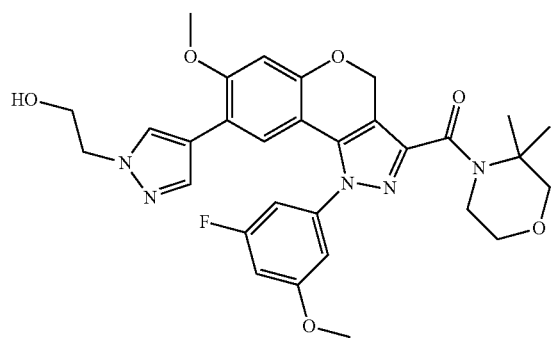 [SMILES: COc1cc(F)cc(-n2nc(C(=O)N3CCOCC3(C)C)c3c2-c2cc(-c4cnn(CCO)c4)c(OC)cc2OC3)c1]
74

TABLE 1-continued
Exemplary compounds of the invention.
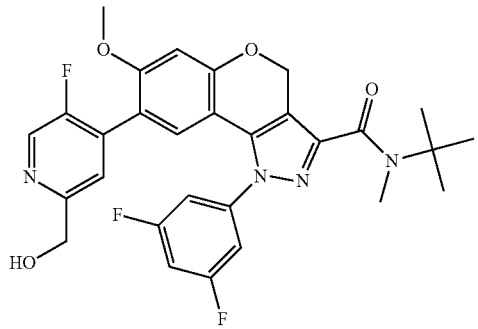 [SMILES: COc1cc2c(cc1-c1cc(CO)ncc1F)-c1c(c(C(=O)N(C)C(C)(C)C)nn1-c1cc(F)cc(F)c1)CO2]
75
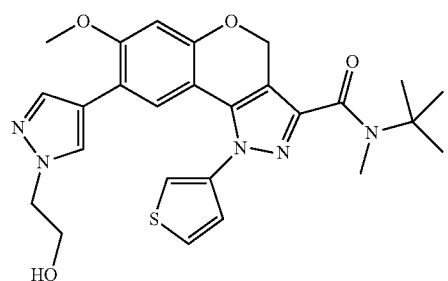 [SMILES: COc1cc2c(cc1-c1cnn(CCO)c1)-c1c(c(C(=O)N(C)C(C)(C)C)nn1-c1ccsc1)CO2]
76
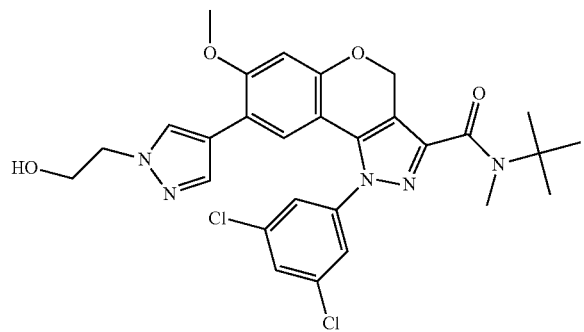 [SMILES: COc1cc2c(cc1-c1cnn(CCO)c1)-c1c(c(C(=O)N(C)C(C)(C)C)nn1-c1cc(Cl)cc(Cl)c1)CO2]
77
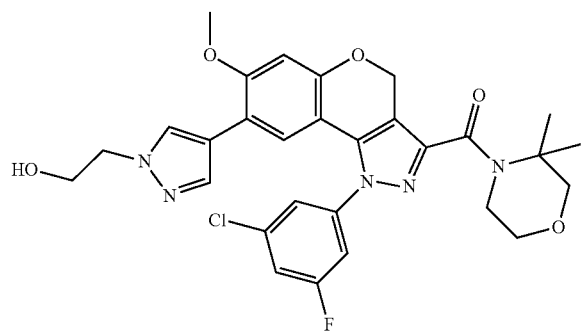 [SMILES: COc1cc2c(cc1-c1cnn(CCO)c1)-c1c(c(C(=O)N3CCOCC3(C)C)nn1-c1cc(F)cc(Cl)c1)CO2]
78

TABLE 1-continued
Exemplary compounds of the invention.
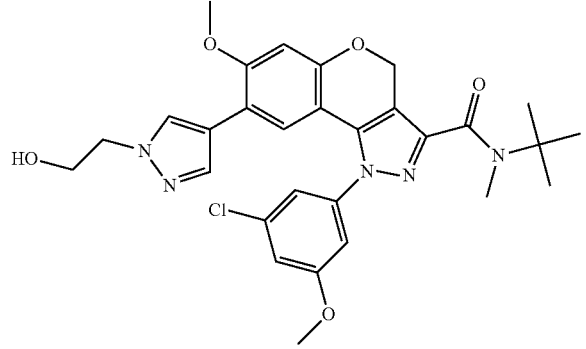 [SMILES: COc1cc(Cl)cc(-n2nc(C(=O)N(C)C(C)(C)C)c3c2-c2cc(-c4cnn(CCO)c4)c(OC)cc2OC3)c1]
79
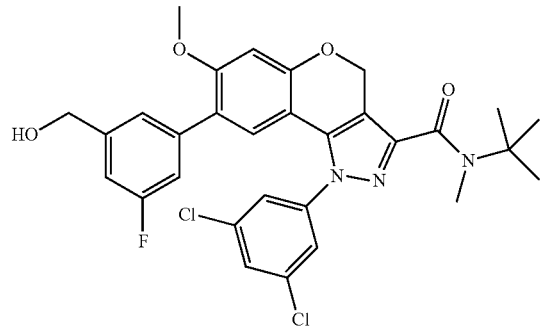 [SMILES: COc1cc2c(cc1-c1cc(F)cc(CO)c1)-c1c(c(C(=O)N(C)C(C)(C)C)nn1-c1cc(Cl)cc(Cl)c1)CO2]
80
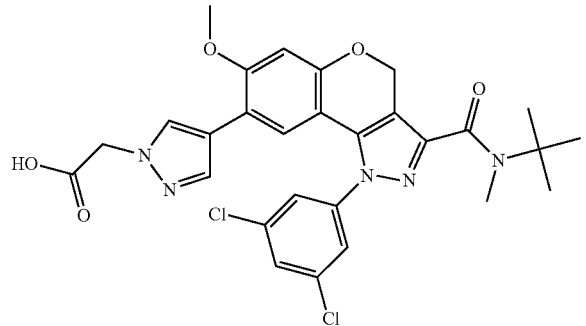 [SMILES: COc1cc2c(cc1-c1cnn(CC(=O)O)c1)-c1c(c(C(=O)N(C)C(C)(C)C)nn1-c1cc(Cl)cc(Cl)c1)CO2]
81
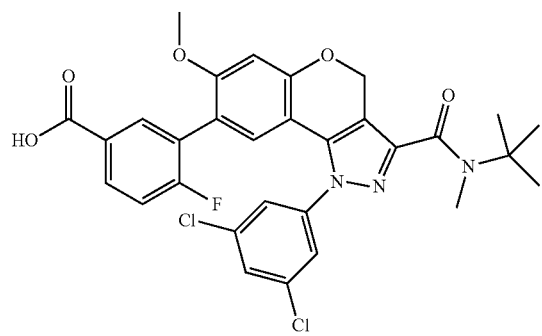 [SMILES: COc1cc2c(cc1-c1cc(C(=O)O)ccc1F)-c1c(c(C(=O)N(C)C(C)(C)C)nn1-c1cc(Cl)cc(Cl)c1)CO2]
82

TABLE 1-continued
Exemplary compounds of the invention.
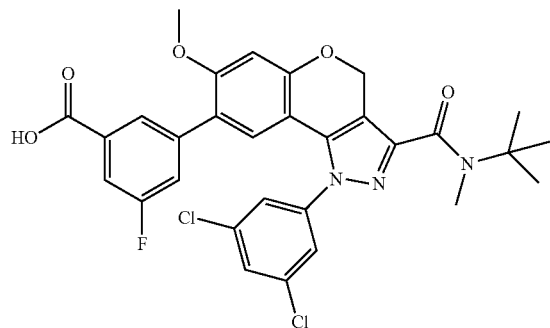 [SMILES: COc1cc2c(cc1-c1cc(F)cc(C(=O)O)c1)-c1c(c(C(=O)N(C)C(C)(C)C)nn1-c1cc(Cl)cc(Cl)c1)CO2]
83
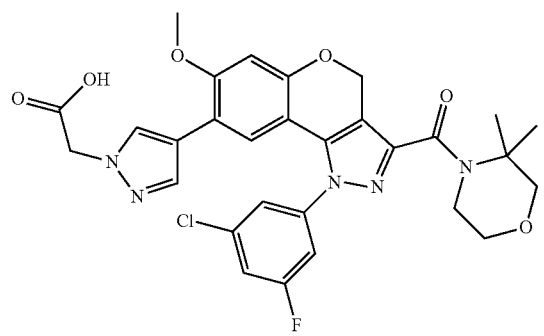 [SMILES: COc1cc2c(cc1-c1cnn(CC(=O)O)c1)-c1c(c(C(=O)N3CCOCC3(C)C)nn1-c1cc(F)cc(Cl)c1)CO2]
84
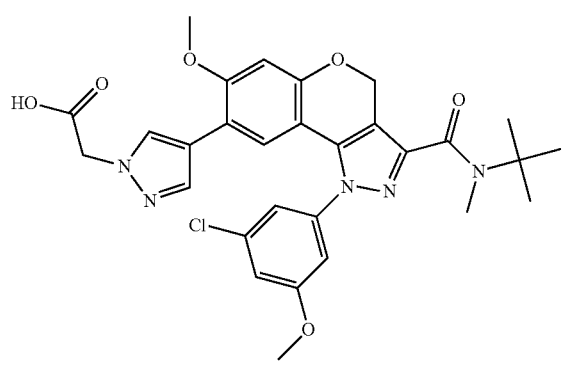 [SMILES: COc1cc(Cl)cc(-n2nc(C(=O)N(C)C(C)(C)C)c3c2-c2cc(-c4cnn(CC(=O)O)c4)c(OC)cc2OC3)c1]
85
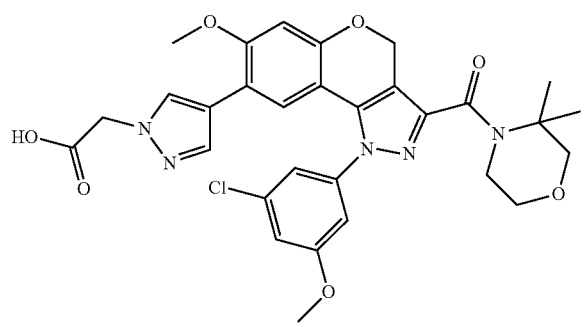 [SMILES: COc1cc(Cl)cc(-n2nc(C(=O)N3CCOCC3(C)C)c3c2-c2cc(-c4cnn(CC(=O)O)c4)c(OC)cc2OC3)c1]
86

TABLE 1-continued
Exemplary compounds of the invention.
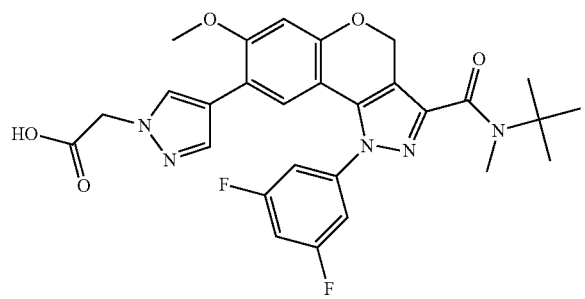 [SMILES: COc1cc2c(cc1-c1cnn(CC(=O)O)c1)-c1c(c(C(=O)N(C)C(C)(C)C)nn1-c1cc(F)cc(F)c1)CO2] 87
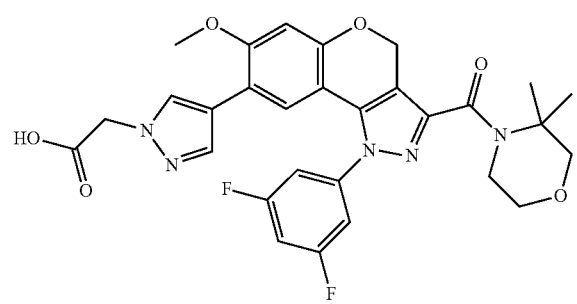 [SMILES: COc1cc2c(cc1-c1cnn(CC(=O)O)c1)-c1c(c(C(=O)N3CCOCC3(C)C)nn1-c1cc(F)cc(F)c1)CO2] 88
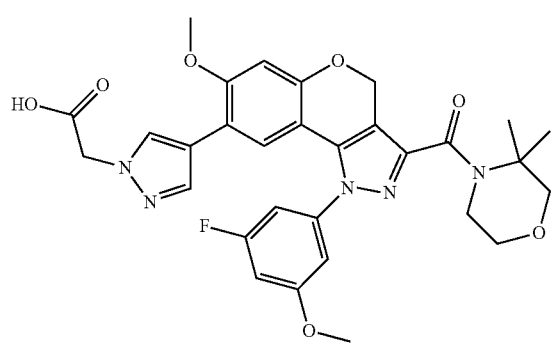 [SMILES: COc1cc(F)cc(-n2nc(C(=O)N3CCOCC3(C)C)c3c2-c2cc(-c4cnn(CC(=O)O)c4)c(OC)cc2OC3)c1] 89
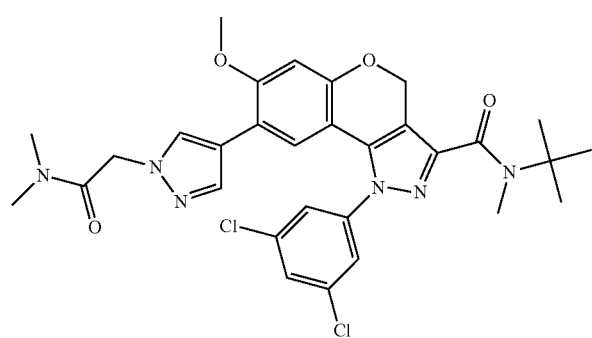 [SMILES: COc1cc2c(cc1-c1cnn(CC(=O)N(C)C)c1)-c1c(c(C(=O)N(C)C(C)(C)C)nn1-c1cc(Cl)cc(Cl)c1)CO2] 90
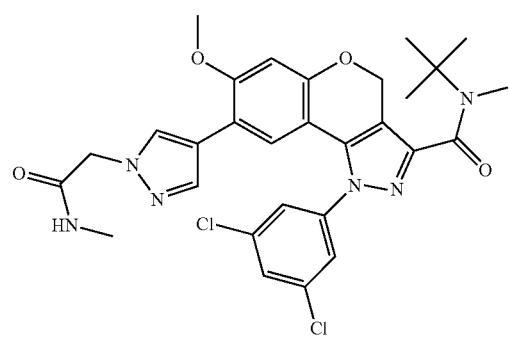 [SMILES: CNC(=O)Cn1cc(-c2cc3c(cc2OC)OCc2c(C(=O)N(C)C(C)(C)C)nn(-c4cc(Cl)cc(Cl)c4)c2-3)cn1] 91

TABLE 1-continued
Exemplary compounds of the invention.
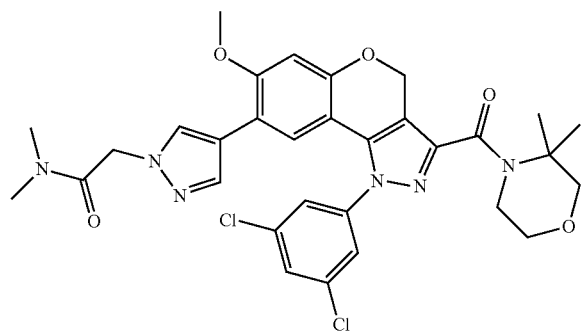
92
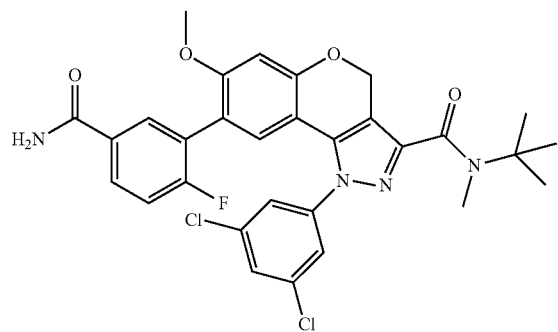 [SMILES: COc1cc2c(cc1-c1cc(C(N)=O)ccc1F)-c1c(c(C(=O)N(C)C(C)(C)C)nn1-c1cc(Cl)cc(Cl)c1)CO2]
93
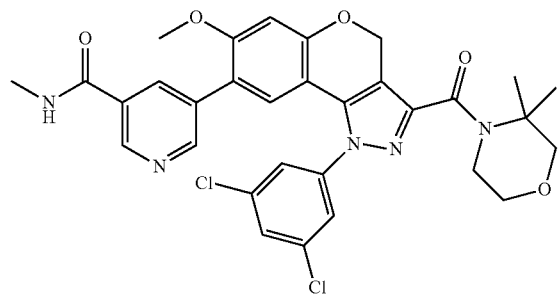
94
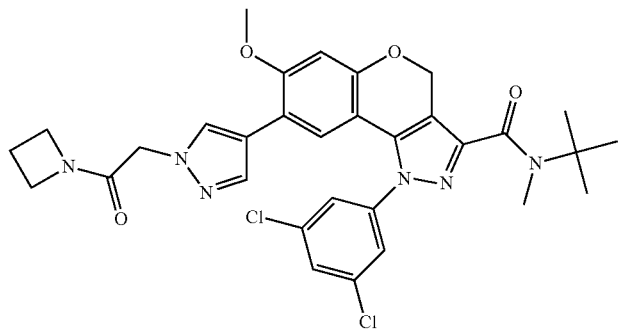 [SMILES: COc1cc2c(cc1-c1cnn(CC(=O)N3CCC3)c1)-c1c(c(C(=O)N(C)C(C)(C)C)nn1-c1cc(Cl)cc(Cl)c1)CO2]
95

TABLE 1-continued
Exemplary compounds of the invention.
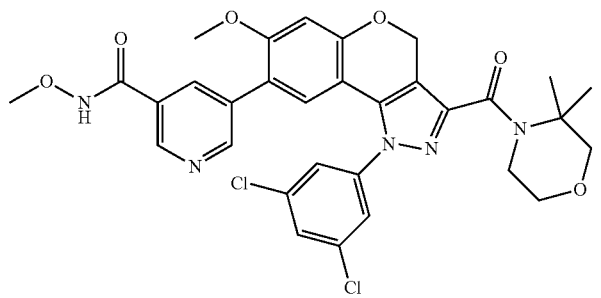
96
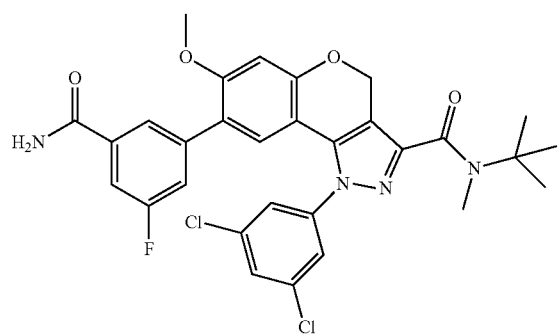 [SMILES: COc1cc2c(cc1-c1cc(F)cc(C(N)=O)c1)-c1c(c(C(=O)N(C)C(C)(C)C)nn1-c1cc(Cl)cc(Cl)c1)CO2]
97
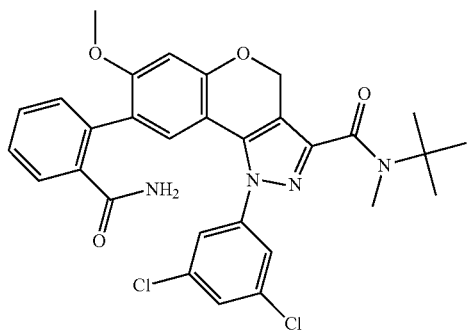 [SMILES: COc1cc2c(cc1-c1ccccc1C(N)=O)-c1c(c(C(=O)N(C)C(C)(C)C)nn1-c1cc(Cl)cc(Cl)c1)CO2]
98
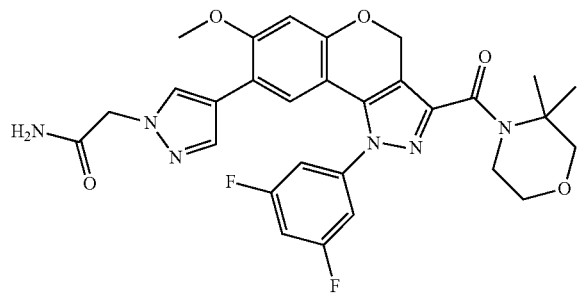 [SMILES: COc1cc2c(cc1-c1cnn(CC(N)=O)c1)-c1c(c(C(=O)N3CCOCC3(C)C)nn1-c1cc(F)cc(F)c1)CO2]
99
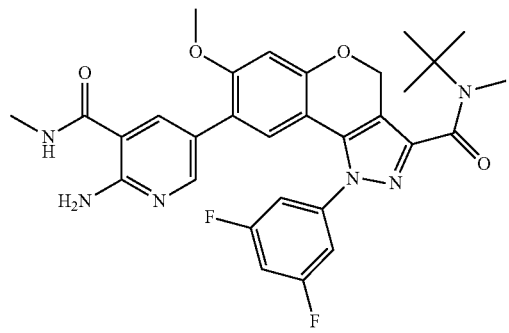
100

TABLE 1-continued
Exemplary compounds of the invention.
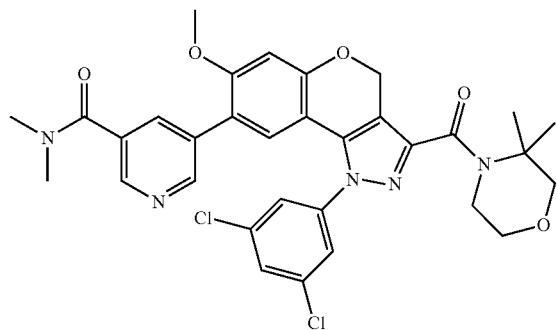 101
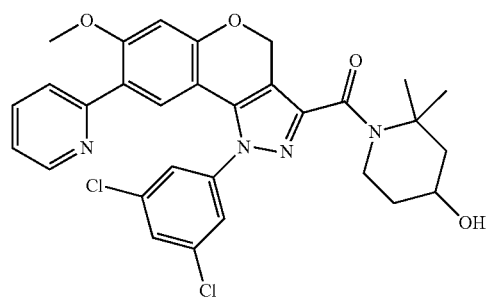 [SMILES: COc1cc2c(cc1-c1ccccn1)-c1c(c(C(=O)N3CCC(O)CC3(C)C)nn1-c1cc(Cl)cc(Cl)c1)CO2] 102
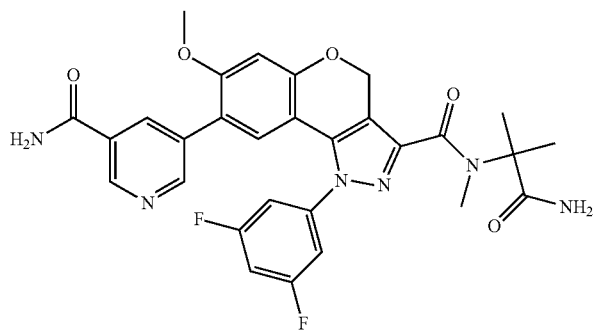 [SMILES: COc1cc2c(cc1-c1cncc(C(N)=O)c1)-c1c(c(C(=O)N(C)C(C)(C)C(N)=O)nn1-c1cc(F)cc(F)c1)CO2] 104
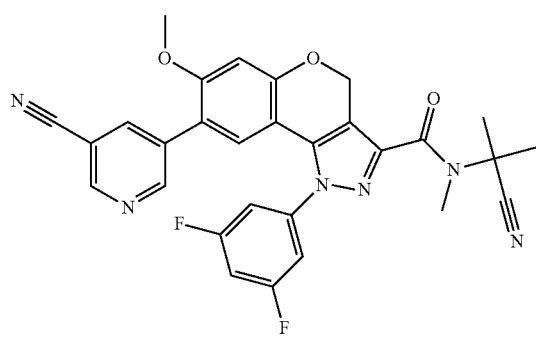 [SMILES: COc1cc2c(cc1-c1cncc(C#N)c1)-c1c(c(C(=O)N(C)C(C)(C)C#N)nn1-c1cc(F)cc(F)c1)CO2] 105

TABLE 1-continued
Exemplary compounds of the invention.
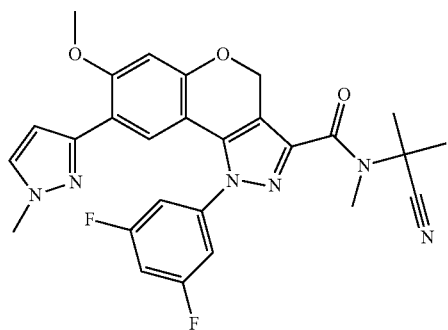 [SMILES: COc1cc2c(cc1-c1ccn(C)n1)-c1c(c(C(=O)N(C)C(C)(C)C#N)nn1-c1cc(F)cc(F)c1)CO2]
106
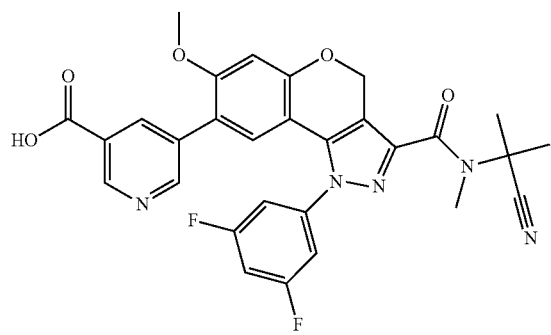 [SMILES: COc1cc2c(cc1-c1cncc(C(=O)O)c1)-c1c(c(C(=O)N(C)C(C)(C)C#N)nn1-c1cc(F)cc(F)c1)CO2]
107
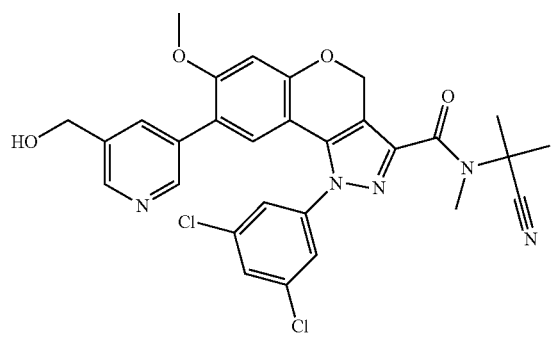 [SMILES: COc1cc2c(cc1-c1cncc(CO)c1)-c1c(c(C(=O)N(C)C(C)(C)C#N)nn1-c1cc(Cl)cc(Cl)c1)CO2]
108
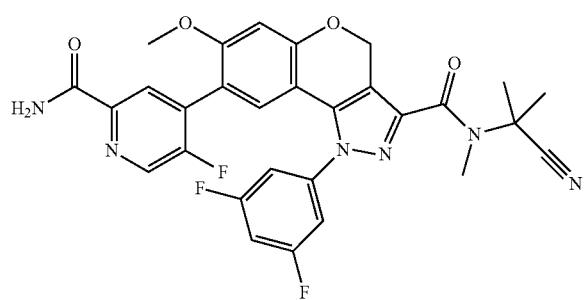 [SMILES: COc1cc2c(cc1-c1cc(C(N)=O)ncc1F)-c1c(c(C(=O)N(C)C(C)(C)C#N)nn1-c1cc(F)cc(F)c1)CO2]
109

TABLE 1-continued
Exemplary compounds of the invention.
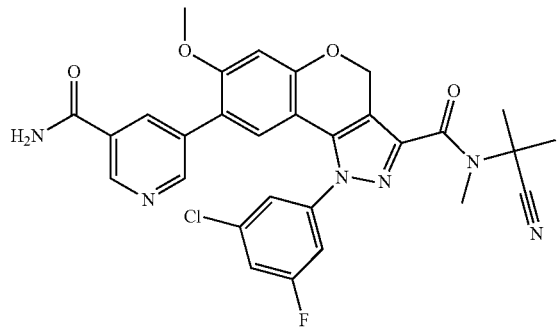 [SMILES: COc1cc2c(cc1-c1cncc(C(N)=O)c1)-c1c(c(C(=O)N(C)C(C)(C)C#N)nn1-c1cc(F)cc(Cl)c1)CO2]
110
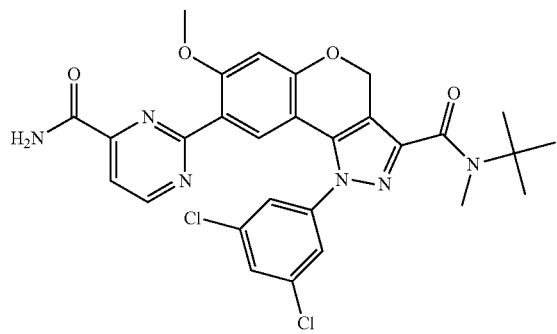 [SMILES: COc1cc2c(cc1-c1nccc(C(N)=O)n1)-c1c(c(C(=O)N(C)C(C)(C)C)nn1-c1cc(Cl)cc(Cl)c1)CO2]
111
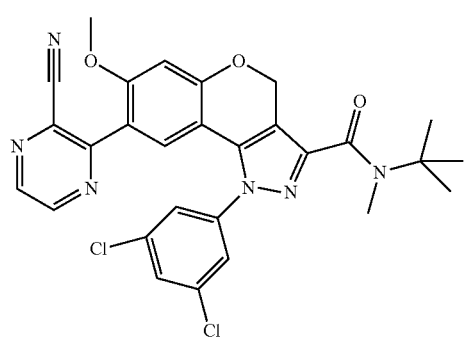 [SMILES: COc1cc2c(cc1-c1nccnc1C#N)-c1c(c(C(=O)N(C)C(C)(C)C)nn1-c1cc(Cl)cc(Cl)c1)CO2]
112
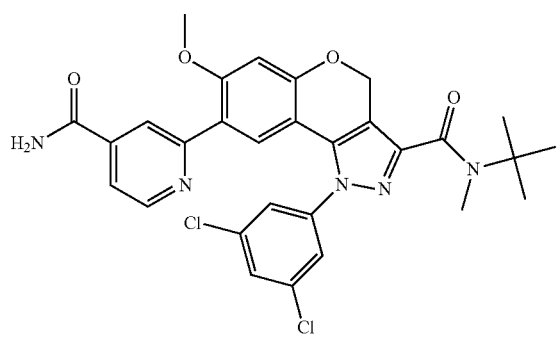 [SMILES: COc1cc2c(cc1-c1cc(C(N)=O)ccn1)-c1c(c(C(=O)N(C)C(C)(C)C)nn1-c1cc(Cl)cc(Cl)c1)CO2]
113

TABLE 1-continued
Exemplary compounds of the invention.
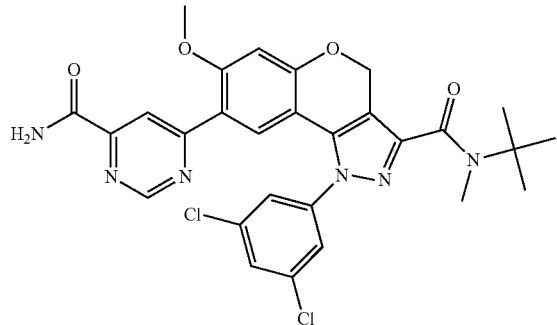 [SMILES: COc1cc2c(cc1-c1cc(C(N)=O)ncn1)-c1c(c(C(=O)N(C)C(C)(C)C)nn1-c1cc(Cl)cc(Cl)c1)CO2]
114
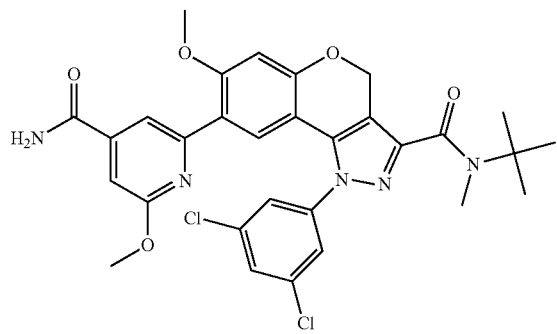 [SMILES: COc1cc(C(N)=O)cc(-c2cc3c(cc2OC)OCc2c(C(=O)N(C)C(C)(C)C)nn(-c4cc(Cl)cc(Cl)c4)c2-3)n1]
115
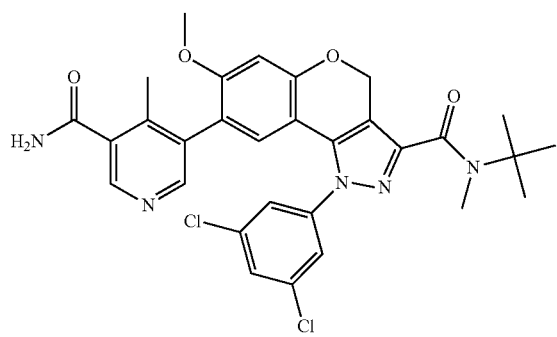 [SMILES: COc1cc2c(cc1-c1cncc(C(N)=O)c1C)-c1c(c(C(=O)N(C)C(C)(C)C)nn1-c1cc(Cl)cc(Cl)c1)CO2]
116
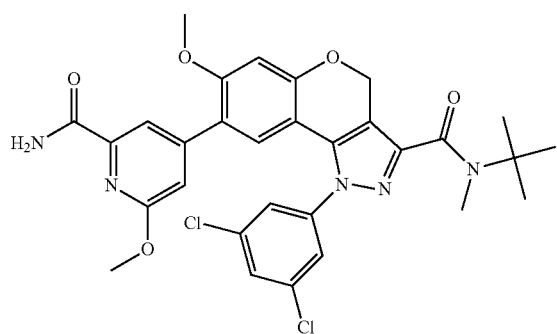 [SMILES: COc1cc(-c2cc3c(cc2OC)OCc2c(C(=O)N(C)C(C)(C)C)nn(-c4cc(Cl)cc(Cl)c4)c2-3)cc(C(N)=O)n1]
117

TABLE 1-continued
Exemplary compounds of the invention.
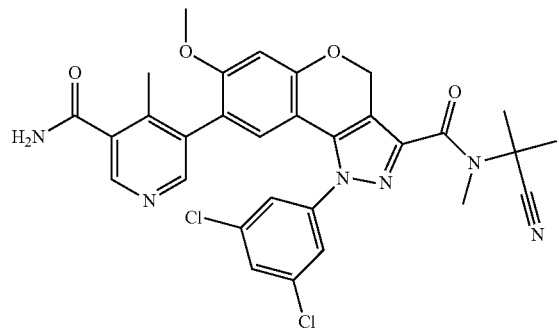 [SMILES: COc1cc2c(cc1-c1cncc(C(N)=O)c1C)-c1c(c(C(=O)N(C)C(C)(C)C#N)nn1-c1cc(Cl)cc(Cl)c1)CO2]
118
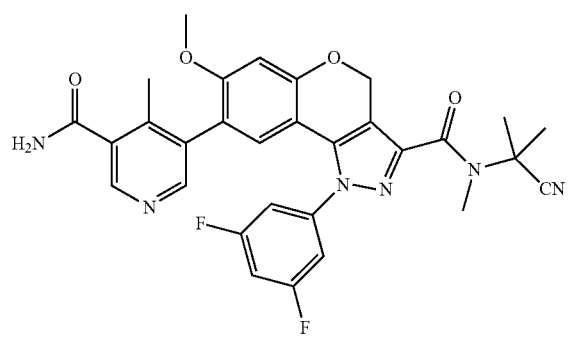 [SMILES: COc1cc2c(cc1-c1cncc(C(N)=O)c1C)-c1c(c(C(=O)N(C)C(C)(C)C#N)nn1-c1cc(F)cc(F)c1)CO2]
119
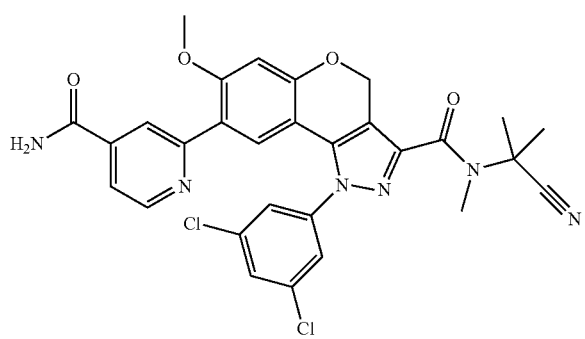 [SMILES: COc1cc2c(cc1-c1cc(C(N)=O)ccn1)-c1c(c(C(=O)N(C)C(C)(C)C#N)nn1-c1cc(Cl)cc(Cl)c1)CO2]
120
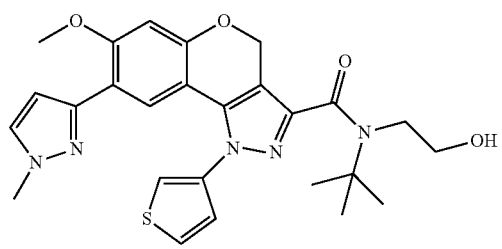 [SMILES: COc1cc2c(cc1-c1ccn(C)n1)-c1c(c(C(=O)N(CCO)C(C)(C)C)nn1-c1ccsc1)CO2]
121
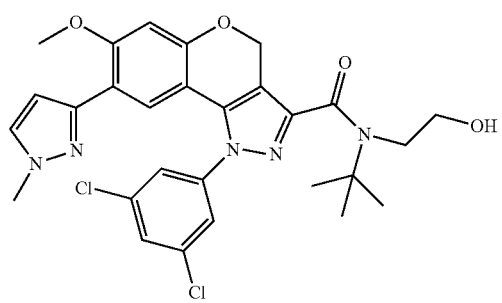 [SMILES: COc1cc2c(cc1-c1ccn(C)n1)-c1c(c(C(=O)N(CCO)C(C)(C)C)nn1-c1cc(Cl)cc(Cl)c1)CO2]
122

TABLE 1-continued
Exemplary compounds of the invention.
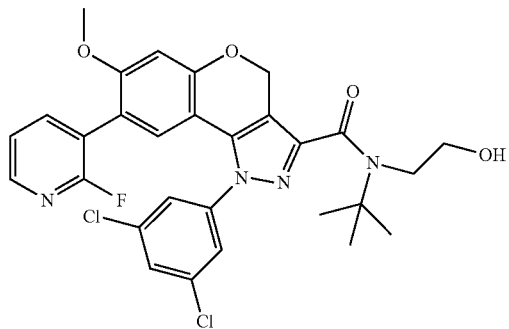 [SMILES: COc1cc2c(cc1-c1cccnc1F)-c1c(c(C(=O)N(CCO)C(C)(C)C)nn1-c1cc(Cl)cc(Cl)c1)CO2]
123
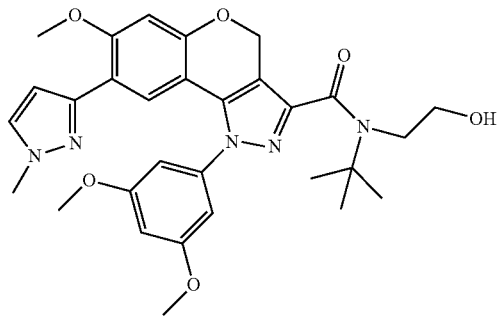 [SMILES: COc1cc(OC)cc(-n2nc(C(=O)N(CCO)C(C)(C)C)c3c2-c2cc(-c4ccn(C)n4)c(OC)cc2OC3)c1]
124
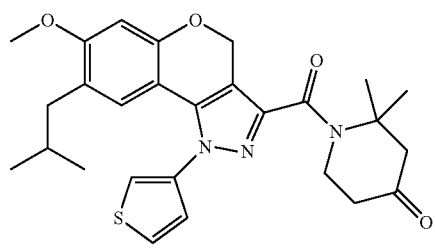 [SMILES: COc1cc2c(cc1CC(C)C)-c1c(c(C(=O)N3CCC(=O)CC3(C)C)nn1-c1ccsc1)CO2]
125
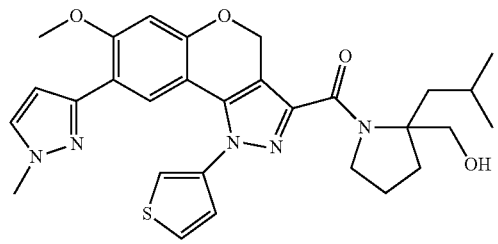 [SMILES: COc1cc2c(cc1-c1ccn(C)n1)-c1c(c(C(=O)N3CCCC3(CO)CC(C)C)nn1-c1ccsc1)CO2]
126
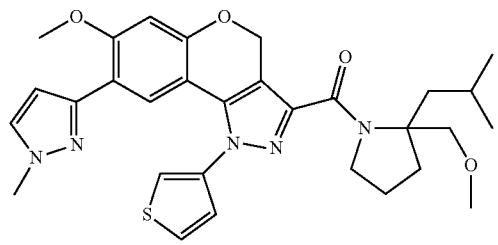 [SMILES: COCC1(CC(C)C)CCCN1C(=O)c1nn(-c2ccsc2)c2c1COc1cc(OC)c(-c3ccn(C)n3)cc1-2]
127

TABLE 1-continued
Exemplary compounds of the invention.
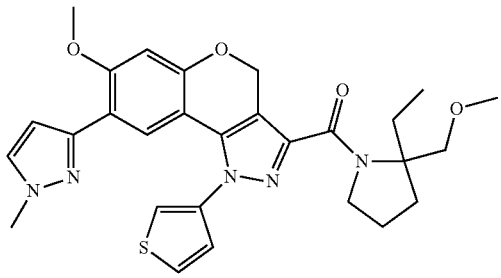 [SMILES: CCC1(COC)CCCN1C(=O)c1nn(-c2ccsc2)c2c1COc1cc(OC)c(-c3ccn(C)n3)cc1-2]
128
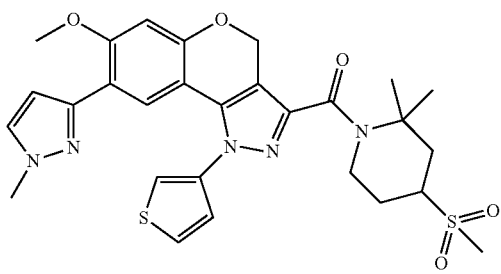 [SMILES: COc1cc2c(cc1-c1ccn(C)n1)-c1c(c(C(=O)N3CCC(S(C)(=O)=O)CC3(C)C)nn1-c1ccsc1)CO2]
129
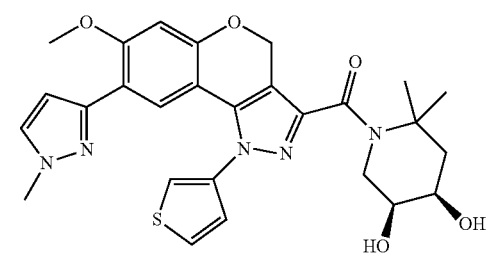 [SMILES: COc1cc2c(cc1-c1ccn(C)n1)-c1c(c(C(=O)N3C[C@H](O)[C@H](O)CC3(C)C)nn1-c1ccsc1)CO2]
130
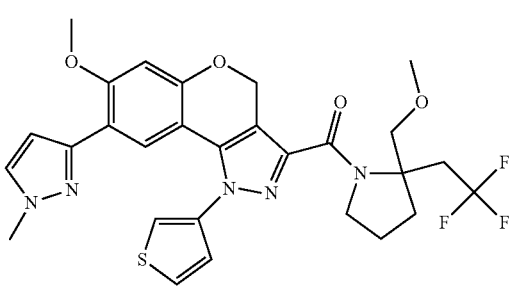 [SMILES: COCC1(CC(F)(F)F)CCCN1C(=O)c1nn(-c2ccsc2)c2c1COc1cc(OC)c(-c3ccn(C)n3)cc1-2]
131
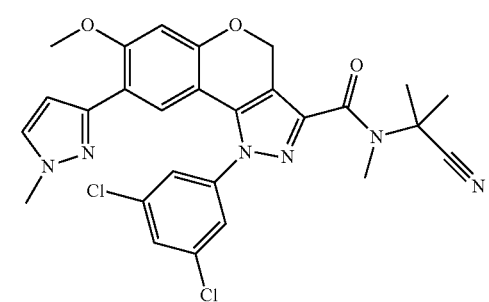
132

TABLE 1-continued
Exemplary compounds of the invention.
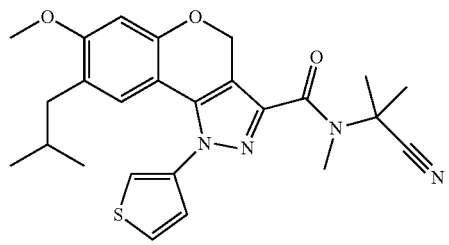 [SMILES: COc1cc2c(cc1CC(C)C)-c1c(c(C(=O)N(C)C(C)(C)C#N)nn1-c1ccsc1)CO2]
133
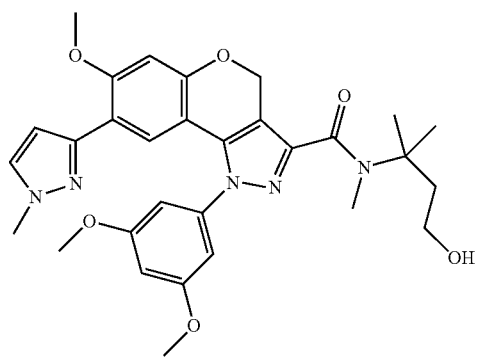 [SMILES: COc1cc(OC)cc(-n2nc(C(=O)N(C)C(C)(C)CCO)c3c2-c2cc(-c4ccn(C)n4)c(OC)cc2OC3)c1]
134
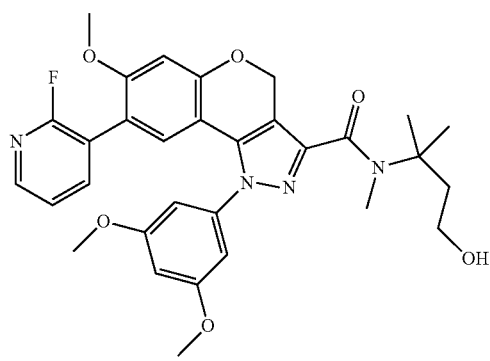 [SMILES: COc1cc(OC)cc(-n2nc(C(=O)N(C)C(C)(C)CCO)c3c2-c2cc(-c4cccnc4F)c(OC)cc2OC3)c1]
135
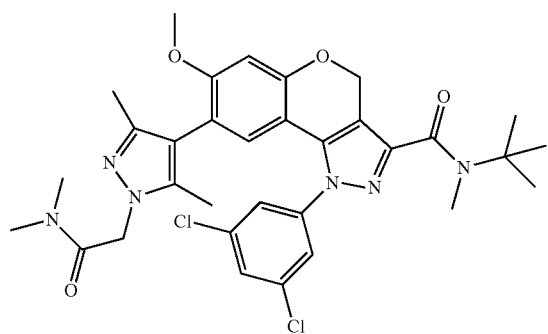 [SMILES: COc1cc2c(cc1-c1c(C)nn(CC(=O)N(C)C)c1C)-c1c(c(C(=O)N(C)C(C)(C)C)nn1-c1cc(Cl)cc(Cl)c1)CO2]
136

TABLE 1-continued
Exemplary compounds of the invention.
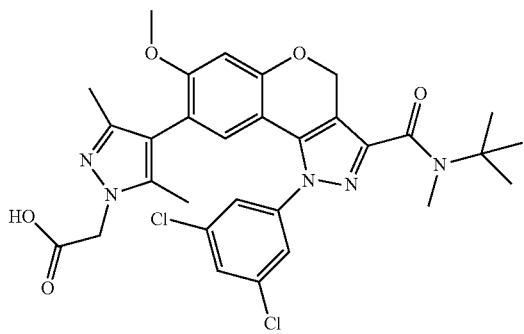 [SMILES: COc1cc2c(cc1-c1c(C)nn(CC(=O)O)c1C)-c1c(c(C(=O)N(C)C(C)(C)C)nn1-c1cc(Cl)cc(Cl)c1)CO2]
137
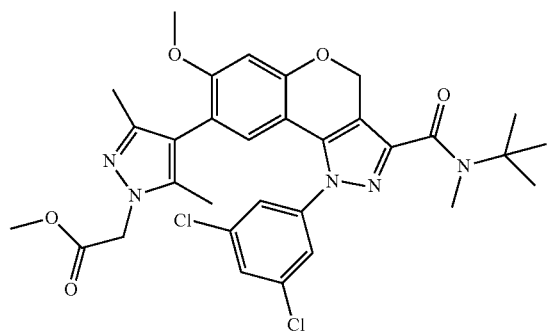 [SMILES: COC(=O)Cn1nc(C)c(-c2cc3c(cc2OC)OCc2c(C(=O)N(C)C(C)(C)C)nn(-c4cc(Cl)cc(Cl)c4)c2-3)c1C]
138
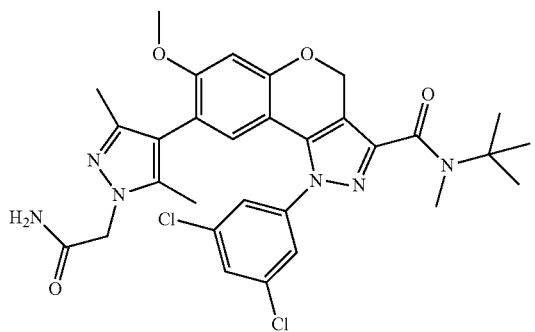 [SMILES: COc1cc2c(cc1-c1c(C)nn(CC(N)=O)c1C)-c1c(c(C(=O)N(C)C(C)(C)C)nn1-c1cc(Cl)cc(Cl)c1)CO2]
139
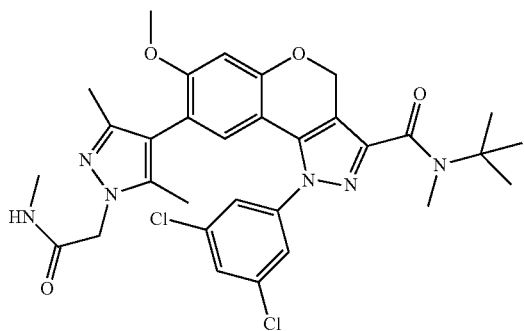 [SMILES: CNC(=O)Cn1nc(C)c(-c2cc3c(cc2OC)OCc2c(C(=O)N(C)C(C)(C)C)nn(-c4cc(Cl)cc(Cl)c4)c2-3)c1C]
140

TABLE 1-continued
Exemplary compounds of the invention.
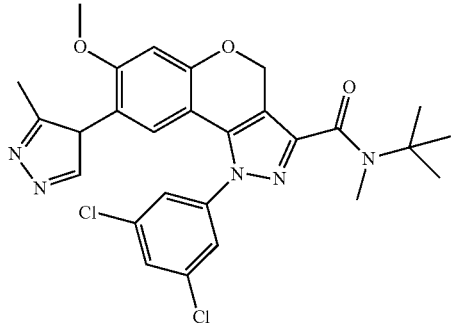 [SMILES: COc1cc2c(cc1C1C=NN=C1C)-c1c(c(C(=O)N(C)C(C)(C)C)nn1-c1cc(Cl)cc(Cl)c1)CO2]
141
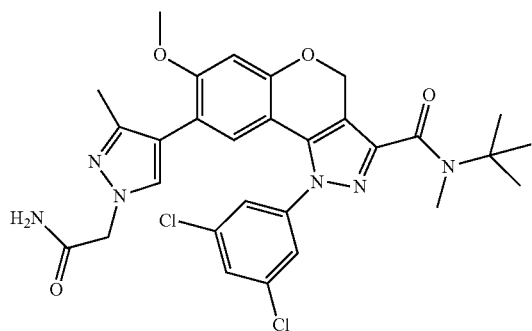 [SMILES: COc1cc2c(cc1-c1cn(CC(N)=O)nc1C)-c1c(c(C(=O)N(C)C(C)(C)C)nn1-c1cc(Cl)cc(Cl)c1)CO2]
142
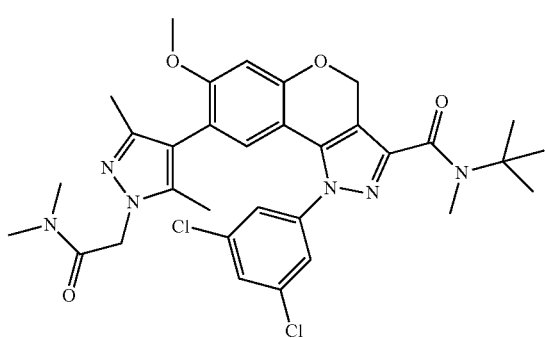 [SMILES: COc1cc2c(cc1-c1c(C)nn(CC(=O)N(C)C)c1C)-c1c(c(C(=O)N(C)C(C)(C)C)nn1-c1cc(Cl)cc(Cl)c1)CO2]
143
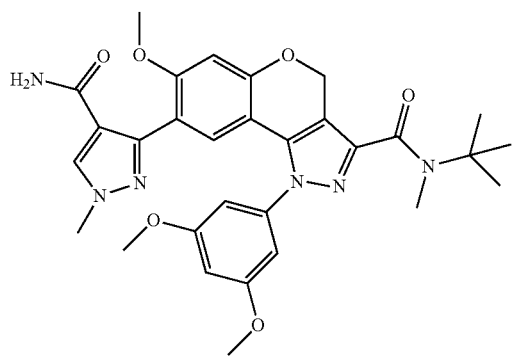 [SMILES: COc1cc(OC)cc(-n2nc(C(=O)N(C)C(C)(C)C)c3c2-c2cc(-c4nn(C)cc4C(N)=O)c(OC)cc2OC3)c1]
144

TABLE 1-continued
Exemplary compounds of the invention.
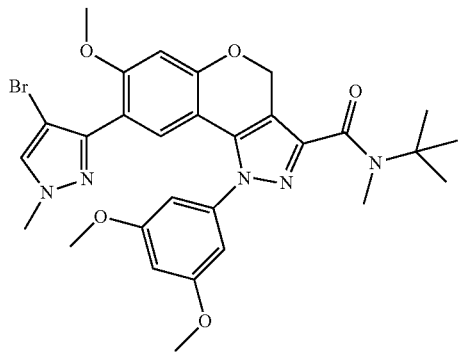 [SMILES: COc1cc(OC)cc(-n2nc(C(=O)N(C)C(C)(C)C)c3c2-c2cc(-c4nn(C)cc4Br)c(OC)cc2OC3)c1]
145
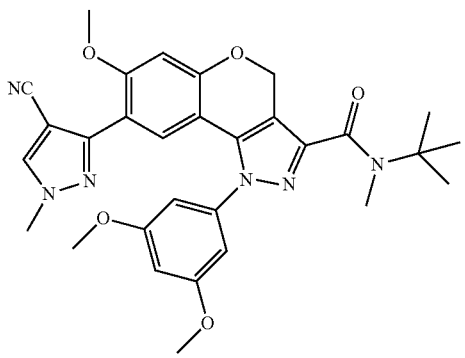 [SMILES: COc1cc(OC)cc(-n2nc(C(=O)N(C)C(C)(C)C)c3c2-c2cc(-c4nn(C)cc4C#N)c(OC)cc2OC3)c1]
146
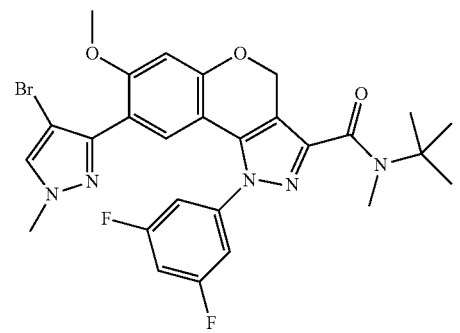
147
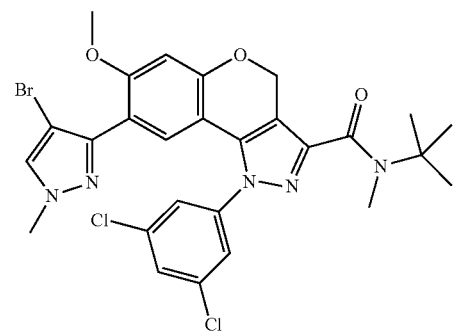 [SMILES: COc1cc2c(cc1-c1nn(C)cc1Br)-c1c(c(C(=O)N(C)C(C)(C)C)nn1-c1cc(Cl)cc(Cl)c1)CO2]
148

TABLE 1-continued
Exemplary compounds of the invention.
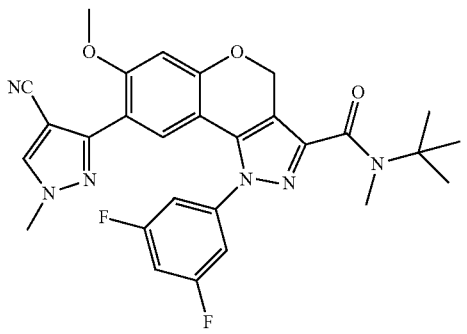 [SMILES: COc1cc2c(cc1-c1nn(C)cc1C#N)-c1c(c(C(=O)N(C)C(C)(C)C)nn1-c1cc(F)cc(F)c1)CO2]
149
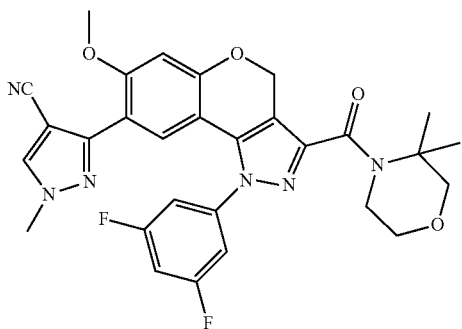 [SMILES: COc1cc2c(cc1-c1nn(C)cc1C#N)-c1c(c(C(=O)N3CCOCC3(C)C)nn1-c1cc(F)cc(F)c1)CO2]
150
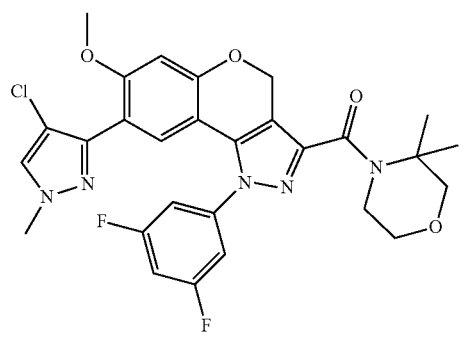 [SMILES: COc1cc2c(cc1-c1nn(C)cc1Cl)-c1c(c(C(=O)N3CCOCC3(C)C)nn1-c1cc(F)cc(F)c1)CO2]
151
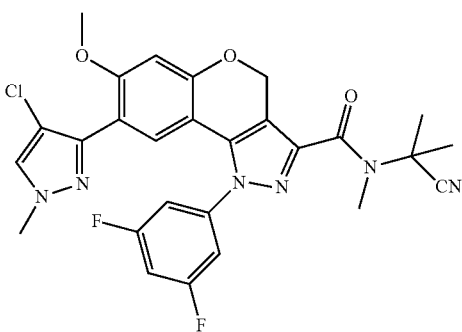 [SMILES: COc1cc2c(cc1-c1nn(C)cc1Cl)-c1c(c(C(=O)N(C)C(C)(C)C#N)nn1-c1cc(F)cc(F)c1)CO2]
152

TABLE 1-continued
Exemplary compounds of the invention.
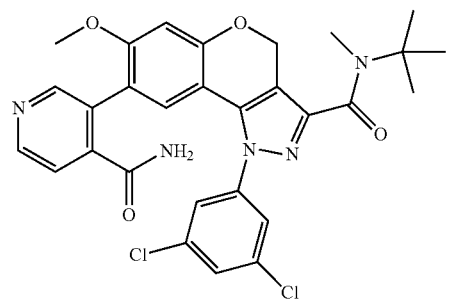 [SMILES: COc1cc2c(cc1-c1cnccc1C(N)=O)-c1c(c(C(=O)N(C)C(C)(C)C)nn1-c1cc(Cl)cc(Cl)c1)CO2] 153
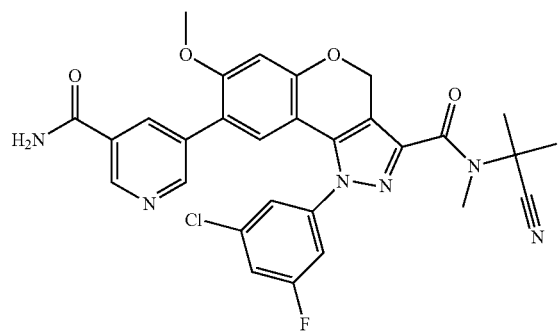 [SMILES: COc1cc2c(cc1-c1cncc(C(N)=O)c1)-c1c(c(C(=O)N(C)C(C)(C)C#N)nn1-c1cc(F)cc(Cl)c1)CO2] 154
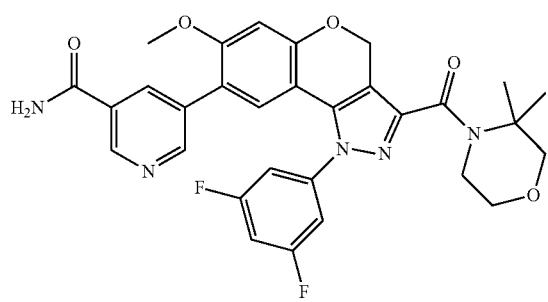 [SMILES: COc1cc2c(cc1-c1cncc(C(N)=O)c1)-c1c(c(C(=O)N3CCOCC3(C)C)nn1-c1cc(F)cc(F)c1)CO2] 155
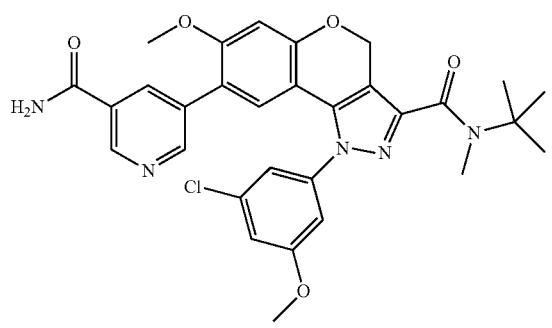 [SMILES: COc1cc(Cl)cc(-n2nc(C(=O)N(C)C(C)(C)C)c3c2-c2cc(-c4cncc(C(N)=O)c4)c(OC)cc2OC3)c1] 156
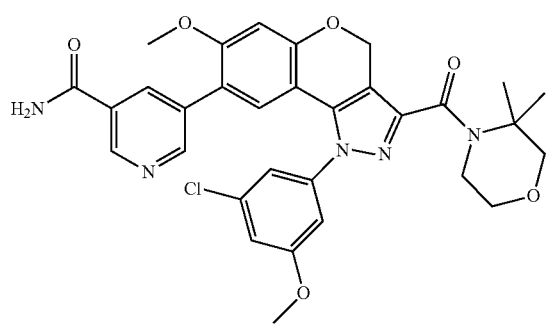 [SMILES: COc1cc(Cl)cc(-n2nc(C(=O)N3CCOCC3(C)C)c3c2-c2cc(-c4cncc(C(N)=O)c4)c(OC)cc2OC3)c1] 157

TABLE 1-continued
Exemplary compounds of the invention.
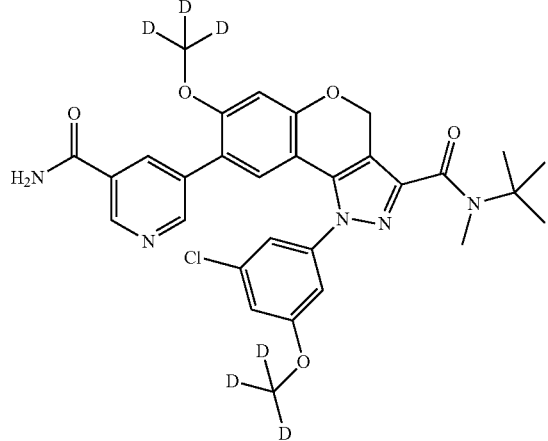 [SMILES: [2H]C([2H])([2H])Oc1cc(Cl)cc(-n2nc(C(=O)N(C)C(C)(C)C)c3c2-c2cc(-c4cncc(C(N)=O)c4)c(OC([2H])([2H])[2H])cc2OC3)c1] 158
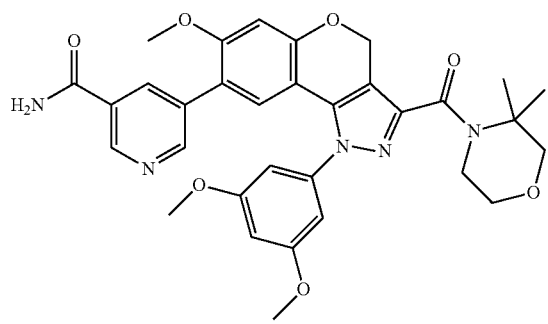 [SMILES: COc1cc(OC)cc(-n2nc(C(=O)N3CCOCC3(C)C)c3c2-c2cc(-c4cncc(C(N)=O)c4)c(OC)cc2OC3)c1] 159
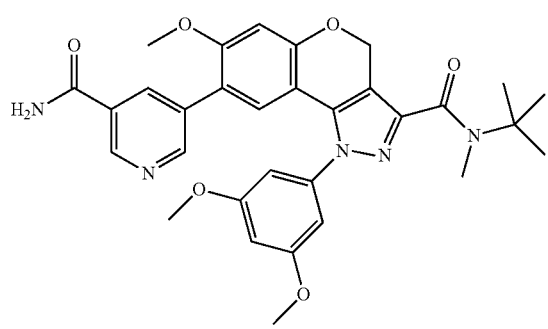 [SMILES: COc1cc(OC)cc(-n2nc(C(=O)N(C)C(C)(C)C)c3c2-c2cc(-c4cncc(C(N)=O)c4)c(OC)cc2OC3)c1] 160
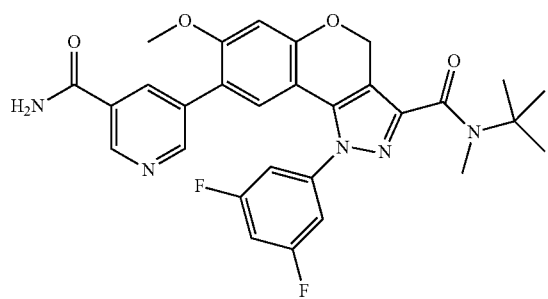 [SMILES: COc1cc2c(cc1-c1cncc(C(N)=O)c1)-c1c(c(C(=O)N(C)C(C)(C)C)nn1-c1cc(F)cc(F)c1)CO2] 161

TABLE 1-continued
Exemplary compounds of the invention.
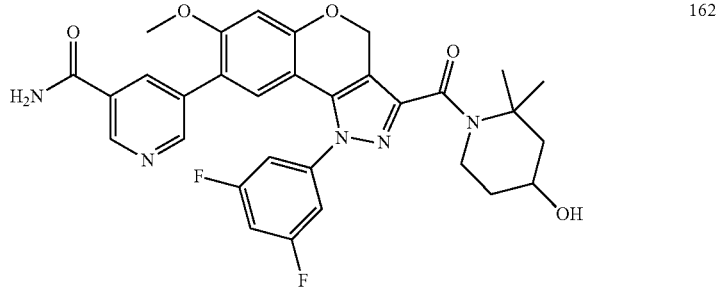
162
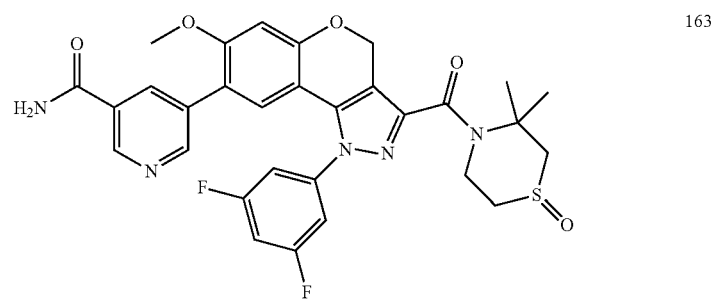
163
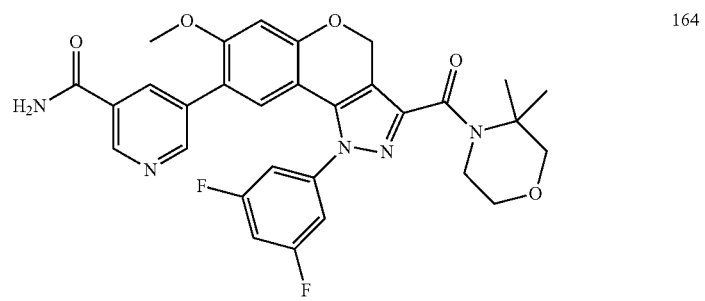
164
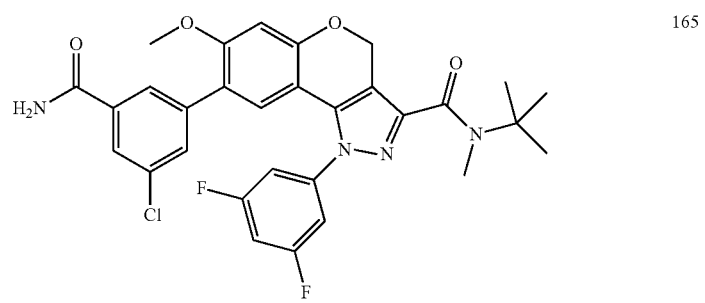
165
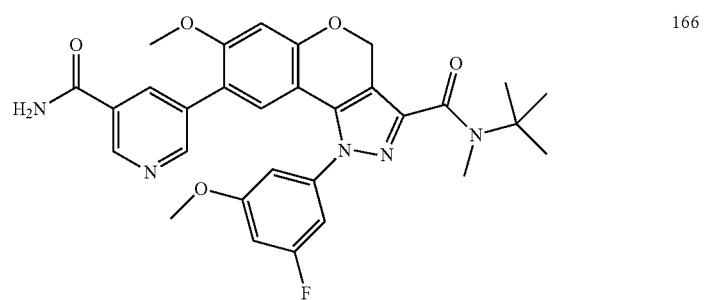
166

TABLE 1-continued
Exemplary compounds of the invention.
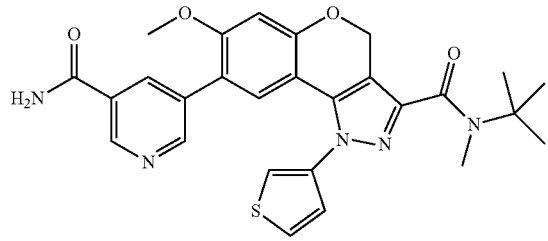 [SMILES: COc1cc2c(cc1-c1cncc(C(N)=O)c1)-c1c(c(C(=O)N(C)C(C)(C)C)nn1-c1ccsc1)CO2] 167
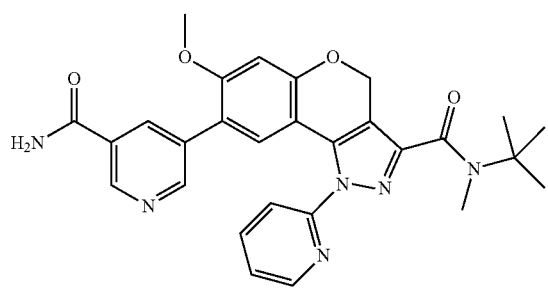 [SMILES: COc1cc2c(cc1-c1cncc(C(N)=O)c1)-c1c(c(C(=O)N(C)C(C)(C)C)nn1-c1ccccn1)CO2] 168
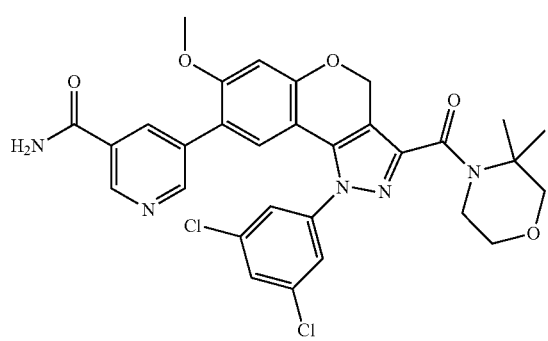 [SMILES: COc1cc2c(cc1-c1cncc(C(N)=O)c1)-c1c(c(C(=O)N3CCOCC3(C)C)nn1-c1cc(Cl)cc(Cl)c1)CO2] 169
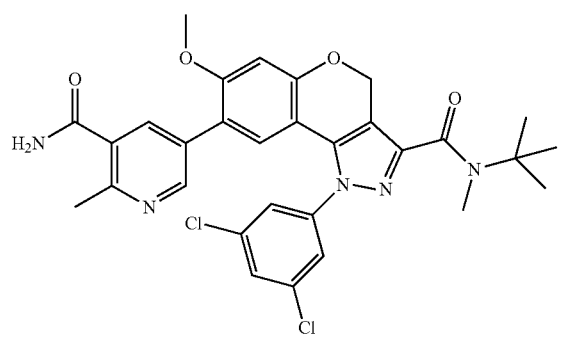 [SMILES: COc1cc2c(cc1-c1cnc(C)c(C(N)=O)c1)-c1c(c(C(=O)N(C)C(C)(C)C)nn1-c1cc(Cl)cc(Cl)c1)CO2] 170
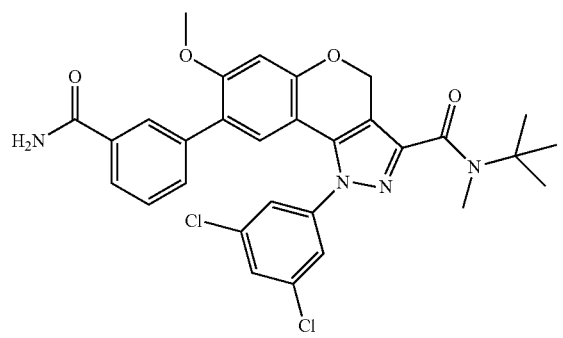 [SMILES: COc1cc2c(cc1-c1cccc(C(N)=O)c1)-c1c(c(C(=O)N(C)C(C)(C)C)nn1-c1cc(Cl)cc(Cl)c1)CO2] 171

TABLE 1-continued
Exemplary compounds of the invention.
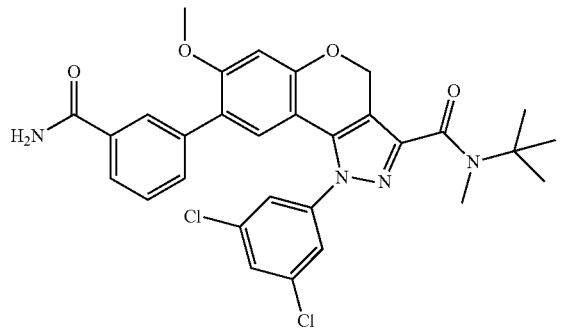 [SMILES: COc1cc2c(cc1-c1cccc(C(N)=O)c1)-c1c(c(C(=O)N(C)C(C)(C)C)nn1-c1cc(Cl)cc(Cl)c1)CO2]
172
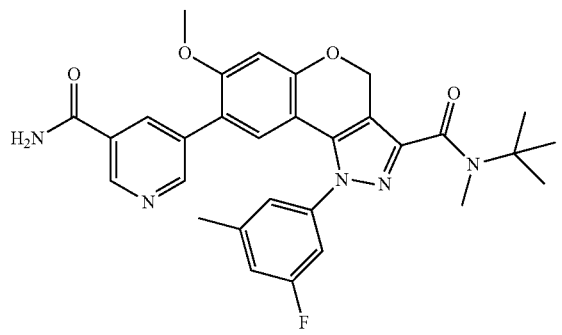 [SMILES: COc1cc2c(cc1-c1cncc(C(N)=O)c1)-c1c(c(C(=O)N(C)C(C)(C)C)nn1-c1cc(C)cc(F)c1)CO2]
173
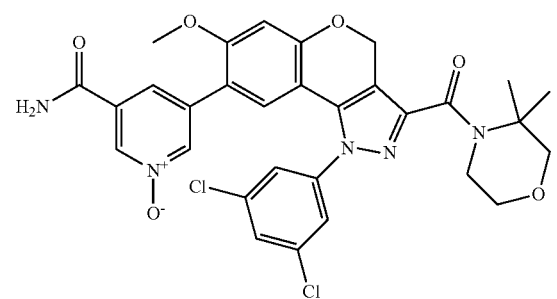 [SMILES: COc1cc2c(cc1-c1cc(C(N)=O)c[n+]([O-])c1)-c1c(c(C(=O)N3CCOCC3(C)C)nn1-c1cc(Cl)cc(Cl)c1)CO2]
174
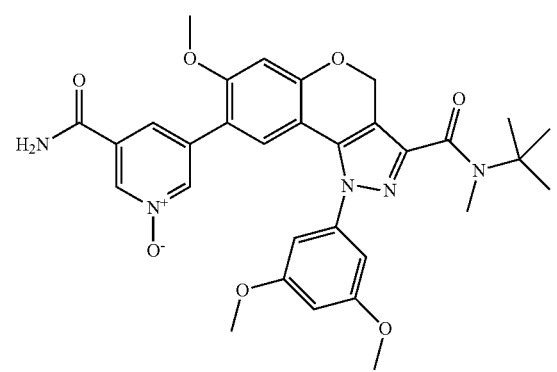 [SMILES: COc1cc(OC)cc(-n2nc(C(=O)N(C)C(C)(C)C)c3c2-c2cc(-c4cc(C(N)=O)c[n+]([O-])c4)c(OC)cc2OC3)c1]
175

TABLE 1-continued
Exemplary compounds of the invention.
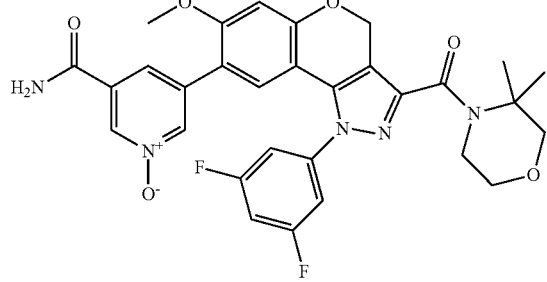
176
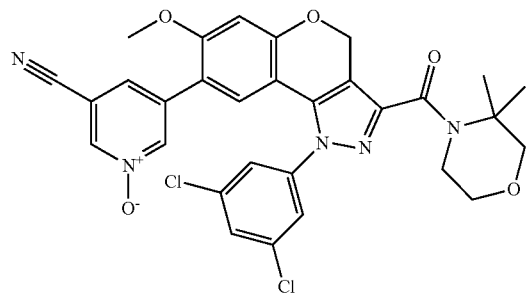 [SMILES: COc1cc2c(cc1-c1cc(C#N)c[n+]([O-])c1)-c1c(c(C(=O)N3CCOCC3(C)C)nn1-c1cc(Cl)cc(Cl)c1)CO2]
177
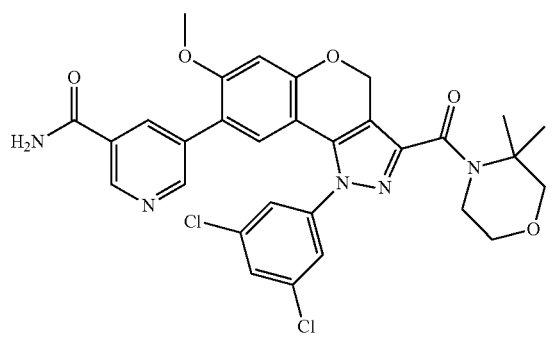 [SMILES: COc1cc2c(cc1-c1cncc(C(N)=O)c1)-c1c(c(C(=O)N3CCOCC3(C)C)nn1-c1cc(Cl)cc(Cl)c1)CO2]
178
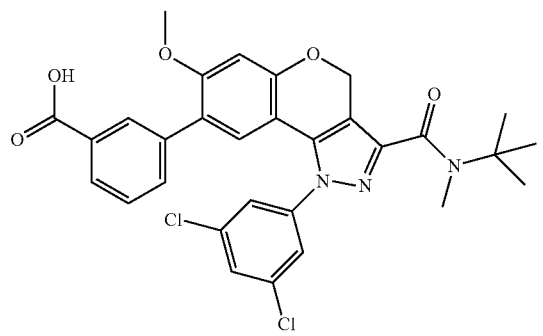 [SMILES: COc1cc2c(cc1-c1cccc(C(=O)O)c1)-c1c(c(C(=O)N(C)C(C)(C)C)nn1-c1cc(Cl)cc(Cl)c1)CO2]
179
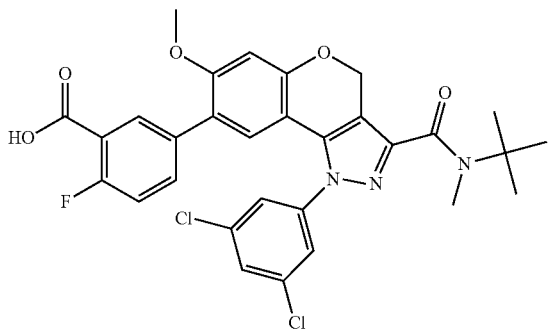 [SMILES: COc1cc2c(cc1-c1ccc(F)c(C(=O)O)c1)-c1c(c(C(=O)N(C)C(C)(C)C)nn1-c1cc(Cl)cc(Cl)c1)CO2]
180

TABLE 1-continued
Exemplary compounds of the invention.
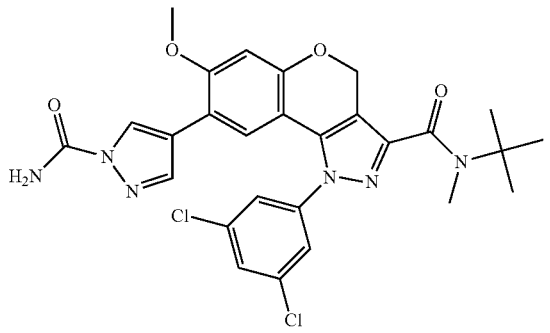 [SMILES: COc1cc2c(cc1-c1cnn(C(N)=O)c1)-c1c(c(C(=O)N(C)C(C)(C)C)nn1-c1cc(Cl)cc(Cl)c1)CO2]
181
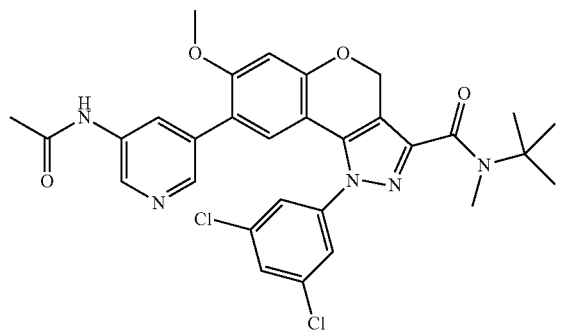 [SMILES: COc1cc2c(cc1-c1cncc(NC(C)=O)c1)-c1c(c(C(=O)N(C)C(C)(C)C)nn1-c1cc(Cl)cc(Cl)c1)CO2]
182
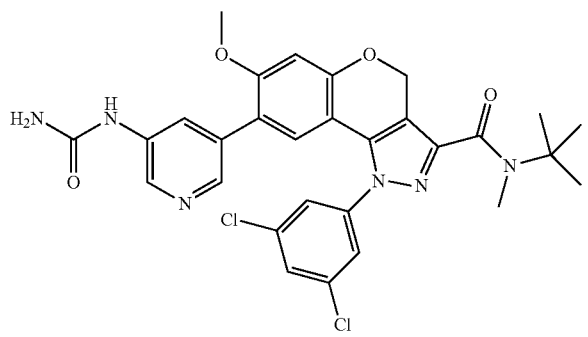 [SMILES: COc1cc2c(cc1-c1cncc(NC(N)=O)c1)-c1c(c(C(=O)N(C)C(C)(C)C)nn1-c1cc(Cl)cc(Cl)c1)CO2]
183
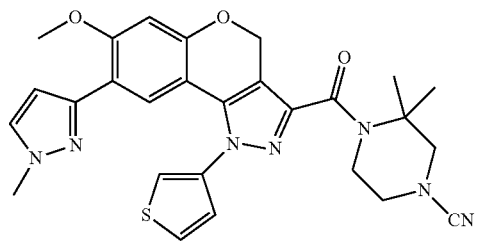 [SMILES: COc1cc2c(cc1-c1ccn(C)n1)-c1c(c(C(=O)N3CCN(C#N)CC3(C)C)nn1-c1ccsc1)CO2]
184
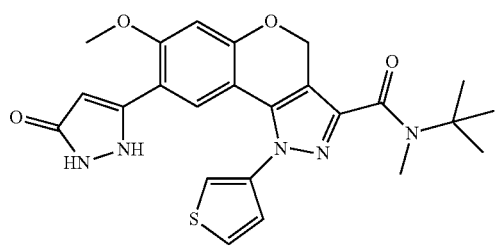 [SMILES: COc1cc2c(cc1-c1cc(=O)[nH][nH]1)-c1c(c(C(=O)N(C)C(C)(C)C)nn1-c1ccsc1)CO2]
185

TABLE 1-continued
Exemplary compounds of the invention.
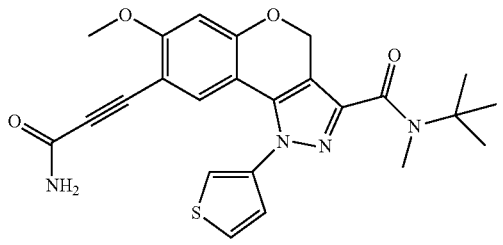 [SMILES: COc1cc2c(cc1C#CC(N)=O)-c1c(c(C(=O)N(C)C(C)(C)C)nn1-c1ccsc1)CO2]
186
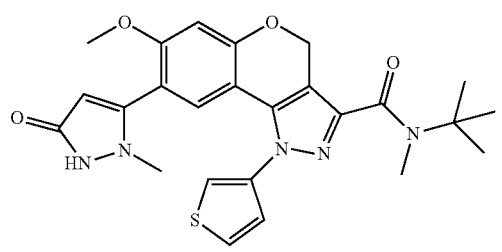 [SMILES: COc1cc2c(cc1-c1cc(=O)[nH]n1C)-c1c(c(C(=O)N(C)C(C)(C)C)nn1-c1ccsc1)CO2]
187
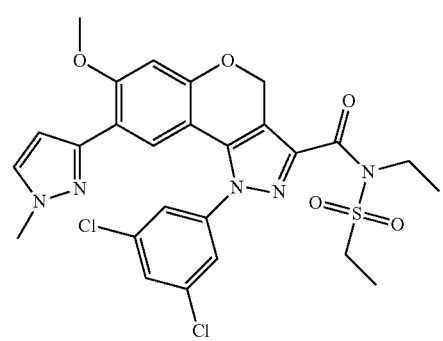 [SMILES: CCN(C(=O)c1nn(-c2cc(Cl)cc(Cl)c2)c2c1COc1cc(OC)c(-c3ccn(C)n3)cc1-2)S(=O)(=O)CC]
188
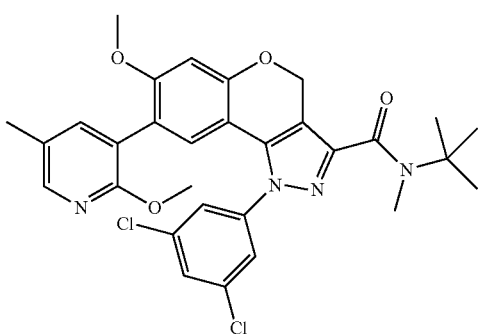 [SMILES: COc1cc2c(cc1-c1cc(C)cnc1OC)-c1c(c(C(=O)N(C)C(C)(C)C)nn1-c1cc(Cl)cc(Cl)c1)CO2]
189
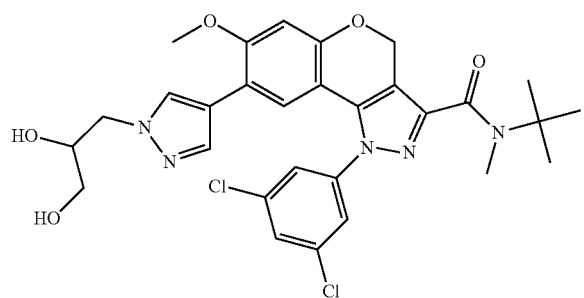 [SMILES: COc1cc2c(cc1-c1cnn(CC(O)CO)c1)-c1c(c(C(=O)N(C)C(C)(C)C)nn1-c1cc(Cl)cc(Cl)c1)CO2]
190

TABLE 1-continued
Exemplary compounds of the invention.
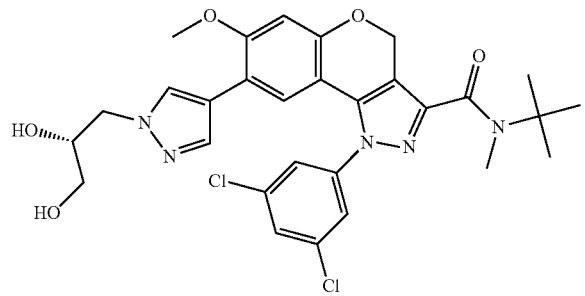 [SMILES: COc1cc2c(cc1-c1cnn(C[C@@H](O)CO)c1)-c1c(c(C(=O)N(C)C(C)(C)C)nn1-c1cc(Cl)cc(Cl)c1)CO2]
191
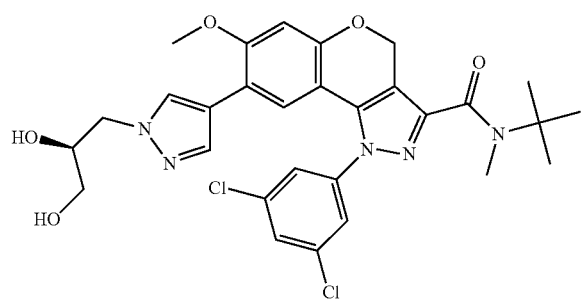 [SMILES: COc1cc2c(cc1-c1cnn(C[C@H](O)CO)c1)-c1c(c(C(=O)N(C)C(C)(C)C)nn1-c1cc(Cl)cc(Cl)c1)CO2]
192
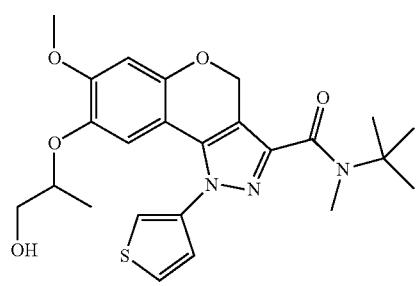 [SMILES: COc1cc2c(cc1OC(C)CO)-c1c(c(C(=O)N(C)C(C)(C)C)nn1-c1ccsc1)CO2]
193
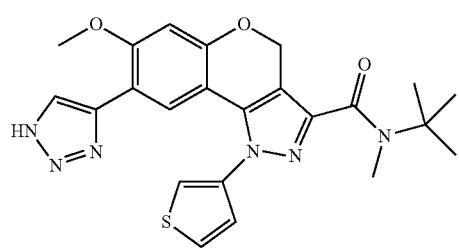 [SMILES: COc1cc2c(cc1-c1c[nH]nn1)-c1c(c(C(=O)N(C)C(C)(C)C)nn1-c1ccsc1)CO2]
194
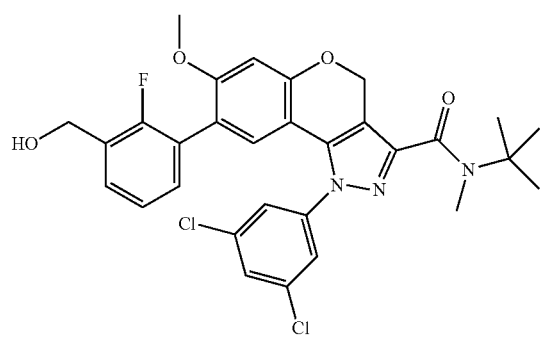 [SMILES: COc1cc2c(cc1-c1cccc(CO)c1F)-c1c(c(C(=O)N(C)C(C)(C)C)nn1-c1cc(Cl)cc(Cl)c1)CO2]
195

TABLE 1-continued
Exemplary compounds of the invention.
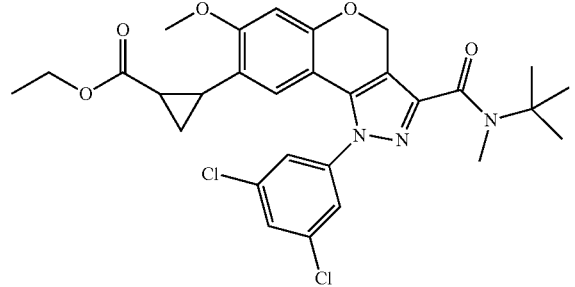 [SMILES: CCOC(=O)C1CC1c1cc2c(cc1OC)OCc1c(C(=O)N(C)C(C)(C)C)nn(-c3cc(Cl)cc(Cl)c3)c1-2]
196
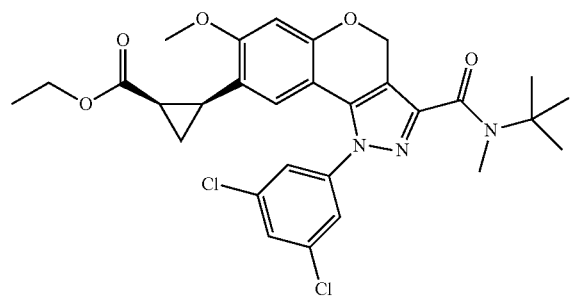 [SMILES: CCOC(=O)[C@@H]1C[C@@H]1c1cc2c(cc1OC)OCc1c(C(=O)N(C)C(C)(C)C)nn(-c3cc(Cl)cc(Cl)c3)c1-2]
197
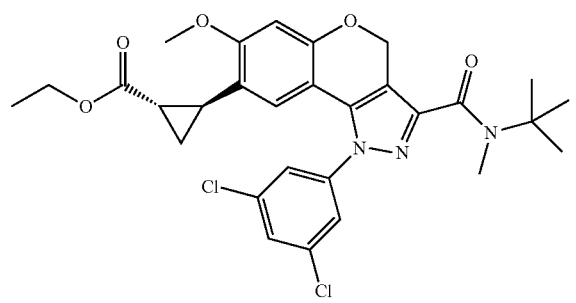 [SMILES: CCOC(=O)[C@H]1C[C@@H]1c1cc2c(cc1OC)OCc1c(C(=O)N(C)C(C)(C)C)nn(-c3cc(Cl)cc(Cl)c3)c1-2]
198
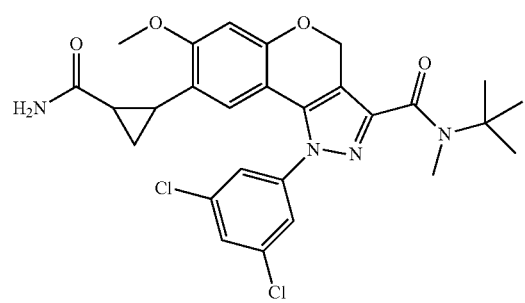 [SMILES: COc1cc2c(cc1C1CC1C(N)=O)-c1c(c(C(=O)N(C)C(C)(C)C)nn1-c1cc(Cl)cc(Cl)c1)CO2]
199
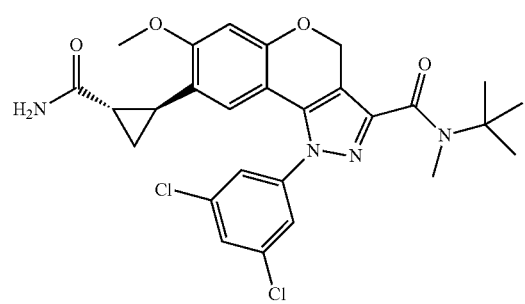 [SMILES: COc1cc2c(cc1[C@H]1C[C@@H]1C(N)=O)-c1c(c(C(=O)N(C)C(C)(C)C)nn1-c1cc(Cl)cc(Cl)c1)CO2]
200

TABLE 1-continued
Exemplary compounds of the invention.
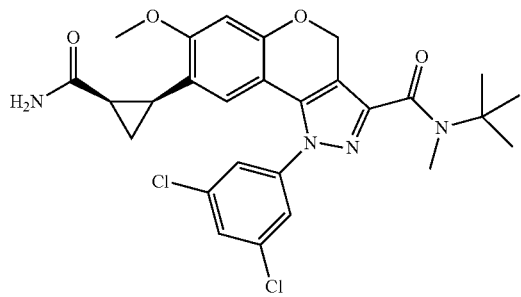 [SMILES: COc1cc2c(cc1[C@H]1C[C@H]1C(N)=O)-c1c(c(C(=O)N(C)C(C)(C)C)nn1-c1cc(Cl)cc(Cl)c1)CO2]
201
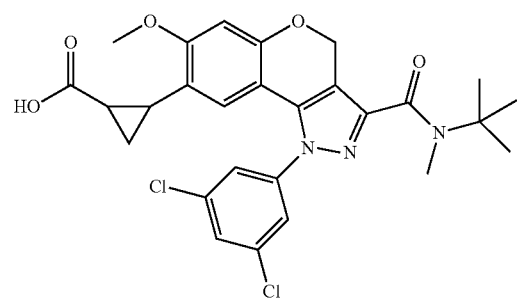 [SMILES: COc1cc2c(cc1C1CC1C(=O)O)-c1c(c(C(=O)N(C)C(C)(C)C)nn1-c1cc(Cl)cc(Cl)c1)CO2]
202
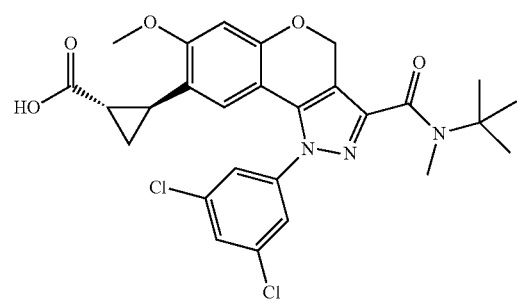 [SMILES: COc1cc2c(cc1[C@H]1C[C@@H]1C(=O)O)-c1c(c(C(=O)N(C)C(C)(C)C)nn1-c1cc(Cl)cc(Cl)c1)CO2]
203
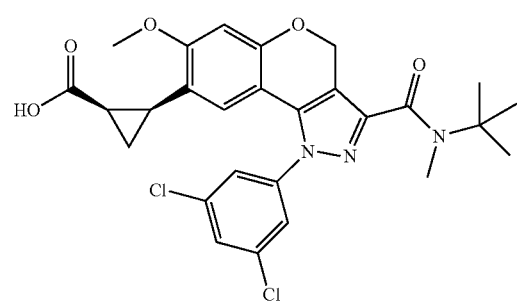 [SMILES: COc1cc2c(cc1[C@H]1C[C@H]1C(=O)O)-c1c(c(C(=O)N(C)C(C)(C)C)nn1-c1cc(Cl)cc(Cl)c1)CO2]
204

205

TABLE 1-continued

Exemplary compounds of the invention.

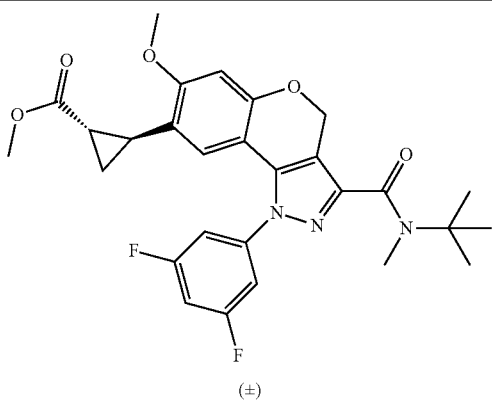

206

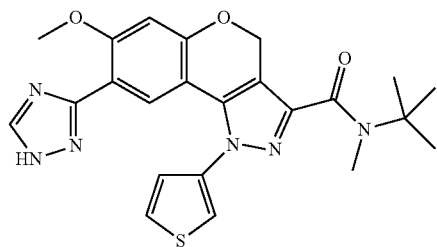 [SMILES: COc1cc2c(cc1-c1nc[nH]n1)-c1c(c(C(=O)N(C)C(C)(C)C)nn1-c1ccsc1)CO2]

207

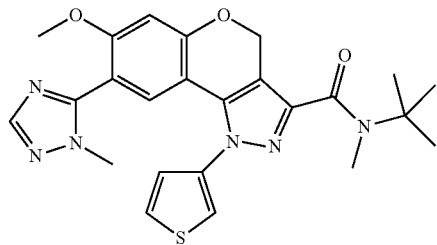 [SMILES: COc1cc2c(cc1-c1ncnn1C)-c1c(c(C(=O)N(C)C(C)(C)C)nn1-c1ccsc1)CO2]

208

In some embodiments, the present invention provides a compound selected from those depicted above, or a pharmaceutically acceptable salt thereof.

Various structural depictions may show a heteroatom without an attached group, radical, charge, or counterion. Those of ordinary skill in the art are aware that such depictions are meant to indicate that the heteroatom is attached to hydrogen (e.g., 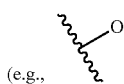

is understood to be

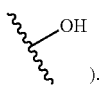).

In certain embodiments, the compounds of the invention were synthesized in accordance with Schemes A-C below. More specific examples of compounds made utilizing Schemes A-C are provided in the Examples below.

Scheme A

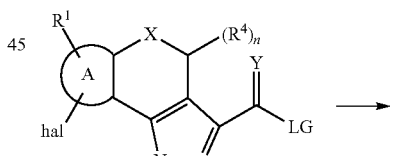

II

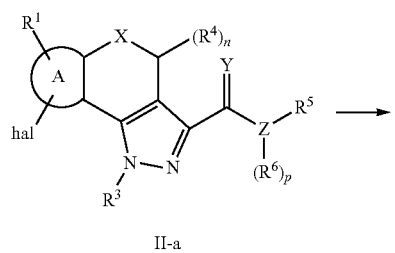

II-a

-continued

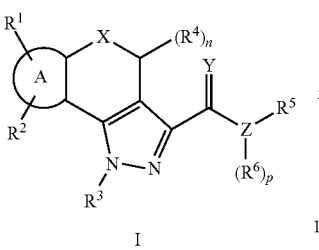

I

Scheme B

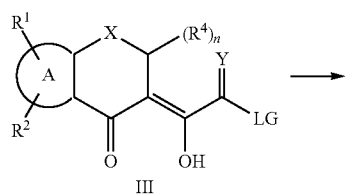

III

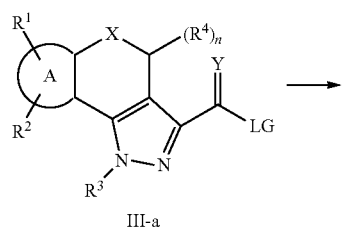

III-a

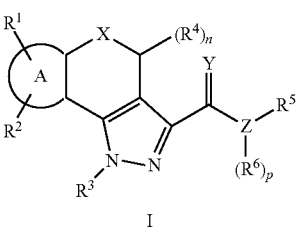

I

Scheme C

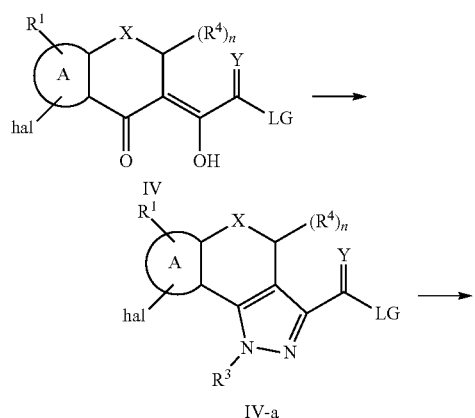

IV

IV-a

-continued

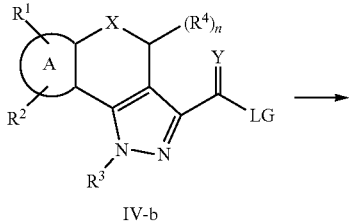

IV-b

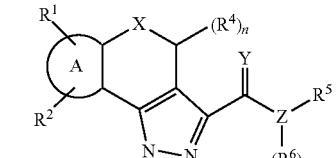

I

4. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably modulate FSHR, or a mutant thereof, in a biological sample or in a patient. In certain embodiments, the amount of compound in compositions of this invention is such that is effective to measurably modulate FSHR, or a mutant thereof, in a biological sample or in a patient. In certain embodiments, a composition of this invention is formulated for administration to a patient in need of such composition.

The term "patient" or "subject", as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that are used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

Compositions of the present invention are administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention include aqueous or oleaginous suspension. These suspensions are formulated according to techniques known in the art using suitable dispersing or wetting agents and suspending agents. The sterile injectable preparation is also be a sterile injectable solution or suspension in a non-toxic parenterally acceptable diluent or solvent, for example as a solution in 1,3-butanediol. Among the acceptable vehicles and solvents that are employed are water, Ringer's solution and isotonic sodium chloride solution. In addition, sterile, fixed oils are conventionally employed as a solvent or suspending medium.

For this purpose, any bland fixed oil employed includes synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms are also be used for the purposes of formulation.

Pharmaceutically acceptable compositions of this invention are orally administered in any orally acceptable dosage form. Exemplary oral dosage forms are capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents are optionally also added.

Alternatively, pharmaceutically acceptable compositions of this invention are administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention are also administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches are also used.

For topical applications, provided pharmaceutically acceptable compositions are formulated in a suitable ointment containing the active component suspended or dissolved in one or more carriers. Exemplary carriers for topical administration of compounds of this areminaral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

Pharmaceutically acceptable compositions of this invention are optionally administered by nasal aerosol or inhalation. Such compositions are prepared according to techniques well-known in the art of pharmaceutical formulation and are prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that are optionally combined with the carrier materials to produce a composition in a single dosage form will vary depending upon the host treated, the particular mode of administration. Preferably, provided compositions should be formulated so that a dosage of between 0.01-100 mg/kg body weight/day of the compound can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

In certain embodiments, the invention provides a method for allosterically agonising FSHR, or a mutant thereof, in a positive manner in a patient or in a biological sample comprising the step of administering to said patient or contacting said biological sample with a compound according to the invention.

In certain embodiments, the invention is directed to the use of compounds of the invention and/or physiologically acceptable salts thereof, for modulating a FSH receptor, particularly in the presence of FSH. The term "modulation" denotes any change in FSHR-mediated signal transduction, which is based on the action of the specific inventive compounds capable to interact with the FSHR target in such a manner that makes recognition, binding and activating possible. The compounds are characterized by such a high affinity to FSHR, which ensures a reliable binding and preferably a positive allosteric modulation of FSHR. In certain embodiments, the substances are mono-specific in order to guarantee an exclusive and directed recognition with the single FSHR target. In the context of the present invention, the term "recognition"—without being limited thereto—relates to any type of interaction between the specific compounds and the target, particularly covalent or non-covalent binding or association, such as a covalent bond, hydrophobic/hydrophilic interactions, van der Waals forces, ion pairs, hydrogen bonds, ligand-receptor interactions, and the like. Such association may also encompass the presence of other molecules such as peptides, proteins or nucleotide sequences. The present receptor/ligand-interaction is characterized by high affinity, high selectivity and minimal or even lacking cross-reactivity to other target molecules to exclude unhealthy and harmful impacts to the treated subject.

In certain embodiments, the present invention relates to a method for modulating an FSH receptor, and in particular in a positive allosteric manner, wherein a system capable of expressing the FSH receptor is contacted, in the presence of FSH, with at least one compound of formula (I) or formula (II) according to the invention and/or physiologically acceptable salts thereof, under conditions such that said FSH receptor is modulated. In certain embodiments, modulation is in a positive allosteric manner. In certain embodiments, the system is a cellular system. In other embodiments, the system is an in-vitro translation which is based on the protein synthesis without living cells. The cellular system is defined to be any subject provided that the subject comprises cells. Hence, the cellular system can be selected from the group of single cells, cell cultures, tissues, organs and animals. In certain embodiments, the method for modulating an FSH receptor is performed in-vitro. The prior teaching of the present specification concerning the compounds of formula (I) or formula (II), including any embodiments thereof, is valid and applicable without restrictions to the compounds according to formula (I) or formula (II) and their salts when used in the method for modulating FSHR. The prior teaching of the present specification concerning the compounds of formula (I) or formula (II), including any embodiments thereof, is valid and applicable without restrictions to the compounds according to formula (I) or formula (II) and their salts when used in the method for modulating FSHR.

In certain embodiments, the compounds according to the invention exhibit an advantageous biological activity, which is easily demonstrated in cell culture-based assays, for example assays as described herein or in prior art (cf. e.g. WO 2002/09706, which is incorporated herein by reference). In such assays, the compounds according to the invention preferably exhibit and cause an agonistic effect. In certain embodiments, the compounds of the invention have an FSHR agonist activity, as expressed by an $EC_{50}$ standard, of less than 5 µM. In certain embodiments, less than 1 µM. In certain embodiments, less than 0.5 µM. In certain embodiments, less than 0.1 µM. "$EC_{50}$" is the effective concentration of a compound at which 50% of the maximal response of that obtained with FSH would be obtained.

As discussed herein, these signaling pathways are relevant for various diseases, including fertility disorders. Disorders/diseases treated by the methods of the invention include but are not limited to, hypogonadotropic hypogonadism, Isolated idiopathic hypogonadotropic hypogonadism, Kallmann syndrome, Idiopathic hypogonadotropic hypogonadism, Craniopharyngiomas, Combined pituitary hormone deficiency, Fertile eunuch syndrome, Abnormal beta subunit of LH, Abnormal beta subunit of FSH, mass lesions, pituitary adenomas, cysts, metastatic cancer to the sella (breast in women, lung and prostate in men), Infiltrative lesions, Hemochromatosis, sarcoidosis, histiocytosis, lymphoma, Lymphocytic hypophysitis, Infections, Meningitis, Pituitary apoplexy, Hyperprolactinemia, hypothyroidism, Intentional (iatrogenic) secondary hypogonadism, Empty sella, Pituitary infarction, Sheehan syndrome, Anorexia nervosa, Congenital adrenal hyperplasia, and disorders related to GnRH deficiency. Accordingly, the compounds according to the invention are useful in the prophylaxis and/or treatment of diseases that are dependent on the said signaling pathways by interaction with one or more of the said signaling pathways. The present invention therefore relates to compounds according to the invention as modulators, preferably agonists, more preferably positive allosteric modulators, of the signaling pathways described herein, preferably of the FSHR-mediated signaling pathway. The compounds of the invention are supposed to bind to the intracellular receptor domain without a competitive interaction with FSH, but they act as an allosteric enhancer of FSH on its receptor. The non-competitive interaction refers to the nature of the agonist activity exhibited by the compounds of the invention, wherein the compounds activate FSHR without substantially reducing the magnitude of binding of FSH to FSHR.

In certain embodiments, the invention is directed towards the stimulation of follicular development, ovulation induction, controlled ovarian hyperstimulation, assisted reproductive technology, including in-vitro fertilization, male hypogonadism and male infertility, including some types of failure of spermatogenesis.

It is another object of the invention to provide a method for treating diseases that are caused, mediated and/or propagated by FSHR activity, wherein at least one compound of formula (I) or formula (II) according to the invention and/or physiologically acceptable salts thereof is administered to a mammal in need of such treatment. In certain embodiments, the invention provides a method for treating fertility disorders, wherein at least one compound of formula (I) or formula (II) according to the invention and/or physiologically acceptable salts thereof is administered to a mammal in need of such treatment. In certain embodiments, the compound is administered in an effective amount as defined above. In certain embodiments, the treatment is an oral administration.

In certain embodiments, the method of treatment aims to achieve ovulation induction and/or controlled ovarian hyperstimulation. In still another embodiment, the method of treatment forms the basis for a method for in-vitro fertilization comprising the steps of: (a) treating a mammal according to the method of treatment as described above, (b) collecting ova from said mammal, (c) fertilizing said ova, and (d) implanting said fertilized ova into a host mammal. The host mammal can be either the treated mammal (i.e. the patient) or a surrogate. The prior teaching of the invention and its embodiments is valid and applicable without restrictions to the methods of treatment if expedient.

The method of the invention can be performed either in-vitro or in-vivo. The susceptibility of a particular cell to treatment with the compounds according to the invention can be particularly determined by in-vitro tests, whether in the course of research or clinical application. Typically, a culture of the cell is combined with a compound according to the invention at various concentrations for a period of time which is sufficient to allow the active agents to modulate FSHR activity, usually between about one hour and one week. In-vitro treatment can be carried out using cultivated cells from a biopsy sample or cell line. In a preferred aspect of the invention, a follicle cell is stimulated for maturation. The viable cells remaining after the treatment are counted and further processed.

The host or patient can belong to any mammalian species, for example a primate species, particularly humans; rodents, including mice, rats and hamsters; rabbits; horses, cows, dogs, cats, etc. Animal models are of interest for experimental investigations, providing a model for treatment of human disease.

For identification of a signal transduction pathway and for detection of interactions between various signal transduction pathways, various scientists have developed suitable models or model systems, for example cell culture models and models of transgenic animals. For the determination of certain stages in the signal transduction cascade, interacting compounds can be utilized in order to modulate the signal. The compounds according to the invention can also be used as reagents for testing FSHR-dependent signal transduction pathways in animals and/or cell culture models or in the clinical diseases mentioned in this application.

The use according to the previous paragraphs of the specification may be either performed in-vitro or in-vivo models. The modulation can be monitored by the techniques described in the course of the present specification. In certain embodiments, the in-vitro use is preferably applied to samples of humans suffering from fertility disorders. Testing of several specific compounds and/or derivatives thereof makes the selection of that active ingredient possible that is best suited for the treatment of the human subject. The in-vivo dose rate of the chosen derivative is advantageously pre-adjusted to the FSHR susceptibility and/or severity of disease of the respective subject with regard to the in-vitro data. Therefore, the therapeutic efficacy is remarkably enhanced. Moreover, the subsequent teaching of the present specification concerning the use of the compounds according to formula (I) or formula (II) and its derivatives for the production of a medicament for the prophylactic or therapeutic treatment and/or monitoring is considered as valid and applicable without restrictions to the use of the compound for the modulation of FSHR activity if expedient.

The invention also relates to the use of compounds according to formula (I) or formula (II) and/or physiologically acceptable salts thereof for the prophylactic or therapeutic treatment and/or monitoring of diseases that are caused, mediated and/or propagated by FSHR activity. Furthermore, the invention relates to the use of compounds according to formula (I) or formula (II) and/or physiologically acceptable salts thereof for the production of a medicament for the prophylactic or therapeutic treatment and/or monitoring of diseases that are caused, mediated and/or propagated by FSHR activity. In certain embodiments, the invention provides the use of a compound according to formula (I) or formula (II) or formula (II) or physiologically acceptable salts thereof, for the production of a medicament for the prophylactic or therapeutic treatment of a FSHR-mediated disorder.

Compounds of formula (I) or formula (II) and/or a physiologically acceptable salt thereof can furthermore be employed as intermediate for the preparation of further medicament active ingredients. The medicament is preferably prepared in a non-chemical manner, e.g. by combining the active ingredient with at least one solid, fluid and/or semi-fluid carrier or excipient, and optionally in conjunction with a single or more other active substances in an appropriate dosage form.

Another object of the present invention are compounds of formula (I) or formula (II) according to the invention and/or physiologically acceptable salts thereof for use in the prophylactic or therapeutic treatment and/or monitoring of diseases that are caused, mediated and/or propagated by FSHR activity. Another preferred object of the invention concerns compounds of formula (I) or formula (II) according to the invention and/or physiologically acceptable salts thereof for use in the prophylactic or therapeutic treatment and/or monitoring of fertility disorders. The prior teaching of the present specification concerning the compounds of formula (I) or formula (II), including any preferred embodiment thereof, is valid and applicable without restrictions to the compounds according to formula (I) or formula (II) and their salts for use in the prophylactic or therapeutic treatment and/or monitoring of fertility disorders.

The compounds of formula (I) or formula (II) according to the invention can be administered before or following an onset of disease once or several times acting as therapy. The aforementioned compounds and medical products of the inventive use are particularly used for the therapeutic treatment. A therapeutically relevant effect relieves to some extent one or more symptoms of a disorder, or returns to normality, either partially or completely, one or more physiological or biochemical parameters associated with or causative of a disease or pathological condition. Monitoring is considered as a kind of treatment provided that the compounds are administered in distinct intervals, e.g. in order to booster the response and eradicate the pathogens and/or symptoms of the disease completely. Either the identical compound or different compounds can be applied. The methods of the invention can also be used to reducing the likelihood of developing a disorder or even prevent the initiation of disorders associated with FSHR activity in advance or to treat the arising and continuing symptoms. In certain embodiments, the disorders are fertility disorders.

In the meaning of the invention, prophylactic treatment is advisable if the subject possesses any preconditions for the aforementioned physiological or pathological conditions, such as a familial disposition, a genetic defect, or a previously passed disease.

The invention furthermore relates to a medicament comprising at least one compound according to the invention and/or pharmaceutically usable derivatives, salts, solvates and stereoisomers thereof, including mixtures thereof in all ratios. In certain embodiments, the invention relates to a medicament comprising at least one compound according to the invention and/or physiologically acceptable salts thereof.

A "medicament" in the meaning of the invention is any agent in the field of medicine, which comprises one or more compounds of formula (I) or formula (II) or preparations thereof (e.g. a pharmaceutical composition or pharmaceutical formulation) and can be used in prophylaxis, therapy, follow-up or aftercare of patients who suffer from diseases, which are associated with FSHR activity, in such a way that a pathogenic modification of their overall condition or of the condition of particular regions of the organism could establish at least temporarily.

In various embodiments, the active ingredient may be administered alone or in combination with other treatments. A synergistic effect may be achieved by using more than one compound in the pharmaceutical composition, i.e. the compound of formula (I) or formula (II) is combined with at least another agent as active ingredient, which is either another compound of formula (I) or formula (II) or a compound of different structural scaffold. The active ingredients can be used either simultaneously or sequentially. The present compounds are suitable for combination with known fertility-inducing agents. In certain embodiments, the other active pharmaceutical ingredient is selected from the group of FSH, α-FSH (Gonal F), β-FSH, LH, hMG and 2-(4-(2-chloro-1,2-diphenylethenyl)-phenoxy)-N,N-diethyl-ethanamine citrate (Chlomifene citrate). Further ovulation adjuncts are known to those of skill in the art (cf. e.g. WO 2002/09706, which is incorporated herein by reference) and are useful with the compounds of the present invention.

In another aspect, the invention provides for a kit consisting of separate packs of an effective amount of a compound according to the invention and/or pharmaceutically acceptable salts, derivatives, solvates and stereoisomers thereof, including mixtures thereof in all ratios, and optionally, an effective amount of a further active ingredient. The kit comprises suitable containers, such as boxes, individual bottles, bags or ampoules. The kit may, for example, comprise separate ampoules, each containing an effective amount of a compound according to the invention and/or pharmaceutically acceptable salts, derivatives, solvates and stereoisomers thereof, including mixtures thereof in all ratios, and an effective amount of a further active ingredient in dissolved or lyophilized form.

As used herein, the terms "treatment," "treat," and "treating" refer to reversing, alleviating, delaying the onset of, or inhibiting the progress of a disease or disorder, or one or more symptoms thereof, as described herein. In some embodiments, treatment is administered after one or more symptoms have developed. In other embodiments, treatment is administered in the absence of symptoms. For example, treatment is administered to a susceptible individual prior to the onset of symptoms (e.g., in light of a history of symptoms and/or in light of genetic or other susceptibility factors). Treatment is also continued after symptoms have resolved, for example to prevent or delay their recurrence.

The compounds and compositions, according to the method of the present invention, are administered using any amount and any route of administration effective for treating or lessening the severity of a disorder provided above. The exact amount required will vary from subject to subject, depending on the species, age, and general condition of the subject, the severity of the infection, the particular agent, its mode of administration, and the like. Compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention are administered orally or parenterally at dosage levels of about 0.01 mg/kg to about 100 mg/kg and preferably from about 1 mg/kg to about 50 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms optionally contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions are formulated according to the known art using suitable dispersing or wetting agents and suspending agents. The sterile injectable preparation are also a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This is accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form also optionally comprises buffering agents.

Solid compositions of a similar type are also employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type are also employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms also comprise, as is normal practice, additional substances other than inert diluents, e.g., tableting lubricants and other tableting aids such a magnesium stearate and microcrystalline cellulose. In the case of capsules, tablets and pills, the dosage forms optionally also comprise buffering agents. They optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to one embodiment, the invention relates to a method of allosterically modulating FSHR activity in a biological sample comprising the step of contacting said biological sample with a compound of this invention, or a composition comprising said compound.

According to another embodiment, the invention relates to a method of allosterically modulating FSHR, or a mutant thereof, activity in a biological sample in a positive manner, comprising the step of contacting said biological sample with a compound of this invention, or a composition comprising said compound.

The compounds of the invention are strong and selective modulators of the FSH receptor. Their selectivity to the FSH receptor is 3 to 10-fold over the LH receptor and even 10 to 100-fold over the TSH receptor while the $EC_{50}$ or $IC_{50}$ amounts to more than 10 µM on unrelated G protein-coupled receptors (GPCR) or non-GPCR targets. The current invention comprises the use of the compounds of the invention in the regulation and/or modulation of the FSHR signal cascade, which can be advantageously applied as research tool, for diagnosis and/or in treatment of any disorder arising from FSHR signaling.

For example, the compounds of the invention are useful in-vitro as unique tools for understanding the biological role of FSH, including the evaluation of the many factors thought to influence, and be influenced by, the production of FSH and the interaction of FSH with the FSHR (e. g. the mechanism of FSH signal transduction/receptor activation). The present compounds are also useful in the development of other compounds that interact with FSHR since the present compounds provide important structure-activity relationship (SAR) information that facilitate that development. Compounds of the present invention that bind to FSHR can be used as reagents for detecting FSHR on living cells, fixed cells, in biological fluids, in tissue homogenates, in purified, natural biological materials, etc. For example, by labeling such compounds, one can identify cells having FSHR on their surfaces. In addition, based on their ability to bind FSHR, compounds of the present invention can be used in in-situ staining, FACS (fluorescence-activated cell sorting), western blotting, ELISA (enzyme-linked immunoadsorptive assay), etc., receptor purification, or in purifying cells expressing FSHR on the cell surface or inside permeabilized cells.

The compounds of the invention can also be utilized as commercial research reagents for various medical research and diagnostic uses. Such uses can include but are not limited to: use as a calibration standard for quantifying the activities of candidate FSH agonists in a variety of functional assays; use as blocking reagents in random compound screening, i.e. in looking for new families of FSH receptor ligands, the compounds can be used to block recovery of the presently claimed FSH compounds; use in the co-crystallization with FSHR receptor, i.e. the compounds of the present invention will allow formation of crystals of the compound bound to FSHR, enabling the determination of receptor/compound structure by x-ray crystallography; other research and diagnostic applications, wherein FSHR is preferably activated or such activation is conveniently calibrated against a known quantity of an FSH agonist, etc.; use in assays as probes for determining the expression of FSHR on the surface of cells; and developing assays for detecting compounds which bind to the same site as the FSHR binding ligands.

The compounds of the invention can be applied either themselves and/or in combination with physical measurements for diagnostics of treatment effectiveness. Pharmaceutical compositions containing said compounds and the use of said compounds to treat FSHR-mediated conditions is a promising, novel approach for a broad spectrum of therapies causing a direct and immediate improvement in the state of health, whether in human or animal. The impact is of special benefit to efficiently combat infertility, either alone or in combination with other fertility-inducing treatments. In particular, the compounds of the invention potentiate the native FSH effect for both ovulation induction and assisted reproductive technology. The orally bioavailable and active new chemical entities of the invention improve convenience for patients and compliance for physicians.

The compounds of the invention are active in the primary screen (CHO with or without FSH), selective in secondary screen (no or low activity against TSHR and LHR) and potent in the granulosa cell estrodiol assay. Neither hERG nor any toxic effects could be observed in-vitro.

In certain embodiments, the invention provides a method for in-vitro fertilization comprising the steps of:
(a) treating a mammal according to the method as described above,
(b) collecting ova from said mammal,
(c) fertilizing said ova, and
(d) implanting said fertilized ova into a host mammal.

The compounds of formula (I) or formula (II), their salts, isomers, tautomers, enantiomeric forms, diastereomers, racemates, derivatives, prodrugs and/or metabolites are characterized by a high specificity and stability, low manufacturing costs and convenient handling. These features form the basis for a reproducible action, wherein the lack of cross-reactivity is included, and for a reliable and safe interaction with the target structure.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Modulation of FSHR, or a mutant thereof, activity in a biological sample is useful for a variety of purposes that are known to one of skill in the art. Examples of such purposes include, but are not limited to, blood transfusion, organ transplantation, biological specimen storage, and biological assays.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

Compound numbers utilized in the Examples below correspond to compound numbers set forth supra.

$^1$H NMR was recorded on a Bruker 400 MHz spectrometer, using the residual signal of deuterated solvent as an internal reference. Chemical shifts (δ) are reported in ppm relative to the residual solvent signal (δ=2.49 ppm for $^1$H NMR in DMSO-d$_6$). $^1$H NMR data are reported as follows: chemical shift (multiplicity, coupling constants, and number of hydrogens). Multiplicity is abbreviated as follows: s (singlet), d (doublet), t (triplet), q (quartet), m (multiplet), br (broad).

LC-MS analysis was performed under the following conditions:
Method: A: 0.1% TFA in H$_2$O, B: 0.1% TFA in ACN; Run time: 6.5 min; Flow Rate: 1.0 mL/min; Gradient: 5-95% B in 4.5 min, wavelengths 254 and 215 nM; Column: Waters Sunfire C18, 3.0×50 mm, 3.5 um, positive mode; Mass Scan: 100-900 Da.

Example 1: N-tert-butyl-1-(3,5-dichlorophenyl)-8-(1-(2-hydroxyethyl)-1H-pyrazol-4-yl)-7-methoxy-N-methyl-1,4-dihydrochromeno[4,3-c]pyrazole-3-carboxamide (Compound 1)

Scheme 1

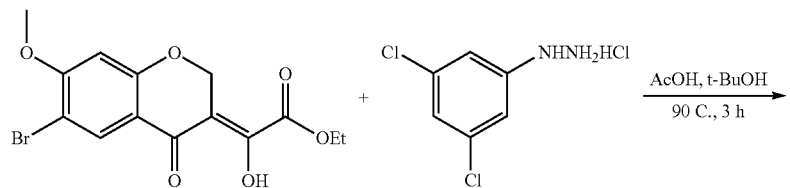

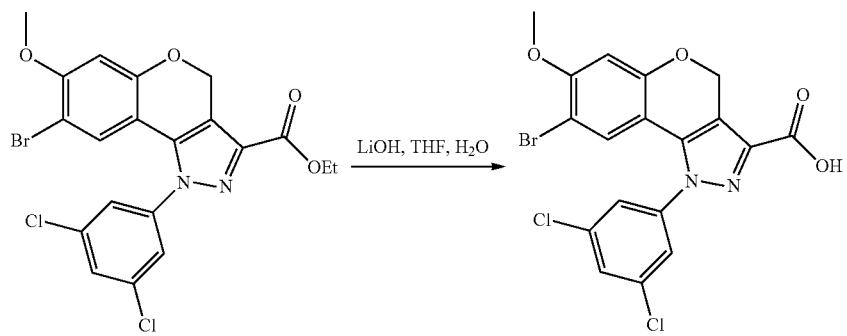

-continued
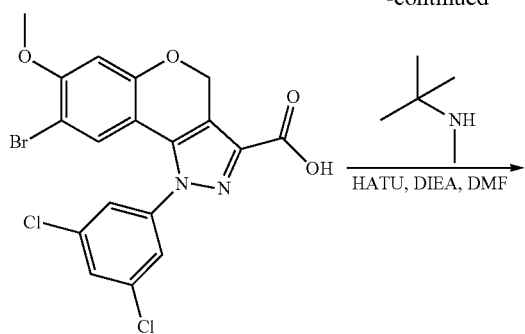
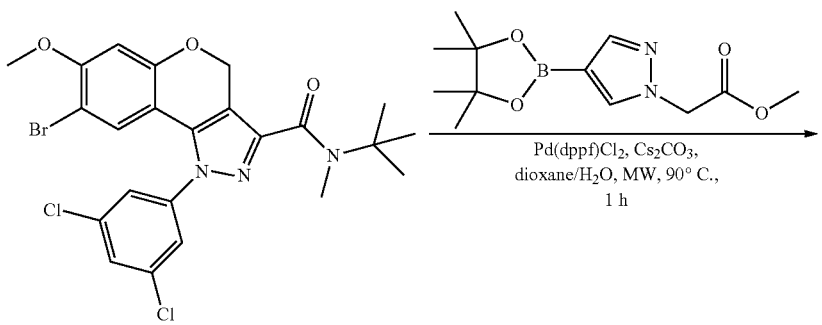
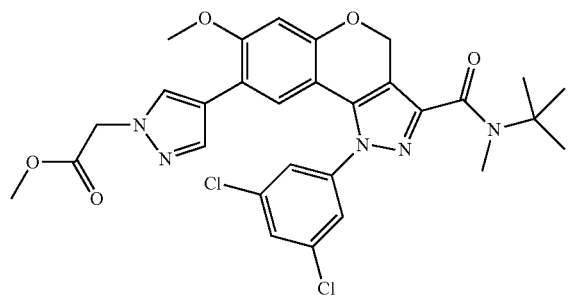
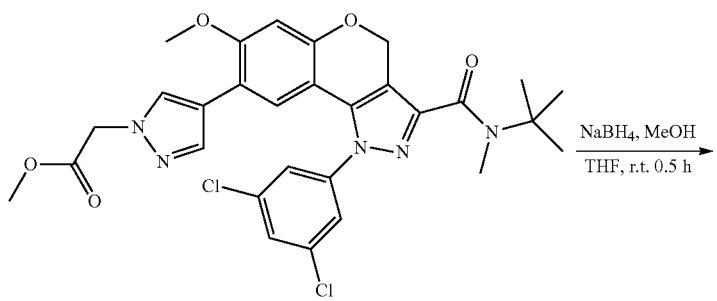
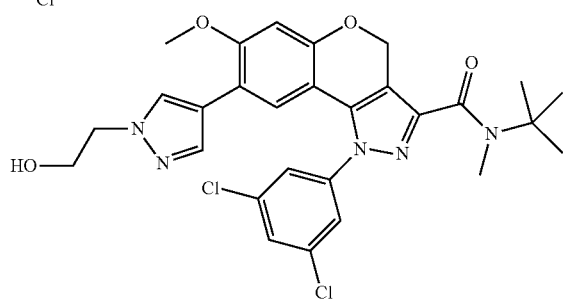

-continued
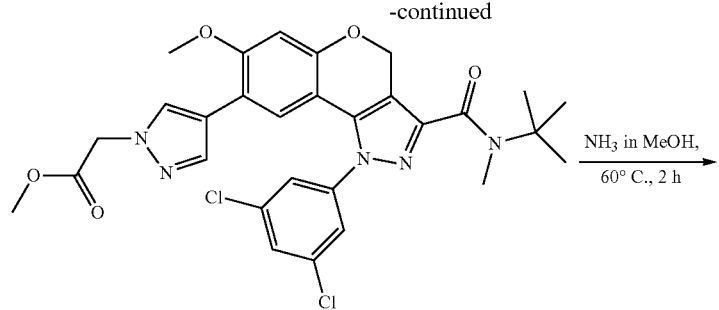
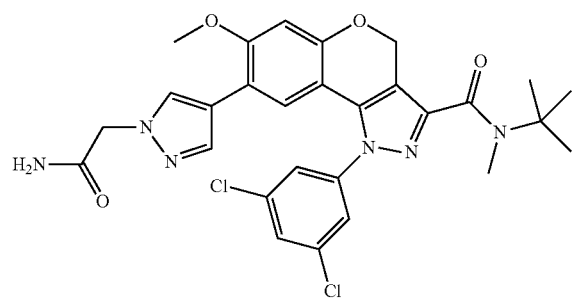
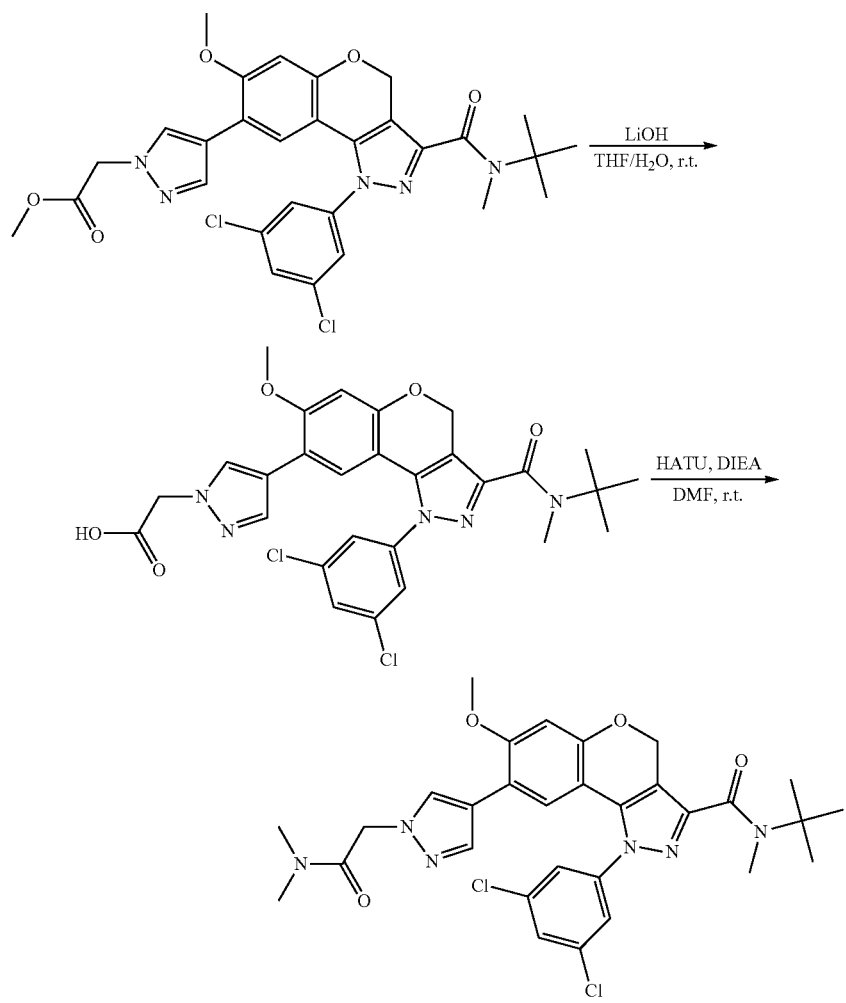

149

Step 1: Ethyl 8-bromo-1-(3,5-dichlorophenyl)-7-methoxy-1,4-dihydrochromeno[4,3-c]pyrazole-3-carboxylate

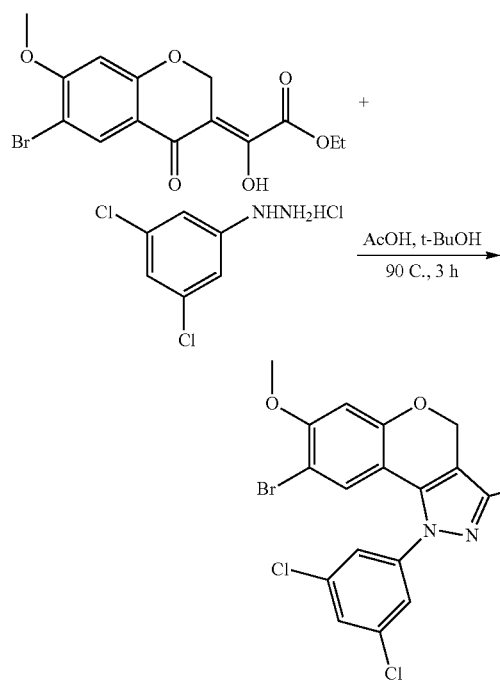

To a solution of (Z)-ethyl 2-(6-bromo-7-methoxy-4-oxochroman-3-ylidene)-2-hydroxyacetate (500 mg, 1.4 mmol) in a mixture of t-BuOH (30 mL) and acetic acid (420 mg, 7 mmol) was added (3,5-dichlorophenyl)hydrazine hydrochloride (290 mg, 1.4 mmol) at RT under nitrogen. The reaction mixture was stirred at 90° C. for 4 h. The reaction mixture was concentrated under high vacuum. The residue was dissolved with ethyl acetate (40 mL), washed with water (10 mL), brine (20 mL), dried over sodium sulphate and concentrated under vacuum. The crude product was purified by column chromatography using pet ether/ethyl acetate as an eluent to afford the titled compound (600 mg, 75%) as a pale yellow solid.

Step 2: 8-bromo-1-(3,5-dichlorophenyl)-7-methoxy-1,4-dihydrochromeno[4,3-c]pyrazole-3-carboxylic acid

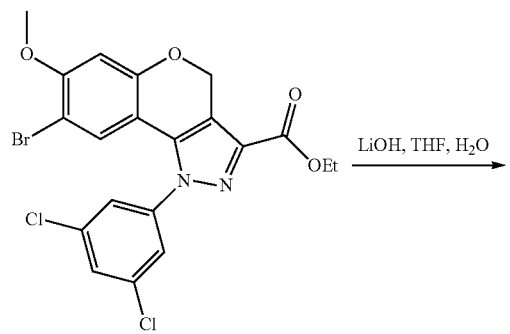

150

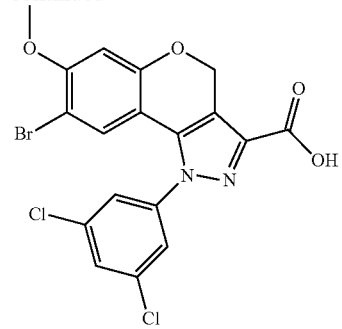

To a solution of ethyl 8-bromo-1-(3,5-dichlorophenyl)-7-methoxy-1,4-dihydrochromeno[4,3-c]pyrazole-3-carboxylate (100 mg, 0.2 mmol) in a mixture of THF (10 mL) and $H_2O$ (10 mL) was added $LiOH \cdot H_2O$ (17 mg, 0.4 mmol) at RT. The reaction mixture was stirred at RT for 4 h. The reaction mixture was evaporated and acidified with a solution of 1.5N HCl. The solid was filtered and dried to afford the desired compound (80 mg, 89%) as an off-white solid.

Step 3: 8-bromo-N-tert-butyl-1-(3,5-dichlorophenyl)-7-methoxy-N-methyl-1,4-dihydro chromeno[4,3-c]pyrazole-3-carboxamide

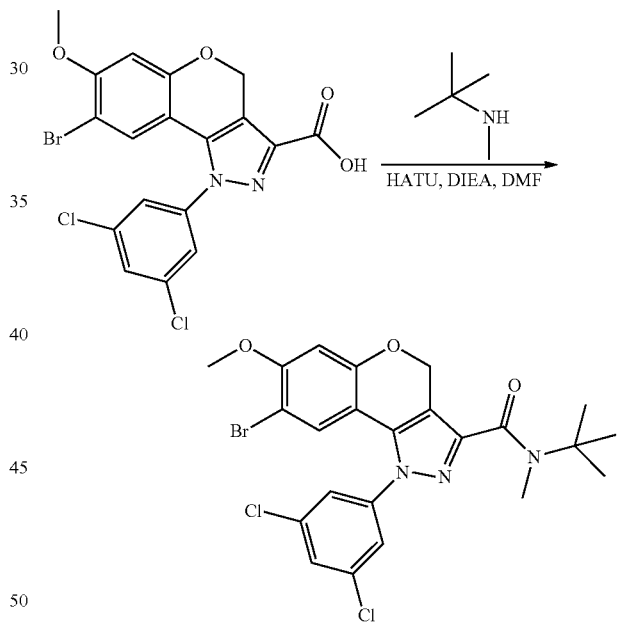

To a solution of 8-bromo-1-(3,5-dichlorophenyl)-7-methoxy-1,4-dihydrochromeno[4,3-c]pyrazole-3-carboxylic acid (500 mg, 0.11 mmol) in DMF (10 mL) was added N-tert-butyl methyl amine (140 mg, 1.6 mmol), HATU (420 mg, 1.1 mmol) and diisopropylethylamine (280 mg, 2.13 mmol) at RT under nitrogen. The reaction mixture was stirred at RT for 3 h. The reaction mixture was quenched to sodium bicarbonate (10 mL, 10%), and extracted with EtOAc (2×50 mL). The combined organic layer was washed with $NaHCO_3$ solution (30 mL, 10% solution), brine (30 mL) and dried over anhydrous sodium sulphate. The solvent was removed under vacuum; the crude product was purified by column chromatography by using pet ether and ethyl acetate (9:1) as an eluent to afford the desired compound (40 mg, 67%) as a white solid.

Step 4: Methyl 2-(4-(3-(tert-butyl(methyl)carbamoyl)-1-(3,5-dichlorophenyl)-7-methoxy-1,4-dihydrochromeno[4,3-c]pyrazol-8-yl)-1H-pyrazol-1-yl)acetate

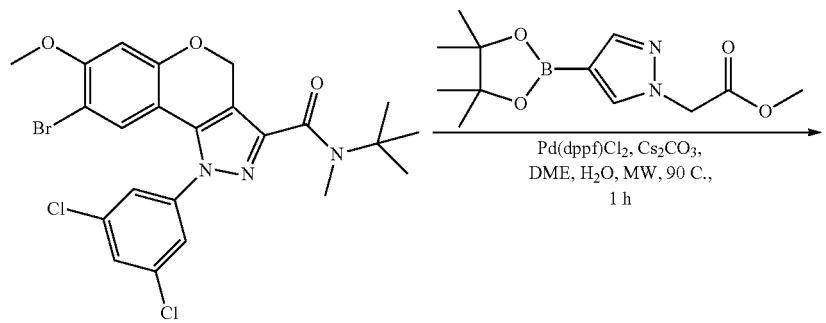

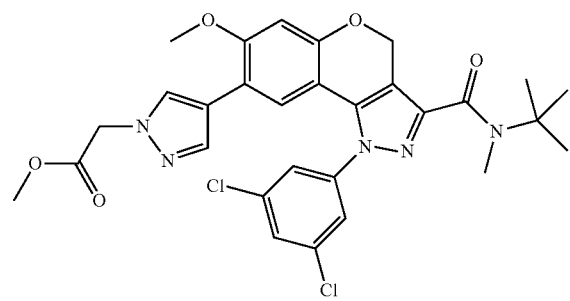

To a solution of 8-bromo-N-tert-butyl-1-(3,5-dichlorophenyl)-7-methoxy-N-methyl-1,4-dihydrochromeno[4,3-c]pyrazole-3-carboxamide (200 mg, 0.37 mmol) in dioxane (6 mL) was added methyl 2-(4-(4,4,5,5-tetramethyl-1,3,2-dioxaborolan-2-yl)-1H-pyrazol-1-yl)acetate (150 mg, 0.56 mmol), PdCl$_2$(dppf) (54 mg, 0.07 mmol) and KF (43 mg, 0.74 mmol) at RT under nitrogen. The reaction mixture was degassed with nitrogen for 20 min and water (4 mL) was added at RT. The reaction mixture was stirred at 90° C. for 1 h under MW conditions. The reaction mixture was filtered through celite and washed with DCM (50 mL). The filtrate was concentrated under vacuum; the crude product was washed with water (10 ml), brine (10 mL) and dried over sodium sulphate. The organic solvent was removed under vacuum; the crude product was purified by column chromatograph using pet ether: ethyl acetate as an eluent to afford the desired compound (90 mg, 51%) as an off-white solid.

Step 5: N-tert-butyl-1-(3,5-dichlorophenyl)-8-(1-(2-hydroxyethyl)-1H-pyrazol-4-yl)-7-methoxy-N-methyl-1,4-dihydrochromeno[4,3-c]pyrazole-3-carboxamide (Compound 1)

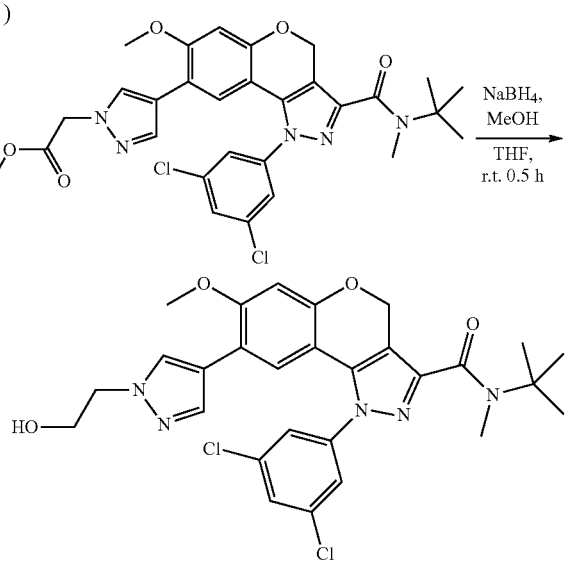

To a stirred solution of methyl 2-(4-(3-(tert-butyl(methyl) carbamoyl)-1-(3,5-dichlorophenyl)-7-methoxy-1,4-dihydrochromeno[4,3-c]pyrazol-8-yl)-1H-pyrazol-1-yl)acetate (200 mg, 0.33 mmol) in MeOH (20 ml) and THF (20 ml) was added NaBH₄ (50 mg, 1.32 mmol) at RT for 0.5 h. Water (10 ml) was added to the mixture and extracted by DCM (100 ml), then dried over sodium sulphate. The organic solvent was removed under vacuum; the crude product was purified by column chromatograph using pet ether: ethyl acetate as an eluent to afford the desired compound (100 mg, 65%) as a white solid. ¹H NMR (400 MHz, CDCl₃): 7.72 (s, 1H), 7.56 (s, 3H), 7.49 (s, 1H), 7.09 (s, 1H), 6.70 (s, 1H), 5.47 (s, 2H), 4.26 (t, 2H), 4.03 (d, 2H), 3.92 (s, 3H), 3.28 (s, 3H), 1.54 (s, 9H).

Example 2: 8-(1-(2-amino-2-oxoethyl)-1H-pyrazol-4-yl)-N-tert-butyl-1-(3,5-dichlorophenyl)-7-methoxy-N-methyl-1,4-dihydrochromeno[4,3-c]pyrazole-3-carboxamide (Compound 2)

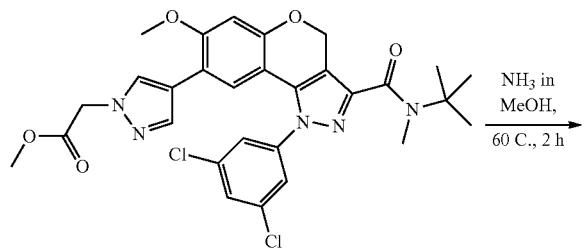

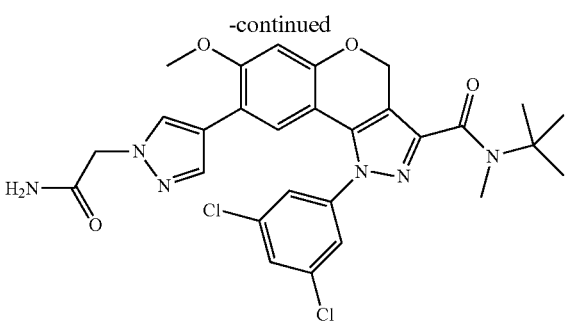

A mixture of methyl 2-(4-(3-(tert-butyl(methyl)carbamoyl)-1-(3,5-dichlorophenyl)-7-methoxy-1,4-dihydrochromeno[4,3-c]pyrazol-8-yl)-1H-pyrazol-1-yl)acetate (100 mg, 0.066 mmol) and NH₃ in MeOH (12 ml) was heated to 60° C. for 2 h. The solvents were removed to provide crude product, which was purified by preparative HPLC to provide the desired product (60 mg, 66%) as a white solid. ¹H NMR (400 MHz, CDCl₃): 7.79 (s, 1H), 7.57 (s, 4H), 7.11 (s, 1H), 6.71 (s, 1H), 5.48 (s, 2H), 4.83 (s, 2H), 3.93 (s, 3H), 3.28 (s, 3H), 1.54 (s, 9H).

The following compounds were prepared using procedures analogous to those disclosed in Scheme 1.

| Compound | Boronic acid Starting material | Amine Starting material | LC/MS | NMR |
|---|---|---|---|---|
| N-tert-butyl-1-(3,5-dichlorophenyl)-8-(2-fluoropyridin-3-yl)-7-methoxy-N-methyl-1,4-dihydrochromeno[4,3-c]pyrazole-3-carboxamide Compound 3 | 2-fluoropyridin-3-yl boronic acid | tert-butyl methylamine | m/z: 555 [M + H]⁺ | ¹H NMR (400 MHz, CDCl₃) δ: 8.14 (d, J = 4.4 Hz, 1H), 7.71-7.66 (m, 1H), 7.49 (d, J = 1.6 Hz, 2H), 7.44-7.43 (m, 1H), 7.20-7.17 (m, 1H), 6.86 (s, 1H), 6.72 (s, 1H), 5.48 (s, 2H), 3.81 (s, 3H), 3.26 (s, 3H), 1.52 (s, 9H). |
| N-tert-butyl-1-(3,5-dichlorophenyl)-7-methoxy-N-methyl-8-(1-methyl-1H-pyrazol-3-yl)-1,4-dihydrochromeno[4,3-c]pyrazole-3-carboxamide Compound 4 | 1-methyl-1H-pyrazole-3-boronic acid pinacol ester | tert-butyl methylamine | m/z: 540 [M + H]⁺ | ¹H NMR (400 MHz, CDCl₃) δ 7.62 (s, 1H), 7.53 (d, J = 2.4 Hz, 2H), 7.48 (t, J = 2.0 Hz, 1H), 7.30 (d, J = 2.0 Hz, 1H), 6.66 (s, 1H), 6.55 (d, J = 2.4 Hz, 1H), 5.45 (s, 2H), 3.88 (s, 3H), 3.86 (s, 3H), 3.26 (s, 3H), 1.52 (s, 9H). |

-continued

| Compound | Boronic acid Starting material | Amine Starting material | LC/MS | NMR |
|---|---|---|---|---|
| 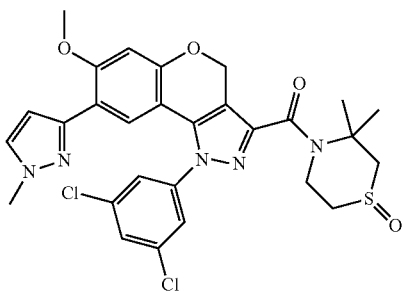 [SMILES: COc1cc2c(cc1-c1ccn(C)n1)-c1c(c(C(=O)N3CCS(=O)CC3(C)C)nn1-c1cc(Cl)cc(Cl)c1)CO2]<br>4-{[1-(3,5-dichlorophenyl)-7-methoxy-8-(1-methyl-1H-pyrazol-3-yl)-1H,4H-chromeno[4,3-c]pyrazol-3-yl]carbonyl}-3,3-dimethyl-1$l^{4}$,4-thiomorpholin-1-one<br>Compound 5 | 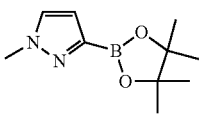 | 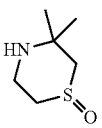 | m/z: 600 [M + H]$^+$ | $^1$H NMR (400 MHz, CDCl$_3$) δ 7.62 (s, 1H), 7.52 (m, 3H), 7.31 (d, J = 2.0 Hz, 1H), 6.66 (s, 1H), 6.56 (d, J = 2.4 Hz, 1H), 5.46 (s, 2H), 4.53-4.32 (m, 2H), 3.88 (s, 3H), 3.87 (s, 3H), 3.61-3.54 (m, 1H), 3.14-3.04 (m, 2H), 2.85-2.80 (m, 1H), 1.57 (s, 6H). |
| 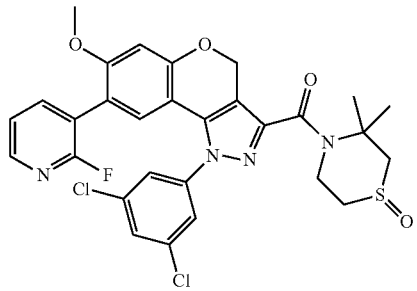 [SMILES: COc1cc2c(cc1-c1cccnc1F)-c1c(c(C(=O)N3CCS(=O)CC3(C)C)nn1-c1cc(Cl)cc(Cl)c1)CO2]<br>(1-(3,5-dichlorophenyl)-8-(2-fluoropyridin-3-yl)-7-methoxy-1H,4H-chromeno[4,3-c]pyrazol-3-yl)(S-oxo-3,3-dimethylthiomorpholino)methanone<br>Compound 6 | 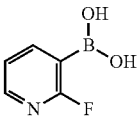 | 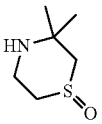 | m/z: 615 [M + H]$^+$ | $^1$H NMR (400 MHz, CDCl$_3$) δ 8.16-8.15 (m, 1H), 7.71-7.66 (m, 1H), 7.48 (s, 3H), 7.21-7.18 (m, 1H), 6.86 (s, 1H), 6.73 (s, 1H), 5.48 (s, 2H), 4.52-4.32 (m, 2H), 3.82 (s, 3H), 3.60-3.52 (m, 1H), 3.15-3.05 (m, 2H), 2.86-2.80 (m, 1H), 1.58 (s, 6H). |
| 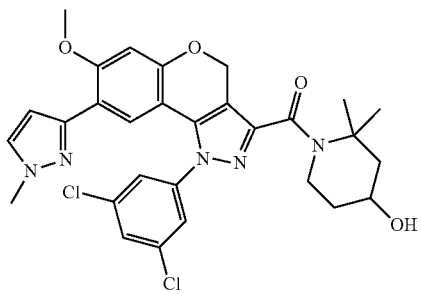 [SMILES: COc1cc2c(cc1-c1ccn(C)n1)-c1c(c(C(=O)N3CCC(O)CC3(C)C)nn1-c1cc(Cl)cc(Cl)c1)CO2]<br>(1-(3,5-dichlorophenyl)-7-methoxy-8-(1-methyl-1H-pyrazol-3-yl)-1,4-dihydrochromeno[4,3-c]pyrazol-3-yl)(4-hydroxy-2,2-dimethylpiperidin-1-yl)methanone<br>Compound 7 | 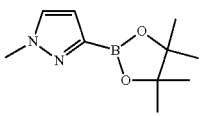 | 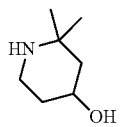 | m/z: 582 [M + H]$^+$ | $^1$H NMR (400 MHz, CDCl$_3$) δ 7.62 (s, 1H), 7.53-7.52 (M, 2H), 7.48-7.47 (M, 1H), 7.31 (d, J = 2.0 Hz, 1H), 6.66 (s, 1H), 6.55 (d, J = 1.6 Hz, 1H), 5.48-5.40 (m, 2H), 4.23-4.17 (m, 1H), 4.10-4.04 (m, 1H), 3.88 (s, sH), 3.87 (s, sH), 3.66-3.59 (m, 1H), 2.19-2.13 (s, 1H), 1.91-1.72 (m, 2H), 1.46 (d, J = 4.4 Hz, 1H), 1.56 (s, 6H). |

-continued

| Compound | Boronic acid Starting material | Amine Starting material | LC/MS | NMR |
|---|---|---|---|---|
| N-tert-butyl-8-(5-cyanopyridin-3-yl)-1-(3,5-dichlorophenyl)-7-methoxy-N-methyl-1,4-dihydrochromeno[4,3-c]pyrazole-3-carboxamide<br>Compound 8 | | | m/z: 562 [M + H]$^+$ | $^1$H NMR (400 MHz, CDCl$_3$) δ 8.76-8.74 (m, 2H), 7.98-7.97 (m, 1H), 7.52 (m, 3H), 6.90 (s, 1H), 6.74 (s, 1H), 5.51 (s, 2H), 3.85 (s, 3H), 3.27 (s, 3H), 1.52 (s, 9H). |
| (1-(3,5-dichlorophenyl)-7-methoxy-8-(1-methyl-1H-pyrazol-3-yl)-1,4-dihydrochromeno[4,3-c]pyrazol-3-yl)(3,3-dimethylmorpholino)methanone<br>Compound 9 | | | m/z: 568 [M + H]$^+$ | $^1$H NMR (400 MHz, CDCl$_3$) δ 7.59 (s, 1H), 7.51-7.48 (m, 3H), 7.31 (d, J = 2.0 Hz, 1H), 6.66 (s, 1H), 6.55 (d, J = 2.0 Hz, 1H), 5.45 (s, 2H), 4.07-4.04 (m, 2H), 3.88-3.94 (m, 8H), 3.49 (s, 2H), 1.53 (s, 6H). |
| (1-(3,5-dichlorophenyl)-7-methoxy-8-(pyridin-2-yl)-1,4-dihydrochromeno[4,3-c]pyrazol-3-yl)(4-hydroxy-2,2-dimethylpiperidin-1-yl)methanone<br>Compound 10 | | | m/z: 579 [M + H]$^+$ | $^1$H NMR (400 MHz, CDCl$_3$) δ 8.56 (d, J = 4.4 Hz, 1H), 7.72 (d, J = 8.0 Hz, 1H), 7.66-7.62 (m, 1H), 7.57 (s, 1H), 7.52 (d, J = 2.0 Hz, 2H), 7.44 (t, J = 2.0 Hz, 1H), 7.15-7.12 (m, 1H), 6.69 (s, 1H), 5.51-5.43 (m, 2H), 4.24-4.17 (m, 1H), 4.13-4.07 (m, 2H), 3.86 (s, 3H), 3.67-3.60 (m, 1H), 2.19-2.12 (m, 1H), 1.92-1.72 (m, 2H), 1.53 (s, 6H). |

| Compound | Boronic acid Starting material | Amine Starting material | LC/MS | NMR |
|---|---|---|---|---|
| (1-(3,5-dichlorophenyl)-7-methoxy-8-(pyridin-2-yl)-1,4-dihydrochromeno[4,3-c]pyrazol-3-yl)(3,3-dimethylmorpholino)methanone<br>Compound 11 | pyridin-2-yl boronic acid | 3,3-dimethylmorpholine | m/z: 565 [M + H]⁺ | ¹H NMR (400 MHz, MeOD) δ 8.72 (s, 1H), 8.43 (t, J = 7.6 Hz, 1H), 7.85 (d, J = 8.0 Hz, 2H), 7.71 (s, 3H), 7.27 (s, 1H), 6.97 (s, 1H), 5.53 (s, 2H), 4.02 (t, J = 5.2 Hz, 2H), 3.97 (s, 3H), 3.85 (t, J = 4.8 Hz, 2H), 3.53 (s, 2H), 1.53 (s, 6H). |
| 5-(1-(3,5-dichlorophenyl)-3-(3,3-dimethylmorpholine-4-carbonyl)-7-methoxy-1,4-dihydrochromeno[4,3-c]pyrazol-8-yl)nicotinonitrile<br>Compound 12 | 5-cyanopyridin-3-yl boronic acid | 3,3-dimethylmorpholine | m/z: 590 [M + H]⁺ | ¹H NMR (400 MHz, CDCl₃) δ 8.76-8.73 (m, 2H), 7.97 (t, J = 2.0 Hz, 1H), 7.54-7.51 (m, 3H), 6.88 (s, 1H), 6.74 (s, 1H), 5.51 (s, 2H), 4.08-4.06 (m, 2H), 3.86 (m, 5H), 3.50 (s, 2H), 1.53 (s, 6H). |
| 4-{[1-(3,5-dichlorophenyl)-7-methoxy-8-(1-methyl-1H-pyrazol-3-yl)-1H,4H-chromeno[4,3-c]pyrazol-3-yl]carbonyl}-3,3-dimethyl-1l{6},4-thiomorpholine-1,1-dione<br>Compound 13 | 1-methyl-1H-pyrazol-3-yl boronic acid pinacol ester | 3,3-dimethylthiomorpholine 1-oxide | m/z: 616 [M + H]⁺ | ¹H NMR (400 MHz, CDCl₃) δ 7.61 (s, 1H), 7.52-7.50 (m, 3H), 7.31 (d, J = 2.0 Hz, 1H), 6.66 (s, 1H), 6.56 (d, J = 2.0 Hz, 1H), 5.46 (s, 2H), 4.45 (t, J = 5.2 Hz, 2H), 3.88 (s, 3H), 3.87 (s, 3H), 3.42 (t, J = 5.6 Hz, 2H), 3.21 (s, 2H), 1.80 (s, 6H). |

-continued

| Compound | Boronic acid Starting material | Amine Starting material | LC/MS | NMR |
|---|---|---|---|---|
| 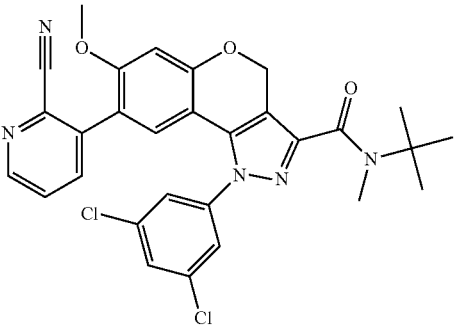 [SMILES: COc1cc2c(cc1-c1cccnc1C#N)-c1c(c(C(=O)N(C)C(C)(C)C)nn1-c1cc(Cl)cc(Cl)c1)CO2]<br>N-tert-butyl-8-(2-cyanopyridin-3-yl)-1-(3,5-dichlorophenyl)-7-methoxy-N-methyl-1,4-dihydrochromeno[4,3-c]pyrazole-3-carboxamide<br>Compound 14 | 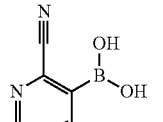 |  | m/z: 562 [M + H]⁺ | ¹H NMR (400 MHz, CDCl₃) δ 8.63-8.62 (m, 1H), 7.66-7.64 (m, 1H), 7.52-7.49 (m, 3H), 7.42-7.41 (m, 1H), 6.82 (s, 1H), 6.75 (s, 1H), 5.52 (s, 2H), 3.85 (s, 3H), 3.25 (s, 3H), 1.52 (s, 9H). |
| 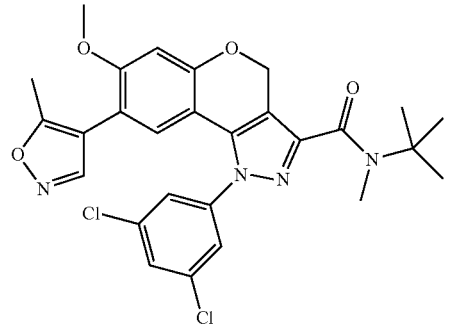 [SMILES: COc1cc2c(cc1-c1cnoc1C)-c1c(c(C(=O)N(C)C(C)(C)C)nn1-c1cc(Cl)cc(Cl)c1)CO2]<br>N-tert-butyl-1-(3,5-dichlorophenyl)-7-methoxy-N-methyl-8-(5-methylisoxazol-4-yl)-1,4-dihydrochromeno[4,3-c]pyrazole-3-carboxamide<br>Compound 15 | 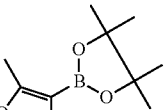 |  | m/z: 541 [M + H]⁺ | ¹H NMR (400 MHz, CDCl₃) δ 8.21 (s, 1H), 7.50 (t, J = 2.0 Hz, 1H), 7.46 (d, J = 1.6 Hz, 2H), 6.69 (d, J = 9.2 Hz, 2H), 5.46 (s, 2H), 3.83 (s, 3H), 3.25 (s, 3H), 2.24 (s, 3H), 1.52 (s, 9H). |
| 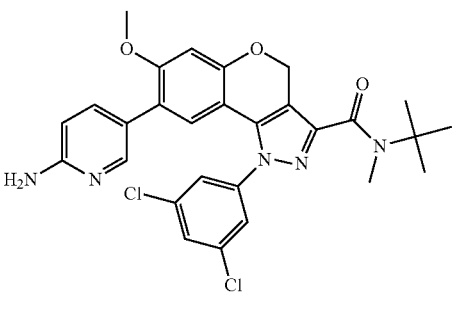 [SMILES: COc1cc2c(cc1-c1ccc(N)nc1)-c1c(c(C(=O)N(C)C(C)(C)C)nn1-c1cc(Cl)cc(Cl)c1)CO2]<br>8-(6-aminopyridin-3-yl)-N-tert-butyl-1-(3,5-dichlorophenyl)-7-methoxy-N-methyl-1,4-dihydrochromeno[4,3-c]pyrazole-3-carboxamide<br>Compound 16 | 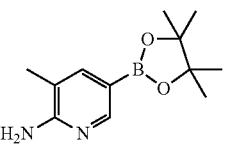 |  | m/z: 552 [M + H]⁺ | ¹H NMR (400 MHz, CDCl₃) δ 8.02 (d, J = 2.0 Hz, 1H), 7.52 (d, J = 2.4 Hz, 2H), 7.48-7.45 (m, 2H), 6.85 (s, 1H), 6.69 (s, 1H), 6.50-6.48 (m, 1H), 5.44 (s, 2H), 3.81 (s, 3H), 3.26 (s, 3H), 1.52 (s, 9H). |

-continued

| Compound | Boronic acid Starting material | Amine Starting material | LC/MS | NMR |
|---|---|---|---|---|
| 8-(6-amino-5-methylpyridin-3-yl)-N-tert-butyl-1-(3,5-dichlorophenyl)-7-methoxy-N-methyl-1,4-dihydrochromeno[4,3-c]pyrazole-3-carboxamide<br>Compound 17 | | | m/z: 566 [M + H]⁺ | ¹H NMR (400 MHz, CDCl₃) δ 7.94 ((1, J = 1.6 Hz, 1H), 7.52 (d, J = 1.6 Hz, 2H), 7.47 (m, 1H), 7.27 (s, 1H), 6.83 (s, 1H), 6.69 (s, 1H), 5.44 (s, 2H), 3.81 (s, 3H), 3.26 (s, 3H), 2.15 (s, 3H), 1.52 (s, 9H). |
| N-tert-butyl-8-(3-cyanophenyl)-1-(3,5-dichlorophenyl)-7-methoxy-N-methyl-1,4-dihydrochromeno[4,3-c]pyrazole-3-carboxamide<br>Compound 18 | | | m/z: 561 [M + H]⁺ | ¹H NMR (400 MHz, CDCl₃) δ 7.66 (t, J = 1.6 Hz, 1H), 7.60-7.51 (m, 4H), 7.50 (t, J = 2.0 Hz, 1H), 7.45 (d, J = 7.7 Hz, 1H), 6.88 (s, 1H), 6.71 (s, 1H), 5.48 (s, 2H), 3.83 (s, 3H), 3.27 (s, 3H), 1.52 (s, 9H). |
| N-tert-butyl-8-(3-cyano-2-fluorophenyl)-1-(3,5-dichlorophenyl)-7-methoxy-N-methyl-1,4-dihydrochromeno[4,3-c]pyrazole-3-carboxamide<br>Compound 19 | | | m/z: 579 [M + H]⁺ | ¹H NMR (400 MHz, CDCl₃) δ 7.58-7.54 (m, 1H), 7.50-7.46 (m, 3H), 7.44 (t, J = 2.0, 1H), 7.24 (s, 1H), 6.82 (s, 1H), 6.72 (s, 1H), 5.49 (s, 2H), 3.81 (s, 3H), 3.26 (s, 3H), 1.52 (s, 9H). |
| 8-(5-aminopyridin-3-yl)-N-tert-butyl-1-(3,5-dichlorophenyl)-7-methoxy-N-methyl-1,4-dihydrochromeno[4,3-c]pyrazole-3-carboxamide<br>Compound 20 | | | m/z: 552 [M + H]⁺ | ¹H NMR (400 MHz, CDCl₃) δ 8.01-7.99 (m, 2H), 7.53 (d, J = 2.0 Hz, 2H), 7.48 (d, J = 2.0 Hz, 1H), 6.98-6.97 (m, 1H), 6.90 (s, 1H), 6.70 (s, 1H), 5.46 (s, 2H), 3.82 (s, 3H), 3.26 (s, 3H), 1.52 (s, 9H). |

-continued

| Compound | Boronic acid Starting material | Amine Starting material | LC/MS | NMR |
|---|---|---|---|---|
| 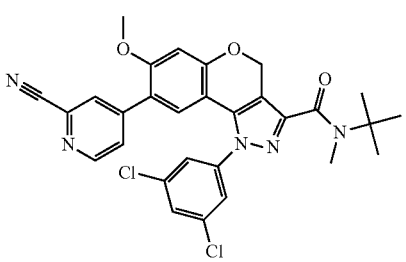 [SMILES: COc1cc2c(cc1-c1ccnc(C#N)c1)-c1c(c(C(=O)N(C)C(C)(C)C)nn1-c1cc(Cl)cc(Cl)c1)CO2]<br>N-tert-butyl-8-(2-cyanopyridin-4-yl)-1-(3,5-dichlorophenyl)-7-methoxy-N-methyl-1,4-dihydrochromeno[4,3-c]pyrazole-3-carboxamide<br>Compound 21 | 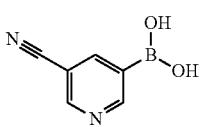 [SMILES: N#Cc1cncc(B(O)O)c1] | 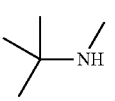 | m/z: 562 [M + H]$^+$ | $^1$H NMR (400 MHz, CDCl$_3$) δ 8.84 (s, 1H), 8.74 (d, J = 5.2 Hz, 1H), 7.50 (d, J = 2.0 Hz, 2H), 7.45 (t, J = 2.0 Hz, 1H), 7.24-7.22 (m, 1H), 6.83 (s, 1H), 6.75 (s, 1H), 5.53 (s, 2H), 3.87 (s, 3H), 3.26 (s, 3H), 1.52 (s, 9H). |
| 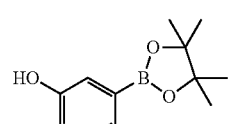<br>N-tert-butyl-1-(3,5-dichlorophenyl)-8-(3-hydroxyphenyl)-7-methoxy-N-methyl-1,4-dihydrochromeno[4,3-c]pyrazole-3-carboxamide<br>Compound 22 |  | 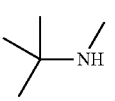 | m/z: 552 [M + H]$^+$ | $^1$H NMR (400 MHz, CDCl$_3$) δ 7.51 (d, J = 2.0 Hz, 2H), 7.45 (t, J = 2.0 Hz, 1H), 7.21 (t, J = 7.6 Hz, 1H), 6.94-6.83 (m, 3H), 6.78-6.75 (m, 1H), 6.68 (s, 1H), 5.43 (s, 2H), 3.80 (s, 3H), 3.25 (s, 3H), 1.52 (s, 9H). |
| 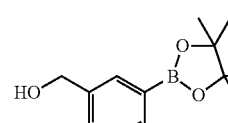<br>N-tert-butyl-1-(3,5-dichlorophenyl)-8-(5-(hydroxymethyl)pyridin-3-yl)-7-methoxy-N-methyl-1,4-dihydrochromeno[4,3-c]pyrazole-3-carboxamide<br>Compound 23 | 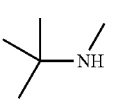 | 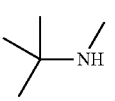 | m/z: 567 [M + H]$^+$ | $^1$H NMR (400 MHz, CDCl$_3$) δ 8.48 (dd, J = 8.8, 2.0 Hz, 2H), 7.66-7.65 (m, 1H), 7.47 (d, J = 1.6 Hz, 3H), 6.87 (s, 1H), 6.71 (s, 1H), 5.46 (s, 2H), 4.74 (s, 2H), 3.82 (s, 3H), 3.26 (s, 3H), 1.52 (s, 9H). |
| 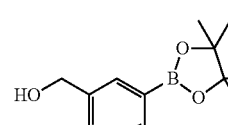<br>(1-(3,5-dichlorophenyl)-8-(5-(hydroxymethyl)pyridin-3-yl)-7-methoxy-1,4-dihydrochromeno[4,3-c]pyrazol-3-yl)(3,3-dimethylmorpholino)methanone<br>Compound 24 | 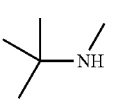 | 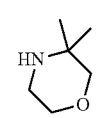 | m/z: 595 [M + H]$^+$ | $^1$H NMR (400 MHz, CDCl$_3$) δ 8.60-8.47 (m, 2H), 7.65 (s, 1H), 7.50 (dd, J = 5.2, 1.7 Hz, 3H), 6.87 (s, 1H), 6.73 (s, 1H), 5.48 (s, 2H), 4.75 (s, 2H), 4.06 (d, J = 5.3 Hz, 2H), 3.94-3.72 (m, 5H), 3.50 (s, 2H), 1.53 (s, 6H). |

| Compound | Boronic acid Starting material | Amine Starting material | LC/MS | NMR |
|---|---|---|---|---|
| N-tert-butyl-8-(2-cyano-3-fluorophenyl)-1-(3,5-dichlorophenyl)-7-methoxy-N-methyl-1,4-dihydrochromeno[4,3-c]pyrazole-3-carboxamide<br>Compound 25 | | | m/z: 579 [M + H]⁺ | ¹H NMR (400 MHz, CDCl₃) δ 7.64-7.48 (m, 3H), 7.42 (t, J = 1.8 Hz, 1H), 7.20-7.04 (m, 2H), 6.82 (s, 1H), 6.73 (s, 1H), 5.50 (s, 2H), 3.86 (s, 3H), 3.25 (s, 3H), 1.52 (s, 9H). |
| N-tert-butyl-8-(4-cyanopyridin-2-yl)-1-(3,5-dichlorophenyl)-7-methoxy-N-methyl-1,4-dihydrochromeno[4,3-c]pyrazole-3-carboxamide<br>Compound 26 | | | m/z: 562 [M + H]⁺ | ¹H NMR (400 MHz, CDCl₃) δ 8.70 (s, 1H), 8.12 (s, 1H), 7.75 (s, 1H), 7.51 (d, J = 14.6 Hz, 3H), 7.33 (d, J = 4.8 Hz, 1H), 6.70 (s, 1H), 5.52 (s, 2H), 3.92 (s, 3H), 3.27 (s, 3H), 1.52 (s, 9H). |
| N-tert-butyl-1-(3-chloro-5-fluorophenyl)-7-methoxy-N-methyl-8-(1-methyl-1H-pyrazol-3-yl)-1,4-dihydrochromeno[4,3-c]pyrazole-3-carboxamide<br>Compound 27 | | | m/z: 524 [M + H]⁺ | ¹H NMR (400 MHz, CDCl₃) δ 7.61 (s, 1H), 7.45-7.44 (m, 1H), 7.30 (d, J = 2.4 Hz, 1H), 7.25-7.22 (m, 1H), 7.21-7.20 (m, 1H), 6.66 (s, 1H), 6.55 (d, J = 2.4 Hz, 1H), 5.46 (s, 2H), 3.88 (s, 3H), 3.85 (s, 3H), 3.26 (s, 3H), 1.51 (s, 9H). |
| 5-(1-(3-chloro-5-fluorophenyl)-3-(3,3-dimethylmorpholine-4-carbonyl)-7-methoxy-1,4-dihydrochromeno[4,3-c]pyrazol-8-yl)nicotinonitrile<br>Compound 28 | | | m/z: 574 [M + H]⁺ | ¹H NMR (400 MHz, CDCl₃) δ 8.73 (dd, J = 22.3, 2.0 Hz, 2H), 7.97 (t, J = 2.0 Hz, 1H), 7.40 (s, 1H), 7.29-7.28 (m, 1H), 7.24-7.23 (m, 1H), 6.87 (s, 1H), 6.74 (s, 1H), 5.51 (s, 2H), 4.07 (t, J = 5.6 Hz, 2H), 3.87-3.85 (m, 5H), 3.50 (s, 2H), 1.53 (s, 6H). |

| Compound | Boronic acid Starting material | Amine Starting material | LC/MS | NMR |
|---|---|---|---|---|
| 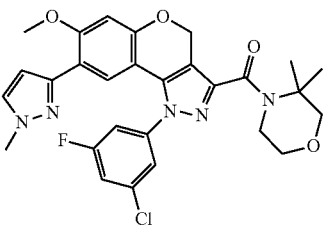 [SMILES: COc1cc2c(cc1-c1ccn(C)n1)-c1c(c(C(=O)N3CCOCC3(C)C)nn1-c1cc(F)cc(Cl)c1)CO2]<br>(1-(3-chloro-5-fluorophenyl)-7-methoxy-8-(1-methyl-1H-pyrazol-3-yl)-1,4-dihydrochromeno[4,3-c]pyrazol-3-yl)(3,3-dimethylmorpholino)methanone<br>Compound 29 | 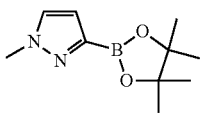 |  | m/z: 552 [M + H]⁺ | ¹H NMR (400 MHz, CDCl₃) δ 7.59 (s, 1H), 7.43-7.42 (m, 1H), 7.30 (d, J = 2.1 Hz, 1H), 7.23 (dd, J = 8.5, 1.7 Hz, 2H), 6.66 (s, 1H), 6.55 (d, J = 2.4 Hz, 1H), 5.46 (s, 2H), 4.06 (t, J = 4.8 Hz, 2H), 3.88 (s, 3H), 3.86-3.84 (m, 5H), 3.49 (s, 2H), 1.53 (s, 6H). |
| 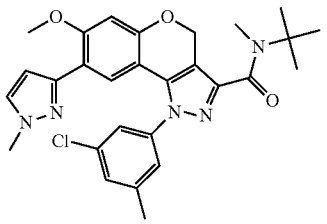 [SMILES: COc1cc2c(cc1-c1ccn(C)n1)-c1c(c(C(=O)N(C)C(C)(C)C)nn1-c1cc(C)cc(Cl)c1)CO2]<br>N-tert-butyl-1-(3-chloro-5-methylphenyl)-7-methoxy-N-methyl-8-(1-methyl-1H-pyrazol-3-yl)-1,4-dihydrochromeno[4,3-c]pyrazole-3-carboxamide<br>Compound 30 | 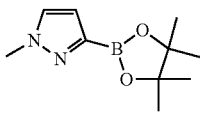 |  | m/z: 520 [M + H]⁺ | ¹H NMR (400 MHz, CDCl₃) δ 7.58 (s, 1H), 7.42 (s, 1H), 7.29-7.28 (m, 3H), 6.64 (s, 1H), 6.51 (d, J = 2.0 Hz, 1H), 5.47 (s, 2H), 3.87 (s, 3H), 3.85 (s, 3H), 3.27 (s, 3H), 2.42 (s, 3H), 1.52 (s, 9H). |
| 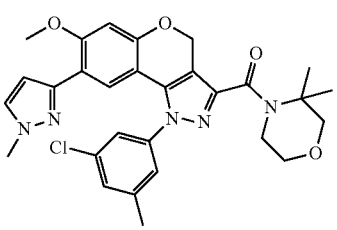 [SMILES: COc1cc2c(cc1-c1ccn(C)n1)-c1c(c(C(=O)N3CCOCC3(C)C)nn1-c1cc(C)cc(Cl)c1)CO2]<br>(1-(3-chloro-5-methylphenyl)-7-methoxy-8-(1-methyl-1H-pyrazol-3-yl)-1,4-dihydrochromeno[4,3-c]pyrazol-3-yl)(3,3-dimethylmorpholino)methanone<br>Compound 31 | 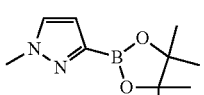 |  | m/z: 548 [M + H]⁺ | ¹H NMR (400 MHz, CDCl₃) δ 7.55 (s, 1H), 7.40 (s, 1H), 7.30-7.27 (m, 3H), 6.65 (s, 1H), 6.51 (d, J = 2.1 Hz, 1H), 5.47 (s, 2H), 4.08 (t, J = 4.8 Hz, 2H), 3.87 (s, 3H), 3.85-3.84 (m, 5H), 3.49 (s, 2H), 2.42 (s, 3H), 1.53 (s, 6H). |
| 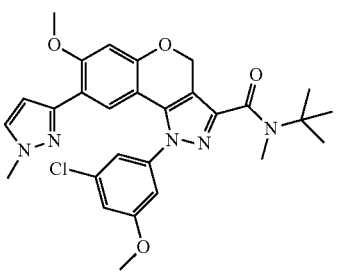 [SMILES: COc1cc(Cl)cc(-n2nc(C(=O)N(C)C(C)(C)C)c3c2-c2cc(-c4ccn(C)n4)c(OC)cc2OC3)c1]<br>N-tert-butyl-1-(3-chloro-5-methoxyphenyl)-7-methoxy-N-methyl-8-(1-methyl-1H-pyrazol-3-yl)-1,4-dihydrochromeno[4,3-c]pyrazole-3-carboxamide<br>Compound 32 | 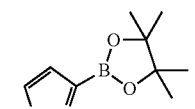 |  | m/z: 536 [M + H]⁺ | ¹H NMR (400 MHz, CDCl₃): 7.68 (s, 1H), 7.31 (d, J = 2.0 Hz, 1H), 7.23 (t, J = 2.0 Hz, 1H), 7.03-7.00 (m, 2H), 6.67 (s, 1H), 6.54 (d, J = 2.0 Hz, 1H), 5.49 (s, 2H), 3.90 (s, 3H), 3.88 (s, 3H), 3.84 (s, 3H), 3.29 (s, 3H), 1.54 (s, 9H). |

-continued

| Compound | Boronic acid Starting material | Amine Starting material | LC/MS | NMR |
|---|---|---|---|---|
| 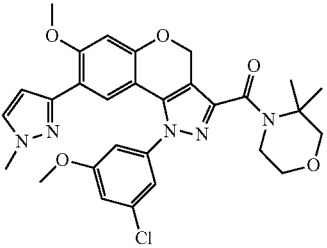<br>(1-(3-chloro-5-methoxyphenyl)-7-methoxy-8-(1-methyl-1H-pyrazol-3-yl)-1,4-dihydrochromeno[4,3-c]pyrazol-3-yl)(3,3-dimethylmorpholino)methanone<br>Compound 33 | 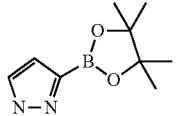 |  | m/z: 564 [M + H]$^+$ | $^1$H NMR (400 MHz, CDCl$_3$) δ 7.64 (s, 1H), 7.30 (d, J = 2.1 Hz, 1H), 7.19-7.18 (m, 1H), 7.04-7.03 (m, 1H), 6.99-6.98 (m, 1H), 6.65 (s, 1H), 6.52 (d, J = 2.2 Hz, 1H), 5.47 (s, 2H), 4.09-4.07 (m, 2H), 3.88 (s, 3H), 3.85 (s, 5H), 3.81 (s, 3H), 3.49 (s, 2H), 1.53 (s, 6H). |
| 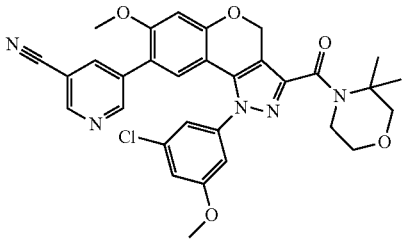 [SMILES: COc1cc(Cl)cc(-n2nc(C(=O)N3CCOCC3(C)C)c3c2-c2cc(-c4cncc(C#N)c4)c(OC)cc2OC3)c1]<br>5-(1-(3-chloro-5-methoxyphenyl)-3-(3,3-dimethylmorpholine-4-carbonyl)-7-methoxy-1,4-dihydrochromeno[4,3-c]pyrazol-8-yl)nicotinonitrile<br>Compound 34 | 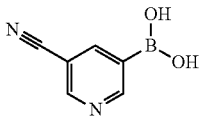 |  | m/z: 586 [M + H]$^+$ | $^1$H NMR (400 MHz, CDCl$_3$) δ 8.74 (t, J = 1.6 Hz, 2H), 7.91 (t, J = 2.0 Hz, 1H), 7.15 (t, J = 2.0 Hz, 1H), 7.07 (t, J = 2.0 Hz, 1H), 7.01 (t, J = 2.0 Hz, 1H), 6.88 (s, 1H), 6.72 (s, 1H), 5.52 (s, 2H), 4.09 (t, J = 2.0 Hz, 2H), 3.88 (s, 3H), 3.87 (s, 1H), 3.84 (s, 4H), 3.49 (s, 2H), 1.53 (s, 6H). |
| 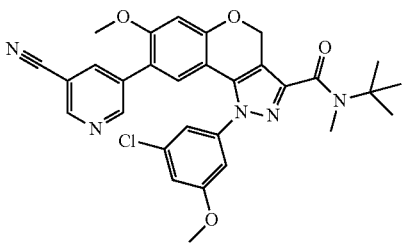 [SMILES: COc1cc(Cl)cc(-n2nc(C(=O)N(C)C(C)(C)C)c3c2-c2cc(-c4cncc(C#N)c4)c(OC)cc2OC3)c1]<br>N-tert-butyl-1-(3-chloro-5-methoxyphenyl)-8-(5-cyanopyridin-3-yl)-7-methoxy-N-methyl-1,4-dihydrochromeno[4,3-c]pyrazole-3-carboxamide<br>Compound 35 | 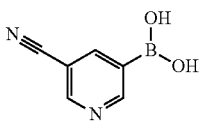 [SMILES: N#Cc1cncc(B(O)O)c1] |  | m/z: 558 [M + H]$^+$ | $^1$H NMR (400 MHz, CDCl$_3$) δ 8.68-8.66 (m, 2H), 7.85-7.84 (m, 1H), 7.10 (t, J = 1.6 Hz, 1H), 7.00-6.95 (m, 2H), 6.83 (s, 1H), 6.65 (s, 1H), 5.45 (s, 2H), 3.81 (s, 3H), 3.77 (s, 3H), 3.21 (s, 3H), 1.45 (s, 9H). |
| 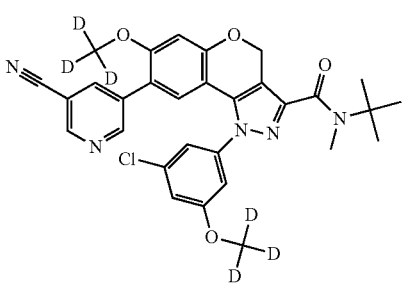 [SMILES: [2H]C([2H])([2H])Oc1cc(Cl)cc(-n2nc(C(=O)N(C)C(C)(C)C)c3c2-c2cc(-c4cncc(C#N)c4)c(OC([2H])([2H])[2H])cc2OC3)c1]<br>N-tert-butyl-1-(3-chloro-5-D$_3$-methoxyphenyl)-8-(5-cyanopyridin-3-yl)-7-D$_3$-methoxy-N-methyl-1H,4H-chromeno[4,3-c]pyrazole-3-carboxamide<br>Compound 36 | 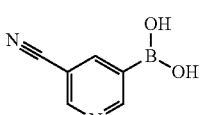 |  | m/z: 564 [M + H]$^+$ | $^1$H NMR (500 MHz, CDCl$_3$): 8.75-8.73 (m, 2H), 7.92 (t, J = 1.6 Hz, 1H), 7.17 (t, J = 1.6 Hz, 1H), 7.05 (t, J = 1.6 Hz, 1H), 7.02 (t, J = 1.6 Hz, 1H), 6.90 (s, 1H), 6.70 (s, 1H), 5.54 (s, 2H), 3.30 (s, 3H), 1.54 (s, 9H). |

-continued

| Compound | Boronic acid Starting material | Amine Starting material | LC/MS | NMR |
|---|---|---|---|---|
| 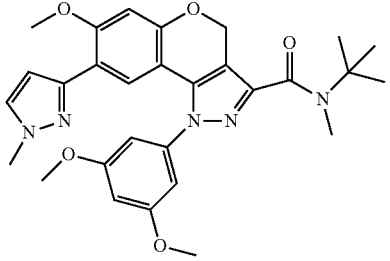 [SMILES: COc1cc(OC)cc(-n2nc(C(=O)N(C)C(C)(C)C)c3c2-c2cc(-c4ccn(C)n4)c(OC)cc2OC3)c1]<br>N-tert-butyl-1-(3,5-dimethoxyphenyl)-7-methoxy-N-methyl-8-(1-methyl-1H-pyrazol-3-yl)-1,4-dihydrochromeno[4,3-c]pyrazole-3-carboxamide<br>Compound 37 | 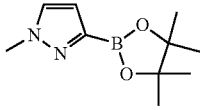 |  | m/z: 532 [M + H]$^+$ | $^1$H NMR (400 MHz, CDCl$_3$) δ ppm 7.69 (s, 1H), 7.29 (d, J = 2 Hz, 1H), 6.73 (s, 2H), 6.64 (s, 1H), 6.57 (s, 1H), 6.48 (d, J = 2.4 Hz, 1H), 5.48 (s, 2H), 3.87 (s, 3H), 3.85 (s, 3H), 3.80 (s, 6H), 3.28 (s, 3H), 1.52 (s, 9H). |
| 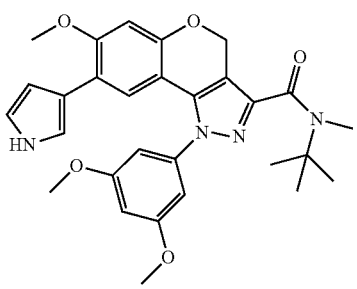 [SMILES: COc1cc(OC)cc(-n2nc(C(=O)N(C)C(C)(C)C)c3c2-c2cc(-c4cc[nH]c4)c(OC)cc2OC3)c1]<br>N-tert-butyl-1-(3,5-dimethoxyphenyl)-7-methoxy-N-methyl-8-(1H-pyrrol-3-yl)-1,4-dihydrochromeno[4,3-c]pyrazole-3-carboxamide<br>Compound 38 | 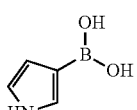 |  | m/z: 517 [M + H]$^+$ | $^1$H NMR (400 MHz, CDCl$_3$): 8.19 (s, 1 H), 7.16-7.11 (m, 2 H), 6.74-6.71 (m, 3 H), 6.63-6.62 (m, 2 H), 6.12-6.10 (m, 1 H), 5.46 (s, 1 H), 3.89 (s, 3 H), 3.79 (s, 6 H), 3.27 (s, 3 H), 1.52 (s, 9 H). |
| 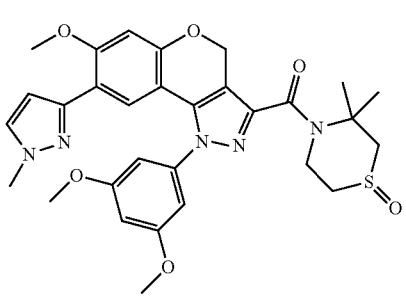 [SMILES: COc1cc(OC)cc(-n2nc(C(=O)N3CCS(=O)CC3(C)C)c3c2-c2cc(-c4ccn(C)n4)c(OC)cc2OC3)c1]<br>(1-(3,5-dimethoxyphenyl)-7-methoxy-8-(1-methyl-1H-pyrazol-3-yl)-1,4-dihydrochromeno[4,3-c]pyrazol-3-yl)-(S-oxo-3,3-dimethylthiomorpholino)methanone<br>Compound 39 | 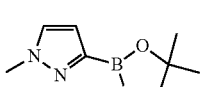 |  | m/z: 592 [M + H]$^+$ | $^1$H NMR (400 MHz, CDCl$_3$) δ 7.72 (s, 1H), 7.30 (d, J = 2.0 Hz, 1H), 6.71 (d, J = 2.4 Hz, 2H), 6.65 (s, 1H), 6.59 (t, J = 2.4 Hz, 1H), 6.50 (d, J = 2.4 Hz, 1H), 5.48 (s, 2H), 4.59-4.53 (m, 1H), 4.40-4.32 (m, 1H), 3.87 (s, 3H), 3.85 (s, 3H), 3.81 (s, 6H), 3.65-3.58 (m, 1H), 3.10 (q, J = 13.6 Hz, 2H), 2.84-2.79 (m, 1H), 1.58 (s, 6H). |

-continued

| Compound | Boronic acid Starting material | Amine Starting material | LC/MS | NMR |
|---|---|---|---|---|
| (1-(3,5-dimethoxyphenyl)-8-(2-fluoropyridin-3-yl)-7-methoxy-1,4-dihydrochromeno[4,3-c]pyrazol-3-yl)(S-oxo-3,3-dimethylthiomorpholino)methanone<br>Compound 40 | 2-fluoropyridin-3-yl boronic acid | S-oxo-3,3-dimethylthiomorpholine | m/z: 607 [M + H]⁺ | ¹H NMR (400 MHz, CDCl₃) δ 8.13 (d, J = 5.2 Hz, 1H), 7.64-77.60 (m, 1H), 7.17-7.13 (m, 1H), 6.86 (s, 1H), 6.69 (s, 1H), 6.63 (d, J = 2.4 Hz, 2H), 6.55 (t, J = 2.0 Hz, 1H), 5.51 (s, 2H), 4.58-4.52 (m, 1H), 4.40-4.33 (m, 1H), 3.80 (s, 9H), 3.63-3.56 (m, 1H), 3.10 (q, J = 13.6 Hz, 2H), 2.84-2.78 (m, 1H), 1.58 (s, 6H). |
| (1-(3,5-dimethoxyphenyl)-7-methoxy-8-(pyridin-2-yl)-1,4-dihydrochromeno[4,3-c]pyrazol-3-yl)(S-oxo-3,3-dimethylthiomorpholino)methanone<br>Compound 41 | pyridin-2-yl boronic acid | S-oxo-3,3-dimethylthiomorpholine | m/z: 589 [M + H]⁺ | ¹H NMR (400 MHz, CDCl₃) δ 8.53 (m, 1H), 7.66 (m, 2H), 7.13 (m, 1H), 6.70-6.68 (m, 2H), 6.62-6.20 (m, 2H), 5.51 (s, 2H), 4.53 (m, 1H), 4.37 (m, 1H), 3.86 (s, 2H), 3.80 (s, 6H), 3.77 (s, 1H), 3.57 (m, 1H), 3.11-3.08 (m, 2H), 2.82 (m, 1H), 1.79 (s, 3H), 1.69 (s, 3H). |
| (1-(3,5-dimethoxyphenyl)-8-(2-fluoropyridin-3-yl)-7-methoxy-1,4-dihydrochromeno[4,3-c]pyrazol-3-yl)(3,3-dimethylmorpholino)methanone<br>Compound 42 | 2-fluoropyridin-3-yl boronic acid | 3,3-dimethylmorpholine | m/z: 575 [M + H]⁺ | ¹H NMR (400 MHz, CDCl₃): 8.13 (d, J = 4.0 Hz, 1H), 7.63-7.59 (m, 1H), 7.16 (t, J = 5.2 Hz, 1H), 6.82 (s, 2H), 6.68 (s, 1H), 6.62 (d, J = 2.0 Hz, 2H), 6.53 (s, 1H), 5.51 (s, 2H), 4.10 (t, J = 1.6 Hz, 2H), 3.84 (t, J = 4.8 Hz, 2H), 3.80 (s, 9H), 3.50 (s, 2H), 1.55 (s, 6H). |

-continued

| Compound | Boronic acid Starting material | Amine Starting material | LC/MS | NMR |
|---|---|---|---|---|
| 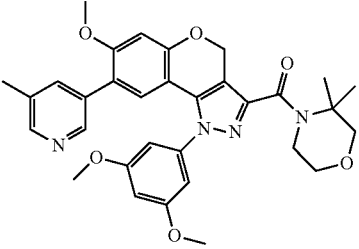<br>(1-(3,5-dimethoxyphenyl)-7-methoxy-8-(5-methylpyridin-3-yl)-1,4-dihydrochromeno[4,3-c]pyrazol-3-yl)(3,3-dimethylmorpholino)methanone<br>Compound 43 | 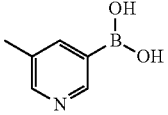 | 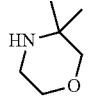 | m/z: 571 [M + H]+ | $^1$H NMR (400 MHz, CDCl$_3$): 8.35-8.30 (m, 2H), 7.37 (s, 1H), 6.86 (s, 1H), 6.7 (s, 1H), 6.68 (d, J = 2.0 Hz, 2H), 6.60 (t, J = 2.0 Hz, 1H), 5.51 (s, 2H), 4.12 (t, J = 4.8 Hz, 2H), 3.86 (t, J = 5.2 Hz, 2H), 3.80 (s, 9H), 3.5 (s, 2H), 2.34 (s, 3H), 1.55 (s, 6H). |
| 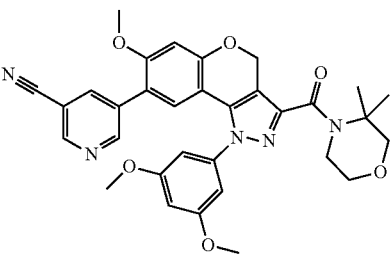 [SMILES: COc1cc(OC)cc(-n2nc(C(=O)N3CCOCC3(C)C)c3c2-c2cc(-c4cncc(C#N)c4)c(OC)cc2OC3)c1]<br>5-(1-(3,5-dimethoxyphenyl)-3-(3,3-dimethylmorpholine-4-carbonyl)-7-methoxy-1,4-dihydrochromeno[4,3-c]pyrazol-8-yl)nicotinonitrile<br>Compound 44 | 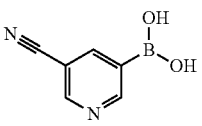 [SMILES: N#Cc1cncc(B(O)O)c1] | 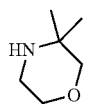 | m/z: 582 [M + H]+ | $^1$H NMR (400 MHz, CDCl$_3$) δ 8.73-8.71 (m, 2H), 7.85-7.84 (m, 1H), 6.87 (s, 1H), 6.69-6.62 (m, 4H), 5.54 (s, 2H), 4.12 4.10 (m, 2H), 3.86-3.84 (m, 8H), ), 3.84 (s, 3H), 3.49 (s, 2H), 1.53 (s, 6H). |
| 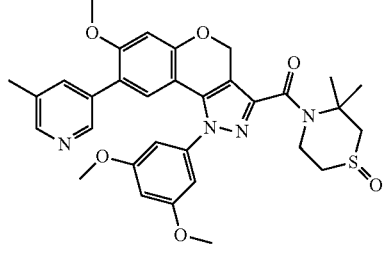 [SMILES: COc1cc(OC)cc(-n2nc(C(=O)N3CCS(=O)CC3(C)C)c3c2-c2cc(-c4cncc(C)c4)c(OC)cc2OC3)c1]<br>(1-(3,5-dimethoxyphenyl)-7-methoxy-8-(5-methylpyridin-3-yl)-1,4-dihydrochromeno[4,3-c]pyrazol-3-yl)(S-oxo-3,3-dimethylthiomorpholino)methanone<br>Compound 45 | 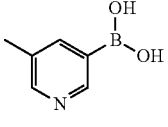 | 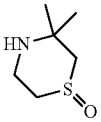 | m/z: 603 [M + H]+ | $^1$H NMR (400 MHz, CDCl$_3$): 8.37-8.32 (m, 2H), 7.39 (s, 1H), 6.90 (s, 1H), 6.70-6.68 (m, 3H), 6.60-6.59 (m, 1H), 5.53 (s, 2H), 4.60-4.54 (m, 1H), 4.41-4.35 (m, 1H), 3.80 (s, 9H), 3.65-3.58 (m, 1H), 3.16-3.06 (m, 2H), 2.85-2.81 (m, 1H), 2.32 (s, 3H) 1.78 (s, 6H). |
| 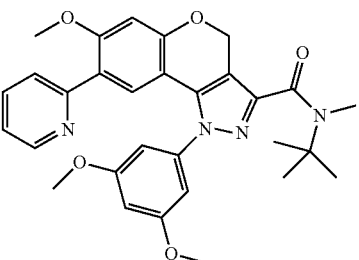<br>N-tert-butyl-1-(3,5-dimethoxyphenyl)-7-methoxy-N-methyl-8-(pyridin-2-yl)-1,4-dihydrochromeno[4,3-c]pyrazole-3-carboxamide<br>Compound 46 | 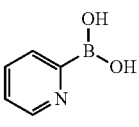 | 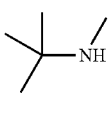 | m/z: 529 [M + H]+ | $^1$H NMR (400 MHz, CDCl$_3$) δ 8.52-8.51 (m, 1H), 7.67-7.58 (m, 3H), 7.12-7.09 (m, 1H), 6.71 (d, J = 2.3 Hz, 2H), 6.67 (s, 1H), 6.53 (t, J = 2.2 Hz, 1H), 5.52 (s, 2H), 3.85 (s, 3H), 3.80 (s, 6H), 3.28 (s, 3H), 1.52 (s, 9H). |

| Compound | Boronic acid Starting material | Amine Starting material | LC/MS | NMR |
|---|---|---|---|---|
| (1-(3,5-dimethoxyphenyl)-7-methoxy-8-(pyridin-2-yl)-1,4-dihydrochromeno[4,3-c]pyrazol-3-yl)(3,3-dimethylmorpholino)methanone<br>Compound 47 | pyridin-2-yl boronic acid | 3,3-dimethylmorpholine | m/z: 557 [M + H]+ | 1H NMR (400 MHz, CDCl3) δ 8.91 (s, 1 H), 7.95-7.90 (m, 1 H), 7.53-7.44 (m, 2 H), 7.21 (s, 1 H), 6.70-6.66 (m, 3 H), 6.55 (s, 1 H), 5.57 (s, 2 H), 3.86-3.79 (m, 12 H), 3.49 (s, 3 H), 1.54 (s, 6 H). |
| N-tert-butyl-1-(3,5-difluorophenyl)-7-methoxy-N-methyl-8-(1-methyl-1H-pyrazol-3-yl)-1,4-dihydrochromeno[4,3-c]pyrazole-3-carboxamide<br>Compound 48 | 1-methyl-1H-pyrazol-3-yl boronic acid pinacol ester | N-methyl-tert-butylamine | m/z: 508 [M + H]+ | 1H NMR (400 MHz, CDCl3) δ = 7.57 (s, 1 H), 7.30 (d, J = 2.0 Hz, 1 H), 7.18-7.15 (m, 2 H), 6.97-6.92 (m, 1 H), 6.66 (s, 1 H), 6.53 (d, J = 2.4 Hz, 1 H), 5.46 (s, 2 H), 3.88 (s, 3 H), 3.85 (s, 3 H), 3.26 (s, 3 H), 1.52 (s, 9 H). |
| 5-[1-(3,5-difluorophenyl)-3-(S-oxo-3,3-dimethylthiomorpholino)-7-methoxy-1H,4H-chromeno[4,3-c]pyrazol-8-yl]pyridine-3-carbonitrile<br>Compound 49 | 5-cyanopyridin-3-yl boronic acid | S-oxo-3,3-dimethylthiomorpholine | m/z: 590 [M + H]+ | 1H NMR (400 MHz, CDCl3) δ 8.76 (d, J = 1.6 Hz, 1H), 8.66 (d, J = 2.2 Hz, 1H), 7.96 (t, J = 2.1 Hz, 1H), 7.15-7.11 (m, 2H), 7.05-7.00 (m, 1H), 6.87 (s, 1H), 6.75 (s, 1H), 5.51 (s, 2H), 4.57-4.44 (m, 1H), 4.44-4.27 (m, 1H), 3.86 (s, 3H), 3.56-3.53 (m, 1H), 3.10 (q, J = 13.7 Hz, 2H), 2.85-2.81 (m, 1H), 1.80 (s, 3H), 1.69 (s, 3H). |
| 5-(1-(3,5-difluorophenyl)-3-(4-hydroxy-2,2-dimethylpiperidine-1-carbonyl)-7-methoxy-1,4-dihydrochromeno[4,3-c]pyrazol-8-yl)nicotinonitrile<br>Compound 50 | 5-cyanopyridin-3-yl boronic acid | 4-hydroxy-2,2-dimethylpiperidine | m/z: 572 [M + H]+ | 1H NMR (400 MHz, CDCl3) δ 8.75 (d, J = 2.0 Hz, 1H), 8.66 (d, J = 2.2 Hz, 1H), 7.96 (t, J = 2.1 Hz, 1H), 7.18-7.12 (m, 2H), 7.01-6.96 (m, 1H), 6.89 (s, 1H), 6.74 (s, 1H), 5.55-5.43 (m, 2H), 4.24-4.17 (m, 1H), 4.09 (m, 1H), 3.85 (s, 3H), 3.84 (m, 1H), 3.69-3.62 (m, 1H), 2.19-2.13 (m, 1H), 1.92-1.88 (m, 1H), 1.79-1.70 (m, 1H), 1.60 (s, 6H). |

-continued

| Compound | Boronic acid Starting material | Amine Starting material | LC/MS | NMR |
|---|---|---|---|---|
| 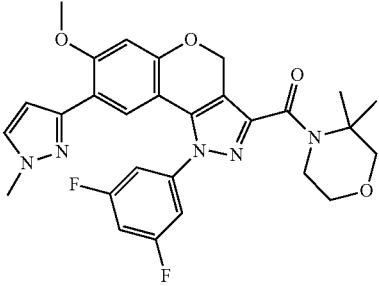 [SMILES: COc1cc2c(cc1-c1ccn(C)n1)-c1c(c(C(=O)N3CCOCC3(C)C)nn1-c1cc(F)cc(F)c1)CO2]<br>(1-(3,5-difluorophenyl)-7-methoxy-8-(1-methyl-1H-pyrazol-3-yl)-1,4-dihydrochromeno[4,3-c]pyrazol-3-yl)(3,3-dimethylmorpholino)methanone<br>Compound 51 | 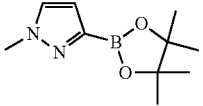 | 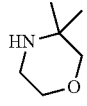 | m/z: 536 [M + H]+ | $^1$H NMR (500 MHz, CDCl$_3$) δ 7.59 (s, 1H), 7.30 (d, J = 2.0 Hz, 1H), 7.19-7.10 (m, 2H), 7.01-6.93 (m, 1H), 6.66 (s, 1H), 6.55 (d, J = 2.0 Hz, 1H), 5.46 (s, 2H), 4.10-4.03 (m, 2H), 3.89-3.78 (m, 8H), 3.49 (s, 2H), 1.53 (s, 6H). |
| 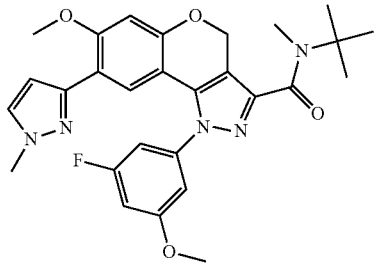 [SMILES: COc1cc(F)cc(-n2nc(C(=O)N(C)C(C)(C)C)c3c2-c2cc(-c4ccn(C)n4)c(OC)cc2OC3)c1]<br>N-tert-butyl-1-(3-fluoro-5-methoxyphenyl)-7-methoxy-N-methyl-8-(1-methyl-1H-pyrazol-3-yl)-1,4-dihydrochromeno[4,3-c]pyrazole-3-carboxamide<br>Compound 52 | 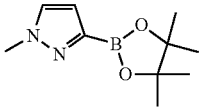 | 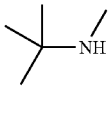 | m/z: 520 [M + H]+ | $^1$H NMR (400 MHz, CDCl$_3$) δ 7.66 (s, 1H), 7.30 (d, J = 2.2 Hz, 1H), 6.96-6.89 (m, 2H), 6.74 (dt, J = 10.3, 2.3 Hz, 1H), 6.65 (s, 1H), 6.52 (d, J = 2.2 Hz, 1H), 5.47 (s, 2H), 3.87 (s, 3H), 3.84 (s, 3H), 3.81 (s, 3H), 3.27 (s, 3H), 1.52 (s, 9H). |
| 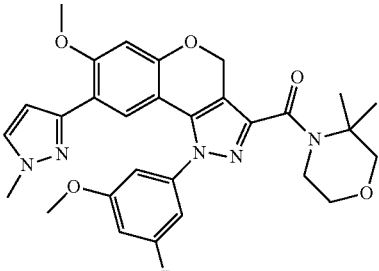<br>(3,3-dimethylmorpholino)(1-(3-fluoro-5-methoxyphenyl)-7-methoxy-8-(1-methyl-1H-pyrazol-3-yl)-1,4-dihydrochromeno[4,3-c]pyrazol-3-yl)methanone<br>Compound 53 | 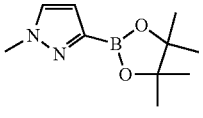 | 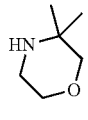 | m/z: 548 [M + H]+ | $^1$H NMR (400 MHz, CDCl$_3$) δ 7.64 (s, 1H), 7.30 (d, J = 2.2 Hz, 1H), 6.95-6.87 (m, 2H), 6.75 (d, J = 10.3 Hz, 1H), 6.65 (s, 1H), 6.52 (d, J = 2.2 Hz, 1H), 5.47 (s, 2H), 4.13-4.04 (m, 2H), 3.91-3.76 (m, 10H), 3.49 (s, 2H), 2.01 (s, 1H), 1.53 (s, 6H). |
| 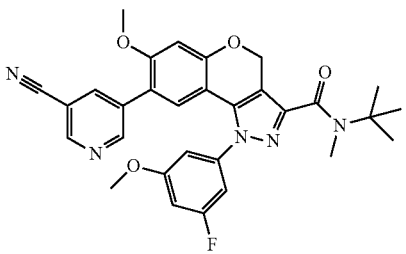 [SMILES: COc1cc(F)cc(-n2nc(C(=O)N(C)C(C)(C)C)c3c2-c2cc(-c4cncc(C#N)c4)c(OC)cc2OC3)c1]<br>N-tert-butyl-8-(5-cyanopyridin-3-yl)-1-(3-fluoro-5-methoxyphenyl)-7-methoxy-N-methyl-1,4-dihydrochromeno[4,3-c]pyrazole-3-carboxamide<br>Compound 54 | 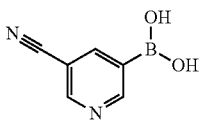 | 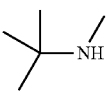 | m/z: 542 [M + H]+ | $^1$H NMR (400 MHz, CDCl$_3$) δ 8.72 (dd, J = 7.4, 2.0 Hz, 2H), 7.90 (t, J = 2.1 Hz, 1H), 6.95-6.86 (m, 3H), 6.79 (d, J = 10.4 Hz, 1H), 6.71 (s, 1H), 5.53 (s, 2H), 3.86 (d, J = 14.5 Hz, 6H), 3.28 (s, 3H), 1.52 (d, J = 4.2 Hz, 9H). |

| Compound | Boronic acid Starting material | Amine Starting material | LC/MS | NMR |
|---|---|---|---|---|
| N-tert-butyl-8-(2-fluoropyridin-3-yl)-7-methoxy-N-methyl-1-(thiophen-3-yl)-1,4-dihydrochromeno[4,3-c]pyrazole-3-carboxamide<br>Compound 55 | 2-fluoropyridin-3-yl boronic acid | N-methyl-tert-butylamine | m/z: 493 [M + H]+ | |
| (1-(thiophen-3-yl)-7-methoxy-8-(1-methyl-1H-pyrazol-3-yl)-1,4-dihydrochromeno[4,3-c]pyrazol-3-yl)(S-oxo-3,3-dimethylthiomorpholino)methanone<br>Compound 56 | 1-methyl-1H-pyrazole-3-boronic acid pinacol ester | 3,3-dimethylthiomorpholine S-oxide | m/z: 538 [M + H]+ | ¹H NMR (400 MHz, CDCl₃): 7.56 (m, 2H), 7.51 (m, 1H), 7.32 (s, 1H), 7.27 (t, 1H), 6.67 (s, 1H), 6.54 (d, 2H), 5.32 (s, 2H), 4.58 (m, 1H), 4.40 (m, 1H), 3.90 (s, 3H), 3.88 (s, 3H), 3.6 (m, 1H), 3.05 (m, 2H), 2.85 (m, 1H), 1.80 (s, 3H), 1.60 (s, 3H). |
| (4-hydroxy-2,2-dimethylpiperidin-1-yl)(7-methoxy-8-(1-methyl-1H-pyrazol-3-yl)-1-(thiophen-3-yl)-1,4-dihydrochromeno[4,3-c]pyrazol-3-yl)methanone<br>Compound 57 | 1-methyl-1H-pyrazole-3-boronic acid pinacol ester | 2,2-dimethyl-4-hydroxypiperidine | m/z: 520 [M + H]+ | ¹H NMR (400 MHz, CDCl₃): 7.534 (s, 1H), 7.457 (m, 1H), 7.363 (s, 1H), 7.326-7.320 (d, 1H), 7.245 (s, 1H), 6.445-6.440 (s, 1H), 5.517-5.438 (m, 2H), 4.240-4.220 (m, 1H), 4.118-4.07 (t, 1H, J = 9.6 Hz), 3.915 (s, 3H), 3.883 (s, 3H), 3.655-3.606 (m, 2H), 2.132 (s, 1H), 2.050 (s, 1H), 1.886-1.756 (m, 2H), 1.704 (s, 3H), 1.525 (s, 3H). |
| N-tert-butyl-7-methoxy-N-methyl-8-(pyridin-2-yl)-1-(thiophen-3-yl)-1,4-dihydrochromeno[4,3-c]pyrazole-3-carboxamide<br>Compound 58 | pyridin-3-yl boronic acid | N-methyl-tert-butylamine | m/z: 475 [M + H]+ | |
| N-tert-butyl-7-methoxy-N-methyl-8-(5-methylpyridin-3-yl)-1-(thiophen-3-yl)-1,4-dihydrochromeno[4,3-c]pyrazole-3-carboxamide<br>Compound 59 | 5-methylpyridin-3-yl boronic acid | N-methyl-tert-butylamine | m/z: 489 [M + H]+ | ¹H NMR (400 MHz, CDCl₃) δ 8.32 (s, 2H), 7.52 (dd, J = 3.2, 1.3 Hz, 1H), 7.48 (d, J = 5.1 Hz, 1H), 7.43 (s, 1H), 7.23 (dd, J = 5.1, 1.3 Hz, 1H), 6.76 (s, 1H), 6.67 (s, 1H), 5.52 (s, 2H), 3.81 (s, 3H), 3.27 (s, 3H), 2.33 (s, 3H), 1.52 (s, 9H). |

-continued

| Compound | Boronic acid Starting material | Amine Starting material | LC/MS | NMR |
|---|---|---|---|---|
| N-tert-butyl-8-(2-chloropyridin-3-yl)-7-methoxy-N-methyl-1-(thiophen-3-yl)-1,4-dihydrochromeno[4,3-c]pyrazole-3-carboxamide<br>Compound 60 | 2-chloropyridin-3-ylboronic acid | N-methyl-tert-butylamine | m/z: 509 [M + H]⁺ | ¹H NMR (400 MHz, CDCl₃) δ 8.33 (dd, J = 4.8, 1.9 Hz, 1H), 7.52-7.45 (m, 2H), 7.39 (dd, J = 5.1, 3.2 Hz, 1H), 7.24-7.16 (m, 2H), 6.71 (s, 1H), 6.68 (s, 1H), 5.52 (s, 2H), 3.76 (s, 3H), 3.26 (s, 3H), 1.51 (s, 9H). |
| (3,3-dimethylmorpholino)(8-(2-fluoropyridin-3-yl)-7-methoxy-1-(thiophen-3-yl)-1,4-dihydrochromeno[4,3-c]pyrazol-3-yl)methanone<br>Compound 61 | 2-fluoropyridin-3-ylboronic acid | 3,3-dimethylmorpholine | m/z: 521 [M + H]⁺ | ¹H NMR (400 MHz, CDCl₃): 8.133 (s, 1H), 7.667-7.632 (m, 1H), 7.488-7.424 (m, 2H), 7.210-7.194 (m, 2H), 6.789-6.787 (d, 1H, J = 0.8 Hz), 6.684 (s, 1H), 5.517 (s, 2H), 4.104-4.078 (t, 2H), 3.859-3.832 (t, 2H), 3.794 (s, 3H), 3.483 (s, 2H), 1.529 (s, 6H). |
| N-tert-butyl-8-(2-fluoro-5-methylpyridin-3-yl)-7-methoxy-N-methyl-1-(thiophen-3-yl)-1,4-dihydrochromeno[4,3-c]pyrazole-3-carboxamide<br>Compound 62 | 2-fluoro-5-methylpyridin-3-ylboronic acid | N-methyl-tert-butylamine | m/z: 507 [M + H]⁺ | ¹H NMR (400 MHz, CDCl₃) δ 7.91 (s, 1H), 7.49 (dd, J = 3.2, 1.3 Hz, 1H), 7.43 (dd, J = 5.0, 3.3 Hz, 2H), 7.21 (dd, J = 5.1, 1.3 Hz, 1H), 6.76 (d, J = 0.8 Hz, 1H), 6.67 (s, 1H), 5.51 (s, 2H), 3.79 (s, 3H), 3.27 (s, 3H), 2.31 (s, 3H), 1.51 (s, 9H). |
| N-tert-butyl-8-(2-fluorophenyl)-7-methoxy-N-methyl-1-(thiophen-3-yl)-1,4-dihydrochromeno[4,3-c]pyrazole-3-carboxamide<br>Compound 63 | 2-fluorophenylboronic acid | N-methyl-tert-butylamine | m/z: 492 [M + H]⁺ | ¹H NMR (400 MHz, CDCl₃) δ 7.49 (dd, J = 3.2, 1.3 Hz, 1H), 7.40 (dd, J = 5.1, 3.2 Hz, 1H), 7.32-7.27 (m, 1H), 7.21 (dd, J = 5.1, 1.3 Hz, 1H), 7.19-7.01 (m, 3H), 6.79 (s, 1H), 6.68 (s, 1H), 5.50 (s, 2H), 3.78 (s, 3H), 3.26 (s, 3H), 1.51 (s, 9H). |

| Compound | Boronic acid Starting material | Amine Starting material | LC/MS | NMR |
|---|---|---|---|---|
| N-tert-butyl-1-(3-chloro-5-(trifluoromethyl)phenyl)-7-methoxy-N-methyl-8-(1-methyl-1H-pyrazol-3-yl)-1,4-dihydrochromeno[4,3-c]pyrazole-3-carboxamide Compound 64 | | | m/z: 574 [M + H]+ | 1H NMR (400 MHz, CDCl3) δ 7.82 (s, 1H), 7.78 (s, 1H), 7.71 (s, 1H), 7.56 (s, 1H), 7.29 (d, J = 2.2 Hz, 1H), 6.67 (s, 1H), 6.56 (d, J = 2.2 Hz, 1H), 5.45 (s, 2H), 3.88 (s, 3H), 3.82 (s, 3H), 3.26 (s, 3H), 1.53 (s, 9H). |
| methyl 2-amino-5-(3-(tert-butyl(methyl)carbamoyl)-1-(3,5-difluorophenyl)-7-methoxy-1,4-dihydrochromeno[4,3-c]pyrazol-8-yl)nicotinate Compound 65 | | | m/z: 578 [M + H]+ | 1H NMR (400 MHz, CDCl3) δ 8.23 (d, J = 2.4 Hz, 1H), 8.02 (d, J = 2.4 Hz, 1H), 7.15 (dt, J = 17.7, 8.8 Hz, 2H), 6.97-6.88 (m, 1H), 6.80 (s, 1H), 6.70 (s, 1H), 5.46 (s, 2H), 3.91 (s, 3H), 3.82 (s, 3H), 3.25 (d, J = 9.5 Hz, 3H), 1.52 (d, J = 3.6 Hz, 9H). |
| N-tert-butyl-1-(3,5-dichlorophenyl)-7-methoxy-N-methyl-8-(5-sulfamoylpyridin-3-yl)-1,4-dihydrochromeno[4,3-c]pyrazole-3-carboxamide Compound 66 | | | m/z: 616 [M + H]+ | 1H NMR (400 MHz, CDCl3) δ 8.99 (d, J = 2.2 Hz, 1H), 8.73 (d, J = 2.0 Hz, 1H), 8.14 (s, 1H), 7.51 (s, 3H), 6.87 (s, 1H), 6.74 (s, 1H), 5.50 (s, 2H), 3.84 (s, 3H), 3.27 (s, 3H), 1.52 (s, 9H). |
| 8-(1-(2-amino-2-oxoethyl)-1H-pyrazol-4-yl)-N-tert-butyl-1-(3,5-dichlorophenyl)-7-methoxy-N-methyl-1,4-dihydrochromeno[4,3-c]pyrazole-3-carboxamide Compound 67 | | | m/z: 583 [M + H]+ | 1H NMR (400 MHz, CDCl3): 7.79 (s, 1H), 7.58-7.57 (m, 4H), 7.11 (s, 1H), 6.71 (s, 1H), 5.48 (s, 2H), 4.83 (s, 2H), 3.93 (s, 3H), 3.28 (s, 3H), 1.54 (s, 9H). |

-continued

| Compound | Boronic acid Starting material | Amine Starting material | LC/MS | NMR |
|---|---|---|---|---|
| N-tert-butyl-8-(2-carbamoyl-5-fluoropyridin-4-yl)-1-(3,5-dichlorophenyl)-7-methoxy-N-methyl-1,4-dihydrochromeno[4,3-c]pyrazole-3-carboxamide Compound 68 | | | m/z: 598 [M + H]⁺ | ¹H NMR (400 MHz, CDCl₃) δ 8.37 (d, J = 1.2 Hz, 1H), 8.17 (d, J = 6.1 Hz, 1H), 7.70 (d, J = 3.9 Hz, 1H), 7.46 (t, J = 1.9 Hz, 2H), 6.88 (s, 1H), 6.73 (s, 1H), 5.51 (d, J = 11.8 Hz, 2H), 3.82 (s, 3H), 3.26 (s, 3H), 1.52 (s, 9H). |
| 2-(4-(1-(3-chloro-5-fluorophenyl)-3-(3,3-dimethylmorpholine-4-carbonyl)-7-methoxy-1,4-dihydrochromeno[4,3-c]pyrazol-8-yl)-1H-pyrazol-1-yl)acetamide Compound 69 | | | m/z: 595 [M + H]⁺ | ¹H NMR (400 MHz, CDCl₃) δ 7.77 (s, 1H), 7.50 (s, 1H), 7.43 (d, J = 0.9 Hz, 1H), 7.35-7.28 (m, 1H), 7.25 (d, J = 2.0 Hz, 1H), 7.07 (s, 1H), 6.69 (s, 1H), 5.46 (s, 2H), 4.80 (s, 2H), 4.11-4.00 (m, 2H), 3.91 (s, 3H), 3.89-3.80 (m, 2H), 3.50 (s, 2H), 1.53 (s, 6H). |
| N-tert-butyl-8-(2-carbamoyl-5-fluoropyridin-4-yl)-1-(3,5-difluorophenyl)-7-methoxy-N-methyl-1,4-dihydrochromeno[4,3-c]pyrazole-3-carboxamide Compound 70 | | | m/z: 566 [M + H]⁺ | ¹H NMR (400 MHz, CDCl₃) δ 8.37 (d, J = 1.4 Hz, 1H), 8.17 (d, J = 6.2 Hz, 1H), 7.12 (d, J = 4.8 Hz, 2H), 6.91 (s, 2H), 6.73 (s, 1H), 5.51 (s, 2H), 3.82 (s, 3H), 3.26 (s, 3H), 1.52 (s, 9H). |
| 24-[1-(3,5-difluorophenyl)-3-(S-oxo-3,3-dimethylthiomorpholino)-7-methoxy-1H,4H-chromeno[4,3-c]pyrazol-8-yl]-(1H-pyrazol-1-yl)acetamide Compound 71 | | | m/z: 611 [M + H]⁺ | ¹H NMR (400 MHz, CDCl₃) δ 7.77 (s, 1H), 7.47 (s, 1H), 7.17 (dd, J = 6.8, 2.1 Hz, 2H), 7.11-7.01 (m, 2H), 6.69 (s, 1H), 6.20 (s, 1H), 5.48 (s, 1H), 5.47 (s, 2H), 4.80 (s, 2H), 4.57-4.30 (m, 2H), 3.91 (s, 3H), 3.56-3.50 (m, 1H), 3.10 (q, J = 13.8 Hz, 2H), 2.83-2.79 (m, 1H), 1.60 (s, 6H). |

| Compound | Boronic acid Starting material | Amine Starting material | LC/MS | NMR |
|---|---|---|---|---|
| 4-(1-(3,5-difluorophenyl)-3-(3,3-dimethylmorpholine-4-carbonyl)-7-methoxy-1,4-dihydrochromeno[4,3-c]pyrazol-8-yl)-5-fluoropicolinamide<br>Compound 72 | | | m/z: 594 [M + H]⁺ | ¹H NMR (400 MHz, CDCl₃) δ 8.37 (d, J = 1.6 Hz, 1H), 8.17 (d, J = 6.2 Hz, 1H), 7.69 (d, J = 4.0 Hz, 1H), 7.13-7.03 (m, 2H), 6.95-6.90 (m, 1H), 6.89 (d, J = 1.2 Hz, 1H), 6.74 (s, 1H), 5.60 (d, J = 4.0 Hz, 1H), 5.53 (s, 2H), 4.13-4.02 (m, 2H), 3.87-3.79 (m, 5H), 3.49 (s, 2H), 1.53 (s, 6H). |
| 2-(4-(3-(3,3-dimethylmorpholine-4-carbonyl)-1-(3-fluoro-5-methoxyphenyl)-7-methoxy-1,4-dihydrochromeno[4,3-c]pyrazol-8-yl)-1H-pyrazol-1-yl)acetamide<br>Compound 73 | | | m/z: 591 [M + H]⁺ | ¹H NMR (400 MHz, CDCl₃) δ 7.76 (s, 1H), 7.45 (s, 1H), 7.08 (s, 1H), 6.90 (d, J = 10.1 Hz, 2H), 6.83 (d, J = 10.3 Hz, 1H), 6.67 (s, 1H), 5.48 (s, 3H), 4.79 (s, 2H), 4.14-4.02 (m, 2H), 3.90 (s, 3H), 3.88-3.78 (m, 4H), 3.49 (s, 2H), 1.53 (s, 6H). |
| (3,3-dimethylmorpholino)(1-(3-fluoro-5-methoxyphenyl)-8-(1-(2-hydroxyethyl)-1H-pyrazol-4-yl)-7-methoxy-1,4-dihydrochromeno[4,3-c]pyrazol-3-yl)methanone<br>Compound 74 | | | m/z: 578 [M + H]⁺ | ¹H NMR (400 MHz, CDCl₃) δ 7.70 (s, 1H), 7.37 (s, 1H), 7.06 (s, 1H), 6.95-6.86 (m, 2H), 6.83 (d, J = 10.3 Hz, 1H), 6.65 (s, 1H), 5.47 (s, 2H), 4.27-4.17 (m, 2H), 4.14-4.03 (m, 2H), 4.00 (d, J = 4.4 Hz, 2H), 3.89 (s, 3H), 3.86 (d, J = 5.4 Hz, 2H), 3.83 (s, 3H), 3.49 (s, 2H), 1.53 (s, 6H). |
| N-tert-butyl-1-(3,5-difluorophenyl)-8-(5-fluoro-2-(hydroxymethyl)pyridin-4-yl)-7-methoxy-N-methyl-1,4-dihydrochromeno[4,3-c]pyrazole-3-carboxamide<br>Compound 75 | | | m/z: 553 [M + H]⁺ | ¹H NMR (400 MHz, CDCl₃) δ 8.38 (d, J = 1.6 Hz, 1H), 7.13 (dd, J = 8.6, 3.9 Hz, 3H), 6.91 (d, J = 18.1 Hz, 2H), 6.72 (s, 1H), 5.50 (s, 2H), 4.72 (d, J = 5.1 Hz, 2H), 3.82 (s, 3H), 3.26 (s, 3H), 1.52 (s, 9H). |

-continued

| Compound | Boronic acid Starting material | Amine Starting material | LC/MS | NMR |
|---|---|---|---|---|
| N-tert-butyl-8-(1-(2-hydroxyethyl)-1H-pyrazol-4-yl)-7-methoxy-N-methyl-1-(thiophen-3-yl)-1,4-dihydrochromeno[4,3-c]pyrazole-3-carboxamide<br>Compound 76 | | | m/z: 508 [M + H]⁺ | ¹H NMR (400 MHz, CDCl₃) δ 7.72 (s, 1H), 7.58-7.50 (m, 2H), 7.41 (s, 1H), 7.25 (s, 1H), 6.95 (d, J = 2.0 Hz, 1H), 6.63 (s, 1H), 5.49 (s, 2H), 4.32-4.18 (m, 2H), 4.01 (d, J = 4.2 Hz, 2H), 3.89 (s, 3H), 3.27 (s, 3H), 1.51 (s, 9H). |
| N-tert-butyl-1-(3,5-dichlorophenyl)-8-(1-(2-hydroxyethyl)-1H-pyrazol-4-yl)-7-methoxy-N-methyl-1,4-dihydrochromeno[4,3-c]pyrazole-3-carboxamide<br>Compound 77 | | | m/z: 570 [M + H]⁺ | ¹H NMR (400 MHz, CDCl₃): 7.70 (s, 1H), 7.54 (s, 3H), 7.47 (s, 1H), 7.07 (s, 1H), 6.67 (s, 1H), 5.44 (s, 2H), 4.24 (t, J = 4.8 Hz, 2H), 4.02-4.01 (m, 2H), 3.90 (s, 3H), 3.26 (s, 3H), 1.52 (s, 9H). |
| (1-(3-chloro-5-fluorophenyl)-8-(1-(2-hydroxyethyl)-1H-pyrazol-4-yl)-7-methoxy-1,4-dihydrochromeno[4,3-c]pyrazol-3-yl)(3,3-dimethylmorpholino)methanone<br>Compound 78 | | | m/z: 582 [M + H]⁺ | ¹H NMR (400 MHz, CDCl₃) δ 7.70 (s, 1H), 7.43 (s, 2H), 7.35-7.28 (m, 1H), 7.25 (d, J = 2.0 Hz, 1H), 7.05 (s, 1H), 6.68 (s, 1H), 5.45 (s, 2H), 4.32-4.15 (m, 2H), 4.05 (dd, J = 13.3, 8.0 Hz, 4H), 3.90 (s, 3H), 3.88-3.79 (m, 2H), 3.49 (s, 2H), 1.53 (s, 6H). |
| N-tert-butyl-1-(3-chloro-5-methoxyphenyl)-8-(1-(2-hydroxyethyl)-1H-pyrazol-4-yl)-7-methoxy-N-methyl-1,4-dihydrochromeno[4,3-c]pyrazole-3-carboxamide<br>Compound 79 | | | m/z: 566 [M + H]⁺ | ¹H NMR (400 MHz, CDCl₃) δ 7.69 (s, 1H), 7.42 (s, 1H), 7.19 (s, 1H), 7.08 (d, J = 2.7 Hz, 2H), 7.01 (s, 1H), 6.65 (s, 1H), 5.46 (s, 2H), 4.28-4.18 (m, 2H), 4.01 (d, J = 4.4 Hz, 2H), 3.89 (s, 3H), 3.84 (s, 3H), 3.27 (s, 3H), 1.50 (d, J = 17.8 Hz, 9H). |

-continued

| Compound | Boronic acid Starting material | Amine Starting material | LC/MS | NMR |
|---|---|---|---|---|
| [structure]<br>N-tert-butyl-1-(3,5-dichlorophenyl)-8-(3-fluoro-5-(hydroxymethyl)phenyl)-7-methoxy-N-methyl-1,4-dihydrochromeno[4,3-c]pyrazole-3-carboxamide<br>Compound 80 | [structure] | [structure] | m/z: 584 [M + H]+ | 1H NMR (400 MHz, CDCl3) δ 7.50 (d, J = 1.8 Hz, 2H), 7.42 (t, J = 1.8 Hz, 1H), 7.35-7.29 (m, 1H), 7.19 (dd, J = 6.9, 2.1 Hz, 1H), 7.10-7.02 (m, 1H), 6.84 (s, 1H), 6.71 (s, 1H), 5.45 (s, 2H), 4.67 (s, 2H), 3.80 (s, 3H), 3.25 (s, 3H), 1.53 (s, 9H). |
| [structure]<br>2-(4-(3-(tert-butyl(methyl)carbamoyl)-1-(3,5-dichlorophenyl)-7-methoxy-1,4-dihydrochromeno[4,3-c]pyrazol-8-yl)-1H-pyrazol-1-yl)acetic acid<br>Compound 81 | [structure] | [structure] | m/z: 584 [M + H]+ | 1H NMR (400 MHz, DMSO) δ 7.97-7.96 (m, 1H), 7.86 (d, J = 1.6 Hz, 2H), 7.75 (s, 1H), 7.09 (s, 1H), 6.99 (s, 1H), 6.79 (s, 1H), 5.35 (s, 2H), 4.31 (s, 2H), 3.86 (s, 3H), 3.17 (s, 3H), 1.44 (s, 9H). |
| [structure]<br>3-(3-(tert-butyl(methyl)carbamoyl)-1-(3,5-dichlorophenyl)-7-methoxy-1,4-dihydrochromeno[4,3-c]pyrazol-8-yl)-4-fluorobenzoic acid<br>Compound 82 | [structure] | [structure] | m/z: 598 [M + H]+ | 1H NMR (400 MHz, MeOD) δ 7.98-.795 (m, 1H), 7.86 (dd, J = 7.2, 2.2 Hz, 1H), 7.60 (s, 3H), 7.14 (t, J = 9.1 Hz, 1H), 6.80 (d, J = 13.0 Hz, 2H), 5.38 (s, 2H), 3.81 (s, 3H), 3.23 (s, 3H), 1.54 (s, 9H). |
| [structure]<br>3-(3-(tert-butyl(methyl)carbamoyl)-1-(3,5-dichlorophenyl)-7-methoxy-1,4-dihydrochromeno[4,3-c]pyrazol-8-yl)-5-fluorobenzoic acid<br>Compound 83 | [structure] | [structure] | m/z: 598 [M + H]+ | 1H NMR (400 MHz, MeOD) δ 7.71-7.69 (m, 4H), 7.57-7.54 (m, 1H), 7.29-7.26 (m, 1H), 6.86 (d, J = 8.4 Hz, 2H), 5.39 (s, 2H), 3.85 (s, 3H), 3.22 (s, 3H), 1.51 (s, 9H). |

-continued

| Compound | Boronic acid Starting material | Amine Starting material | LC/MS | ¹H NMR |
|---|---|---|---|---|
| 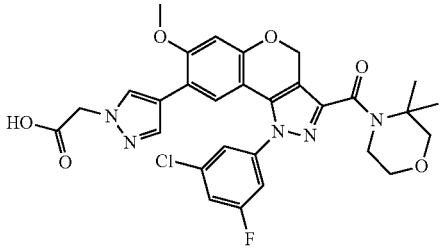<br>2-(4-(1-(3-chloro-5-fluorophenyl)-3-(3,3-dimethylmorpholine-4-carbonyl)-7-methoxy-1,4-dihydrochromeno[4,3-c]pyrazol-8-yl)-1H-pyrazol-1-yl)acetic acid<br>Compound 84 | 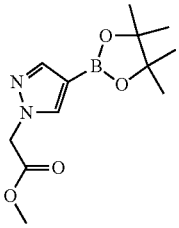 |  | m/z: 596 [M + H]⁺ | ¹H NMR (400 MHz, CDCl₃) δ 7.75 (s, 1H), 7.49-7.42 (m, 2H), 7.29-7.24 (m, 2H), 7.06 (s, 1H), 6.67 (s, 1H), 5.45 (s, 2H), 4.95 (s, 2H), 4.06 (m, 2H), 3.89-3.86 (m, 5H), 3.50 (s, 2H), 1.53 (s, 6H). |
| 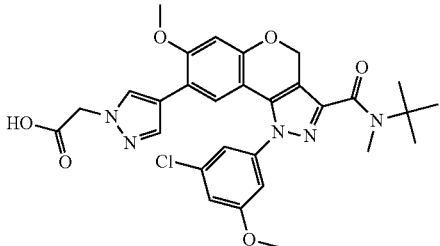<br>2-(4-(3-(tert-butyl(methyl)carbamoyl)-1-(3-chloro-5-methoxyphenyl)-7-methoxy-1,4-dihydrochromeno[4,3-c]pyrazol-8-yl)-1H-pyrazol-1-yl)acetic acid<br>Compound 85 | 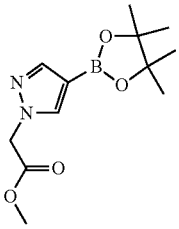 |  | m/z: 580 [M + H]⁺ | ¹H NMR (400 MHz, CDCl₃) δ 7.73 (s, 1H), 7.46 (s, 1H), 7.17 (s, 1H), 7.08-7.04 (m, 2H), 7.00 (s, 1H), 6.63 (s, 1H), 5.45 (s, 2H), 4.95 (s, 2H), 3.86 (s, 3H), 3.77 (s, 3H), 3.25 (s, 3H), 1.2 (s, 9H). |
| 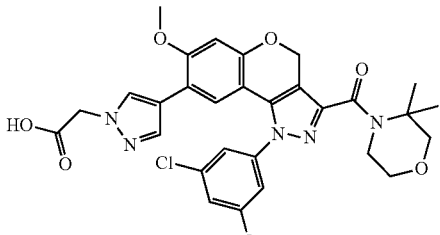<br>2-(4-(1-(3-chloro-5-methoxyphenyl)-3-(3,3-dimethylmorpholine-4-carbonyl)-7-methoxy-1,4-dihydrochromeno[4,3-c]pyrazol-8-yl)-1H-pyrazol-1-yl)acetic acid<br>Compound 86 | 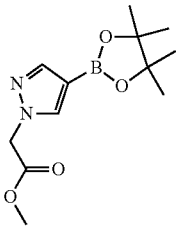 |  | m/z: 608 [M + H]⁺ | ¹H NMR (400 MHz, CDCl₃) δ 7.75 (s, 1H), 7.49 (s, 1H), 7.17-7.00 (m, 4H), 6.66 (s, 1H), 5.47 (s, 2H), 4.95 (s, 2H), 4.07 (m, 2H), 3.95-3.74 (m, 8H), 3.49 (s, 2H), 1.53 (s, 6H) |
| 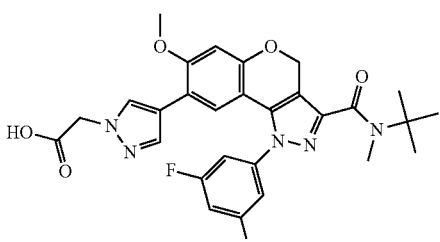<br>2-(4-(3-(tert-butyl(methyl)carbamoyl)-1-(3,5-difluorophenyl)-7-methoxy-1,4-dihydrochromeno[4,3-c]pyrazol-8-yl)-1H-pyrazol-1-yl)acetic acid<br>Compound 87 | 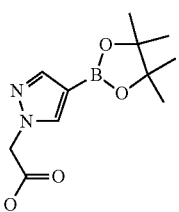 |  | m/z: 552 [M + H]⁺ | ¹H NMR (400 MHz, CDCl₃) δ 7.69 (s, 1H), 7.39 (s, 1H), 7.14-7.13 (m, 2H), 7.03-6.96 (m, 2H), 6.62-6.60 (m, 1H), 5.43 (s, 2H), 4.87 (s, 2H), 3.84 (s, 3H), 3.25 (s, 3H), 1.52 (s, 9H). |

-continued

| Compound | Boronic acid Starting material | Amine Starting material | LC/MS | NMR |
|---|---|---|---|---|
| 2-(4-(1-(3,5-difluorophenyl)-3-(3,3-dimethylmorpholine-4-carbonyl)-7-methoxy-1,4-dihydrochromeno[4,3-c]pyrazol-8-yl)-1H-pyrazol-1-yl)acetic acid<br>Compound 88 | | | m/z: 580 [M + H]⁺ | ¹H NMR (400 MHz, DMSO) δ 7.81 (s, 1H), 7.68-7.53 (m, 3H), 7.12 (s, 1H), 6.94 (s, 1H), 6.80 (s, 1H), 5.37 (s, 2H), 4.62 (s, 2H), 3.96-3.90 (m, 2H), 3.86 (s, 3H), 3.76-3.70 (m, 2H), 3.42 (s, 2H), 1.42 (s, 6H). |
| 2-(4-(3-(3,3-dimethylmorpholine-4-carbonyl)-1-(3-fluoro-5-methoxyphenyl)-7-methoxy-1,4-dihydrochromeno[4,3-c]pyrazol-8-yl)-1H-pyrazol-1-yl)acetic acid<br>Compound 89 | | | m/z: 592 [M + H]⁺ | ¹H NMR (400 MHz, CDCl₃) δ 7.54 (s, 1H), 7.23 (s, 1H), 6.89-6.73 (m, 4H), 6.48 (s, 1H), 5.40 (s, 2H), 4.73 (s, 2H), 4.06 (s, 2H), 3.84 (s, 2H), 3.71 (s, 6H), 3.49 (s, 3H), 1.53 (s, 6H). |
| N-tert-butyl-1-(3,5-dichlorophenyl)-8-(1-(2-(dimethylamino)-2-oxoethyl)-1H-pyrazol-4-yl)-7-methoxy-N-methyl-1,4-dihydrochromeno[4,3-c]pyrazole-3-carboxamide<br>Compound 90 | | | m/z: 611 [M + H]⁺ | 1H NMR (400 MHz, CDCl3) δ 7.84 (s, 1H), 7.53 (s, 3H), 7.44 (s, 1H), 7.09 (s, 1H), 6.66 (s, 1H), 5.44 (s, 2H), 4.97 (s, 2H), 3.88 (s, 3H), 3.26 (s, 3H), 3.08 (s, 3H), 2.99 (s, 3H), 1.52 (s, 9H). |
| N-tert-butyl-1-(3,5-dichlorophenyl)-7-methoxy-N-methyl-8-(1-(2-(methylamino)-2-oxoethyl)-1H-pyrazol-4-yl)-1,4-dihydrochromeno[4,3-c]pyrazole-3-carboxamide<br>Compound 91 | | | m/z: 597 [M + H]⁺ | 1H NMR(400 MHz, CDCl3) δ 7.74 (s, 1H), 7.53 (d, J = 10.4 Hz, 3H), 7.09 (s, 1H), 6.69 (s, 1H), 6.21 (s, 1H), 5.45 (s, 2H), 4.80 (s, 2H), 3.91 (s, 3H), 3.26 (s, 3H), 2.79 (d, J = 4.9 Hz, 3H), 1.52 (s, 9H). |

| Compound | Boronic acid Starting material | Amine Starting material | LC/MS | NMR |
|---|---|---|---|---|
| 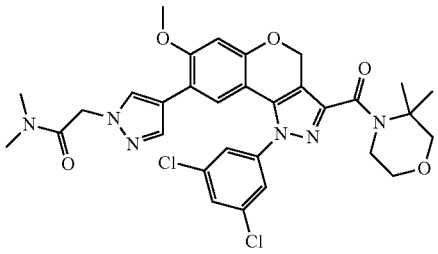 [SMILES: COc1cc2c(cc1-c1cnn(CC(=O)N(C)C)c1)-c1c(c(C(=O)N3CCOCC3(C)C)nn1-c1cc(Cl)cc(Cl)c1)CO2]<br>2-(4-(1-(3,5-dichlorophenyl)-3-(3,3-dimethylmorpholine-4-carbonyl)-7-methoxy-1,4-dihydrochromeno[4,3-c]pyrazol-8-yl)-1H-pyrazol-1-yl)-N,N-dimethylacetamide<br>Compound 92 | 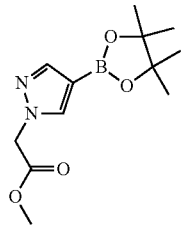 | 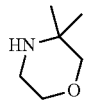 | m/z: 639 [M + H]⁺ | ¹H NMR (400 MHz, CDCl3) δ 7.83 (s, 1H), 7.53 (dd, J = 10.4, 1.8 Hz, 3H), 7.43 (s, 1H), 7.07 (s, 1H), 6.66 (s, 1H), 5.44 (s, 2H), 4.97 (s, 2H), 4.05 (s, 2H), 3.90-3.83 (m, 5H), 3.49 (s, 2H), 3.08 (s, 3H), 2.99 (s, 3H), 1.53 (s, 6H). |
| 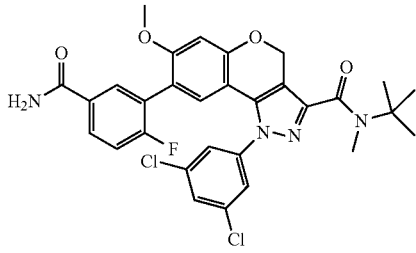 [SMILES: COc1cc2c(cc1-c1cc(C(N)=O)ccc1F)-c1c(c(C(=O)N(C)C(C)(C)C)nn1-c1cc(Cl)cc(Cl)c1)CO2]<br>N-tert-butyl-8-(5-carbamoyl-2-fluorophenyl)-1-(3,5-dichlorophenyl)-7-methoxy-N-methyl-1,4-dihydrochromeno[4,3-c]pyrazole-3-carboxamide<br>Compound 93 | 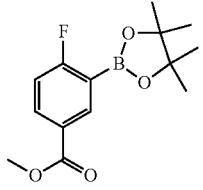 | 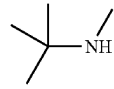 | m/z: 597 [M + H]⁺ | 1H NMR (400 MHz, CDCl3) δ 7.86-7.76 (m, 1H), 7.62 (dd, J = 6.8, 2.3 Hz, 1H), 7.49 (d, J = 1.8 Hz, 2H), 7.42 (t, J = 1.8 Hz, 1H), 7.15 (t, J = 8.9 Hz, 1H), 6.82 (s, 1H), 6.72 (s, 1H), 5.47 (s, 2H), 3.80 (s, 3H), 3.26 (s, 3H), 1.50 (d, J = 17.4 Hz, 9H). |
| 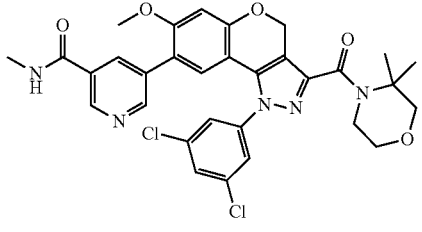 [SMILES: CNC(=O)c1cncc(-c2cc3c(cc2OC)OCc2c(C(=O)N4CCOCC4(C)C)nn(-c4cc(Cl)cc(Cl)c4)c2-3)c1]<br>5-(1-(3,5-dichlorophenyl)-3-(3,3-dimethylmorpholine-4-carbonyl)-7-methoxy-1,4-dihydrochromeno[4,3-c]pyrazol-8-yl)-N-methylnicotinamide<br>Compound 94 | 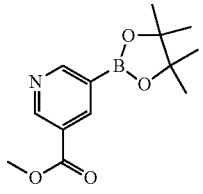 | 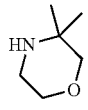 | m/z: 622 [M + H]⁺ | ¹H NMR (400 MHz, CDCl₃) δ 8.86 (d, J = 2.1 Hz, 1H), 8.62 (d, J = 2.1 Hz, 1H), 8.03 (t, J = 2.1 Hz, 1H), 7.53-7.46 (m, 3H), 6.86 (s, 1H), 6.74 (s, 1H), 6.13 (d, J = 4.0 Hz, 1H), 5.48 (s, 2H), 4.11-4.02 (m, 2H), 3.89-3.80 (m, 5H), 3.50 (s, 2H), 3.06 (d, J = 4.8 Hz, 3H), 1.53 (s, 6H). |
| 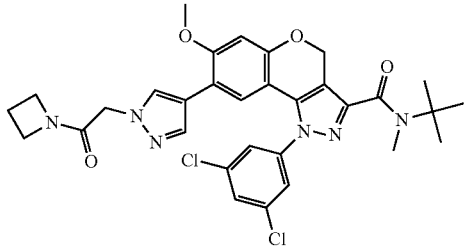 [SMILES: COc1cc2c(cc1-c1cnn(CC(=O)N3CCC3)c1)-c1c(c(C(=O)N(C)C(C)(C)C)nn1-c1cc(Cl)cc(Cl)c1)CO2]<br>8-(1-(2-(azetidin-1-yl)-2-oxoethyl)-1H-pyrazol-4-yl)-N-tert-butyl-1-(3,5-dichlorophenyl)-7-methoxy-N-methyl-1,4-dihydrochromeno[4,3-c]pyrazole-3-carboxamide<br>Compound 95 | 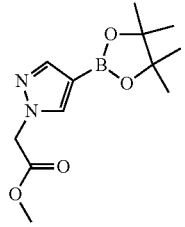 | 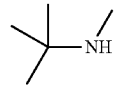 | m/z: 623 [M + H]⁺ | ¹H NMR (400 MHz, CDCl₃) δ 7.83 (s, 1H), 7.53 (s, 3H), 7.43 (s, 1H), 7.08 (s, 1H), 6.67 (s, 1H), 5.44 (s, 2H), 4.75 (s, 2H), 4.08 (t, J = 7.8 Hz, 2H), 3.99 (t, J = 7.7 Hz, 2H), 3.89 (s, 3H), 3.26 (s, 3H), 2.31-2.19 (m, 2H), 1.52 (s, 9H). |

-continued

| Compound | Boronic acid Starting material | Amine Starting material | LC/MS | NMR |
|---|---|---|---|---|
| 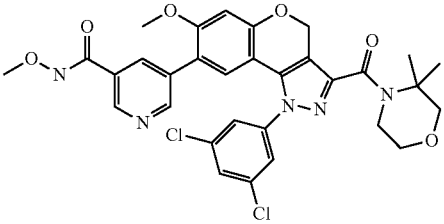 [SMILES: CONC(=O)c1cncc(-c2cc3c(cc2OC)OCc2c(C(=O)N4CCOCC4(C)C)nn(-c4cc(Cl)cc(Cl)c4)c2-3)c1]<br>5-(1-(3,5-dichlorophenyl)-3-(3,3-dimethylmorpholine-4-carbonyl)-7-methoxy-1,4-dihydrochromeno[4,3-c]pyrazol-8-yl)-N-methoxynicotinamide<br>Compound 96 | 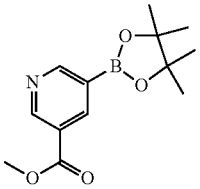 |  | m/z: 638 [M + H]$^+$ | $^1$H NMR (400 MHz, CDCl$_3$) δ 8.82 (s, 1H), 8.66 (s, 1H), 8.02 (t, J = 2.1 Hz, 1H), 7.53-7.46 (m, 3H), 6.85 (s, 1H), 6.73 (s, 1H), 5.48 (s, 2H), 4.09-4.02 (m, 2H), 3.93 (s, 3H), 3.88-3.81 (m, 5H), 3.50 (s, 2H), 1.53 (s, 6H). |
| 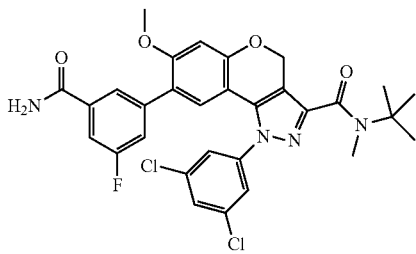 [SMILES: COc1cc2c(cc1-c1cc(F)cc(C(N)=O)c1)-c1c(c(C(=O)N(C)C(C)(C)C)nn1-c1cc(Cl)cc(Cl)c1)CO2]<br>N-tert-butyl-8-(3-carbamoyl-5-fluorophenyl)-1-(3,5-dichlorophenyl)-7-methoxy-N-methyl-1,4-dihydrochromeno[4,3-c]pyrazole-3-carboxamide<br>Compound 97 | 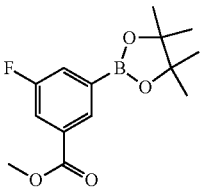 |  | m/z: 597 [M + H]$^+$ | $^1$H NMR (400 MHz, CDCl$_3$) δ 7.52 (d, J = 1.8 Hz, 2H), 7.50-7.42 (m, 3H), 7.26-7.21 (m, 1H), 6.86 (s, 1H), 6.72 (s, 1H), 5.48 (s, 2H), 3.83 (s, 3H), 3.26 (s, 3H), 1.52 (s, 9H). |
| 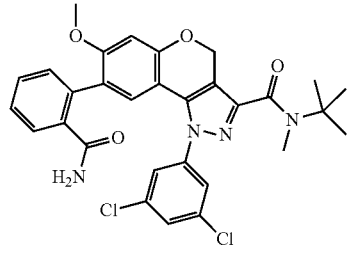 [SMILES: COc1cc2c(cc1-c1ccccc1C(N)=O)-c1c(c(C(=O)N(C)C(C)(C)C)nn1-c1cc(Cl)cc(Cl)c1)CO2]<br>N-tert-butyl-8-(2-carbamoylphenyl)-1-(3,5-dichlorophenyl)-7-methoxy-N-methyl-1,4-dihydrochromeno[4,3-c]pyrazole-3-carboxamide<br>Compound 98 | 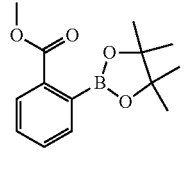 |  | m/z: 579 [M + H]$^+$ | $^1$H NMR (500 MHz, CDCl$_3$) δ 7.73 (d, J = 7.5 Hz, 1H), 7.54-7.45 (m, 3H), 7.39-7.35 (m, 2H), 7.16 (d, J = 7.5 Hz, 1H), 6.90 (s, 1H), 6.65 (s, 1H), 5.49 (d, J = 28.7 Hz, 2H), 3.76 (s, 3H), 3.25 (s, 3H), 1.50 (s, 9H). |
| 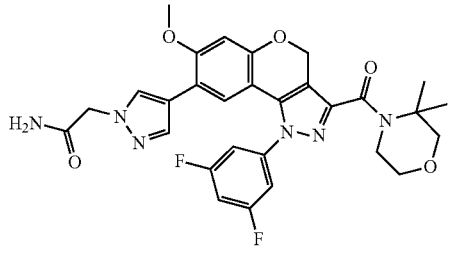 [SMILES: COc1cc2c(cc1-c1cnn(CC(N)=O)c1)-c1c(c(C(=O)N3CCOCC3(C)C)nn1-c1cc(F)cc(F)c1)CO2]<br>2-(4-(1-(3,5-difluorophenyl)-3-(3,3-dimethylmorpholine-4-carbonyl)-7-methoxy-1,4-dihydrochromeno[4,3-c]pyrazol-8-yl)-1H-pyrazol-1-yl)acetamide<br>Compound 99 | 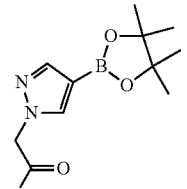 |  | m/z: 579 [M + H]$^+$ | $^1$H NMR (400 MHz, CDCl$_3$) δ 7.77 (s, 1H), 7.47 (s, 1H), 7.21-7.11 (m, 2H), 7.08-6.96 (m, 2H), 6.69 (s, 1H), 6.21 (s, 1H), 5.52 (s, 1H), 5.46 (s, 2H), 4.80 (s, 2H), 4.12-3.99 (m, 2H), 3.91 (s, 3H), 3.89-3.80 (m, 2H), 3.50 (s, 2H), 1.53 (s, 6H). |

-continued

| Compound | Boronic acid Starting material | Amine Starting material | LC/MS | NMR |
|---|---|---|---|---|
| 8-(6-amino-5-(methylcarbamoyl)pyridin-3-yl)-N-tert-butyl-1-(3,5-difluorophenyl)-7-methoxy-N-methyl-1,4-dihydrochromeno[4,3-c]pyrazole-3-carboxamide<br>Compound 100 | | | m/z: 577 [M + H]+ | $^1$H NMR (500 MHz, CDCl$_3$) δ 8.12 (d, J = 2.0 Hz, 1H), 7.49 (d, J = 1.9 Hz, 1H), 7.23-7.14 (m, 2H), 6.93 (t, J = 8.7 Hz, 1H), 6.81 (s, 1H), 6.70 (s, 1H), 6.38 (s, 2H), 6.03 (s, 1H), 5.45 (s, 2H), 3.82 (s, 3H), 3.26 (s, 3H), 3.00 (d, J = 4.8 Hz, 3H), 1.52 (s, 9H). |
| 5-(1-(3,5-dichlorophenyl)-3-(3,3-dimethylmorpholine-4-carbonyl)-7-methoxy-1,4-dihydrochromeno[4,3-c]pyrazol-8-yl)-N,N-dimethylnicotinamide<br>Compound 101 | | | m/z: 636 [M + H]+ | $^1$H NMR (500 MHz, CDCl$_3$) δ 8.57 (d, J = 1.8 Hz, 2H), 7.74 (t, J = 2.1 Hz, 1H), 7.50-7.47 (m, 3H), 6.88 (s, 1H), 6.73 (s, 1H), 5.49 (s, 2H), 4.09-4.04 (m, 2H), 3.88-3.84 (m, 2H), 3.83 (s, 3H), 3.50 (s, 2H), 3.15 (s, 3H), 3.00 (s, 3H), 1.53 (s, 6H). |

Example 3: (1-(3,5-dichlorophenyl)-7-methoxy-8-(pyridin-2-yl)-1,4-dihydrochromeno[4,3-c]pyrazol-3-yl)(4-hydroxy-2,2-dimethylpiperidin-1-yl)methanone (Compound 102)

Scheme 2

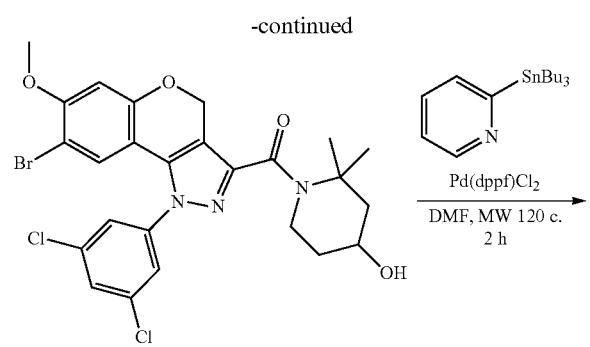

-continued

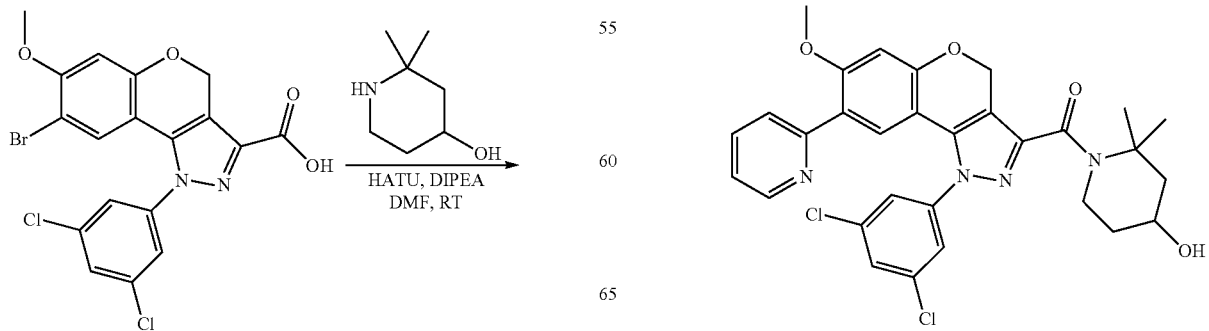

Step 1: Synthesis of (8-bromo-1-(3,5-dichlorophenyl)-7-methoxy-1,4-dihydrochromeno[4,3-c]pyrazol-3-yl)(4-hydroxy-2,2-dimethylpiperidin-1-yl)methanone

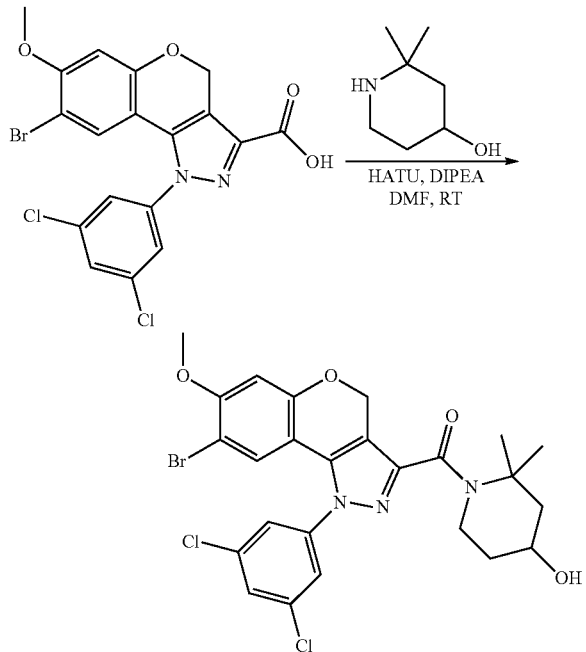

To a solution of 8-bromo-1-(3,5-dichlorophenyl)-7-methoxy-1,4-dihydrochromeno[4,3-c]pyrazole-3-carboxylic acid (500 mg, 1.07 mmol) in DMF (20 mL) was added 2,2-dimethylpiperidin-4-ol (166 mg, 1.28 mmol), HATU (407 mg, 1.07 mmol) and diisopropyl ethyl amine (0.57 mL, 3.21 mmol) at RT under nitrogen. The reaction mixture was stirred at RT for 3 h. The reaction mixture was quenched with sodium bicarbonate (10 mL, 10%), and extracted with EtOAc (2×50 mL). The combined organic layer was washed with brine (30 mL) and dried over anhydrous $Na_2SO_4$. The solvent was removed under vacuum; the crude product was purified by column chromatography by using pet ether and ethyl acetate (5:1) as eluents to afford the desired compound (500 mg, 80%) as a white solid.

Step 2: Synthesis of (1-(3,5-dichlorophenyl)-7-methoxy-8-(pyridin-2-yl)-1,4-dihydrochromeno[4,3-c]pyrazol-3-yl)(4-hydroxy-2,2-dimethylpiperidin-1-yl)methanone (Compound 102)

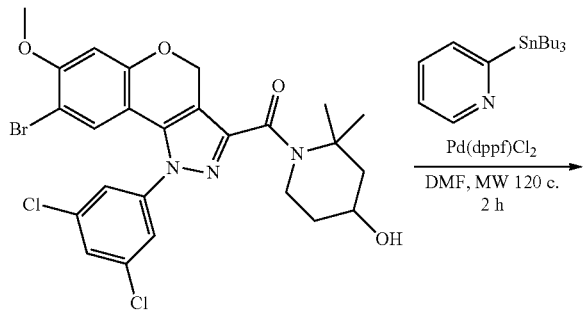

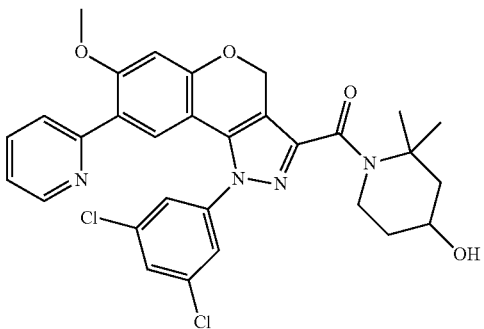

To a solution of (8-bromo-1-(3,5-dichlorophenyl)-7-methoxy-1,4-dihydrochromeno[4,3-c]pyrazol-3-yl)(4-hydroxy-2,2-dimethylpiperidin-1-yl)methanone (200 mg, 0.35 mmol) in DMF (5 mL) was added 2-(tributylstannyl)pyridine (193 mg, 0.53 mmol) and $Pd(dppf)Cl_2$ (29 mg, 0.07 mmol) at RT under nitrogen. The reaction was microwaved at 120° C. for 2 hours. LCMS showed the reaction was completed. The mixture was purified by preparative HPLC to afford the desired compound (30 mg, 15%) as a yellow solid. $^1H$ NMR (400 MHz, $CDCl_3$): δ 8.98 (d, 1H), 8.07 (t, J=7.8 Hz, 1H), 7.67 (d, J=7.8 Hz, 1H), 7.53 (d, J=1.8 Hz, 3H), 7.46 (t, J=1.8 Hz, 1H), 7.22 (s, 1H), 6.74 (s, 1H), 5.54 (q, J=13.8 Hz, 2H), 4.23-4.04 (m, 2H), 3.87 (s, 3H), 3.68-3.59 (m, 1H), 2.16 (s, 1H), 1.90 (dd, J=13.5, 4.9 Hz, 1H), 1.75 (dd, J=24.2, 10.9 Hz, 1H), 1.68 (s, 3H), 1.53 (s, 3H).

Example 4. N-(1-amino-2-methyl-1-oxopropan-2-yl)-8-(5-carbamoylpyridin-3-yl)-1-(3,5-difluorophenyl)-7-methoxy-N-methyl-1,4-dihydrochromeno[4,3-c]pyrazole-3-carboxamide (Compound 104)

Scheme 3

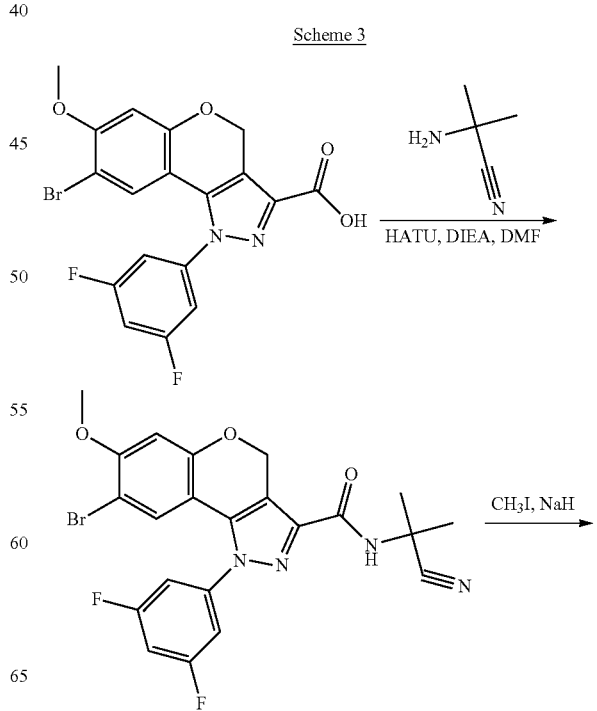

-continued

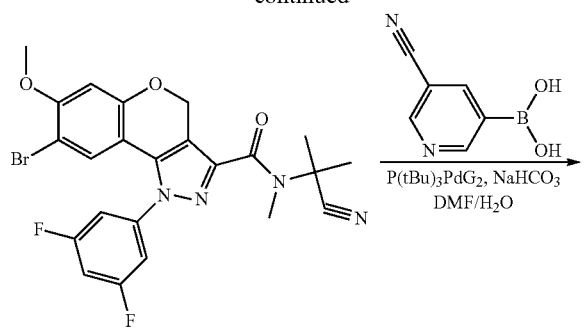

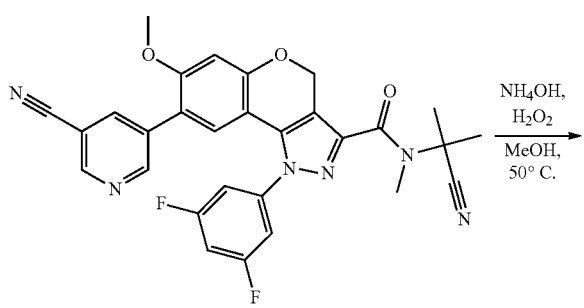

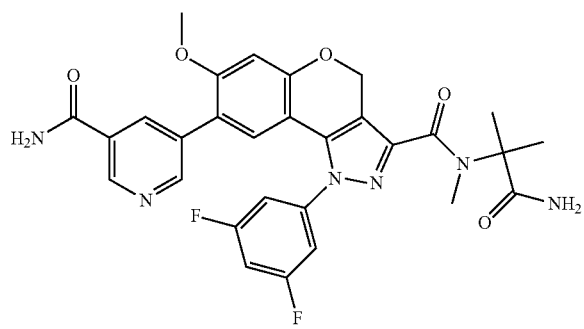

Step 1: 8-bromo-N-(2-cyanopropan-2-yl)-1-(3,5-difluorophenyl)-7-methoxy-1,4-dihydrochromeno[4,3-c]pyrazole-3-carboxamide A mixture of 8-bromo-1-(3,5-difluorophenyl)-7-methoxy-1,4-dihydrochromeno[4,3-c]pyrazole-3-carboxylic acid (100 mg, 0.229 mmol), HATU 9104 mg, 0.275 mmol), 2-amino-2-methylpropanenitrile (29 mg, 0.344 mmol) and DIPEA (89 mg, 0.687 mmol0 in DMF (4 ml) was stirred at RT for 2 h. Then The mixture was purified by Combi-Flash (mobile phase: acetonitrile/water (10 mM NH$_4$HCO$_3$) to afford 8-bromo-N-(2-cyanopropan-2-yl)-1-(3,5-difluorophenyl)-7-methoxy-1,4-dihydrochromeno[4,3-c]pyrazole-3-carboxamide (95 mg, 82%). LCMS m/z [M+H]$^+$ 503.0.

Step 2: 8-bromo-N-(2-cyanopropan-2-yl)-1-(3,5-difluorophenyl)-7-methoxy-N-methyl-1,4-dihydrochromeno[4,3-c]pyrazole-3-carboxamide At 0° C., to a solution of 8-bromo-N-(2-cyanopropan-2-yl)-1-(3,5-difluorophenyl)-7-methoxy-1,4-dihydrochromeno[4,3-c]pyrazole-3-carboxamide (95 mg, 0.19 mmol) in DMF (4 mL), was added NaH (31 mg, 0.76 mmol) and CH$_3$I (54 mg, 0.38 mmol). The mixture was stirred at RT under N$_2$ for 2 h, quenched by sat, NH$_4$Cl, purified by Combi-Flash (mobile phase: acetonitrile/water (10 mM NH$_4$HCO$_3$) to afford 8-bromo-N-(2-cyanopropan-2-yl)-1-(3,5-difluorophenyl)-7-methoxy-N-methyl-1,4-dihydrochromeno[4,3-c]pyrazole-3-carboxamide (70 mg, 71.4%) as white solid. LCMS m/z [M+H]$^+$ 516.8.

Step 3: N-(2-cyanopropan-2-yl)-8-(5-cyanopyridin-3-yl)-1-(3,5-difluorophenyl)-7-methoxy-N-methyl-1,4-dihydrochromeno[4,3-c]pyrazole-3-carboxamide (Compound 105)

A mixture of 8-bromo-N-(2-cyanopropan-2-yl)-1-(3,5-difluorophenyl)-7-methoxy-N-methyl-1,4-dihydrochromeno[4,3-c]pyrazole-3-carboxamide (70 mg, 0.136 mmol), 5-cyanopyridin-3-ylboronic acid (40 mg, 0.272 mmol), P(tBu)$_3$PdG$_2$ (7 mg, 0.0136 mmol) and NaHCO$_3$ (34 mg, 0.408 mmol) in DMF (3 ml) and water (0.6 ml) was heated at 120° C. by Microwave for 1 h. Then the mixture was purified by preparative HPLC to get N-(2-cyanopropan-2-yl)-8-(5-cyanopyridin-3-yl)-1-(3,5-difluorophenyl)-7-methoxy-N-methyl-1,4-dihydrochromeno[4,3-c]pyrazole-3-carboxamide (30 mg, 41%) as white solid. LCMS m/z [M+H]$^+$ 541.0. $^1$H NMR (400 MHz, CDCl$_3$): 8.75 (d, 1H, J=1.6 Hz), 8.65 (d, 1H, J=2.0 Hz), 7.96 (t, 1H, J=2.0 Hz), 7.17-7.14 (m, 2H), 7.04-6.99 (m, 1H), 6.86 (s, 1H), 6.75 (s, 1H), 5.58 (s, 2H), 3.86 (s, 3H), 3.47 (s, 3H), 1.84 (s, 6H).

Step 4: N-(1-amino-2-methyl-1-oxopropan-2-yl)-8-(5-carbamoylpyridin-3-yl)-1-(3,5-difluorophenyl)-7-methoxy-N-methyl-1,4-dihydrochromeno[4,3-c]pyrazole-3-carboxamide (Compound 104)

A mixture of N-(2-cyanopropan-2-yl)-8-(5-cyanopyridin-3-yl)-1-(3,5-difluorophenyl)-7-methoxy-N-methyl-1,4-dihydrochromeno[4,3-c]pyrazole-3-carboxamide (20 mg, 0.037 mmol), NH$_4$OH (0.5 ml) and H$_2$O$_2$(0.5 ml) in MeOH (2 ml) was stirred at 50° C. for 2 h. Then the mixture was purified by preparative HPLC to get N-(1-amino-2-methyl-1-oxopropan-2-yl)-8-(5-carbamoylpyridin-3-yl)-1-(3,5-difluorophenyl)-7-methoxy-N-methyl-1,4-dihydrochromeno[4,3-c]pyrazole-3-carboxamide (12 mg, 56%) as white solid. LCMS m/z [M+H]+ 577.0. $^1$H NMR (400 MHz, CDCl$_3$): 8.75 (d, 1H, J=1.6 Hz), 8.65 (d, 1H, J=2.0 Hz), 7.96 (t, 1H, J=2.0 Hz), 7.168-7.145 (m, 2H), 7.04-6.99 (m, 1H), 6.86 (s, 1H), 6.75 (s, 1H), 5.58 (s, 2H), 3.86 (s, 3H), 3.47 (s, 3H), 1.84 (s, 6H).

The following compounds were prepared using procedures analogous to those disclosed in Scheme 3.

| Compound | Boronic Acid Starting Material | Amine Starting Material | LC-MS | NMR |
|---|---|---|---|---|
| N-(2-cyanopropan-2-yl)-1-(3,5-difluorophenyl)-7-methoxy-N-methyl-8-(1-methyl-1H-pyrazol-3-yl)-1,4-dihydrochromeno[4,3-c]pyrazole-3-carboxamide<br>Compound 106 | | | MZ: 519 [M + H]⁺ | $^1$H NMR (500 MHz, CDCl$_3$) δ 7.59 (s, 1H), 7.30 (d, J = 2.0 Hz, 1H), 7.17 (dd, J = 6.7, 2.0 Hz, 2H), 6.97 (s, 1H), 6.67 (s, 1H), 6.55 (d, J = 2.1 Hz, 1H), 5.52 (s, 2H), 3.86 (d, J = 22.6 Hz, 6H), 3.46 s, 3H), 1.83 (d, J = 7.1 Hz, 6H). |
| 5-(3-((2-cyanopropan-2-yl)(methyl)carbamoyl)-1-(3,5-difluorophenyl)-7-methoxy-1,4-dihydrochromeno[4,3-c]pyrazol-8-yl)nicotinic acid<br>Compound 107 | | | MZ: 560 [M + H]⁺ | $^1$H NMR (400 MHz, CDCl$_3$): 9.158-9.153 (d, 1H, J = 2.0 Hz), 8.764-8.758 (d, 1H, J = 2.4 Hz), 8.265-8.260 (d, 1H, J = 2.0 Hz), 7.163-7.146 (m, 2H), 7.034-6.981 (m, 2H), 7.034-6.981 (m, 1H), 6.877 (s, 1H), 6.748 (s, 1H), 5.572 (s, 2H), 3.853 (s, 3H), 3.468 (s, 3H), 1.814 (s, 6H). |
| N-(2-cyanopropan-2-yl)-1-(3,5-dichlorophenyl)-8-(5-(hydroxymethyl)pyridin-3-yl)-7-methoxy-N-methyl-1,4-dihydrochromeno[4,3-c]pyrazole-3-carboxamide<br>Compound 108 | | | m/z: 578 [M + H]⁺ | $^1$H NMR (400 MHz, CDCl$_3$) δ 8.52 (s, 2H), 7.66 (s, 1H), 7.52 (dd, J = 6.8, 1.8 Hz, 3H), 6.87 (s, 1H), 6.73 (s, 1H), 5.55 (s, 2H), 4.76 (d, J = 5.5 Hz, 2H), 3.83 (s, 3H), 3.46 (s, 3H), 1.84 (s, 6H). |
| 8-(2-carbamoyl-5-fluoropyridin-4-yl)-N-(2-cyanopropan-2-yl)-1-(3,5-difluorophenyl)-7-methoxy-N-methyl-1,4-dihydrochromeno[4,3-c]pyrazole-3-carboxamide<br>Compound 109 | | | m/z: 577 [M + H]⁺ | $^1$H NMR (400 MHz, CDCl$_3$) δ 8.37 (d, J = 1.6 Hz, 1H), 8.17 (d, J = 6.2 Hz, 1H), 7.69 (d, J = 4.0, 1H), 7.12-7.09 (m, 2H), 6.99-6.92 (m, 1H), 6.90 (d, J = 1.1 Hz, 1H), 6.74 (s, 1H), 5.56 (s, 2H), 5.54 (d, J = 4.0 Hz, 1H), 3.83 (s, 3H), 3.45 (S, 3H), 1.84 (s, 6H). |

| Compound | Boronic Acid Starting Material | Amine Starting Material | LC-MS | NMR |
|---|---|---|---|---|
| 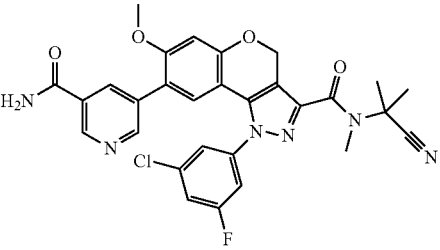 [SMILES: COc1cc2c(cc1-c1cncc(C(N)=O)c1)-c1c(c(C(=O)N(C)C(C)(C)C#N)nn1-c1cc(F)cc(Cl)c1)CO2]<br>8-(5-carbamoylpyridin-3-yl)-1-(3-chloro-5-fluorophenyl)-N-(2-cyanopropan-2-yl)-7-methoxy-N-methyl-1,4-dihydrochromeno[4,3-c]pyrazole-3-carboxamide<br>Compound 110 | 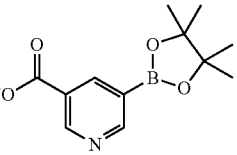 | 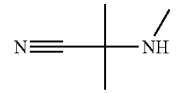 | m/z: 575 [M + H]+ | 1H NMR (400 MHz, CDCl3) δ 8.92 (s, 1H), 8.68 (s, 1H), 8.10 (s, 1H), 7.80 (m, 1H), 7.56 (m, 1H), 7.44 (s, 1H), 6.90 (s, 1H), 6.76 (s, 1H), 5.58 (s, 2H), 3.90 (s, 3H), 3.48 (s, 3H), 1.49 (s, 6H). |

Example 5. N-tert-butyl-8-(4-carbamoylpyrimidin-2-yl)-1-(3,5-dichlorophenyl)-7-methoxy-N-methyl-1,4-dihydrochromeno[4,3-c]pyrazole-3-carboxamide (Compound 111)

Scheme 4

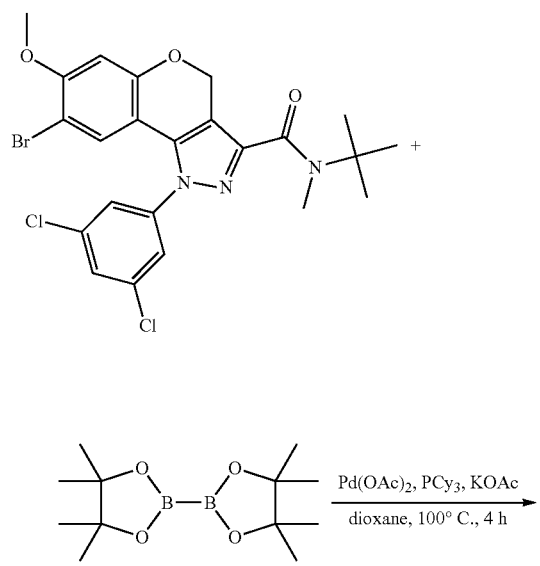

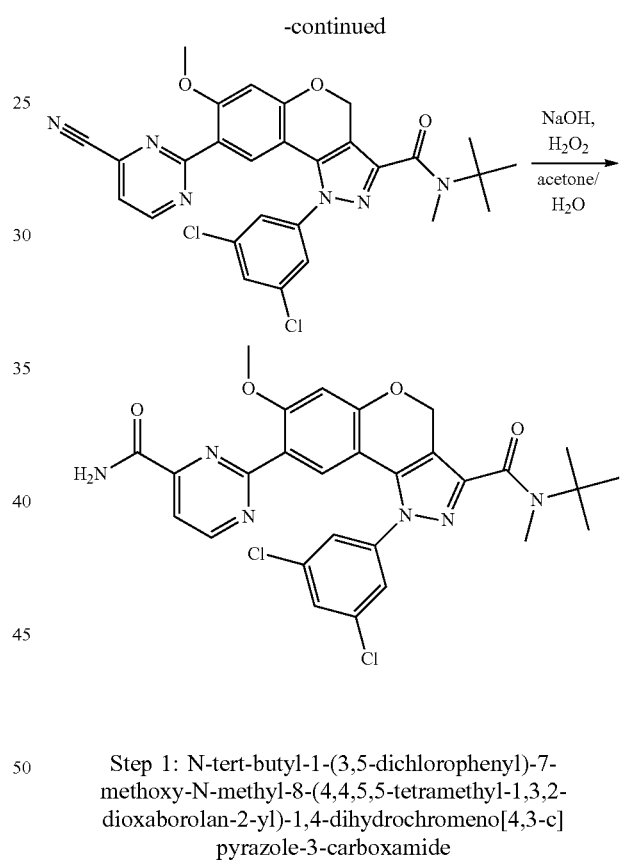

Step 1: N-tert-butyl-1-(3,5-dichlorophenyl)-7-methoxy-N-methyl-8-(4,4,5,5-tetramethyl-1,3,2-dioxaborolan-2-yl)-1,4-dihydrochromeno[4,3-c]pyrazole-3-carboxamide To a solution of 8-bromo-N-tert-butyl-1-(3,5-dichlorophenyl)-7-methoxy-N-methyl-1,4-dihydrochromeno[4,3-c]pyrazole-3-carboxamide (100 mg, 0.19 mmol) in dioxane (3 mL) were added Pd(OAc)2 (9 mg, 0.04 mmol), PCy3 (11 mg, 0.04 mmol) and KOAc (56 mg, 0.57 mmol). The mixture was heated at 100° C. for 4 h. After cooling to r.t, the mixture was concentrated. The residue was purified by Combi-Flash (mobile phase: acetonitrile/water (10 mM NH4HCO3)) to afford N-tert-butyl-1-(3,5-dichlorophenyl)-7-methoxy-N-methyl-8-(4,4,5,5-tetramethyl-1,3,2-dioxaborolan-2-yl)-1,4-dihydrochromeno[4,3-c]pyrazole-3-carboxamide (30 mg, 27%) as a yellow solid.

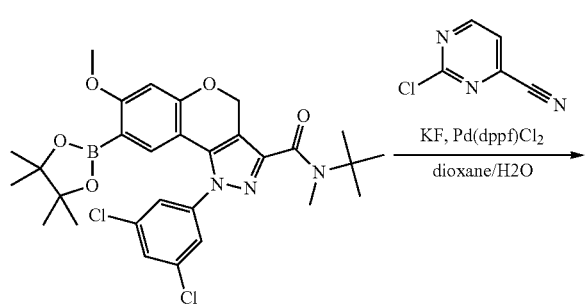

Step 2: N-tert-butyl-8-(4-cyanopyrimidin-2-yl)-1-(3,5-dichlorophenyl)-7-methoxy-N-methyl-1,4-dihydrochromeno[4,3-c]pyrazole-3-carboxamide To a solution of N-tert-butyl-1-(3,5-dichlorophenyl)-7-methoxy-N-methyl-8-(4,4,5,5-tetramethyl-1,3,2-dioxaborolan-2-yl)-1,4-dihydrochromeno[4,3-c]pyrazole-3-carboxamide (20 mg, 0.03 mmol) in dioxane (1.5 mL) and water (0.3 mL) was added 2-chloropyrimidine-4-carbonitrile (10 mg, 0.06 mmol), Pd (dppf) Cl$_2$ (3 mg, 0.003 mmol) and KF (3 mg, 0.06 mmol) at RT under nitrogen. The mixture was stirred at 90° C. for 2 h under MW conditions. Then the mixture was directly purified by Combi-Flash (mobile phase: acetonitrile/water (10 mM NH$_4$HCO$_3$)) to afford N-tert-butyl-8-(4-cyanopyrimidin-2-yl)-1-(3,5-dichlorophenyl)-7-methoxy-N-methyl-1,4-dihydrochromeno[4,3-c]pyrazole-3-carboxamide (12 mg, 75%) as a white solid. LCMS: m/z=563(M+H).

Step 3: N-tert-butyl-8-(4-carbamoylpyrimidin-2-yl)-1-(3,5-dichlorophenyl)-7-methoxy-N-methyl-1,4-dihydrochromeno[4,3-c]pyrazole-3-carboxamide (Compound 111)

To a solution of N-tert-butyl-8-(4-cyanopyrimidin-2-yl)-1-(3,5-dichlorophenyl)-7-methoxy-N-methyl-1,4-dihydrochromeno[4,3-c]pyrazole-3-carboxamide in acetone/H$_2$O (2 mL/0.4 mL) was added NaOH (4 mg, 0.1 mmol) and H$_2$O$_2$(0.5 mL, 30%). The mixture was heated at 40° C. for 3 h. The solvent was removed and the crude was purified by Combi-Flash (mobile phase: acetonitrile/water (10 mM NH$_4$HCO$_3$)) to afford N-tert-butyl-8-(4-carbamoylpyrimidin-2-yl)-1-(3,5-dichlorophenyl)-7-methoxy-N-methyl-1,4-dihydrochromeno[4,3-c]pyrazole-3-carboxamide (5 mg, 45%) as a white solid. LCMS m/z=581 [M+H]$^+$. $^1$H NMR (400 MHz, CDCl$_3$) δ 8.98 (d, J=4.9 Hz, 1H), 7.92 (d, J=4.9 Hz, 1H), 7.71 (s, 1H), 7.53-7.49 (m, 3H), 7.47 (t, J=1.8 Hz, 1H), 6.75 (s, 1H), 5.68 (s, 1H), 5.53 (s, 2H), 3.90 (s, 3H), 3.27 (s, 3H), 1.52 (s, 9H).

The following compounds were prepared using procedures analogous to those disclosed in Scheme 4.

| Compound | Boronic Acid Starting Material | Amine Starting Material | LC-MS | NMR |
|---|---|---|---|---|
| 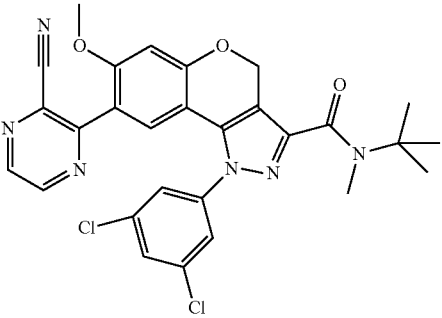 [SMILES: COc1cc2c(cc1-c1nccnc1C#N)-c1c(c(C(=O)N(C)C(C)(C)C)nn1-c1cc(Cl)cc(Cl)c1)CO2]<br>N-tert-butyl-8-(3-cyanopyrazin-2-yl)-1-(3,5-dichlorophenyl)-7-methoxy-N-methyl-1,4-dihydrochromeno[4,3-c]pyrazole-3-carboxamide<br>Compound 112 | 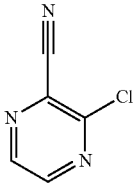 |  | m/z: 563 [M + H]$^+$ | $^1$H NMR (400 MHz, CDCl$_3$) δ 8.74 (d, J = 2.4 Hz, 1H), 8.55 (d, J = 2.4 Hz, 1H), 7.51 (d, J = 1.8 Hz, 2H), 7.42 (t, J = 1.8 Hz, 1H), 7.17 (s, 1H), 6.74 (s, 1H), 5.54 (s, 2H), 3.91 (s, 3H), 3.26 (s, 3H), 1.52 (s, 9H). |
| 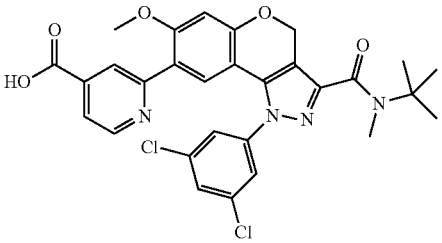 [SMILES: COc1cc2c(cc1-c1cc(C(=O)O)ccn1)-c1c(c(C(=O)N(C)C(C)(C)C)nn1-c1cc(Cl)cc(Cl)c1)CO2]<br>N-tert-butyl-8-(4-carbamoylpyridin-2-yl)-1-(3,5-dichlorophenyl)-7-methoxy-N-methyl-1,4-dihydrochromeno[4,3-c]pyrazole-3-carboxamide<br>Compound 113 | 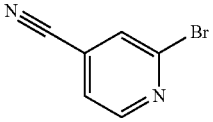 | 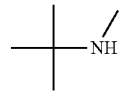 | m/z: 580 [M + H]$^+$ | $^1$H NMR (400 MHz, DMSO) δ 8.58 (d, J = 5.2 Hz, 1H), 8.20 (d, J = 4.0 Hz, 2H), 7.87 (t, J = 1.9 Hz, 1H), 7.81 (d, J = 1.8 Hz, 2H), 7.70 (s, 1H), 7.60 (dd, J = 5.0, 1.5 Hz, 1H), 7.57 (s, 1H), 6.89 (s, 1H), 5.44 (s, 2H), 3.89 (s, 3H), 3.19 (s, 3H), 1.45 (s, 9H). |

-continued

| Compound | Boronic Acid Starting Material | Amine Starting Material | LC-MS | NMR |
|---|---|---|---|---|
| N-tert-butyl-8-(6-carbamoylpyrimidin-4-yl)-1-(3,5-dichlorophenyl)-7-methoxy-N-methyl-1,4-dihydrochromeno[4,3-c]pyrazole-3-carboxamide<br>Compound 114 | methyl 6-bromopyrimidine-4-carboxylate | tert-butyl(methyl)amine | m/z: 581 [M + H]⁺ | $^1$H NMR (400 MHz, CDCl$_3$) δ 9.07 (d, J = 1.3 Hz, 1H), 8.70 (d, J = 1.3 Hz, 1H), 8.01 (s, 1H), 7.53 (s, 3H), 6.70 (s, 1H), 5.55 (s, 2H), 3.96 (s, 3H), 3.28 (s, 3H), 1.52 (s, 9H). |
| N-tert-butyl-8-(4-carbamoyl-6-methoxypyridin-2-yl)-1-(3,5-dichlorophenyl)-7-methoxy-N-methyl-1,4-dihydrochromeno[4,3-c]pyrazole-3-carboxamide<br>Compound 115 | methyl 2-chloro-6-methoxyisonicotinate | tert-butyl(methyl)amine | m/z: 610 [M + H]⁺ | $^1$H NMR (400 MHz, CDCl$_3$) δ 7.85 (d, J = 1.1 Hz, 1H), 7.66 (s, 1H), 7.48 (d, J = 1.8 Hz, 2H), 7.44 (s, 1H), 6.91 (d, J = 1.1 Hz, 1H), 6.73 (s, 1H), 5.48 (s, 2H), 3.92 (s, 3H), 3.70 (s, 3H), 3.25 (s, 3H), 1.52 (s, 9H). |
| N-tert-butyl-8-(5-carbamoyl-4-methylpyridin-3-yl)-1-(3,5-dichlorophenyl)-7-methoxy-N-methyl-1,4-dihydrochromeno[4,3-c]pyrazole-3-carboxamide<br>Compound 116 | methyl 5-bromo-4-methylnicotinate | tert-butyl(methyl)amine | m/z: 594 [M + H]⁺ | $^1$H NMR (500 MHz, CDCl$_3$) δ 8.60 (s, 1H), 8.32 (s, 1H), 7.47 (d, J = 1.7 Hz, 2H), 7.39 (s, 1H), 6.70 (d, J = 13.0 Hz, 2H), 5.51-5.44 (m, 2H), 3.76 (s, 3H), 3.26 (s, 3H), 2.23 (s, 3H), 1.52 (s, 9H). |
| N-tert-butyl-8-(2-carbamoyl-6-methoxypyridin-4-yl)-1-(3,5-dichlorophenyl)-7-methoxy-N-methyl-1,4-dihydrochromeno[4,3-c]pyrazole-3-carboxamide<br>Compound 117 | methyl 4-bromo-6-methoxypicolinate | tert-butyl(methyl)amine | m/z: 610 [M + H]⁺ | $^1$H NMR (400 MHz, CDCl$_3$) δ 7.79 (d, J = 1.3 Hz, 1H), 7.67 (d, J = 4.4 Hz, 1H), 7.53-7.48 (m, 3H), 6.92 (s, 1H), 6.89 (d, J = 1.3 Hz, 1H), 6.71 (s, 1H), 5.55 (d, J = 4.3 Hz, 1H), 5.48 (s, 2H), 3.97 (s, 3H), 3.83 (d, J = 4.4 Hz, 3H), 3.26 (s, 3H), 1.52 (s, 9H). |

-continued

| Compound | Boronic Acid Starting Material | Amine Starting Material | LC-MS | NMR |
|---|---|---|---|---|
| 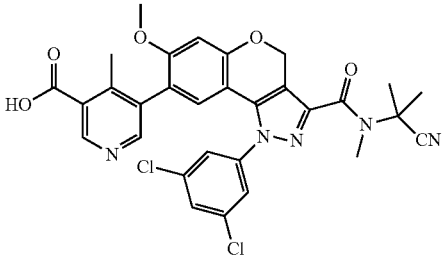 [SMILES: COc1cc2c(cc1-c1cncc(C(=O)O)c1C)-c1c(c(C(=O)N(C)C(C)(C)C#N)nn1-c1cc(Cl)cc(Cl)c1)CO2]<br>8-(5-carbamoyl-4-methylpyridin-3-yl)-N-(2-cyanopropan-2-yl)-1-(3,5-dichlorophenyl)-7-methoxy-N-methyl-1,4-dihydrochromeno[4,3-c]pyrazole-3-carboxamide<br>Compound 118 | 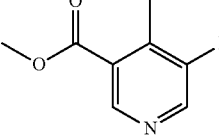 | 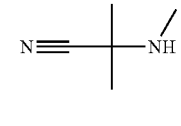 | m/z: 605 [M + H]⁺ | ¹H NMR (500 MHz, CDCl₃) δ 8.61 (s, 1H), 8.32 (s, 1H), 7.47-7.42 (m, 3H), 6.71 (d, J = 16.4 Hz, 2H), 5.62-5.48 (m, 2H), 3.77 (s, 3H), 3.46 (s, 3H), 2.23 (s, 3H), 1.84 (s, 6H). |
| 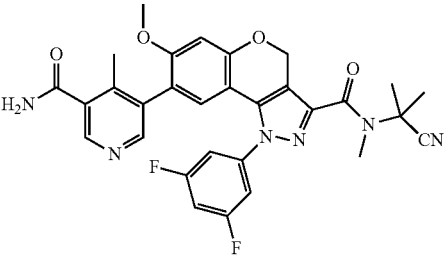 [SMILES: COc1cc2c(cc1-c1cncc(C(N)=O)c1C)-c1c(c(C(=O)N(C)C(C)(C)C#N)nn1-c1cc(F)cc(F)c1)CO2]<br>8-(5-carbamoyl-4-methylpyridin-3-yl)-N-(2-cyanopropan-2-yl)-1-(3,5-difluorophenyl)-7-methoxy-N-methyl-1,4-dihydrochromeno[4,3-c]pyrazole-3-carboxamide<br>Compound 119 | 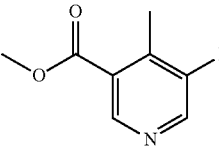 | 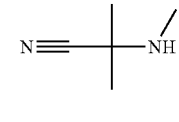 | m/z: 573 [M + H]⁺ | ¹H NMR (400 MHz, CDCl₃) δ 8.59 (s, 1H), 8.26 (s, 1H), 7.11 (dd, J = 6.8, 2.1 Hz, 2H), 6.96-6.86 (m, 1H), 6.71 (d, J = 15.7 Hz, 2H), 5.88 (d, J = 16.5 Hz, 2H), 5.55 (d, J = 14.3 Hz, 2H), 3.77 (s, 3H), 3.46 (s, 3H), 2.23 (s, 3H), 1.84 (s, 6H). |
| 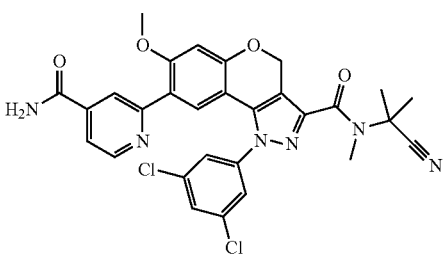 [SMILES: COc1cc2c(cc1-c1cc(C(N)=O)ccn1)-c1c(c(C(=O)N(C)C(C)(C)C#N)nn1-c1cc(Cl)cc(Cl)c1)CO2]<br>8-(4-carbamoylpyridin-2-yl)-N-(2-cyanopropan-2-yl)-1-(3,5-dichlorophenyl)-7-methoxy-N-methyl-1,4-dihydrochromeno[4,3-c]pyrazole-3-carboxamide<br>Compound 120 | 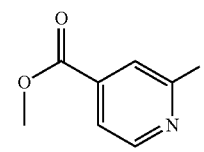 | 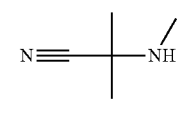 | m/z: 591 [M + H]⁺ | ¹H NMR (400 MHz, DMSO) δ 8.58 (d, J = 4.3 Hz, 1H), 8.20 (s, 2H), 7.89 (d, J = 16.4 Hz, 3H), 7.71 (s, 1H), 7.58 (d, J = 19.5 Hz, 2H), 6.91 (s, 1H), 5.51 (s, 2H), 3.89 (s, 3H), 1.74 (s, 6H). |

Example 6. N-tert-butyl-N-(2-hydroxyethyl)-7-methoxy-8-(1-methyl-1H-pyrazol-3-yl)-1-(thiophen-3-yl)-1,4-dihydrochromeno[4,3-c]pyrazole-3-carboxamide (Compound 121)

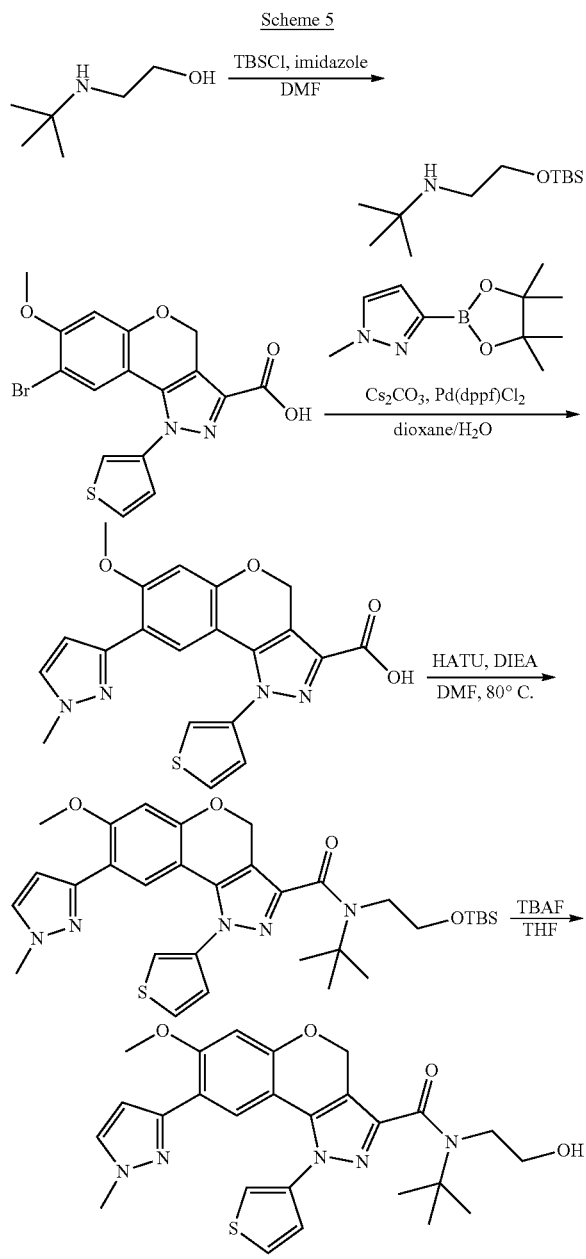

Scheme 5

Step 1: N-(2-(tert-butyldimethylsilyloxy)ethyl)-2-methylpropan-2-amine

To a solution of 2-(tert-butylamino)ethanol (500 mg, 4.27 mmol) in DMF (5 mL) was added imidazle (581 mg, 8.54 mmol) and TBSCl (962 mg, 63.41 mmol) at 0° C. The mixture was stirred at RT overnight. Then the mixture was extracted with EtOAc (100 mL), washed with water (20 mL×4) and dried over anhydrous $Na_2SO_4$. The organic phase was concentrated to afford N-(2-(tert-butyldimethylsilyloxy)ethyl)-2-methylpropan-2-amine (770 mg, 78%) as a colorless oil. LCMS m/z [M+H]$^+$ 232.2.

Step 2: 7-methoxy-8-(1-methyl-1H-pyrazol-3-yl)-1-(thiophen-3-yl)-1,4-dihydrochromeno[4,3-c]pyrazole-3-carboxylic acid To a solution of 8-bromo-7-methoxy-1-(thiophen-3-yl)-1,4-dihydrochromeno[4,3-c]pyrazole-3-carboxylic acid (100 mg, 0.25 mmol) in dioxane/H2O (5/1, 2 mL) were added 1-methyl-3-(4,4,5,5-tetramethyl-1,3,2-dioxaborolan-2-yl)-1H-pyrazole (104 mg, 0.50 mmol), $PdCl_2$(dppf) (36.6 mg, 0.05 mmol) and Cs2CO3 (161 mg, 0.50 mmol) at RT under nitrogen. The reaction mixture was stirred at 90° C. for 1 h under MW conditions. The reaction mixture was then filtered through celite and washed with DCM (50 mL). The filtrate was concentrated under vacuum; the crude product was purified by HPLC (mobile phase: acetonitrile/water (10 mM $NH_4HCO_3$) to afford the desired compound (100 mg, 90%) as an off-white solid. LCMS m/z=409 [M+H]$^+$

Step 3: N-tert-butyl-N-(2-(tert-butyldimethylsilyloxy)ethyl)-7-methoxy-8-(1-methyl-1H-pyrazol-3-yl)-1-(thiophen-3-yl)-1,4-dihydrochromeno[4,3-c]pyrazole-3-carboxamide To a solution of 7-methoxy-8-(1-methyl-1H-pyrazol-3-yl)-1-(thiophen-3-yl)-1,4-dihydrochromeno[4,3-c]pyrazole-3-carboxylic acid (50 mg, 0.123 mmol) in DMF (1 mL) was added N-(2-(tert-butyldimethylsilyloxy)ethyl)-2-methylpropan-2-amine (57 mg, 0.246 mmol), DIEA (48 mg, 0.369 mmol) and HATU (70 mg, 0.185 mmol). The mixture was stirred at 80° C. for 4 h, then directly purified by CombiFlash (mobile phase: acetonitrile/water (10 mM $NH_4HCO_3$)) to afford N-tert-butyl-N-(2-(tert-butyldimethylsilyloxy)ethyl)-7-methoxy-8-(1-methyl-1H-pyrazol-3-yl)-1-(thiophen-3-yl)-1,4-dihydrochromeno[4,3-c]pyrazole-3-carboxamide (20 mg, 26%) as a white solid. LCMS m/z [M+H]$^+$ 622.

Step 4: N-tert-butyl-N-(2-hydroxyethyl)-7-methoxy-8-(1-methyl-1H-pyrazol-3-yl)-1-(thiophen-3-yl)-1,4-dihydrochromeno[4,3-c]pyrazole-3-carboxamide (Compound 121)

To a solution of N-tert-butyl-N-(2-(tert-butyldimethylsilyloxy)ethyl)-7-methoxy-8-(1-methyl-1H-pyrazol-3-yl)-1-(thiophen-3-yl)-1,4-dihydrochromeno[4,3-c]pyrazole-3-carboxamide (20 mg, 0.032 mmol) in THF (1 mL) was added TBAF (25 mg, 0.096 mmol). The mixture was stirred at RT for 4 h. Then the mixture was directly purified by CombiFlash (mobile phase: acetonitrile/water (10 mM $NH_4HCO_3$)) to afford N-tert-butyl-N-(2-hydroxyethyl)-7-methoxy-8-(1-methyl-1H-pyrazol-3-yl)-1-(thiophen-3-yl)-1,4-dihydrochromeno[4,3-c]pyrazole-3-carboxamide (3 mg, 19%) as a white solid. LCMS m/z [M+H]$^+$ 507.9. $^1$H NMR (400 MHz, CDCl$_3$): 7.54-7.53 (m, 1H), 7.52 (s, 1H), 7.49-7.47 (m, 1H), 7.30 (d, J=2 Hz, 1H), 7.25-7.23 (m, 1H), 6.65 (s, 1H), 6.51 (d, J=2 Hz, 1H), 5.47 (s, 2H), 3.92-3.90 (m, 2H), 3.88 (s, 3H), 3.86 (s, 3H), 3.83-3.82 (m, 2H), 1.57 (s, 9H).

The following compounds were prepared using procedures analogous to those disclosed in Scheme 5.

| Compound | Boronic Acid Starting Material | Amine Starting Material | LC-MS | NMR |
|---|---|---|---|---|
| 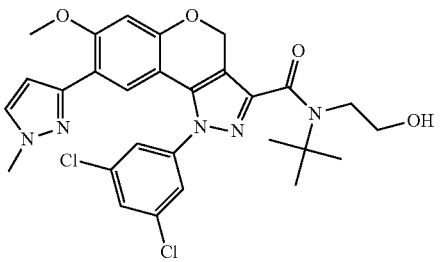 [SMILES: COc1cc2c(cc1-c1ccn(C)n1)-c1c(c(C(=O)N(CCO)C(C)(C)C)nn1-c1cc(Cl)cc(Cl)c1)CO2]<br>N-tert-butyl-1-(3,5-dichlorophenyl)-N-(2-hydroxyethyl)-7-methoxy-8-(1-methyl-1H-pyrazol-3-yl)-1,4-dihydrochromeno[4,3-c]pyrazole-3-carboxamide<br>Compound 122 | 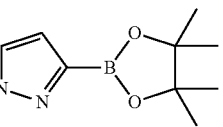 | 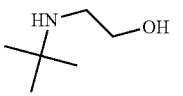 | m/z: 570 [M + H]$^+$ | $^1$H NMR (400 MHz, CDCl$_3$) δ 7.59 (s, 1H), 7.50 (s, 3H), 7.31 (d, J = 2.2 Hz, 1H), 6.66 (s, 1H), 6.55 (d, J = 2.2 Hz, 1H), 5.44 (s, 2H), 3.19 (t, J = 5.7 Hz, 2H), 3.89 (d, J = 3.8 Hz, 3H), 3.86 (s, 3H), 3.86-3.79 (m, 2H), 1.56 (s, 9H). |
| 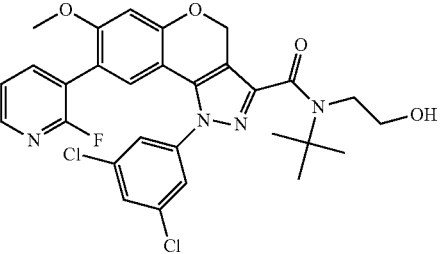 [SMILES: COc1cc2c(cc1-c1cccnc1F)-c1c(c(C(=O)N(CCO)C(C)(C)C)nn1-c1cc(Cl)cc(Cl)c1)CO2]<br>N-tert-butyl-1-(3,5-dichlorophenyl)-8-(2-fluoropyridin-3-yl)-N-(2-hydroxyethyl)-7-methoxy-1,4-dihydrochromeno[4,3-c]pyrazole-3-carboxamide<br>Compound 123 | 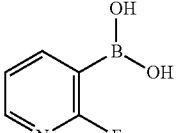 | 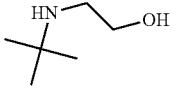 | m/z: 585 [M + H]$^+$ | $^1$H NMR (400 MHz, CDCl$_3$) δ 8.15 (d, J = 4.1 Hz, 1H), 7.68 (ddd, J = 9.4, 7.4, 1.9 Hz, 1H), 7.46 (s, 3H), 7.19 (ddd, J = 7.0, 4.9, 1.7 Hz, 1H), 6.83 (s, 1H), 6.72 (s, 1H), 5.46 (s, 2H), 3.98-3.85 (m, 2H), 3.82 (d, J = 5.8 Hz, 5H), 1.56 (s, 9H). |
| 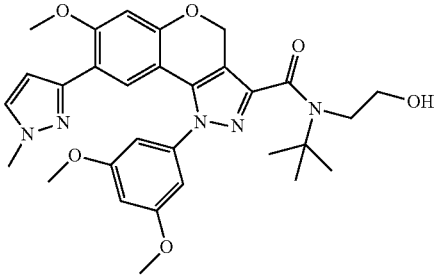 [SMILES: COc1cc(OC)cc(-n2nc(C(=O)N(CCO)C(C)(C)C)c3c2-c2cc(-c4ccn(C)n4)c(OC)cc2OC3)c1]<br>N-tert-butyl-1-(3,5-dimethoxyphenyl)-N-(2-hydroxyethyl)-7-methoxy-8-(1-methyl-1H-pyrazol-3-yl)-1,4-dihydrochromeno[4,3-c]pyrazole-3-carboxamide<br>Compound 124 | 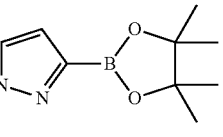 | 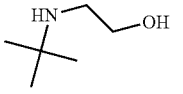 | m/z: 562 [M + H]$^+$ | $^1$H NMR (400 MHz, CDCl$_3$): δ = 7.66 (s, 1 H), 7.22 (s, 1 H), 6.63 (s, 2H), 6.58 (s, 1 H), 6.50 (s, 1 H), 6.43 (s, 1 H), 3.86-3.73 (m, 16 H), 1.51 (s, 9 H). |
| 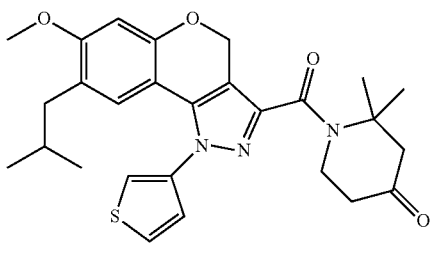 [SMILES: COc1cc2c(cc1CC(C)C)-c1c(c(C(=O)N3CCC(=O)CC3(C)C)nn1-c1ccsc1)CO2]<br>1-(8-isobutyl-7-methoxy-1-(thiophen-3-yl)-1,4-dihydrochromeno[4,3-c]pyrazole-3-carbonyl)-2,2-dimethylpiperidin-4-one<br>Compound 125 | | 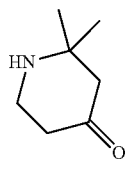 | m/z: 494 [M + H]$^+$ | |

| Compound | Boronic Acid Starting Material | Amine Starting Material | LC-MS | NMR |
|---|---|---|---|---|
| (2-(hydroxymethyl)-2-isobutylpyrrolidin-1-yl)(7-methoxy-8-(1-methyl-1H-pyrazol-3-yl)-1-(thiophen-3-yl)-1,4-dihydrochromeno[4,3-c]pyrazol-3-yl)methanone<br>Compound 126 | | | m/z: 548 [M + H]+ | $^1$H NMR (400 MHz, CDCl$_3$): δ = 7.54-6.65 (m, 7 H), 6.64 (s, 1H), 6.49 (d, J = 2.4 Hz, 1 H), 5.55 (s, 2 H), 4.32-4.25 (m, 1 H), 4.07-4.00 (m, 1 H), 3.88-3.87 (m, 6 H), 3.80 (s, 2 H), 2.17-1.65 (m, 7 H), 1.15-0.98 (m, 6 H). |
| (2-isobutyl-2-(methoxymethyl)pyrrolidin-1-yl)(7-methoxy-8-(1-methyl-1H-pyrazol-3-yl)-1-(thiophen-3-yl)-1,4-dihydrochromeno[4,3-c]pyrazol-3-yl)methanone<br>Compound 127 | | | m/z: 562 [M + H]+ | $^1$H NMR (400 MHz, CDCl$_3$): δ = 7.53-7.52 (m, 1 H), 7.49 (s, 1 H), 7.47-7.45 (m, 1 H), 6.63 (s, 1 H), 6.50 (d, J = 2.4 Hz, 1 H), 5.60-5.52 (m, 2 H), 4.15-4.08 (m, 2 H), 4.02 (d, J = 9.2 Hz, 1 H), 3.87 (s, 3 H), 3.86 (s, 3 H), 3.60 (d, J = 8.8 Hz, 1 H), 3.36 (s, 3 H), 2.05-1.90 (m, 7 H), 1.05 (m, 6 H). |
| (2-ethyl-2-(methoxymethyl)pyrroli-din-1-yl)(7-methoxy-8-(1-methyl-1H-pyrazol-3-yl)-1-(thiophen-3-yl)-1,4-dihydrochromeno[4,3-c]pyrazole-3-yl)methanone<br>Compound 128 | | | m/z: 534 [M + H]+ | $^1$H NMR (400 MHz, CDCl$_3$) δ 7.53 (dd, J = 3.2, 1.3 Hz, 1H), 7.49 (s, 1H), 7.46 (dd, J = 5.1, 3.2 Hz, 1H), 7.29 (d, J = 2.2 Hz, 1H), 7.27-7.25 (m, 2H), 6.64 (s, 1H), 6.51 (d, J = 2.2 Hz, 1H), 5.62-5.51 (m, 2H), 4.21-4.12 m, 1H), 4.05-3.96 (m, 2H), 3.87 (t, J = 6.4 Hz, 6H), 3.60 (d, J = 9.1 Hz, 1H), 3.36 (s, 3H), 2.34-2.16 (m, 1H), 2.10 (dt, J = 11.4, 5.3 Hz, 1H), 1.94-1.71 (m, 4H), 0.88 (t, J = 7.5 Hz, 3H). |

| Compound | Boronic Acid Starting Material | Amine Starting Material | LC-MS | NMR |
|---|---|---|---|---|
| 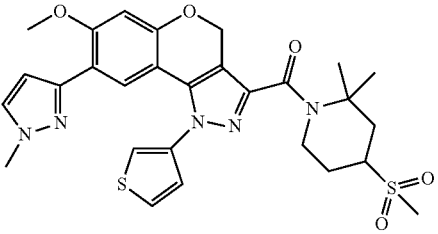 [SMILES: COc1cc2c(cc1-c1ccn(C)n1)-c1c(c(C(=O)N3CCC(S(C)(=O)=O)CC3(C)C)nn1-c1ccsc1)CO2]<br>(2,2-dimethyl-4-(methylsulfonyl)piperidin-1-yl)(7-methoxy-8-(1-methyl-1H-pyrazol-3-yl)-1-(thiophen-3-yl)-1,4-dihydrochromeno[4,3-c]pyrazol-3-yl)methanone<br>Compound 129 | 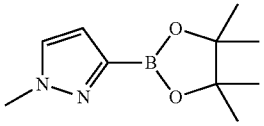 | 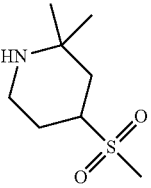 | m/z: 582 [M + H]$^+$ | $^1$H NMR (400 MHz, CDCl$_3$): 7.55 (m, 2H), 7.48 (m, 1H), 7.32 (d, 1H), 7.27 (m, 1H), 6.67 (s, 1H), 6.54 (d, 2H), 5.32 (s, 2H), 4.20 (m, 1H), 4.10 (m, 1H), 3.90 (s, 6H), 3.38 (m, 1H), 2.90 (s, 3H), 2.38 (m, 1H), 2.12 (m, 2H), 2.00 (m, 1H), 1.70 (s, 3H), 1.45 (s, 3H). |
| 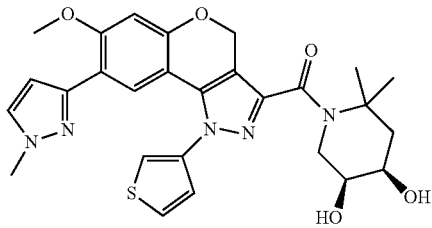 [SMILES: COc1cc2c(cc1-c1ccn(C)n1)-c1c(c(C(=O)N3C[C@H](O)[C@H](O)CC3(C)C)nn1-c1ccsc1)CO2]<br>((4R,5S)-4,5-dihydroxy-2,2-dimethylpiperidin-1-yl)(7-methoxy-8-(1-methyl-1H-pyrazol-3-yl)-1-(thiophen-3-yl)-1,4-dihydrochromeno[4,3-c]pyrazol-3-yl)methanone<br>Compound 130 | 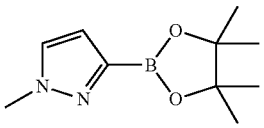 | 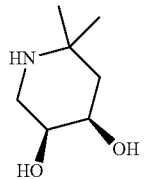 | m/z: 536 [M + H]$^+$ | $^1$H NMR (400 MHz, CDCl$_3$): 7.55 (m, 2H), 7.48 (m, 1H), 7.32 (d, 1H), 7.27 (m, 1H), 6.67 (s, 1H), 6.54 (d, 2H), 5.32 (s, 2H), 4.28 (m, 1H), 4.00 (d, 1H), 3.88 (s, 6H), 3.45 (m, 2H), 1.90 (m, 2H), 1.70 (s, 3H), 1.45 (s, 3H). |
| 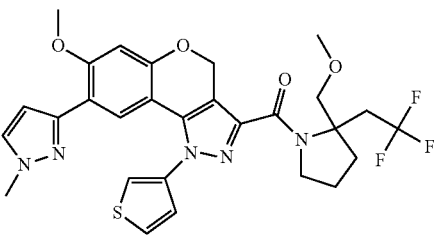 [SMILES: COCC1(CC(F)(F)F)CCCN1C(=O)c1nn(-c2ccsc2)c2c1COc1cc(OC)c(-c3ccn(C)n3)cc1-2]<br>(7-methoxy-8-(1-methyl-1H-pyrazol-3-yl)-1-(thiophen-3-yl)-1,4-dihydrochromeno[4,3-c]pyrazol-3-yl)(2-(methoxymethyl)-2-(2,2,2-trifluoroethyl)pyrrolidin-1-yl)methanone<br>Compound 131 | 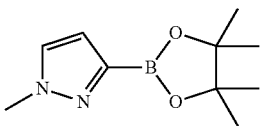 | 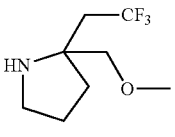 | m/z: 588 [M + H]$^+$ | $^1$H NMR (400 MHz, CDCl$_3$): 7.541-7.455 (m, 3H), 7.298-7.254 (m, 2H) 6.638 (s, 1H), 6.510-6.505 (d, 1H), 5.544 (s, 2H), 4.129-4.087 (m, 2H), 3.871 (s, 3H), 3.860 (s, 3H), 3.827-3.821 (d, 2H), 3.365 (s, 3H), 3.290-3.213 (m, 1H), 2.890-2.761 (m, 1H), 2.294-2.173 (m, 2H), 1.933-1.879 (m, 2H). |
| 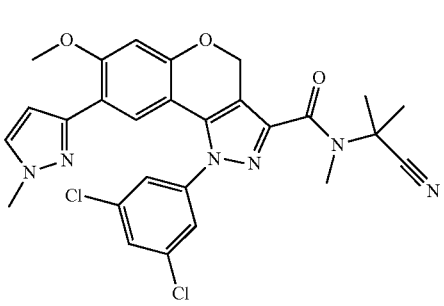 [SMILES: COc1cc2c(cc1-c1ccn(C)n1)-c1c(c(C(=O)N(C)C(C)(C)C#N)nn1-c1cc(Cl)cc(Cl)c1)CO2]<br>N-(2-cyanopropan-2-yl)-1-(3,5-dichlorophenyl)-7-methoxy-N-methyl-8-(1-methyl-1H-pyrazol-3-yl)-1,4-dihydrochromeno[4,3-c]pyrazole-3-carboxamide<br>Compound 132 | 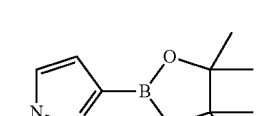 | 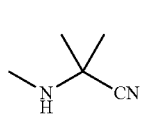 | m/z: 551 [M + H]$^+$ | $^1$H NMR (400 MHz, CDCl$_3$): 7.611 (s, 1H), 7.535-7.529 (d, 2H, J = 2.4 Hz), 7.513-7.507 (d, 1H, J = 2.4 Hz), 7.312-7.306 (d, 1H, J = 2.4 Hz), 6.663 (s, 1H), 6.561-6.556 (d, 1H, J = 2.0 Hz), 5.526 (s, 2H), 3.884 (s, 3H), 3.866 (s, 3H), 3.460 (s, 3H), 1.828 (s, 6H). |

| Compound | Boronic Acid Starting Material | Amine Starting Material | LC-MS | NMR |
|---|---|---|---|---|
| 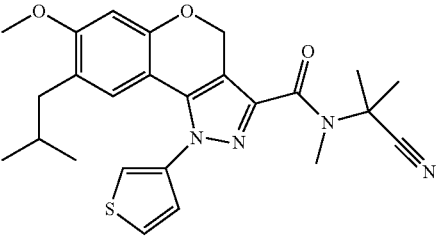 [SMILES: COc1cc2c(cc1CC(C)C)-c1c(c(C(=O)N(C)C(C)(C)C#N)nn1-c1ccsc1)CO2]<br>N-(2-cyanopropan-2-yl)-8-isobutyl-7-methoxy-N-methyl-1-(thiophen-3-yl)-1,4-dihydrochromeno[4,3-c]pyrazole-3-carboxamide<br>Compound 133 | | 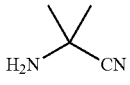 | m/z: 465 [M + H]+ | 1H NMR (400 MHz, CDCl3): 7.498-7.460 (m, 2H), 7.223-7.207 (1H), 6.543 (s, 1H), 6.511 (s, 1H), 5.479 (s, 2H), 3.779 (s, 3H), 3.450 (s, 3H), 2.218-2.201 (d, 2H), 1.828 (s, 6H), 1.726-1.659 (m, 1H), 0.792 (s, 3H), 0.775 (s, 3H). |

Example 7. 1-(3,5-dimethoxyphenyl)-N-(4-hydroxy-2-methylbutan-2-yl)-7-methoxy-N-methyl-8-(1-methyl-1H-pyrazol-3-yl)-1,4-dihydrochromeno[4,3-c]pyrazole-3-carboxamide (Compound 134)

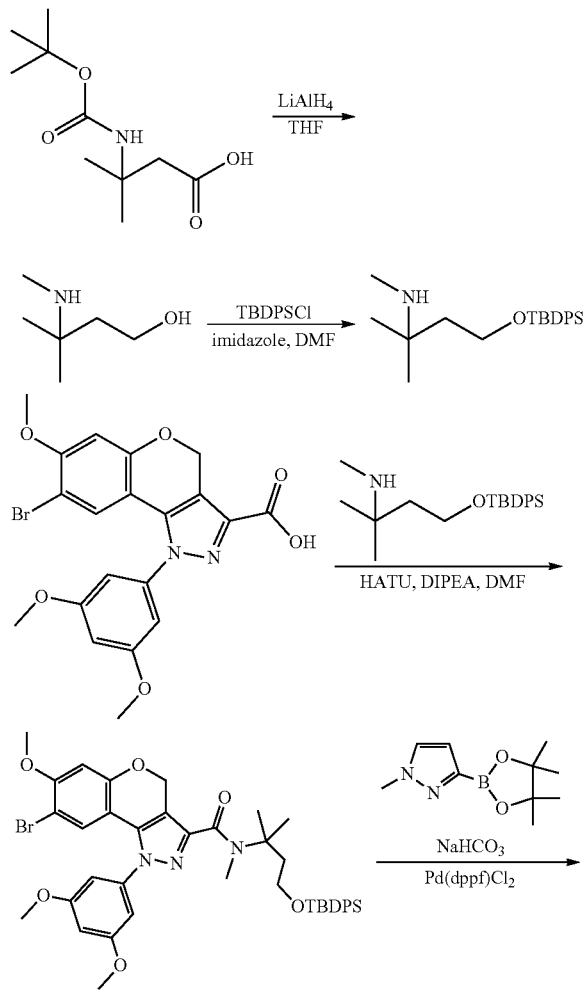

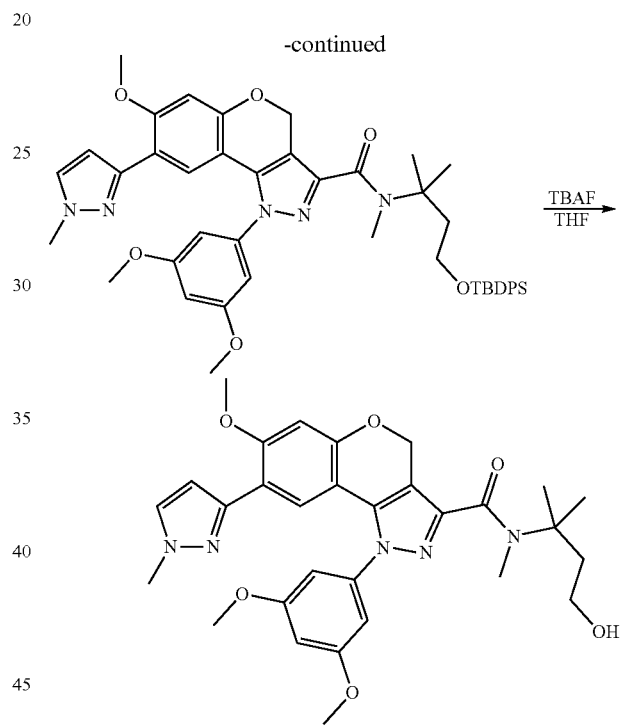

Step 1: 3-methyl-3-(methylamino)butan-1-ol

A mixture of 3-(tert-butoxycarbonylamino)-3-methylbutanoic acid (434 mg, 2.0 mmol) and LiAlH4 (10 mL, 10 mmol, 1 mol/L in THF) in THF (10 mL) was heated at 60° C. under N2 overnight. After cooling to room temperature, water (4 mL) was added, followed by 15% NaOH (1 mL aq). The mixture was then extracted with DCM:MeOH 10:1 (20 mL×3), washed with brine (10 mL), dried (Na2SO4), and evaporated to afford 3-methyl-3-(methylamino)butan-1-ol (117 mg, yield 50%). m/z=118.2 [M+H]+

Step 2: 4-(tert-butyldiphenylsilyloxy)-N,2-dimethylbutan-2-amine

A mixture of 3-methyl-3-(methylamino)butan-1-ol (117 mg, 1.0 mmol), TBDPSCl (274 mg, 1.0 mmol) and imidazole (210 mg, 3.0 mmol) in DMF (10 mL) was stirred at room temperature under N$_2$ for 4 hrs. Then the mixture was diluted with EtOAc (80 mL) and washed with water (20 mL×3), brine (20 mL), dried (Na$_2$SO$_4$), and evaporated. The residue was purified by prep-TLC (silica gel:PE:EA=1:1) to afford 4-(tert-butyldiphenylsilyloxy)-N,2-dimethylbutan-2-amine (80 mg, yield 23%).

Step 3: 8-bromo-N-(4-(tert-butyldiphenylsilyloxy)-2-methylbutan-2-yl)-1-(3,5-dimethoxyphenyl)-7-methoxy-N-methyl-1,4-dihydrochromeno[4,3-c]pyrazole-3-carboxamide To a solution of 8-bromo-1-(3,5-dimethoxyphenyl)-7-methoxy-1,4-dihydrochromeno[4,3-c]pyrazole-3-carboxylic acid (69 mg, 0.15 mmol) in DMF (5 mL) was added 4-(tert-butyldiphenylsilyloxy)-N,2-dimethylbutan-2-amine (54 mg, 0.15 mmol), HATU (57 mg, 0.15 mmol) and diisopropyl ethylamine (59 mg, 0.45 mmol) at RT under nitrogen. The reaction mixture was stirred at RT for 3 h. then quenches with sodium bicarbonate (10 mL, 10%) and extracted with EtOAc (2×30 mL). The combined organic layers were washed with NaHCO$_3$ solution (10 mL, 10% solution), brine (10 mL), and dried (Na$_2$SO$_4$). The solvent was removed under vacuum, and the crude product was purified by column chromatography by using pet ether and ethyl acetate (3:1) as eluent to afford 8-bromo-N-(4-(tert-butyldiphenylsilyloxy)-2-methylbutan-2-yl)-1-(3,5-dimethoxyphenyl)-7-methoxy-N-methyl-1,4-dihydrochromeno[4,3-c]pyrazole-3-carboxamide (65 mg, 54%) as a light-yellow solid. m/Z=820.2 [M+Na]

Step 4: N-(4-(tert-butyldiphenylsilyloxy)-2-methylbutan-2-yl)-1-(3,5-dimethoxyphenyl)-7-methoxy-N-methyl-8-(1-methyl-1H-pyrazol-3-yl)-1,4-dihydrochromeno[4,3-c]pyrazole-3-carboxamide To a solution of 8-bromo-N-(4-(tert-butyldiphenylsilyloxy)-2-methylbutan-2-yl)-1-(3,5-dimethoxyphenyl)-7-methoxy-N-methyl-1,4-dihydrochromeno[4,3-c]pyrazole-3-carboxamide (27 mg, 0.034 mmol) in DMF (1.5 mL) was added 1-methyl-3-(4,4,5,5-tetramethyl-1,3,2-dioxaborolan-2-yl)-1H-pyrazole (21 mg, 0.10 mmol), Pd(dppf)Cl$_2$ (4 mg, 0.0068 mmol) and NaHCO$_3$ (9 mg, 0.10 mmol) at RT under nitrogen. The reaction mixture was degassed with nitrogen for 20 min and water (0.3 mL) was added at RT. The reaction mixture was stirred at 120° C. for 1 h under MW conditions. The reaction mixture was filtered through celite and washed with DCM (50 mL). The filtrate was concentrated under vacuum; the crude product was washed with water (10 ml), brine (10 mL) and dried over sodium sulphate. The organic solvent was removed under vacuum; the crude product was purified by preparative HPLC(C18, A 10 mmol NH$_4$HCO$_3$, B. CH$_3$CN) to afford N-(4-(tert-butyldiphenylsilyloxy)-2-methylbutan-2-yl)-1-(3,5-dimethoxyphenyl)-7-methoxy-N-methyl-8-(1-methyl-1H-pyrazol-3-yl)-1,4-dihydrochromeno[4,3-c]pyrazole-3-carboxamide (15 mg, 55%) as a white solid. m/Z=822.3 [M+Na]

Step 5: 1-(3,5-dimethoxyphenyl)-N-(4-hydroxy-2-methylbutan-2-yl)-7-methoxy-N-methyl-8-(1-methyl-1H-pyrazol-3-yl)-1,4-dihydrochromeno[4,3-c]pyrazole-3-carboxamide (Compound 134)

A mixture of N-(4-(tert-butyldiphenylsilyloxy)-2-methylbutan-2-yl)-1-(3,5-dimethoxyphenyl)-7-methoxy-N-methyl-8-(1-methyl-1H-pyrazol-3-yl)-1,4-dihydrochromeno[4,3-c]pyrazole-3-carboxamide (15 mg, 0.019 mmol) and TBAF (0.06 mL, 0.06 mmol, 1.0 mol·L$^-$) in THF (2 mL) was stirred at room temperature overnight. Then concentrated and the residue was purified by Preparative HPLC (C18, A 10 mmol NH$_4$HCO$_3$, B. CH$_3$CN) to afford 1-(3,5-dimethoxyphenyl)-N-(4-hydroxy-2-methylbutan-2-yl)-7-methoxy-N-methyl-8-(1-methyl-1H-pyrazol-3-yl)-1,4-dihydrochromeno[4,3-c]pyrazole-3-carboxamide (6 mg, 57%) as a light-yellow solid. m/Z=562.3 [M+H]$^+$; $^1$H NMR (400 MHz, CDCl$_3$) δ ppm 7.69 (s, 1H), 7.30 (s, 1H), 6.73-6.72 (m, 2H), 6.64 (s, 1H), 6.58 (s, 1H), 6.49 (d, J=2.4 Hz, 1H), 5.46 (s, 2H), 3.87 (s, 3H), 3.85 (s, 3H), 3.81 (s, 6H), 3.77-3.73 (m, 2H), 3.28 (s, 3H), 2.20-2.17 (m, 2H), 1.54 (s, 6H).

The following compounds were prepared using procedures analogous to those disclosed in Scheme 6.

| Compound | Boronic Acid Starting Material | Amine Starting Material | LC-MS | NMR |
|---|---|---|---|---|
| 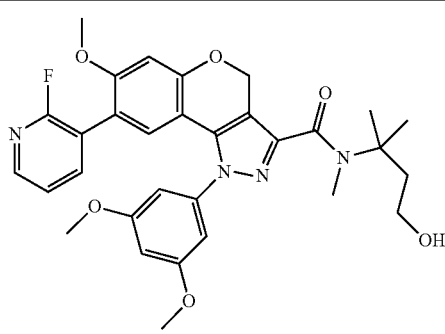<br>1-(3,5-dimethoxyphenyl)-8-(2-fluoropyridin-3-yl)-N-(4-hydroxy-2-methylbutan-2-yl)-7-methoxy-N-methyl-1,4-dihydrochromeno[4,3-c]pyrazole-3-carboxamide<br>Compound 135 | 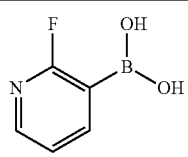 | 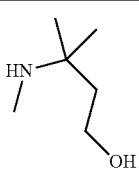 | m/z: 577 [M + H]$^+$ | $^1$H NMR (400 MHz, CDCl$_3$) δ 8.12 (d, J = 4.1 Hz, 1H), 7.61 (s, 1H), 7.15 (s, 1H), 6.83 (s, 1H), 6.68 (s, 1H), 6.64 (d, J = 2.2 Hz, 2H), 6.53 (t, J = 2.2 Hz, 1H), 5.49 (s, 2H), 3.86-3.70 (m, 11H), 3.28 (s, 3H), 2.20 (dd, J = 12.8, 6.3 Hz, 2H), 1.54 (s, 6H). |

233

Example 8. N-tert-butyl-1-(3,5-dichlorophenyl)-8-(1-(2-(dimethylamino)-2-oxoethyl)-3,5-dimethyl-1H-pyrazol-4-yl)-7-methoxy-N-methyl-1,4-dihydrochromeno[4,3-c]pyrazole-3-carboxamide (Compound 136)

Scheme 7

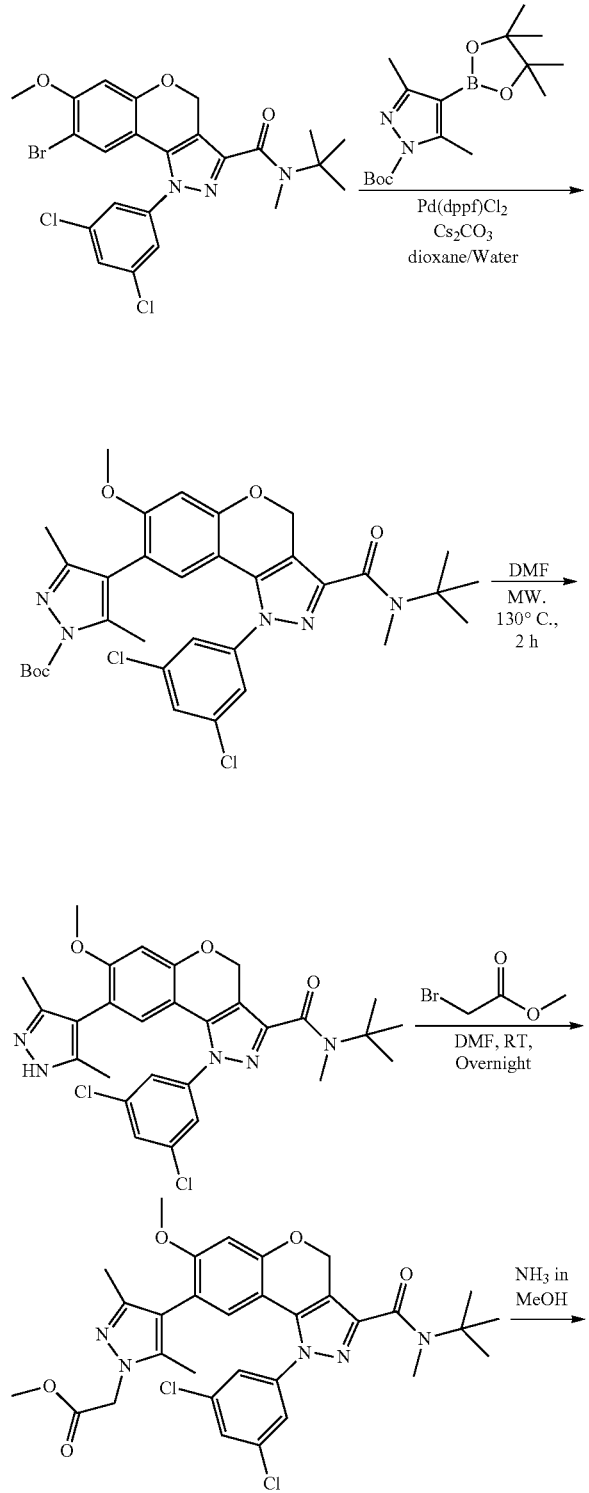

234

-continued

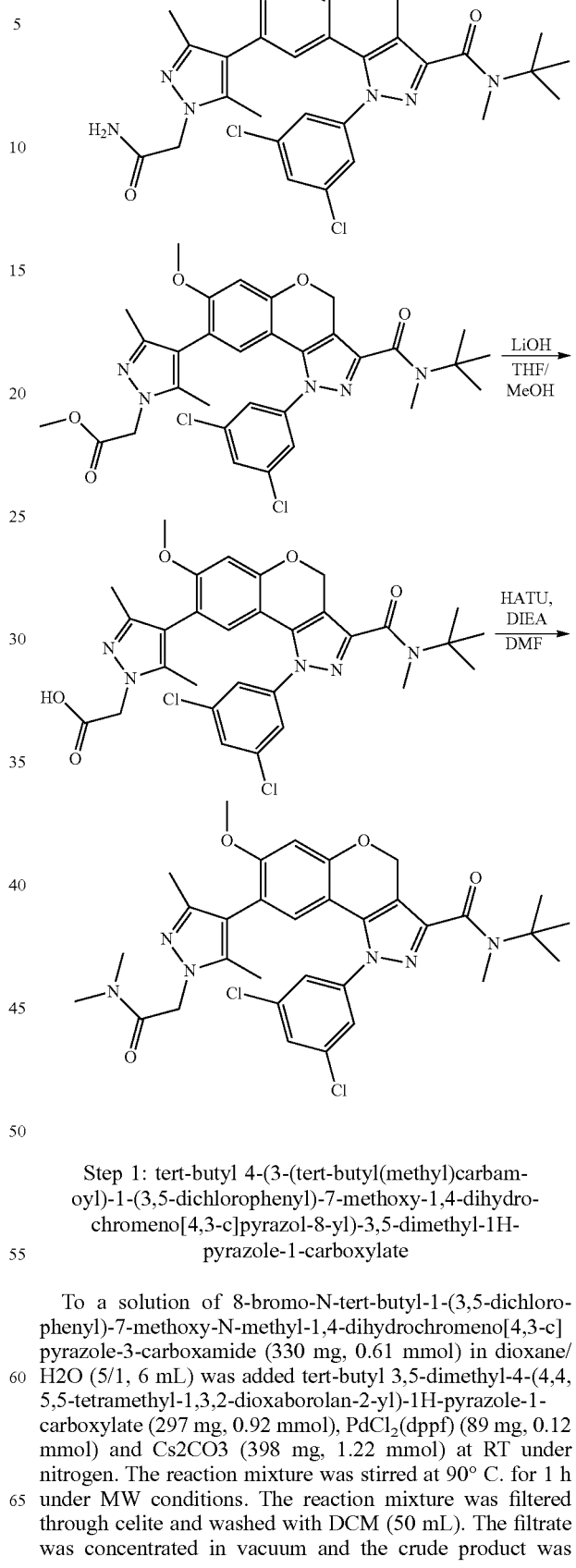

Step 1: tert-butyl 4-(3-(tert-butyl(methyl)carbamoyl)-1-(3,5-dichlorophenyl)-7-methoxy-1,4-dihydrochromeno[4,3-c]pyrazol-8-yl)-3,5-dimethyl-1H-pyrazole-1-carboxylate To a solution of 8-bromo-N-tert-butyl-1-(3,5-dichlorophenyl)-7-methoxy-N-methyl-1,4-dihydrochromeno[4,3-c]pyrazole-3-carboxamide (330 mg, 0.61 mmol) in dioxane/H2O (5/1, 6 mL) was added tert-butyl 3,5-dimethyl-4-(4,4,5,5-tetramethyl-1,3,2-dioxaborolan-2-yl)-1H-pyrazole-1-carboxylate (297 mg, 0.92 mmol), PdCl$_2$(dppf) (89 mg, 0.12 mmol) and Cs2CO3 (398 mg, 1.22 mmol) at RT under nitrogen. The reaction mixture was stirred at 90° C. for 1 h under MW conditions. The reaction mixture was filtered through celite and washed with DCM (50 mL). The filtrate was concentrated in vacuum and the crude product was purified by column chromatograph using pet ether: ethyl acetate as eluent to afford the desired compound (230 mg, 56%) as an off-white solid.

Step 2: N-tert-butyl-1-(3,5-dichlorophenyl)-8-(3,5-dimethyl-1H-pyrazol-4-yl)-7-methoxy-N-methyl-1,4-dihydrochromeno[4,3-c]pyrazole-3-carboxamide A solution of tert-butyl 4-(3-(tert-butyl(methyl)carbamoyl)-1-(3,5-dichlorophenyl)-7-methoxy-1,4-dihydrochromeno[4,3-c]pyrazol-8-yl)-3,5-dimethyl-1H-pyrazole-1-carboxylate (120 mg, 0.18 mmol) in DMF (5 mL) was stirred at 120° C. for 2 h under MW conditions. The solution was diluted with $H_2O$ (50 mL), exacted with EA (20 mL×3). The combined organics were washed with brine (20 mL×2), dried with Na2SO4, and concentrated to give the crude product (100 mg, 99%) as a pale yellow solid. m/z=654 $[M+H]^+$.

Step 3: methyl 2-(4-(3-(tert-butyl(methyl)carbamoyl)-1-(3,5-dichlorophenyl)-7-methoxy-1,4-dihydrochromeno[4,3-c]pyrazol-8-yl)-3,5-dimethyl-1H-pyrazol-1-yl)acetate (Compound 138)

To a solution of N-tert-butyl-1-(3,5-dichlorophenyl)-8-(3,5-dimethyl-1H-pyrazol-4-yl)-7-methoxy-N-methyl-1,4-dihydrochromeno[4,3-c]pyrazole-3-carboxamide (100 mg, 0.18 mmol) in DMF (3 mL) was added $Cs_2CO_3$ (117 mg, 0.36 mmol) and methyl 2-bromoacetate (55 mg, 0.36 mmol). The reaction mixture was stirred at RT overnight, then directly purified by Combi-Flash (mobile phase: acetonitrile/water (10 mM $NH_4HCO_3$)) to afford methyl 2-(4-(3-(tert-butyl(methyl)carbamoyl)-1-(3,5-dichlorophenyl)-7-methoxy-1,4-dihydrochromeno[4,3-c]pyrazol-8-yl)-3,5-dimethyl-1H-pyrazol-1-yl)acetate (100 mg, 88%) as a white solid. LCMS m/z=626 $[M+H]^+$. $^1$H NMR (400 MHz, $CDCl_3$) δ 7.44-7.43 (m, 3H), 6.69 (s, 1H), 6.61 (s, 1H), 5.45 (s, 2H), 4.79 (s, 2H), 3.78 (d, J=1.7 Hz, 6H), 3.24 (s, 3H), 2.00 (d, J=9.6 Hz, 6H), 1.52 (s, 9H).

Step 4: 8-(1-(2-amino-2-oxoethyl)-3,5-dimethyl-1H-pyrazol-4-yl)-N-tert-butyl-1-(3,5-dichlorophenyl)-7-methoxy-N-methyl-1,4-dihydrochromeno[4,3-c]pyrazole-3-carboxamide (Compound 139)

A mixture of methyl 2-(4-(3-(tert-butyl(methyl)carbamoyl)-1-(3,5-dichlorophenyl)-7-methoxy-1,4-dihydrochromeno[4,3-c]pyrazol-8-yl)-3,5-dimethyl-1H-pyrazol-1-yl)acetate (10 mg, 0.016 mmol) and $NH_3$ in MeOH (2 ml) was sealed up and heated to 60° C. for 2 h. The solvents were removed to give the crude product, which was purified by preparative HPLC to give desired product (7 mg, 70%) as a white solid. LCMS m/z=611 $[M+H]^+$. $^1$H NMR (400 MHz, $CDCl_3$) δ 7.44-7.43 (m, 3H), 6.69 (s, 1H), 6.61 (s, 1H), 5.45 (s, 2H), 4.79 (s, 2H), 3.78 (d, J=1.7 Hz, 6H), 3.24 (s, 3H), 2.00 (d, J=9.6 Hz, 6H), 1.52 (s, 9H).

Step 5: 2-(4-(3-(tert-butyl(methyl)carbamoyl)-1-(3,5-dichlorophenyl)-7-methoxy-1,4-dihydrochromeno[4,3-c]pyrazol-8-yl)-3,5-dimethyl-1H-pyrazol-1-yl)acetic acid (Compound 137)

To a solution of methyl 2-(4-(3-(tert-butyl(methyl)carbamoyl)-1-(3,5-dichlorophenyl)-7-methoxy-1,4-dihydrochromeno[4,3-c]pyrazol-8-yl)-3,5-dimethyl-1H-pyrazol-1-yl)acetate (90 mg, 0.14 mmol) in the mixture of THF (3 mL) and $H_2O$ (3 mL) was added $LiOH.H_2O$ (29 mg, 0.7 mmol) at RT. The reaction mixture was stirred at RT for 16 h. The reaction mixture was and concentrated. The residue was purified by Combi-Flash (mobile phase: acetonitrile/water (10 mM $NH_4HCO_3$)) to afford 2-(4-(3-(tert-butyl(methyl)carbamoyl)-1-(3,5-dichlorophenyl)-7-methoxy-1,4-dihydrochromeno[4,3-c]pyrazol-8-yl)-3,5-dimethyl-1H-pyrazol-1-yl)acetic acid (80 mg, 91%) as a white solid. LCMS m/z=612 $[M+H]^+$. $^1$H NMR (400 MHz, $CDCl_3$) δ 7.47-7.43 (m, 3H), 6.71 (s, 1H), 6.58 (s, 1H), 5.46 (s, 2H), 4.93 (s, 2H), 3.78 (s, 3H), 3.24 (s, 3H), 2.06-2.01 (m, 6H), 1.52 (s, 9H).

Step 6: N-tert-butyl-1-(3,5-dichlorophenyl)-8-(1-(2-(dimethylamino)-2-oxoethyl)-3,5-dimethyl-1H-pyrazol-4-yl)-7-methoxy-N-methyl-1,4-dihydrochromeno[4,3-c]pyrazole-3-carboxamide (Compound 136)

To a solution of 2-(4-(3-(tert-butyl(methyl)carbamoyl)-1-(3,5-dichlorophenyl)-7-methoxy-1,4-dihydrochromeno[4,3-c]pyrazol-8-yl)-3,5-dimethyl-1H-pyrazol-1-yl)acetic acid (45 mg, 0.074 mmol) in DMF (1 mL) was added dimethylamine hydrochloride (12 mg, 0.147 mmol), HATU (42 mg, 0.11 mmol) and DIEA (38.2 mg, 0.296 mmol). The mixture was stirred at RT overnight. Then the mixture was directly purified by Combi-Flash (mobile phase: acetonitrile/water (10 mM $NH_4HCO_3$)) to afford N-tert-butyl-1-(3,5-dichlorophenyl)-8-(1-(2-(dimethylamino)-2-oxoethyl)-3,5-dimethyl-1H-pyrazol-4-yl)-7-methoxy-N-methyl-1,4-dihydrochromeno[4,3-c]pyrazole-3-carboxamide (20 mg, 43%) as a white solid. LCMS m/z=639 $[M+H]^+$. $^1$H NMR (400 MHz, $CDCl_3$) δ 7.43 (s, 3H), 6.69 (s, 1H), 6.64 (s, 1H), 5.44 (s, 2H), 4.84 (s, 2H), 3.77 (s, 3H), 3.24 (s, 3H), 3.08 (s, 3H), 2.98 (s, 3H), 2.00 (s, 6H), 1.51 (s, 9H).

The following compounds were prepared using procedures analogous to those disclosed in Scheme 7.

| Compound | Boronic Acid Starting Material | Amine Starting Material | LC-MS | NMR |
|---|---|---|---|---|
| 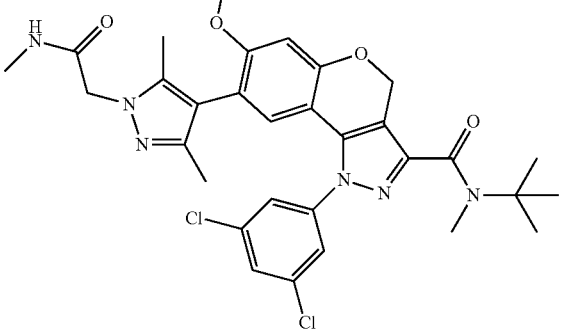<br>N-tert-butyl-1-(3,5-dichlorophenyl)-8-(3,5-dimethyl-1-(2-(methylamino)-2-oxoethyl)-1H-pyrazol-4-yl)-7-methoxy-N-methyl-1,4-dihydrochromeno[4,3-c]pyrazole-3-carboxamide<br>Compound 140 | 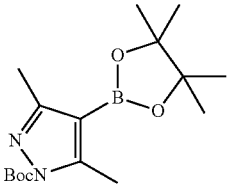 |  | m/z: 625 [M + H]$^+$ | $^1$H NMR (400 MHz, CDCl$_3$) δ 7.46-7.44 (m, 3H), 6.70 (s, 1H), 6.57 (s, 1H), 6.23-6.21 (m, 1H), 5.46 (s, 2H), 4.66 (s, 2H), 3.79 (s, 3H), 3.24 (s, 3H), 2.81 (d, J = 4.8 Hz, 3H), 2.01 (d, J = 15.0 Hz, 6H), 1.52 (s, 9H). |
| 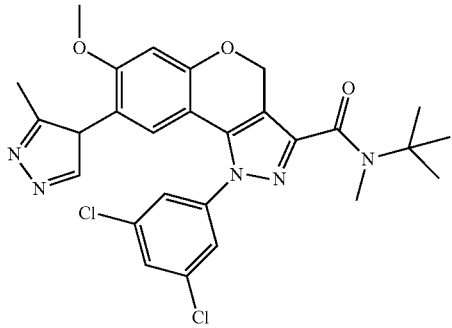 [SMILES: COc1cc2c(cc1C1C=NN=C1C)-c1c(c(C(=O)N(C)C(C)(C)C)nn1-c1cc(Cl)cc(Cl)c1)CO2]<br>N-tert-butyl-1-(3,5-dichlorophenyl)-7-methoxy-N-methyl-8-(5-methyl-1H-pyrazol-4-yl)-1,4-dihydrochromeno[4,3-c]pyrazole-3-carboxamide<br>Compound 141 | 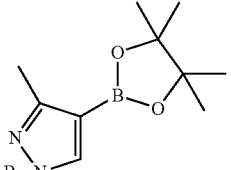 |  | m/z: 540 [M + H]$^+$ | $^1$H NMR (400 MHz, CDCl$_3$) δ 7.56-7.43 (m, 4H), 6.76 (s, 1H), 6.69 (s, 1H), 5.45 (s, 2H), 3.82 (s, 3H), 3.25 (s, 3H), 2.11 (s, 3H), 1.52 (s, 9H). |
| 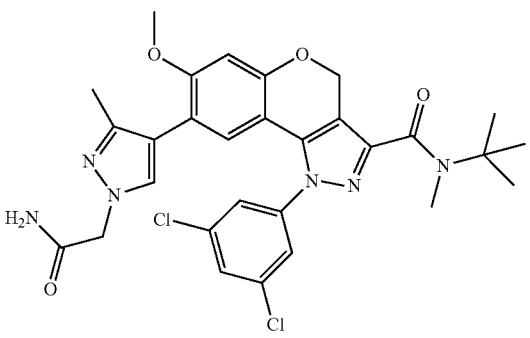 [SMILES: COc1cc2c(cc1-c1cn(CC(N)=O)nc1C)-c1c(c(C(=O)N(C)C(C)(C)C)nn1-c1cc(Cl)cc(Cl)c1)CO2]<br>8-(1-(2-amino-2-oxoethyl)-3-methyl-1H-pyrazol-4-yl)-N-tert-butyl-1-(3,5-dichlorophenyl)-7-methoxy-N-methyl-1,4-dihydrochromeno[4,3-c]pyrazole-3-carboxamide<br>Compound 142 | 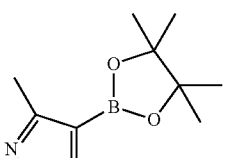 |  | m/z: 597 [M + H]$^+$ | $^1$H NMR (500 MHz, CDCl$_3$) δ 7.48 (s, 4H), 6.79 (s, 1H), 6.69 (s, 1H), 6.40 (s, 1H), 5.60 (s, 1H), 5.45 (s, 2H), 4.71 (s, 2H), 3.83 (s, 3H), 3.25 (s, 3H), 2.05 (s, 3H), 1.50 (s, 9H). |

| Compound | Boronic Acid Starting Material | Amine Starting Material | LC-MS | NMR |
|---|---|---|---|---|
| 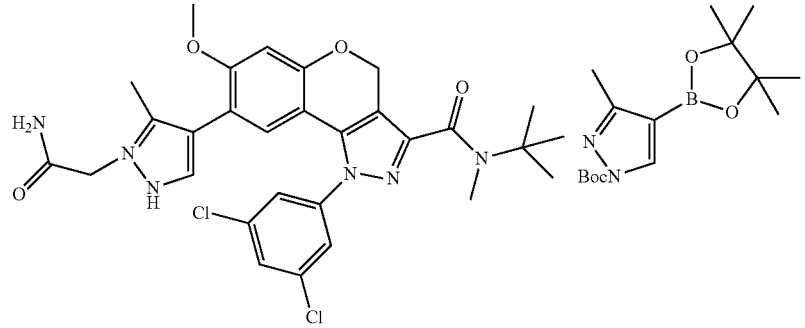<br>8-(1-(2-amino-2-oxoethyl)-5-methyl-1H-pyrazol-4-yl)-N-tert-butyl-1-(3,5-dichlorophenyl)-7-methoxy-N-methyl-1,4-dihydrochromeno[4,3-c]pyrazole-3-carboxamide<br>Compound 143 | 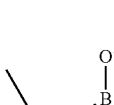 |  | m/z: 597 [M + H]+ | $^1$H NMR (400 MHz, CDCl$_3$) δ 7.50-7.48 (m, 4H), 6.71 (d, J = 6.0 Hz, 2H), 6.10 (s, 1H), 5.60 (s, 1H), 5.45 (s, 2H), 4.74 (s, 2H), 3.82 (s, 3H), 3.25 (s, 3H), 2.09 (s, 3H), 1.52 (s, 9H). |

Example 9. N-tert-butyl-8-(4-carbamoyl-1-methyl-1H-pyrazol-3-yl)-1-(3,5-dimethoxyphenyl)-7-methoxy-N-methyl-1,4-dihydrochromeno[4,3-c]pyrazole-3-carboxamide (Compound 144)

Scheme 8

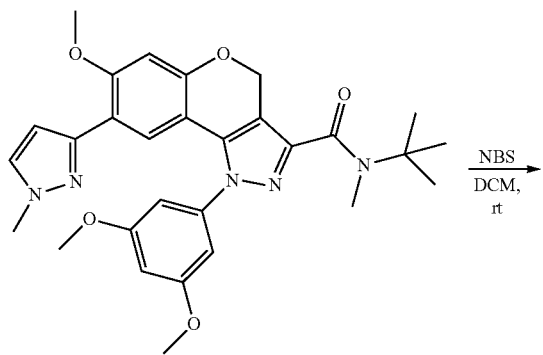

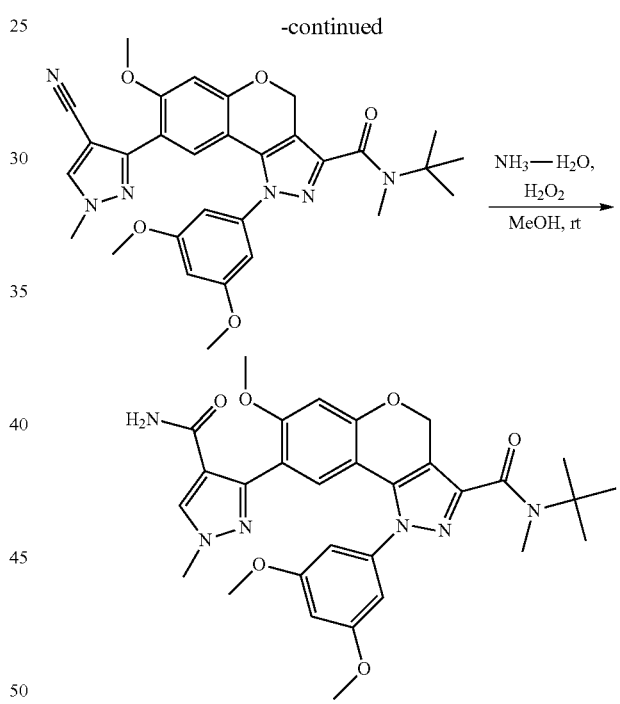

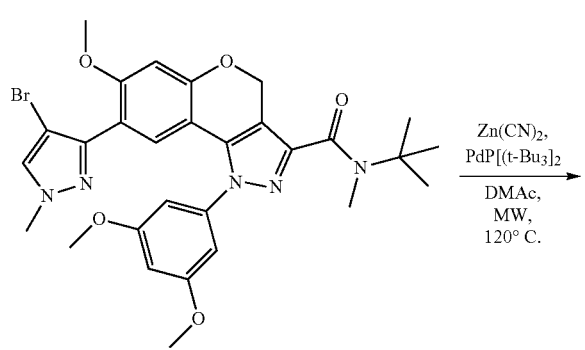

Step 1: 8-(4-bromo-1-methyl-1H-pyrazol-3-yl)-N-tert-butyl-1-(3,5-dimethoxyphenyl)-7-methoxy-N-methyl-1,4-dihydrochromeno[4,3-c]pyrazole-3-carboxamide (Compound 145)

To a solution of N-tert-butyl-1-(3,5-dimethoxyphenyl)-7-methoxy-N-methyl-8-(1-methyl-1H-pyrazol-3-yl)-1,4-dihydrochromeno[4,3-c]pyrazole-3-carboxamide (250 mg, 0.47 mmol) in DCM (10 mL) was added NBS (84 mg, 0.47 mmol). The mixture was stirred at RT for 6 h. Then the mixture was directly purified by pre-TLC (peth:EA=3:2) to afford 8-(4-bromo-1-methyl-1H-pyrazol-3-yl)-N-tert-butyl-1-(3,5-dimethoxyphenyl)-7-methoxy-N-methyl-1,4 dihydrochromeno[4,3-c]pyrazole-3-carboxamide (200 mg, 70%)

as a white solid. LCMS m/z=610[M+H]⁺. ¹H NMR (400 MHz, CDCl₃): 7.39 (s, 1H), 7.05 (s, 1H), 6.69 (s, 1H), 6.67 (d, 2H), 6.51 (t, 1H), 5.51 (s, 2H), 3.88 (s, 3H), 3.83 (s, 3H), 3.80 (s, 6H), 3.28 (s, 3H), 1.53 (s, 9H).

Step 2: N-tert-butyl-8-(4-cyano-1-methyl-1H-pyrazol-3-yl)-1-(3,5-dimethoxyphenyl)-7-methoxy-N-methyl-1,4-dihydrochromeno[4,3-c]pyrazole-3-carboxamide (Compound 146)

To a solution of 8-(4-bromo-1-methyl-1H-pyrazol-3-yl)-N-tert-butyl-1-(3,5-dimethoxyphenyl)-7-methoxy-N-methyl-1,4-dihydrochromeno[4,3-c]pyrazole-3-carboxamide (90 mg, 0.15 mmol) in DMAc (3 mL) was added zinc cyanide (52 mg, 0.45 mmol), zinc powder (30 mg, 0.45 mmol) and PdP[(t-Bu)3]2 (15 mg, 0.3 mmol) at RT under nitrogen. The mixture was stirred at 120° C. for 1 h under MW conditions. The mixture was filtered and directly purified by purified by Combi-Flash (mobile phase: acetonitrile/water (10 mM NH₄HCO₃)) to afford N-tert-butyl-8-(4-cyano-1-methyl-1H-pyrazol-3-yl)-1-(3,5-dimethoxyphenyl)-7-methoxy-N-methyl-1,4-dihydrochromeno[4,3-c]pyrazole-3-carboxamide (60 mg, 73%) as a white solid. LCMS m/z 557 [M+H]⁺. ¹H NMR (400 MHz, CDCl₃): 7.77 (s, 1H), 7.29 (s, 1H), 6.69 (m, 3H), 6.55 (t, 1H), 5.54 (s, 2H), 3.91 (s, 3H), 3.89 (s, 3H), 3.82 (s, 6H), 3.29 (s, 3H), 1.54 (s, 9H).

Step 3: N-tert-butyl-8-(4-carbamoyl-1-methyl-1H-pyrazol-3-yl)-1-(3,5-dimethoxyphenyl)-7-methoxy-N-methyl-1,4-dihydrochromeno[4,3-c]pyrazole-3-carboxamide (Compound 144)

To a solution of N-tert-butyl-8-(4-cyano-1-methyl-1H-pyrazol-3-yl)-1-(3,5-dimethoxyphenyl)-7-methoxy-N-methyl-1,4-dihydrochromeno[4,3-c]pyrazole-3-carboxamide (20 mg, 0.36 mmol) in MeOH (1 mL) was added NH₃.H₂O (0.5 mL) and H₂O₂(0.5 mL, 30%) at RT. The mixture was stirred at RT overnight. The mixture was concentrated in vacuum and the residue was directly purified by Combi-Flash (mobile phase: acetonitrile/water (10 mM NH₄HCO₃)) to afford N-tert-butyl-8-(4-carbamoyl-1-methyl-1H-pyrazol-3-yl)-1-(3,5-dimethoxyphenyl)-7-methoxy-N-methyl-1,4-dihydrochromeno[4,3-c]pyrazole-3-carboxamide (6 mg, 29%) as a white solid. LCMS m/z=575 [M+H]⁺. ¹H NMR (400 MHz, CDCl₃): 7.92 (s, 1H), 7.03 (s, 1H), 6.71 (s, 1H), 6.64 (d, 2H), 6.53 (t, 1H), 5.53 (s, 2H), 3.89 (s, 3H), 3.82 (s, 6H), 3.80 (s, 3H), 3.29 (s, 3H), 1.53 (s, 9H).

The following compounds were prepared using procedures analogous to those disclosed in Scheme 8.

| Compound | Boronic acid Starting material | Amine Starting material | LC/MS | NMR |
|---|---|---|---|---|
| 8-(4-bromo-1-methyl-1H-pyrazol-3-yl)-N-(2-cyanopropan-2-yl)-1-(3,5-difluorophenyl)-7-methoxy-N-methyl-1,4-dihydrochromeno[4,3-c]pyrazole-3-carboxamide Compound 147 | | | m/z: 597 [M + H]⁺ | ¹H NMR (400 MHz,CDCl₃) δ 7.39 (s, 1H), 7.17-7.07 (m, 2H), 6.97-6.87 (m, 2H), 6.70 (s, 1H), 5.54 (s, 2H), 3.87 (s, 3H), 3.82 (s, 3H), 3.45 (s, 3H), 1.83 (s, 6H). |
| 8-(4-bromo-1-methyl-1H-pyrazol-3-yl)-N-tert-butyl-1-(3,5-dichlorophenyl)-7-methoxy-N-methyl-1,4-dihydrochromeno[4,3-c]pyrazole-3-carboxamide Compound 148 | | | m/z: 618 [M + H]⁺ | ¹H NMR (400 MHz, CDCl₃) δ 7.50-7.44 (m, 2H), 7.42 (t, J = 1.8 Hz, 1H), 7.39 (s, 1H), 6.93 (s, 1H), 6.69 (s, 1H), 5.46 (s, 2H), 3.88 (s, 3H), 3.82 (s, 3H), 3.24 (s, 3H), 1.51 (s, 9H). |

-continued

| Compound | Boronic acid Starting material | Amine Starting material | LC/MS | NMR |
|---|---|---|---|---|
| 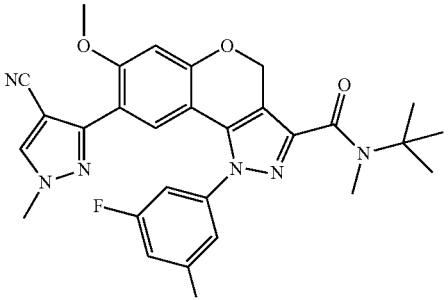<br>N-tert-butyl-8-(4-cyano-1-methyl-1H-pyrazol-3-yl)-1-(3,5-difluorophenyl)-7-methoxy-N-methyl-1,4-dihydrochromeno[4,3-c]pyrazole-3-carboxamide<br>Compound 149 | 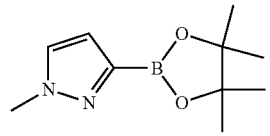 | 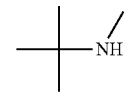 | m/z: 533 [M + H]⁺ | ¹H NMR (400 MHz, CDCl₃) δ 7.76 (s, 1H), 7.22 (s, 1H), 7.18-7.10 (m, 2H), 6.924-6.90 (m, 1H), 6.69 (s, 1H), 5.49 (s, 2H), 3.90 (s, 3H), 3.88 (s, 3H), 3.26 (s, 3H), 1.52 (s, 9H). |
| 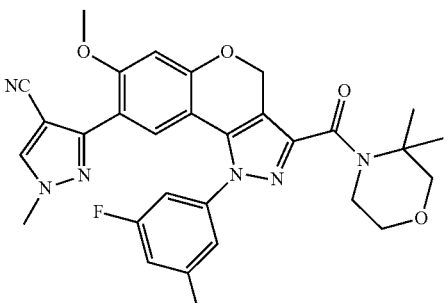<br>3-(1-(3,5-difluorophenyl)-3-(3,3-dimethylmorpholine-4-carbonyl)-7-methoxy-1,4-dihydrochromeno[4,3-c]pyrazol-8-yl)-1-methyl-1H-pyrazole-4-carbonitrile<br>Compound 150 | 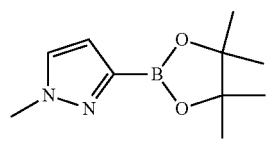 | 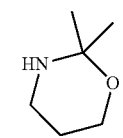 | m/z: 561 [M + H]⁺ | ¹H NMR (400 MHz, CDCl₃) δ 7.77 (s, 1H), 7.20 (s, 1H), 7.16-7.09 (m, 2H), 6.95-6.90 (m, 1H), 6.69 (s, 1H), 5.49 (s, 2H), 4.05-4.03 (m, 2H), 3.90 (s, 3H), 3.89 (s, 3H), 3.87-3.82 (m, 2H), 3.49 (s, 2H), 1.53 (s, 6H). |
| 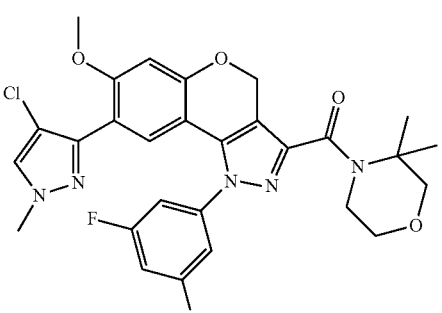<br>(8-(4-chloro-1-methyl-1H-pyrazol-3-yl)-1-(3,5-difluorophenyl)-7-methoxy-1,4-dihydrochromeno[4,3-c]pyrazol-3-yl)(3,3-dimethylmorpholino)methanone<br>Compound 151 | 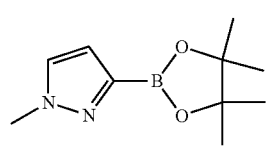 | 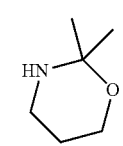 | m/z: 570 [M + H]⁺ | ¹H NMR (400 MHz, CDCl₃) δ 7.36 (s, 1H), 7.17-7.05 (m, 2H), 6.96 (s, 1H), 6.95-6.85 (m, 1H), 6.70 (s, 1H), 5.47 (s, 2H), 4.15-4.00 (m, 2H), 3.85-3.83 (m, 8H), 3.48 (s, 2H), 1.53 (s, 6H). |

| Compound | Boronic acid Starting material | Amine Starting material | LC/MS | NMR |
|---|---|---|---|---|
| 8-(4-chloro-1-methyl-1H-pyrazol-3-yl)-N-(2-cyanopropan-2-yl)-1-(3,5-difluorophenyl)-7-methoxy-N-methyl-1,4-dihydrochromeno[4,3-c]pyrazole-3-carboxamide<br>Compound 152 | | | m/z: 553 [M + H]$^+$ | $^1$H NMR (400 MHz, CDCl$_3$) δ 7.37 (s, 1H), 7.15-7.10 (m, 2H), 6.96, 6.90 (m, 2H), 6.71 (s, 1H), 5.54 (s, 2H), 3.86 (s, 3H), 3.83 (s, 3H), 3.45 (s, 3H), 1.84 (s, 6H). |
| N-tert-butyl-8-(4-carbamoylpyridin-3-yl)-1-(3,5-dichlorophenyl)-7-methoxy-N-methyl-1,4-dihydrochromeno[4,3-c]pyrazole-3-carboxamide<br>Compound 153 | | | m/z: 580 [M + H]$^+$ | $^1$H NMR (400 MHz, CDCl$_3$): 8.669-8.656 (d, 1H, J = 5.2 Hz), 8.416 (s, 1H), 7.592-7.579 (d, 1H, J = 5.2 Hz), 7.499-7.494 (d, 2H, J = 2.0 Hz), 7.453-7.444 (t, 1H, J = 1.6 Hz), 6.883 (s, 1H), 6.690 (s, 1H), 5.632-5.484 (m, 4H), 3.765 (s, 3H), 3.260 (s, 3H), 1.510 (s, 9H). |
| N-tert-butyl-8-(5-carbamoylpyridin-3-yl)-1-(3-chloro-5-fluorophenyl)-7-methoxy-N-methyl-1,4-dihydrochromeno[4,3-c]pyrazole-3-carboxamide<br>Compound 154 | | | m/z: 564 [M + H]$^+$ | $^1$H NMR (400 MHz, CDCl$_3$): 8.91 (d, 1H), 8.67 (d, 1H), 7.08 (t, 1H), 7.43 (s, 1H), 7.25 (m, 2H), 6.90 (s, 1H), 6.75 (s, 1H), 5.50 (s, 2H), 3.84 (s, 3H), 3.28 (s, 3H), 1.53 (s, 9H). |

| Compound | Boronic acid Starting material | Amine Starting material | LC/MS | NMR |
|---|---|---|---|---|
| 5-(1-(3-chloro-5-fluorophenyl)-3-(3,3-dimethylmorpholine-4-carbonyl)-7-methoxy-1,4-dihydrochromeno[4,3-c]pyrazol-8-yl)nicotinamide<br>Compound 155 | 5-cyanopyridine-3-boronic acid pinacol ester | 3,3-dimethylmorpholine | m/z: 592 [M + H]⁺ | $^1$H NMR (400 MHz, CDCl$_3$) δ 8.90 (d, J = 2.1 Hz, 1H), 8.67 (d, J = 2.1 Hz, 1H), 8.08 (t, J = 2.1 Hz, 1H), 7.40 (s, 1H), 7.26-7.22 (m, 2H), 6.87 (s, 1H), 6.74 (s, 1H), 5.49 (s, 2H), 4.11-4.01 (m, 2H), 3.89-3.78 (m, 5H), 3.50 (s, 2H), 1.53 (s, 6H). |
| N-tert-butyl-8-(5-carbamoylpyridin-3-yl)-1-(3-chloro-5-methoxyphenyl)-7-methoxy-N-methyl-1,4-dihydrochromeno[4,3-c]pyrazole-3-carboxamide<br>Compound 156 | 5-cyanopyridine-3-boronic acid pinacol ester | N-tert-butyl-N-methylamine | m/z: 576 [M + H]⁺ | $^1$H NMR (400 MHz, CDCl$_3$) δ 8.91 (d, J = 2.0 Hz, 1H), 8.66 (d, J = 2.0 Hz, 1H), 8.03 (t, J = 2.1 Hz, 1H), 7.16 (t, J = 1.7 Hz, 1H), 7.03-7.00 (m, 2H), 6.87 (s, 1H), 6.70 (d, J = 5.7 Hz, 1H), 5.50 (s, 2H), 3.84 (d, J = 4.1 Hz, 3H), 3.82 (s, 3H), 3.27 (s, 3H), 1.52 (s, 9H). |
| 5-(1-(3-chloro-5-methoxyphenyl)-3-(3,3-dimethylmorpholine-4-carbonyl)-7-methoxy-1,4-dihydrochromeno[4,3-c]pyrazol-8-yl)nicotinamide<br>Compound 157 | 5-cyanopyridine-3-boronic acid pinacol ester | 3,3-dimethylmorpholine | m/z: 604 [M + H]⁺ | $^1$H NMR (400 MHz, CDCl$_3$) δ 8.90 (d, J = 2.1 Hz, 1H), 8.67 (d, J = 2.1 Hz, 1H), 8.02 (t, J = 2.1 Hz, 1H), 7.14 (t, J = 1.7 Hz, 1H), 7.04 (t, J = 2.0 Hz, 1H), 7.00 (t, J = 2.0 Hz, 1H), 6.86 (s, 1H), 6.72 (s, 1H), 5.51 (s, 2H), 4.13-4.04 (m, 2H), 3.87-3.83 (m, 8H), 3.49 (s, 2H), 1.53 (s, 6H). |

-continued

| Compound | Boronic acid Starting material | Amine Starting material | LC/ MS | NMR |
|---|---|---|---|---|
| 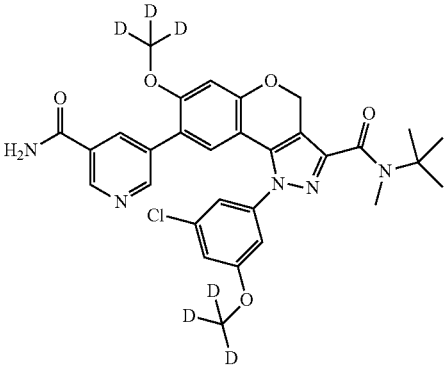 [SMILES: [2H]C([2H])([2H])Oc1cc(Cl)cc(-n2nc(C(=O)N(C)C(C)(C)C)c3c2-c2cc(-c4cncc(C(N)=O)c4)c(OC([2H])([2H])[2H])cc2OC3)c1]<br>5-{3-[tert-butyl(methyl)carbamoyl]-1-(3-chloro-5-D₃-methoxyphenyl)-7-D₃-methoxy-1H,4H-chromeno[4,3-c]pyrazol-8-yl}pyridine-3-carboxamide<br>Compound 158 | 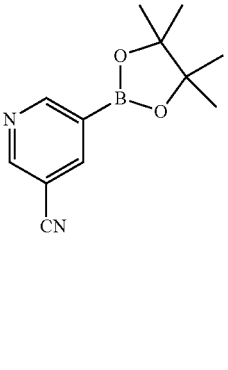 |  | m/z: 582 [M + H]⁺ | ¹H NMR (500 MHz, CDCl₃): 8.93 (d, 1H), 8.69 (d, 1H), 8.04 (t, 1H), 7.17 (t, 1H), 7.04 (m, 2H), 6.89 (s, 1H), 6.72 (s, 1H), 5.52 (s, 2H), 3.29 (s, 3H), 1.54 (s, 9H). |
| 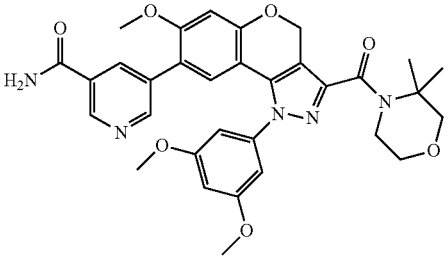<br>5-(1-(3,5-dimethoxyphenyl)-3-(3,3-dimethylmorpholine-4-carbonyl)-7-methoxy-1,4-dihydrochromeno[4,3-c]pyrazol-8-yl)nicotinamide<br>Compound 159 | 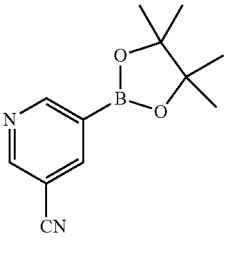 [SMILES: CC1(C)OB(c2cncc(C#N)c2)OC1(C)C] | 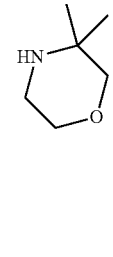 | m/z: 600 [M + H]⁺ | ¹H NMR (400 MHz, CDCl₃) δ 8.91 (d, J = 2.1 Hz, 1H), 8.68 (d, J = 2.1 Hz, 1H), 7.92 (t, J = 2.1 Hz, 1H), 6.84 (s, 1H), 6.72-6.64 (m, 3H), 6.60 (t, J = 2.3 Hz, 1H), 5.53 (s, 2H), 4.16-4.08 (m, 2H), 3.89-3.78 (m, 11H), 3.49 (s, 2H), 1.54 (s, 6H). |
| 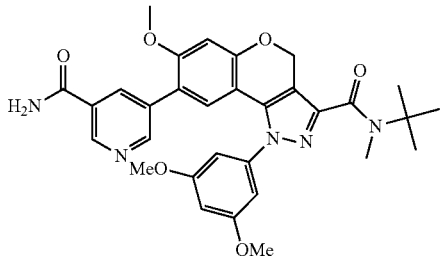 [SMILES: COc1cc(OC)cc(-n2nc(C(=O)N(C)C(C)(C)C)c3c2-c2cc(-c4cncc(C(N)=O)c4)c(OC)cc2OC3)c1]<br>N-tert-butyl-8-(5-carbamoylpyridin-3-yl)-1-(3,5-dimethoxyphenyl)-7-methoxy-N-methyl-1,4-dihydrochromeno[4,3-c]pyrazole-3-carboxamide<br>Compound 160 | 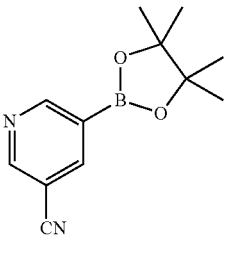 |  | m/z: 572 [M + H]⁺ | ¹H NMR (400 MHz, CDCl₃) δ 8.92 (d, J = 2.1 Hz, 1H), 8.69 (d, J = 2.0 Hz, 1H), 7.92 (t, J = 2.0 Hz, 1H), 6.85 (s, 1H), 6.72-6.67 (m, 3H), 6.59 (t, J = 2.2 Hz, 1H), 5.53 (s, 2H), 3.82-3.81 (m, 9H), 3.28 (s, 3H), 1.52 (s, 9H). |

| Compound | Boronic acid Starting material | Amine Starting material | LC/MS | NMR |
|---|---|---|---|---|
| N-tert-butyl-8-(5-carbamoylpyridin-3-yl)-1-(3,5-difluorophenyl)-7-methoxy-N-methyl-1,4-dihydrochromeno[4,3-c]pyrazole-3-carboxamide<br>Compound 161 | 5-cyanopyridin-3-yl boronic acid | N-methyl-tert-butylamine | m/z: 548 [M + H]⁺ | ¹H NMR (400 MHz, CDCl₃) δ 8.90 (d, J = 2.1 Hz, 1H), 8.66 (d, J = 2.1 Hz, 1H), 8.07 (t, J = 2.1 Hz, 1H), 71.8-7.13 (m, 2H), 7.02-6.92 (m, 1H), 6.89 (s, 1H), 6.73 (s, 1H), 5.49 (s, 2H), 3.83 (s, 3H), 3.27 (s, 3H), 1.52 (s, 9H). |
| 5-(1-(3,5-difluorophenyl)-3-(4-hydroxy-2,2-dimethylpiperidine-1-carbonyl)-7-methoxy-1,4-dihydrochromeno[4,3-c]pyrazol-8-yl)nicotinamide<br>Compound 162 | 5-cyanopyridin-3-yl boronic acid pinacol ester | 2,2-dimethyl-4-hydroxypiperidine | m/z: 590 [M + H]⁺ | ¹H NMR (400 MHz, DMSO) δ 8.89 (d, J = 2.0 Hz, 1H), 8.50 (d, J = 2.0 Hz, 1H), 8.11-8.10 (m, 1H), 7.64-7.45 (m, 3H), 6.93 (s, 1H), 6.83 (s, 1H), 5.41 (s, 2H), 4.73 (d, J = 4.5 Hz, 1H), 3.82 (s, 3H), 1.55 (s, 3H), 1.42 (s, 3H). |
| 5-[1-(3,5-difluorophenyl)-3-[(3,3-dimethyl-1-oxo-1$1^{4}$,4-thiomorpholin-4-yl)carbonyl]-7-methoxy-1H,4H-chromeno[4,3-c]pyrazol-8-yl]pyridine-3-carboxamide<br>Compound 163 | 5-cyanopyridin-3-yl boronic acid pinacol ester | 3,3-dimethylthiomorpholine 1-oxide | m/z: 608 [M + H]⁺ | ¹H NMR (400 MHz, CDCl₃) δ 8.90 (d, J = 2.1 Hz, 1H), 8.67 (d, J = 2.1 Hz, 1H), 8.07 (t, J = 2.1 Hz, 1H), 7.15 (dd, J = 6.8, 2.1 Hz, 2H), 7.04-6.95 (m, 1H), 6.89 (s, 1H), 6.74 (s, 1H), 5.50 (s, 2H), 4.53-4.47 (m, 1H), 4.39-4.32 (m, 1H), 3.84 (s, 3H), 3.61-3.52 (m, 1H), 3.10 (q, J = 13.8 Hz, 2H), 2.86-2.80 (m, 1H), 1.79 (s, 3H), 1.69 (s, 3H). |

-continued

| Compound | Boronic acid Starting material | Amine Starting material | LC/MS | NMR |
|---|---|---|---|---|
| 5-(1-(3,5-difluorophenyl)-3-(3,3-dimethylmorpholine-4-carbonyl)-7-methoxy-1,4-dihydrochromeno[4,3-c]pyrazol-8-yl)nicotinamide<br>Compound 164 | 5-cyano-pyridine-3-boronic acid pinacol ester | 3,3-dimethylmorpholine | m/z: 576 [M + H]+ | ¹H NMR (400 MHz, CDCl₃) δ 8.90 (d, J = 2.1 Hz, 1H), 8.66 (d, J = 2.1 Hz, 1H), 8.07 (t, J = 2.1 Hz, 1H), 7.17-7.12 (m, 2H), 7.02-6.92 (m, 1H), 6.88 (s, 1H), 6.74 (s, 1H), 5.50 (s, 2H), 4.13-4.03 (m, 2H), 3.90-3.80 (m, 5H), 3.50 (s, 2H), 1.53 (s, 6H). |
| N-tert-butyl-8-(3-carbamoyl-5-chlorophenyl)-1-(3,5-difluorophenyl)-7-methoxy-N-methyl-1,4-dihydrochromeno[4,3-c]pyrazole-3-carboxamide<br>Compound 165 | methyl 3-chloro-5-(4,4,5,5-tetramethyl-1,3,2-dioxaborolan-2-yl)benzoate | N-tert-butyl-N-methylamine | m/z: 581 [M + H]+ | ¹H NMR (400 MHz, CDCl₃) δ 7.73 (t, J = 1.8 Hz, 1H), 7.56 (t, J = 1.5 Hz, 1H), 7.46 (t, J = 1.8 Hz, 1H), 7.22-7.11 (m, 2H), 7.00-6.95 (m, 1H), 6.85 (s, 1H), 6.71 (s, 1H), 5.48 (s, 2H), 3.83 (s, 3H), 3.27 (s, 3H), 1.52 (s, 9H). |
| N-tert-butyl-8-(5-carbamoylpyridin-3-yl)-1-(3-fluoro-5-methoxyphenyl)-7-methoxy-N-methyl-1,4-dihydrochromeno[4,3-c]pyrazole-3-carboxamide<br>Compound 166 | 5-cyano-pyridine-3-boronic acid pinacol ester | N-tert-butyl-N-methylamine | m/z: 560 [M + H]+ | ¹H NMR (400 MHz, CDCl₃) δ 8.90 (d, J = 2.1 Hz, 1H), 8.67 (d, J = 2.1 Hz, 1H), 8.01 (t, J = 2.1 Hz, 1H), 6.95-6.85 (m, 3H), 6.78-6.74 (m, 1H), 6.71 (s, 1H), 5.51 (s, 2H), 3.84 (s, 3H), 3.83 (s, 3H), 3.27 (s, 3H), 1.52 (s, 9H). |
| N-tert-butyl-8-(5-carbamoylpyridin-3-yl)-7-methoxy-N-methyl-1-(thiophen-3-yl)-1,4-dihydrochromeno[4,3-c]pyrazole-3-carboxamide<br>Compound 167 | 5-cyano-pyridine-3-boronic acid pinacol ester | N-tert-butyl-N-methylamine | m/z: 518 [M + H]+ | ¹H NMR (400 MHz, CDCl₃) δ 8.86 (d, J = 2.0 Hz, 1H), 8.66 (d, J = 2.0 Hz, 1H), 8.10 (t, J = 2.0 Hz, 1H), 7.56-7.47 (m, 2H), 7.24-7.22 (m, 1H), 6.77 (s, 1H), 6.69 (s, 1H), 5.53 (s, 2H), 3.82 (s, 3H), 3.28 (s, 3H), 1.52 (s, 9H). |

-continued

| Compound | Boronic acid Starting material | Amine Starting material | LC/MS | NMR |
|---|---|---|---|---|
| 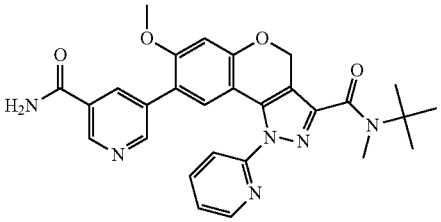 [SMILES: COc1cc2c(cc1-c1cncc(C(N)=O)c1)-c1c(c(C(=O)N(C)C(C)(C)C)nn1-c1ccccn1)CO2]<br>N-tert-butyl-8-(5-carbamoylpyridin-3-yl)-7-methoxy-N-methyl-1-(pyridin-2-yl)-1,4-dihydrochromeno[4,3-c]pyrazole-3-carboxamide<br>Compound 168 | 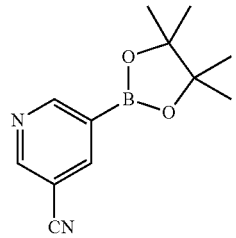 | 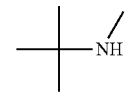 | m/z: 513 [M + H]⁺ | ¹H NMR (400 MHz, CDCl₃): 8.86 (d, 1H, J = 2.0 Hz), 8.78 (d, 1H, J = 2.0 Hz), 8.64-8.62 (m, 1H), 8.24 (t, 1H, J = 2.4 Hz), 7.93-7.89 (m, 1H), 7.77 (d, 1H, J = 8.4 Hz), 7.58 (s, 1H), 7.42-7.39 (m, 1H), 6.70 (s, 1H), 6.26 (brs, 1H), 5.78 (brs, 1H), 5.47 (s, 2H), 3.83 (s, 3H), 3.28 (s, 3H), 1.53 (s, 9H). |
| 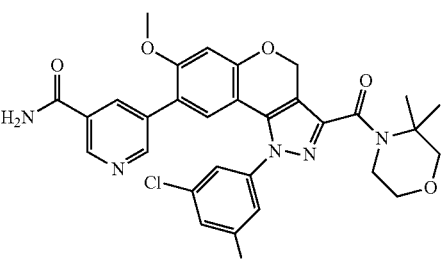<br>5-(1-(3,5-dichlorophenyl)-3-(3,3-dimethylmorpholine-4-carbonyl)-7-methoxy-1,4-dihydrochromeno[4,3-c]pyrazol-8-yl)nicotinamide<br>Compound 169 | 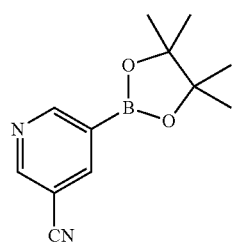 | 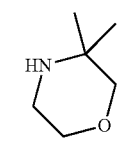 | m/z: 608 [M + H]⁺ | ¹H NMR (400 MHz, CDCl₃) δ 8.90 (d, J = 2.1 Hz, 1H), 8.67 (d, J = 2.1 Hz, 1H), 8.09 (t, J = 2.1 Hz, 1H), 7.50 (s, 3H), 6.86 (s, 1H), 6.74 (s, 1H), 5.49 (s, 2H), 4.11-4.03 (m, 2H), 3.90-3.81 (m, 5H), 3.50 (s, 2H), 1.53 (s, 6H). |
| 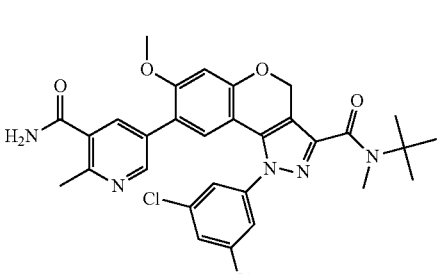<br>N-tert-butyl-8-(5-carbamoyl-6-methylpyridin-3-yl)-1-(3,5-dichlorophenyl)-7-methoxy-N-methyl-1,4-dihydrochromeno[4,3-c]pyrazole-3-carboxamide<br>Compound 170 | 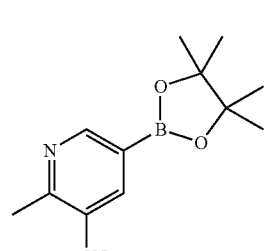 | 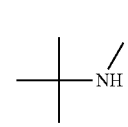 | m/z: 594 [M + H]⁺ | ¹H NMR (400 MHz, CDCl₃) δ 8.52 (d, J = 2.2 Hz, 1H), 7.70 (d, J = 2.2 Hz, 1H), 7.54-7.44 (m, 3H), 6.86 (s, 1H), 6.73 (s, 1H), 5.76 (s, 2H), 5.47 (s, 2H), 3.82 (s, 3H), 3.26 (s, 3H), 2.72 (s, 3H), 1.52 (s, 9H). |

-continued

| Compound | Boronic acid Starting material | Amine Starting material | LC/MS | NMR |
|---|---|---|---|---|
| 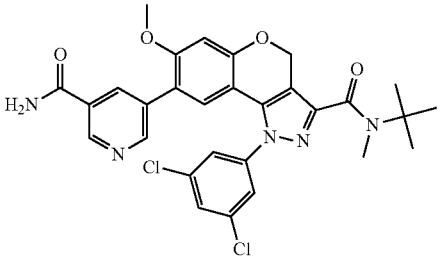 [SMILES: COc1cc2c(cc1-c1cncc(C(N)=O)c1)-c1c(c(C(=O)N(C)C(C)(C)C)nn1-c1cc(Cl)cc(Cl)c1)CO2]<br>5-{3-[tert-butyl(methyl)carbamoyl]-1-(3,5-dichlorophenyl)-7-methoxy-1H,4H-chromeno[4,3-c]pyrazol-8-yl}pyridine-3-carboxamide<br>Compound 171 | 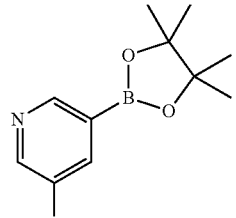 |  | m/z: 580 [M + H]⁺ | ¹H NMR (400 MHz, CDCl₃) δ 8.84 (d, J = 1.9 Hz, 1H), 8.60 (d, J = 1.9 Hz, 1H), 8.03 (t, J = 1.9 Hz, 1H), 7.45-7.41 (m, 3H), 6.81 (s, 1H), 6.66 (s, 1H), 5.41 (s, 2H), 3.76 (s, 3H), 3.19 (s, 3H), 1.45 (s, 9H). |
| 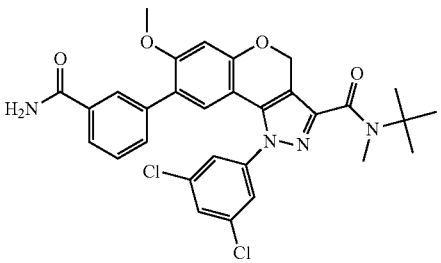 [SMILES: COc1cc2c(cc1-c1cccc(C(N)=O)c1)-c1c(c(C(=O)N(C)C(C)(C)C)nn1-c1cc(Cl)cc(Cl)c1)CO2]<br>N-tert-butyl-8-(3-carbamoylphenyl)-1-(3,5-dichlorophenyl)-7-methoxy-N-methyl-1,4-dihydrochromeno[4,3-c]pyrazole-3-carboxamide<br>Compound 172 | 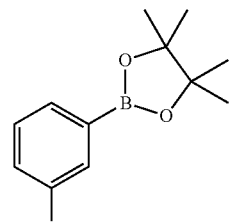 |  | m/z: 579 [M + H]⁺ | ¹H NMR (400 MHz, CDCl₃) δ 7.79-7.69 (m, 2H), 7.56-7.40 (m, 5H), 6.88 (s, 1H), 6.72 (s, 1H), 5.47 (s, 2H), 3.82 (s, 3H), 3.26 (s, 3H), 15.2 (s, 9H). |
| 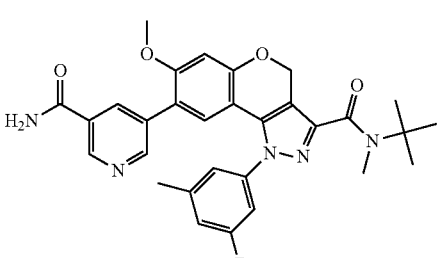<br>N-tert-butyl-8-(5-carbamoylpyridin-3-yl)-1-(3-fluoro-5-methylphenyl)-7-methoxy-N-methyl-1,4-dihydrochromeno[4,3-c]pyrazole-3-carbxoamide<br>Compound 173 | 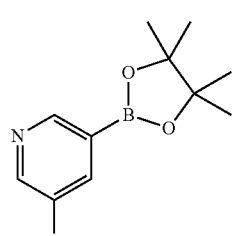 |  | m/z: 544 [M + H]⁺ | ¹H NMR (400 MHz, CDCl₃) δ 8.88 (d, J = 2.0 Hz, 1H), 8.63 (d, J = 2.0 Hz, 1H), 8.03 (t, J = 2.1 Hz, 1H), 7.18 (s, 1H), 7.09-7.03 (m, 2H), 6.82 (s, 1H), 6.71 (s, 1H), 5.52 (s, 2H), 3.82 (s, 3H), 3.28 (s, 3H), 2.44 (s, 3H), 1.52 (s, 9H). |

259

Example 10. 3-carbamoyl-5-(1-(3,5-dichlorophenyl)-3-(3,3-dimethylmorpholine-4-carbonyl)-7-methoxy-1,4-dihydrochromeno[4,3-c]pyrazol-8-yl)pyridine 1-oxide (Compound 174)

Scheme 9

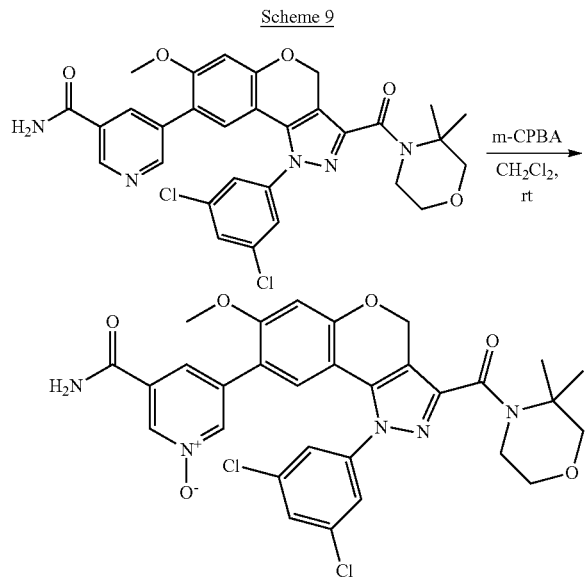

260

Step 1: 3-carbamoyl-5-(1-(3,5-dichlorophenyl)-3-(3,3-dimethylmorpholine-4-carbonyl)-7-methoxy-1,4-dihydrochromeno[4,3-c]pyrazol-8-yl)pyridine 1-oxide To a solution of 5-(1-(3,5-dichlorophenyl)-3-(3,3-dimethylmorpholine-4-carbonyl)-7-methoxy-1,4-dihydrochromeno[4,3-c]pyrazol-8-yl)nicotinamide (30 mg, 0.05 mmol) in $CH_2Cl_2$ (10 mL) was added m-CPBA (26 mg, 0.15 mmol) at 0° C. The mixture was stirred at RT overnight. The mixture was concentrated in vacuum and the residue was purified by Combi-Flash (mobile phase: acetonitrile/water (10 mM $NH_4HCO_3$)) to afford 3-carbamoyl-5-(1-(3,5-dichlorophenyl)-3-(3,3-dimethylmorpholine-4-carbonyl)-7-methoxy-1,4-dihydrochromeno[4,3-c]pyrazol-8-yl)pyridine 1-oxide (20 mg, 65%) as a white solid. LCMS m/z=624 [M+H]$^+$. $^1$H NMR (400 MHz, DMSO) δ 8.51 (t, J=1.4 Hz, 1H), 8.24 (t, J=1.5 Hz, 1H), 8.14 (s, 1H), 7.80 (dd, J=3.0, 1.3 Hz, 4H), 7.56 (t, J=1.4 Hz, 1H), 6.92 (d, J=13.1 Hz, 2H), 5.43 (s, 2H), 3.96-3.88 (m, 2H), 3.84 (s, 3H), 3.73 (t, J=5.0 Hz, 2H), 3.43 (s, 2H), 1.42 (s, 6H).

The following compounds were prepared using procedures analogous to those disclosed in Scheme 9.

| Compound | Boronic Acid Starting Material | Amine Starting Material | LC-MS | NMR |
|---|---|---|---|---|
| 3-carbamoyl-5-(1-(3,5-dichlorophenyl)-3-(3,3-dimethylmorpholine-4-carbonyl)-7-methoxy-1,4-dihydrochromeno[4,3-c]pyrazol-8-yl)pyridine 1-oxide Compound 174 | | | m/z: 624 [M + H]$^+$ | $^1$H NMR (400 mHz, DMSO) δ 8.51 (t, J = 1.4 Hz, 1H), 8.24 (t, J = 1.5 Hz, 1H), 8.14 (s, 1H), 7.80 (dd, J = 3.0, 1.3 Hz, 4H), 7.56 (t, J = 1.4 Hz, 1H), 6.92 (d, J = 13.1 Hz, 2H), 5.43 (s, 2H), 3.96-3.88 (m, 2H), 3.84 (s, 3H), 3.73 (t, J = 5.0 Hz, 2H), 3.43 (s, 2H), 1.42 (s, 6H). |
| 3-(3-(tert-butyl(methyl)carbamoyl)-1-(3,5-dimethoxyphenyl)-7-methoxy-1,4-dihydrochromeno[4,3-c]pyrazol-8-yl)-5-carbamoylpyridine 1-oxide Compound 175 | | | m/z: 588 [M + H]$^+$ | $^1$H NMR (400 MHz, CDCl$_3$) δ 8.56 (t, J = 1.6 Hz, 1H), 8.43 (t, J = 1.6 Hz, 1H), 7.33-7.32 (m, 1H), 6.84 (s, 1H), 6.70-6.69 (dm, 3H), 6.62 (t,, J = 2.0 Hz, 1H), 5.54 (s, 2H), 3.84 (s, 9H), 3.29 (s, 3H), 1.52 (s, 9H). |

-continued

| Compound | Boronic Acid Starting Material | Amine Starting Material | LC-MS | NMR |
|---|---|---|---|---|
| 3-carbamoyl-5-(1-(3,5-difluorophenyl)-3-(3,3-dimethylmorpholine-4-carbonyl)-7-methoxy-1,4-dihydrochromeno[4,3-c]pyrazol-8-yl)pyridine 1-oxide<br>Compound 176 | | | m/z: 592 [M + H]+ | $^1$H NMR (500 MHz, CDCl$_3$) δ 8.77 (s, 1H), 8.40 (s, 1H), 7.58 (s, 1H), 7.12 (d, J = 4.9 Hz, 2H), 7.03 (t, J = 8.5 Hz, 1H), 6.88 (s, 1H), 6.72 (s, 1H), 5.51 (s, 2H), 4.07 (t, J = 3.6 Hz, 2H), 3.85 (m, 5H), 3.50 (s, 2H), 1.53 (s, 6H). |
| 3-cyano-5-(1-(3,5-dichlorophenyl)-3-(3,3-dimethylmorpholine-4-carbonyl)-7-methoxy-1,4-dihydrochromeno[4,3-c]pyrazol-8-yl)pyridine 1-oxide<br>Compound 177 | | | m/z: 606 [M + H]+ | $^1$H NMR (500 MHz, CDCl$_3$) δ 8.44 (s, 1H), 8.30 (s, 1H), 7.57 (t, J = 1.6 Hz, 1H), 7.49 (d, J = 1.6 Hz, 2H), 7.36 (s, 1H), 6.86 (s, 1H), 6.73 (s, 1H), 5.52 (s, 2H), 4.14-4.02 (m, 2H), 3.90-3.81 (m, 5H), 3.50 (s, 2H), 1.53 (s, 6H). |

Example 11. 5-(1-(3,5-dichlorophenyl)-3-(3,3-dimethylmorpholine-4-carbonyl)-7-methoxy-1,4-dihydrochromeno[4,3-c]pyrazol-8-yl)nicotinic acid (Compound 178)

Scheme 10

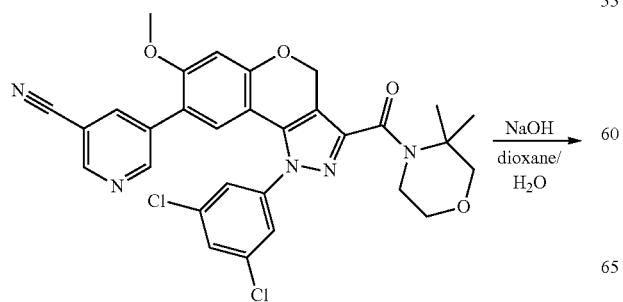

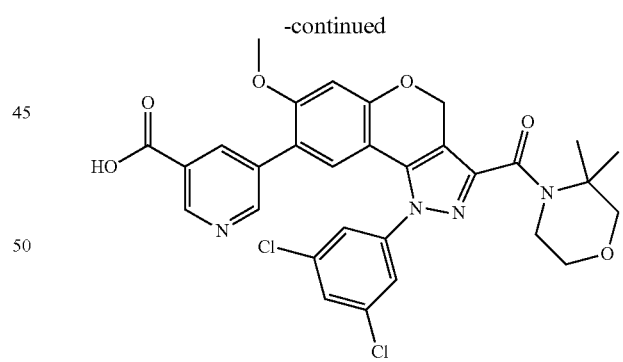

Step 15-(1-(3,5-dichlorophenyl)-3-(3,3-dimethylmorpholine-4-carbonyl)-7-methoxy-1,4-dihydrochromeno[4,3-c]pyrazol-8-yl)nicotinic acid To a solution of 5-(1-(3,5-dichlorophenyl)-3-(3,3-dimethylmorpholine-4-carbonyl)-7-methoxy-1,4-dihydrochromeno[4,3-c]pyrazol-8-yl)nicotinonitrile (50 mg, 0.085 mmol) in dioxane/H$_2$O (1/1, 2 mL) was added NaOH (17 mg, 0.42 mmol). The mixture was stirred at 100° C. for 2 h under MW conditions. The mixture was directly purified by Combi-Flash (mobile phase: acetonitrile/water (10 mM NH₄HCO₃)) to afford 5-(1-(3,5-dichlorophenyl)-3-(3,3-dimethylmorpholine-4-carbonyl)-7-methoxy-1,4-dihydrochromeno[4,3-c]pyrazol-8-yl)nicotinic acid (33 mg, 65%) as a white solid. LCMS m/z=609 [M+H]⁺. ¹H NMR (400 MHz, CDCl₃) δ 8.75 (dd, J=11.8, 1.9 Hz, 2H), 7.97 (t, J=2.1 Hz, 1H), 7.56-7.47 (m, 3H), 6.88 (s, 1H), 6.74 (s, 1H), 5.51 (s, 2H), 4.11-4.02 (m, 2H), 3.86 (d, J=7.8 Hz, 5H), 3.50 (s, 2H), 1.53 (s, 6H).

The following compounds were prepared using procedures analogous to those disclosed in Scheme 10.

| Compound | Boronic Acid Starting Material | Amine Starting Material | LC-MS | NMR |
|---|---|---|---|---|
| 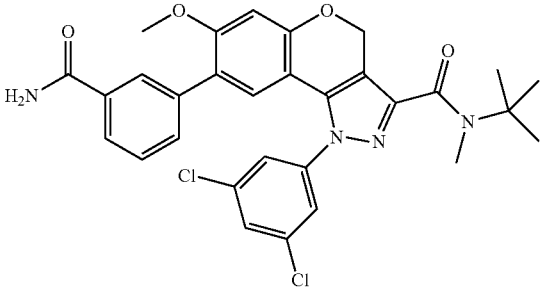 [SMILES: COc1cc2c(cc1-c1cccc(C(N)=O)c1)-c1c(c(C(=O)N(C)C(C)(C)C)nn1-c1cc(Cl)cc(Cl)c1)CO2]<br>3-(3-(tert-butyl(methyl)carbamoyl)-1-(3,5-dichlorophenyl)-7-methoxy-1,4-dihydrochromeno[4,3-c]pyrazol-8-yl)benzoic acid<br>Compound 179 | 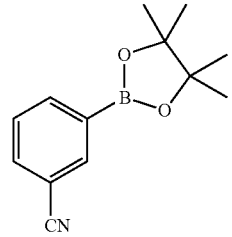 | 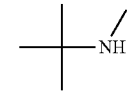 | m/z: 580 [M + H]⁺ | ¹H NMR (400 MHz, MeOD) δ 8.01-7.87 (m, 2H), 7.67-7.66 (m, 3H), 7.47 (d, J = 7.6 Hz, 1H), 7.39 (t, J = 7.7 Hz, 1H), 6.86 (s, 2H), 5.39 (s, 1H), 6.83 (s, 2H), 5.39 (s, 1H), 3.85 (s, 3H), 3.24 (s, 3H), 1.56 (s, 9H). |
| 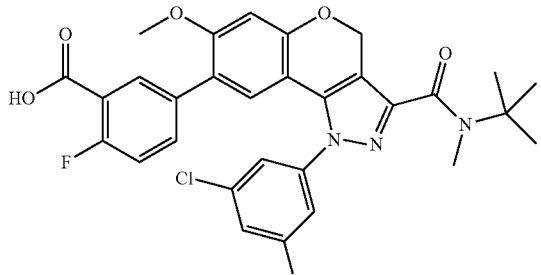<br>5-(3-(tert-butyl(methyl)carbamoyl)-1-(3,5-dichlorophenyl)-7-methoxy-1,4-dihydrochromeno[4,3-c]pyrazol-8-yl)-2-fluorobenzoic acid<br>Compound 180 | 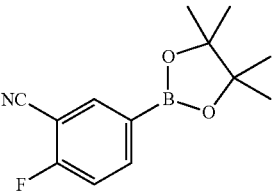 | 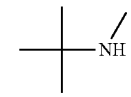 | m/z: 598 [M + H]⁺ | ¹H NMR (400 MHz, MeOD) δ 7.74 (dd, J = 7.0, 2.4 Hz, 1H), 7.67 (t, J = 1.8 Hz, 1H), 7.63 (d, J = 1.9 Hz, 2H), 7.48-7.44 (m, 1H), 7.13-7.08 (m, 1H), 6.80 (d, J = 7.5 Hz, 2H), 5.37 (s, 2H), 3.82 (s, 3H), 3.24 (s, 3H), 1.55 (s, 9H). |

Example 12. N-tert-butyl-8-(1-carbamoyl-1H-pyrazol-4-yl)-1-(3,5-dichlorophenyl)-7-methoxy-N-methyl-1,4-dihydrochromeno[4,3-c]pyrazole-3-carboxamide (Compound 181)

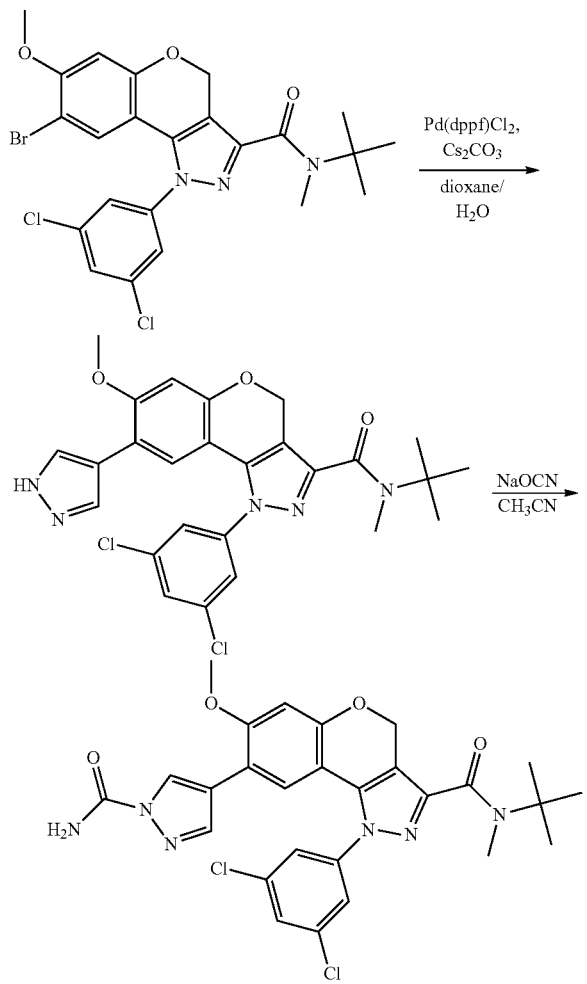

Step 1: N-tert-butyl-1-(3,5-dichlorophenyl)-7-methoxy-N-methyl-8-(1H-pyrazol-4-yl)-1,4-dihydrochromeno[4,3-c]pyrazole-3-carboxamide To a solution of 8-bromo-N-tert-butyl-1-(3,5-dichlorophenyl)-7-methoxy-N-methyl-1,4-dihydrochromeno[4,3-c]pyrazole-3-carboxamide (300 mg, 0.56 mmol) in dioxane/H$_2$O (10/1, 3 mL) were added 4-(4,4,5,5-tetramethyl-1,3,2-dioxaborolan-2-yl)-1H-pyrazole (217 mg, 1.12 mmol), Cs$_2$CO$_3$ (364 mg, 1.12 mmol), and Pd(dppf)Cl$_2$ (45 mg, 0.056 mmol) at RT under nitrogen. The reaction mixture was stirred at 90° C. for 1 h under MW conditions. The reaction mixture was directly purified by Combi-Flash (mobile phase: acetonitrile/water (10 mM NH$_4$HCO$_3$)) to afford N-tert-butyl-1-(3,5-dichlorophenyl)-7-methoxy-N-methyl-8-(1H-pyrazol-4-yl)-1,4-dihydrochromeno[4,3-c]pyrazole-3-carboxamide (280 mg, 95%) as a white solid. LC-MS m/z=526 [M+H]$^+$.

Step 2: N-tert-butyl-8-(1-carbamoyl-1H-pyrazol-4-yl)-1-(3,5-dichlorophenyl)-7-methoxy-N-methyl-1,4-dihydrochromeno[4,3-c]pyrazole-3-carboxamide To a solution of N-tert-butyl-1-(3,5-dichlorophenyl)-7-methoxy-N-methyl-8-(1H-pyrazol-4-yl)-1,4-dihydrochromeno[4,3-c]pyrazole-3-carboxamide (50 mg, 0.095 mmol) in CH$_3$CN (3 mL) were added NaOCN (10 mg, 0.19 mmol), HOAc (0.2 mL), and H$_2$O (0.2 mL). The reaction mixture was stirred at RT overnight. The mixture was diluted with NaHCO$_3$ (aq.) (10 mL), extracted with CH$_2$Cl$_2$ (10 mL*2). The combined organics were dried over Na$_2$SO$_4$, and concentrated. The residue was purified by HPLC (mobile phase: acetonitrile/water (10 mM NH$_4$HCO$_3$) to afford N-tert-butyl-8-(1-carbamoyl-1H-pyrazol-4-yl)-1-(3,5-dichlorophenyl)-7-methoxy-N-methyl-1,4-dihydrochromeno[4,3-c]pyrazole-3-carboxamide (20 mg, 38%) as a white solid. LCMS m/z=569 [M+H]$^+$. $^1$H NMR (400 MHz, CDCl$_3$) δ 8.45 (d, J=0.5 Hz, 1H), 7.58-7.50 (m, 4H), 7.10 (s, 1H), 6.70 (s, 1H), 5.46 (s, 2H), 3.92 (s, 3H), 3.26 (s, 3H), 1.52 (s, 9H).

Example 13. N-tert-butyl-1-(3,5-dichlorophenyl)-7-methoxy-N-methyl-8-(5-ureidopyridin-3-yl)-1,4-dihydrochromeno[4,3-c]pyrazole-3-carboxamide

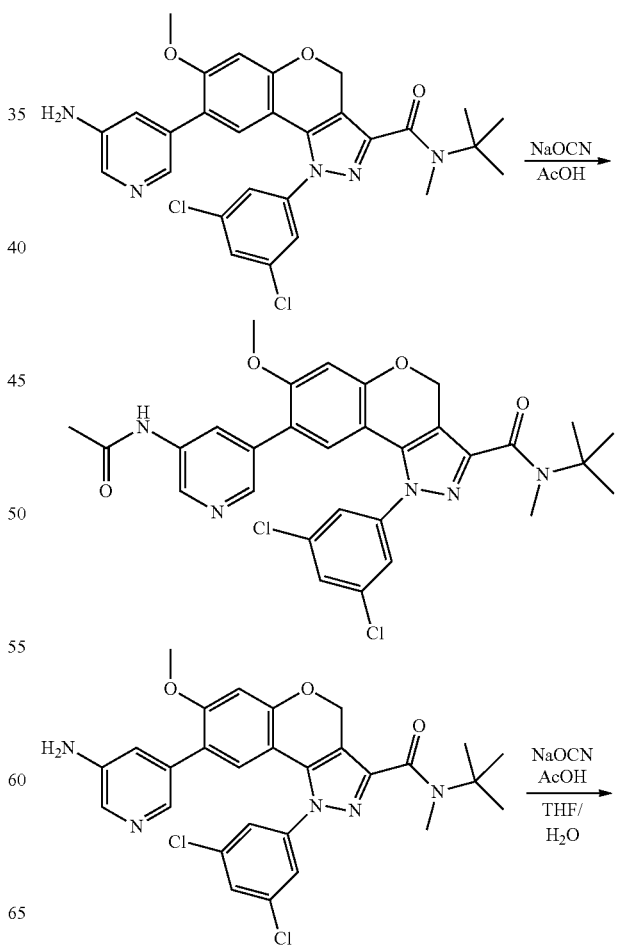

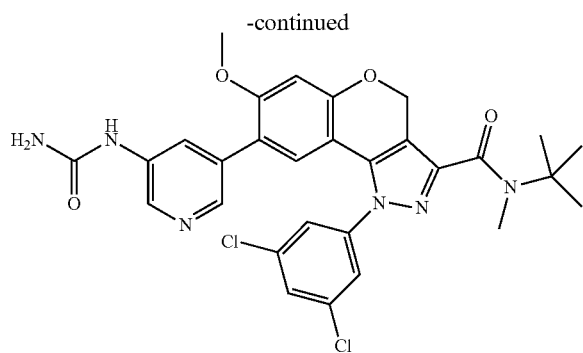

Step 1: 8-(5-acetamidopyridin-3-yl)-N-tert-butyl-1-(3,5-dichlorophenyl)-7-methoxy-N-methyl-1,4-dihydrochromeno[4,3-c]pyrazole-3-carboxamide (Compound 182)

To a solution of N 8-(5-aminopyridin-3-yl)-N-tert-butyl-1-(3,5-dichlorophenyl)-7-methoxy-N-methyl-1,4-dihydrochromeno[4,3-c]pyrazole-3-carboxamide (5 mg, 0.01 mmol), in AcOH (1 mL) were added NaOCN (2 mg, 0.03 mmol). The reaction mixture was stirred at RT for 1 h. The mixture was poured into NaHCO$_3$ (aq.) (5 mL), extracted with CH2Cl2 (5 mL*2). The combined organics were dried over Na$_2$SO$_4$, and concentrated. The solution was purified by HPLC (mobile phase: acetonitrile/water (10 mM NH$_4$HCO$_3$) to afford 8-(5-acetamidopyridin-3-yl)-N-tert-butyl-1-(3,5-dichlorophenyl)-7-methoxy-N-methyl-1,4-dihydrochromeno[4,3-c]pyrazole-3-carboxamide (2 mg, 33%) as a as a white solid. LCMS m/z=594 [M+H]$^+$. $^1$H NMR (400 MHz, CDCl$_3$) δ 8.59 (d, J=2.3 Hz, 1H), 8.27 (d, J=1.6 Hz, 1H), 7.99 (s, 1H), 7.52 (d, J=1.8 Hz, 2H), 7.46 (t, J=1.8 Hz, 1H), 7.37 (s, 1H), 6.90 (s, 1H), 6.71 (s, 1H), 5.47 (s, 2H), 3.83 (s, 3H), 3.26 (s, 3H), 2.22 (s, 3H), 1.52 (s, 9H).

Step 2: N-tert-butyl-1-(3,5-dichlorophenyl)-7-methoxy-N-methyl-8-(5-ureidopyridin-3-yl)-1,4-dihydrochromeno[4,3-c]pyrazole-3-carboxamide (Compound 183)

A solution of 8-(5-aminopyridin-3-yl)-N-tert-butyl-1-(3,5-dichlorophenyl)-7-methoxy-N-methyl-1,4-dihydrochromeno[4,3-c]pyrazole-3-carboxamide (20 mg, 0.036 mmol) in NaOCN (7 mg, 0.11 mmol), HOAc (0.05 mL), and THF/H$_2$O (1/1, 0.1 Ml) was stirred at RT overnight. The mixture was poured into NaHCO$_3$ (aq.) (10 mL), extracted with CH2Cl2 (10 mL*2). The combined organics were dried over Na$_2$SO$_4$, and concentrated. The solution was purified by HPLC (mobile phase: acetonitrile/water (10 mM NH$_4$HCO$_3$) to afford N-tert-butyl-1-(3,5-dichlorophenyl)-7-methoxy-N-methyl-8-(5-ureidopyridin-3-yl)-1,4-dihydrochromeno[4,3-c]pyrazole-3-carboxamide (5 mg, 24%) as a as a white solid. LCMS m/z=595 [M+H]$^+$. $^1$H NMR (400 MHz, CDCl$_3$) δ 8.36 (s, 1H), 8.11 (s, 1H), 7.88 (d, J=16.0 Hz, 2H), 7.47 (d, J=1.6 Hz, 2H), 7.40 (d, J=1.6 Hz, 1H), 6.84 (s, 1H), 6.65 (s, 1H), 5.42 (s, 2H), 5.13 (s, 2H), 3.75 (s, 3H), 3.24 (s, 3H), 1.52 (s, 9H).

Example 14. 4-(7-methoxy-8-(1-methyl-1H-pyrazol-3-yl)-1-(thiophen-3-yl)-1,4-dihydrochromeno[4,3-c]pyrazole-3-carbonyl)-3,3-dimethylpiperazine-1-carbonitrile (Compound 184)

Scheme 15

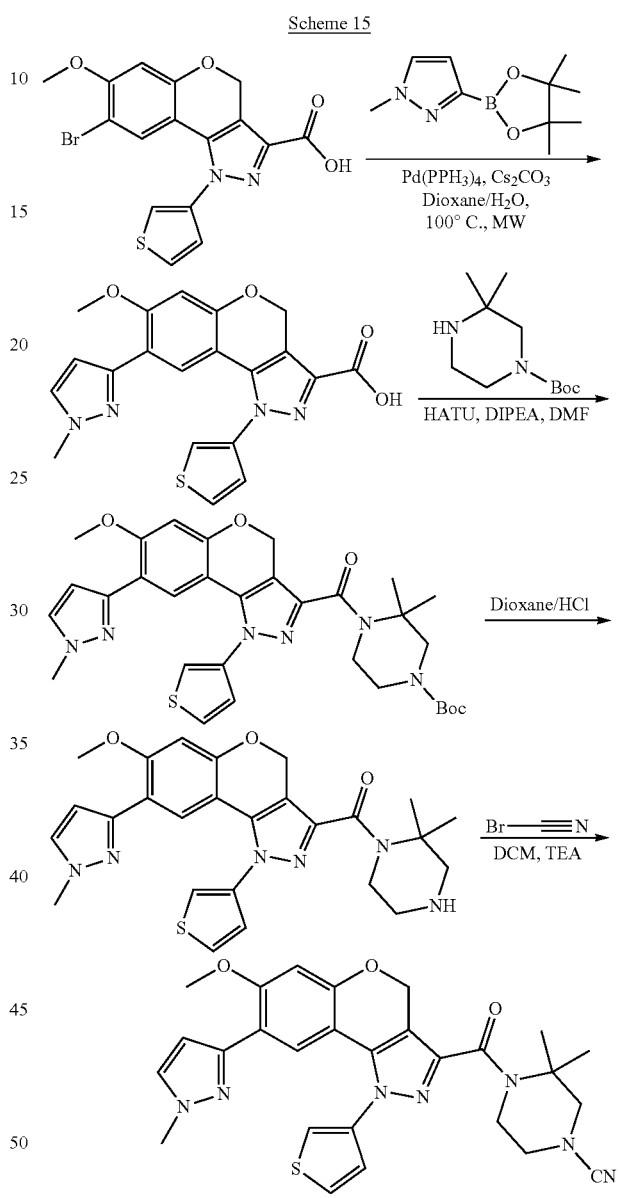

Step 1: 7-methoxy-8-(1-methyl-1H-pyrazol-3-yl)-1-(thiophen-3-yl)-1,4-dihydrochromeno[4,3-c]pyrazole-3-carboxylic acid To a solution of 8-bromo-7-methoxy-1-(thiophen-3-yl)-1,4-dihydrochromeno[4,3-c]pyrazole-3-carboxylic acid (1 g, 2.46 mmol) in dioxane/H2O (5/1, 10 mL) was added methyl 2-(4-(4,4,5,5-tetramethyl-1,3,2-dioxaborolan-2-yl)-1H-pyrazol-1-yl)acetate (1.02 g, 4.93 mmol), PdCl$_2$(dppf) (360 mg, 0.49 mmol) and Cs2CO3 (1.6 g, 4.93 mmol) at RT under nitrogen. The reaction mixture was stirred at 100° C. for 1 h under MW conditions. The reaction mixture was filtered through celite and washed with DCM (50 mL). The filtrate was concentrated under vacuum; the crude product was purified by HPLC (mobile phase: acetonitrile/water (10 mM NH₄HCO₃) to afford the desired compound (300 mg, 30%) as an off-white solid. LCMS m/z=409 [M+H]⁺.

Step 2: tert-butyl 4-(7-methoxy-8-(1-methyl-1H-pyrazol-3-yl)-1-(thiophen-3-yl)-1,4-dihydrochromeno[4,3-c]pyrazole-3-carbonyl)-3,3-dimethylpiperazine-1-carboxylate A mixture of 7-methoxy-8-(1-methyl-1H-pyrazol-3-yl)-1-(thiophen-3-yl)-1,4-dihydrochromeno[4,3-c]pyrazole-3-carboxylic acid (50 mg, 0.123 mmol), HATU (51 mg, 0.135 mmol), tert-butyl 3,3-dimethylpiperazine-1-carboxylate (34 mg, 0.135 mmol) and DIPEA (48 mg, 0.369 mmol) in DMF (3 ml) was stirred at RT overnight. Then the mixture was purified by Combi-Flash (mobile phase: acetonitrile/water (10 mM NH₄HCO₃) to afford tert-butyl 4-(7-methoxy-8-(1-methyl-1H-pyrazol-3-yl)-1-(thiophen-3-yl)-1,4-dihydrochromeno[4,3-c]pyrazole-3-carbonyl)-3,3-dimethylpiperazine-1-carboxylate (55 mg, 37.2%) as a white solid. LCMS m/z=605 [M+H]⁺.

Step 3: (2,2-dimethylpiperazin-1-yl)(7-methoxy-8-(1-methyl-1H-pyrazol-3-yl)-1-(thiophen-3-yl)-1,4-dihydrochromeno[4,3-c]pyrazol-3-yl)methanone hydrochloride A mixture of tert-butyl 4-(7-methoxy-8-(1-methyl-1H-pyrazol-3-yl)-1-(thiophen-3-yl)-1,4-dihydrochromeno[4,3-c]pyrazole-3-carbonyl)-3,3-dimethylpiperazine-1-carboxylate (55 mg, 0.091 mmol) and Dioxane/HCl (4M, 1 ml) in DCm (2 ml) was stirred at RT overnight. Then the mixture was concentrated to get (2,2-dimethylpiperazin-1-yl)(7-methoxy-8-(1-methyl-1H-pyrazol-3-yl)-1-(thiophen-3-yl)-1,4-dihydrochromeno[4,3-c]pyrazol-3-yl)methanone hydrochloride (40 mg, 54%) as a white solid. LCMS m/z=505 [M+H]+.

Step 4: 4-(7-methoxy-8-(1-methyl-1H-pyrazol-3-yl)-1-(thiophen-3-yl)-1,4-dihydrochromeno[4,3-c]pyrazole-3-carbonyl)-3,3-dimethylpiperazine-1-carbonitrile A mixture of (2,2-dimethylpiperazin-1-yl)(7-methoxy-8-(1-methyl-1H-pyrazol-3-yl)-1-(thiophen-3-yl)-1,4-dihydrochromeno[4,3-c]pyrazol-3-yl)methanone hydrochloride (20 mg, 0.037 mmol), cyanic bromide (8 mg, 0.074 mmol) and TEA (12 mg, 0.111 mol) was stirred at RT overnight. Then the mixture was purified by column chromatography (silica gel: 200-300 mesh, PE:EtOAc=1:1) to get 4-(7-methoxy-8-(1-methyl-1H-pyrazol-3-yl)-1-(thiophen-3-yl)-1,4-dihydrochromeno[4,3-c]pyrazole-3-carbonyl)-3,3-dimethylpiperazine-1-carbonitrile (10 mg, 50%) as a white solid. LCMS m/z=530.2 [M+H]⁺. ¹H NMR (400 MHz, CDCl₃): 7.53-7.52 (m, 1H), 7.49-7.47 (m, 2H), 7.30-7.29 (m, 1H), 7.24-7.23 (m, 1H), 6.51 (d, J=2.4 Hz, 1H), 5.48 (s, 2H), 4.29-4.27 (m, 2H), 3.87 (s, 3H), 3.86 (s, 3H), 3.56 (m, 2H), 3.25 (s, 2H), 1.65 (s, 6H).

Example 15. N-tert-butyl-7-methoxy-N-methyl-8-(5-oxo-2,5-dihydro-1H-pyrazol-3-yl)-1-(thiophen-3-yl)-1,4-dihydrochromeno[4,3-c]pyrazole-3-carboxamide (Compound 185)

Scheme 14

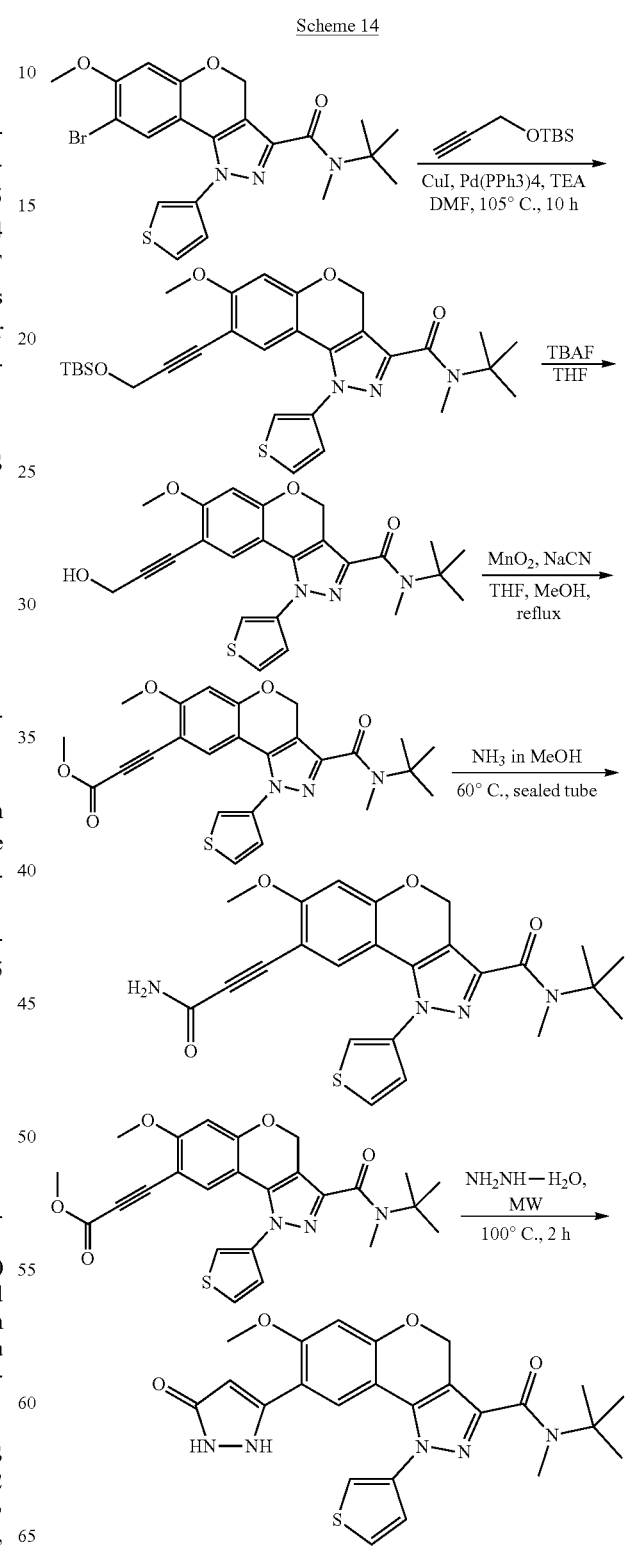

Step 1: N-tert-butyl-8-(3-(tert-butyldimethylsilyloxy)prop-1-ynyl)-7-methoxy-N-methyl-1-(thiophen-3-yl)-1,4-dihydrochromeno[4,3-c]pyrazole-3-carboxamide A mixture of 8-bromo-N-tert-butyl-7-methoxy-N-methyl-1-(thiophen-3-yl)-1,4-dihydrochromeno[4,3-c]pyrazole-3-carboxamide (47.5 mg, 0.1 mmol), tert-butyldimethyl(prop-2-ynyloxy)silane (51 mg, 0.3 mmol), CuI (6 mg, 0.03 mmol), Pd(PPh$_3$)$_4$(14 mg, 0.012 mmol), TEA (0.15 ml) in DMF (2 ml) was stirred at 105° C. for 10 h. The crude product was purified by preparative HPLC to give the desired pure product (15 mg, 33%) as a yellow liquid. $^1$H NMR (400 MHz, CDCl$_3$): 7.48-7.51 (m, 2H), 7.21-7.22 (m, 1H), 6.91 (s, 1H), 6.56 (s, 1H), 5.50 (s, 2H), 4.53 (s, 2H), 3.85 (s, 3H), 3.28 (s, 3H), 1.53 (s, 9H), 0.94 (s, 9H), 0.15 (s, 6H). m/z=566.2 [M+H]$^+$.

Step 2: N-tert-butyl-8-(3-hydroxyprop-1-ynyl)-7-methoxy-N-methyl-1-(thiophen-3-yl)-1,4-dihydrochromeno[4,3-c]pyrazole-3-carboxamide To a solution of N-tert-butyl-8-(3-(tert-butyldimethylsilyloxy)prop-1-ynyl)-7-methoxy-N-methyl-1-(thiophen-3-yl)-1,4-dihydrochromeno[4,3-c]pyrazole-3-carboxamide (56.5 mg, 0.1 mmol) in THF (5 mL) was added TBAF (1 ml, 0.2 mmol) at RT. The reaction mixture was stirred at RT for 2 h. The reaction mixture was evaporated and diluted with EtOAc (50 ml) and washed with brine. The mixture was filtered and concentrated to afford the desired crude compound N-tert-butyl-8-(3-hydroxyprop-1-ynyl)-7-methoxy-N-methyl-1-(thiophen-3-yl)-1,4-dihydrochromeno[4,3-c]pyrazole-3-carboxamide (30 mg, 66%) as an off-white solid, which was used to the next step without further purification. m/z=452.1 [M+H$^+$.

Step 3: Methyl 3-(3-(tert-butyl(methyl)carbamoyl)-7-methoxy-1-(thiophen-3-yl)-1,4-dihydrochromeno[4,3-c]pyrazol-8-yl)propiolate A mixture of N-tert-butyl-8-(3-hydroxyprop-1-ynyl)-7-methoxy-N-methyl-1-(thiophen-3-yl)-1,4-dihydrochromeno[4,3-c]pyrazole-3-carboxamide (50 mg, 0.11 mmol), NaCN (6 mg, 0.11 mmol), MnO$_2$ (145 mg, 1.65 mmol) in THF (5 ml) and MeOH (5 ml) was refluxed for 5 h. The crude product was purified by preparative HPLC to give the desired pure product (5 mg, 12%) as a white solid. $^1$H NMR (400 MHz, CDCl$_3$): 7.51-7.54 (m, 2H), 7.20-7.22 (m, 1H), 7.00 (s, 1H), 6.58 (s, 1H), 5.56 (s, 2H), 3.89 (s, 3H), 3.82 (s, 3H), 3.29 (s, 3H), 1.53 (s, 9H). m/z=480.0 [M+H]$^+$. and 6 (5 mg, 13%) as a white solid. $^1$H NMR (400 MHz, CDCl$_3$): 7.51-7.54 (m, 2H), 7.19 (s, 1H), 6.98 (s, 1H), 6.57 (s, 1H), 3.88 (s, 3H), 3.28 (s, 3H), 1.52 (s, 9H). m/z=466.0 [M+H]$^+$.

Step 4: 8-(3-amino-3-oxoprop-1-ynyl)-N-tert-butyl-7-methoxy-N-methyl-1-(thiophen-3-yl)-1,4-dihydrochromeno[4,3-c]pyrazole-3-carboxamide (Compound 186)

A solution of methyl 3-(3-(tert-butyl(methyl)carbamoyl)-7-methoxy-1-(thiophen-3-yl)-1,4-dihydrochromeno[4,3-c]pyrazol-8-yl)propiolate (10 mg, 0.021 mmol) and NH$_3$ in MeOH (3 ml) was heated to 60° C. for 2 h in a sealed tube. The solvent was removed to give crude product, which was purified by preparative HPLC to give desired product (5 mg, 50%) as a white solid. $^1$H NMR (400 MHz, CDCl$_3$): 7.50-7.54 (m, 2H), 7.20-7.22 (m, 1H), 6.98 (s, 1H), 6.59 (s, 1H), 5.55 (s, 2H), 3.88 (s, 3H), 3.28 (s, 3H), 1.53 (s, 9H). m/z=465.2 [M+H]$^+$.

Step 5: N-tert-butyl-7-methoxy-N-methyl-8-(5-oxo-2,5-dihydro-1H-pyrazol-3-yl)-1-(thiophen-3-yl)-1,4-dihydrochromeno[4,3-c]pyrazole-3-carboxamide (Compound 185)

A solution of methyl 3-(3-(tert-butyl(methyl)carbamoyl)-7-methoxy-1-(thiophen-3-yl)-1,4-dihydrochromeno[4,3-c]pyrazol-8-yl)propiolate (6 mg, 0.0125 mmol) in NH$_2$NH$_2$H2O (2 ml) was heated to 100° C. for 2 h under MW conditions. The solvent was removed to give crude product, which was purified by preparative HPLC to give N-tert-butyl-7-methoxy-N-methyl-8-(5-oxo-2,5-dihydro-1H-pyrazol-3-yl)-1-(thiophen-3-yl)-1,4-dihydrochromeno[4,3-c]pyrazole-3-carboxamide (2 mg, 25%) as a white solid. $^1$H NMR (400 MHz, CDCl$_3$): 7.57-7.59 (m, 2H), 7.25-7.26 (m, 1H), 7.04 (s, 1H), 6.69 (s, 1H), 5.56 (s, 2H), 5.37 (s, 1H), 3.98 (s, 3H), 3.30 (s, 3H), 1.54 (s, 9H). m/z=480.0 [M+H]$^+$.

The following compound was prepared using procedures analogous to those disclosed in Scheme 14.

| Compound | Hydrazinyl Starting material | Amine Starting Material | LC-MS | NMR |
|---|---|---|---|---|
| 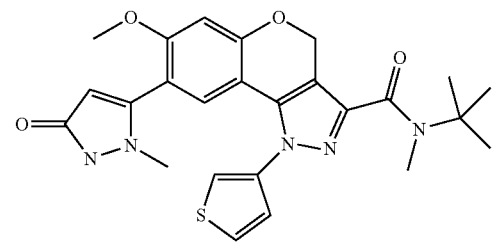 [SMILES: COc1cc2c(cc1-c1cc(=O)[nH]n1C)-c1c(c(C(=O)N(C)C(C)(C)C)nn1-c1ccsc1)CO2]  N-tert-butyl-7-methoxy-N-methyl-8-(1-methyl-3-oxo-2,3-dihydro-1H-pyrazol-5-yl)-1-(thiophen-3-yl)-1,4-dihydrochlromeno[4,3-c]pyrazole-3-carboxamide Compound 187 | | CH$_3$NH$_2$NH$_2$ | m/z: 494 [M + H]$^+$ | $^1$H NMR (500 MHz, CDCl$_3$) δ 7.57-7.44 (m, 2H), 7.23-7.17 (m, 1H), 6.72 (s, 1H), 6.67 (s, 1H), 5.54 (s, 2H), 5.43 (s, 1H), 3.83 (s, 3H), 3.45 (s, 3H), 3.29 (s, 3H), 1.53 (s, 9H). |

Example 16. 1-(3,5-dichlorophenyl)-N-ethyl-N-(ethylsulfonyl)-7-methoxy-8-(1-methyl-1H-pyrazol-3-yl)-1,4-dihydrochromeno[4,3-c]pyrazole-3-carboxamide (Compound 188)

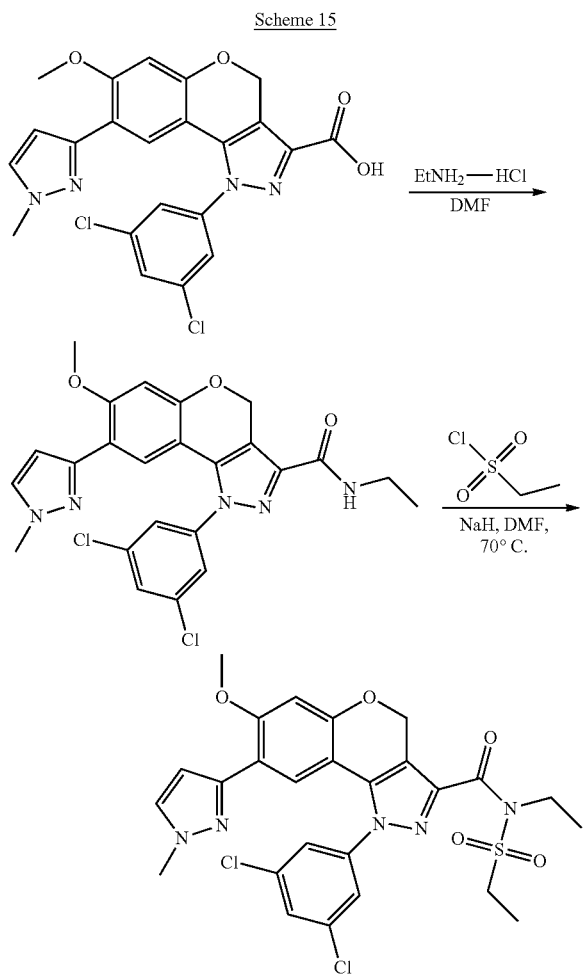

Scheme 15

Step 1: 1-(3,5-dichlorophenyl)-N-ethyl-7-methoxy-8-(1-methyl-1H-pyrazol-3-yl)-1,4-dihydrochromeno[4,3-c]pyrazole-3-carboxamide A mixture of 1-(3,5-dichlorophenyl)-7-methoxy-8-(1-methyl-1H-pyrazol-3-yl)-1,4-dihydrochromeno[4,3-c]pyrazole-3-carboxylic acid (100 mg, 0.212 mmol), HATU (97 mg, 0.255 mmol), ethanamine hydrochloride (21 mg, 0.255 mmol) in DMF (3 ml) was stirred at RT overnight. Then the mixture was purified by Combi-Flash (mobile phase: acetonitrile/water (10 mM NH$_4$HCO$_3$) to afford 1-(3, 5-dichlorophenyl)-N-ethyl-7-methoxy-8-(1-methyl-1H-pyrazol-3-yl)-1,4-dihydrochromeno[4,3-c]pyrazole-3-carboxamide (100 mg, 94%) as a white solid. LCMS m/z [M+H]$^+$ 498.1. $^1$H NMR (400 MHz, CDCl$_3$): 7.598 (s, 1H), 7.551-7.546 (d, 2H, J=2.0 Hz), 7.509-7.504 (d, 1H, J=2.0 Hz), 7.310-7.304 (d, 1H, J=2.4 Hz), 6.863-6.850 (m, 1H), 6.652 (s, 1H), 6.555-6.550 (d, 1H, J=2.0 Hz), 5.617 (s, 2H), 3.880 (s, 3H), 3.863 (s, 3H), 3.510-3.441 (m, 2H), 1.273-1.237 (t, 3H, J=2.0 Hz).

Step 2: 1-(3,5-dichlorophenyl)-N-ethyl-N-(ethylsulfonyl)-7-methoxy-8-(1-methyl-1H-pyrazol-3-yl)-1,4-dihydrochromeno[4,3-c]pyrazole-3-carboxamide (Compound 188)

At 0° C., to a solution of 1-(3, 5-dichlorophenyl)-N-ethyl-7-methoxy-8-(1-methyl-1H-pyrazol-3-yl)-1,4-dihydrochromeno[4,3-c]pyrazole-3-carboxamide (100 mg, 0.2 mmol) in DMF, was added NaH (24 mg, 0.6 mmol) and ethanesulfonyl chloride (77 mg, 0.6 mmol). The mixture was stirred at 70° C. under N$_2$ overnight, quenched by sat NH$_4$Cl and purified by preparative HPLC to get 1-(3,5-dichlorophenyl)-N-ethyl-N-(ethylsulfonyl)-7-methoxy-8-(1-methyl-1H-pyrazol-3-yl)-1,4-dihydrochromeno[4,3-c]pyrazole-3-carboxamide (15 mg, 12.7%) as a white solid. LCMS m/z [M+H]$^+$ 590.1. $^1$H NMR (400 MHz, CDCl$_3$): 7.63 (s, 1H), 7.53 (m, 3H,), 7.33-7.31 (m, 1H), 6.65 (s, 1H), 6.56 (d, 1H, J=2.0 Hz), 5.53 (s, 2H), 4.41-4.35 (m, 2H), 3.89 (s, 3H), 3.87 (s, 3H), 3.74-3.69 (m, 2H), 1.45-1.41 (m, 6H).

Example 17. N-tert-butyl-1-(3,5-dichlorophenyl)-7-methoxy-8-(2-methoxy-5-methylpyridin-3-yl)-N-methyl-1,4-dihydrochromeno[4,3-c]pyrazole-3-carboxamide (Compound 189)

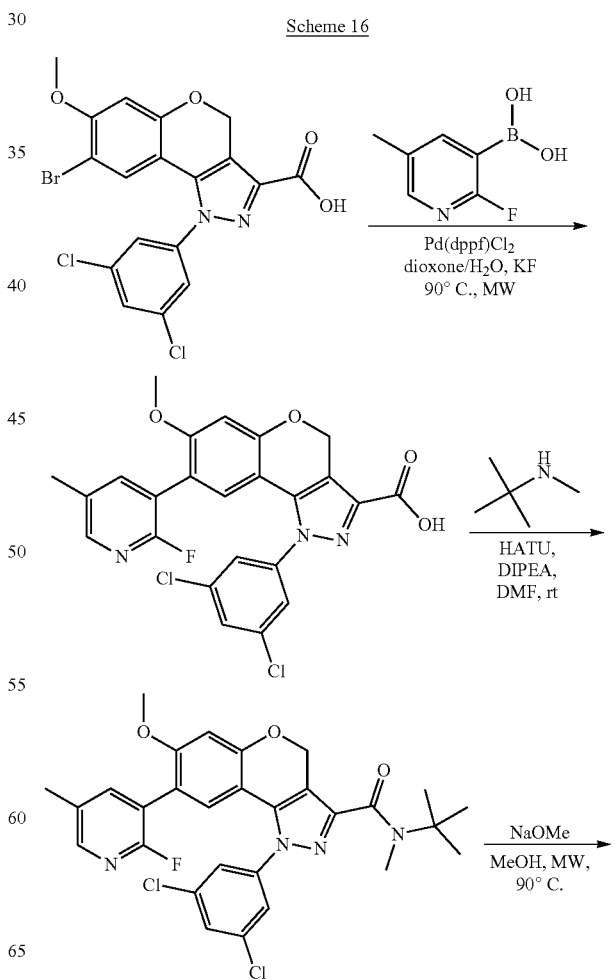

Scheme 16

-continued

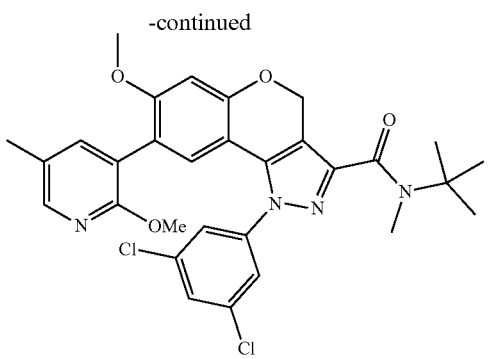

Step 1: 1-(3,5-dichlorophenyl)-8-(2-fluoro-5-methylpyridin-3-yl)-7-methoxy-1,4-dihydrochromeno[4,3-c]pyrazole-3-carboxylic acid To a solution of 8-bromo-1-(3,5-dichlorophenyl)-7-methoxy-1,4-dihydrochromeno[4,3-c]pyrazole-3-carboxylic acid (160 mg, 0.34 mmol) in dioxane/H$_2$O (5/1, 5 mL) was added 2-fluoro-5-methylpyridin-3-ylboronic acid (106 mg, 0.68 mmol), PdCl$_2$(dppf) (50 mg, 0.068 mmol) and KF (39 mg, 0.68 mmol) at RT under nitrogen. The reaction mixture was stirred at 90° C. for 2 h under MW conditions. The reaction mixture was filtered through celite and washed with DCM (50 mL). The filtrate was concentrated in vacuum and the crude product was purified by purified by preparative HPLC to afford the desired compound (80 mg, 47%) as an off-white solid. LCMS m/z [M+H]$^+$ 500.

Step 2: N-tert-butyl-1-(3,5-dichlorophenyl)-8-(2-fluoro-5-methylpyridin-3-yl)-7-methoxy-N-methyl-1,4-dihydrochromeno[4,3-c]pyrazole-3-carboxamide To a solution of 1-(3,5-dichlorophenyl)-8-(2-fluoro-5-methylpyridin-3-yl)-7-methoxy-1,4-dihydrochromeno[4,3-c]pyrazole-3-carboxylic acid (40 mg, 0.08 mol) in DMF (3 mL) was added N,2-dimethylpropan-2-amine (14 mg, 0.16 mmol), HATU (45 mg, 0.12 mmol) and diisopropyl ethyl amine (21 mg, 0.16 mmol) at RT under nitrogen. The reaction mixture was stirred at RT for 3 h, then the mixture was purified by Combi-Flash (mobile phase: acetonitrile/water (10 mM NH$_4$HCO$_3$) to afford the desired compound (10 mg, 22%) as a white solid. LCMS (ESI) m/z=569 [M+H]$^+$.

Step 3: N-tert-butyl-1-(3,5-dichlorophenyl)-7-methoxy-8-(2-methoxy-5-methylpyridin-3-yl)-N-methyl-1,4-dihydrochromeno[4,3-c]pyrazole-3-carboxamide (Compound 189)

To a solution of N-tert-butyl-1-(3,5-dichlorophenyl)-8-(2-fluoro-5-methylpyridin-3-yl)-7-methoxy-N-methyl-1,4-dihydrochromeno[4,3-c]pyrazole-3-carboxamide (5 mg, 0.009 mol) in CH3OH (1 mL) was added sodium methanolate (1.5 mg, 0.027 mmol) at RT. The reaction mixture was stirred at 90° C. for 2 h under MW conditions. The mixture was purified by Combi-Flash (mobile phase: acetonitrile/water (10 mM NH$_4$HCO$_3$) to afford the desired compound (2 mg, 39%) as a white solid. LCMS (ESI) m/z=581 [M+H]$^+$. $^1$H NMR (400 MHz, CDCl$_3$) δ 7.93 (d, J=1.6 Hz, 1H), 7.49 (d, J=1.8 Hz, 2H), 7.41 (t, J=1.8 Hz, 1H), 7.24 (d, J=2.3 Hz, 1H), 6.77 (s, 1H), 6.68 (s, 1H), 5.45 (s, 2H), 3.84 (s, 3H), 3.78 (s, 3H), 3.25 (s, 3H), 2.26 (s, 3H), 1.52 (s, 9H).

Example 18. N-tert-butyl-1-(3,5-dichlorophenyl)-8-(1-(2,3-dihydroxypropyl)-1H-pyrazol-4-yl)-7-methoxy-N-methyl-1,4-dihydrochromeno[4,3-c]pyrazole-3-carboxamide (Compounds 190, 191 and 192)

Scheme 17

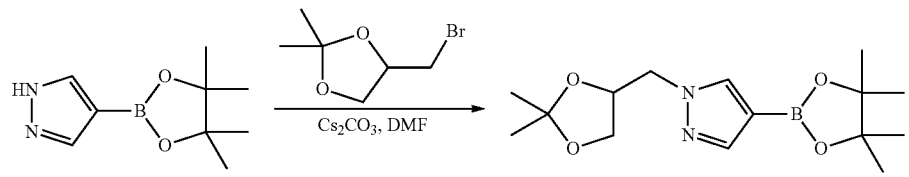

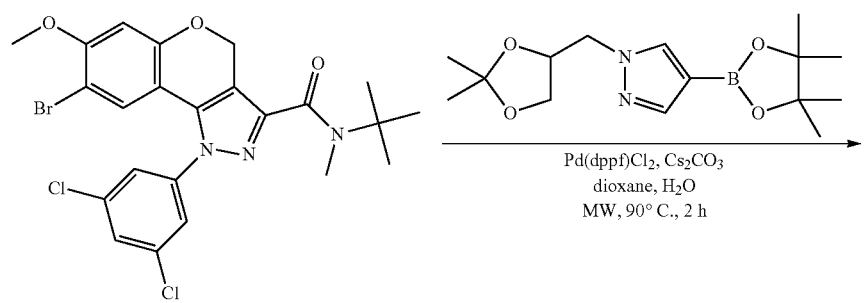

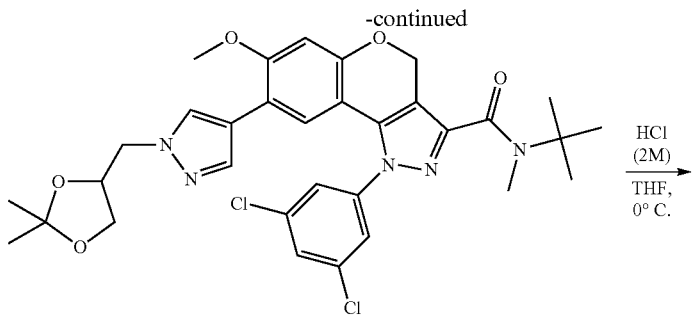

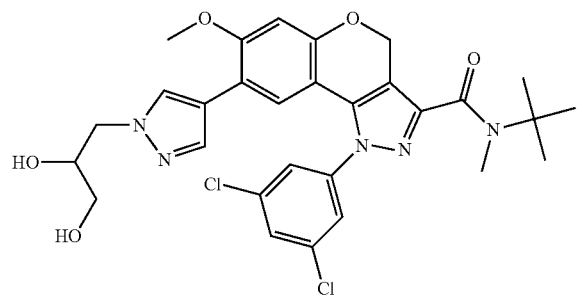

Step 1: 1-((2,2-dimethyl-1,3-dioxolan-4-yl)methyl)-4-(4,4,5,5-tetramethyl-1,3,2-dioxaborolan-2-yl)-1H-pyrazole To a solution of 4-(4,4,5,5-tetramethyl-1,3,2-dioxaborolan-2-yl)-1H-pyrazole (500 mg, 2.57 mmol) and 4-(bromomethyl)-2,2-dimethyl-1,3-dioxolane (501 mg, 2.57 mmol) in DMF (10 mL) was added Cs$_2$CO$_3$, DMF, OC (1.25 g, 3.85 mmol). The reaction mixture was stirred at RT overnight. The solution was filtered and concentrated to give the desired compound (500 mg, 63%) as a yellow oil. LCMS (ESI) m/z=309 [M+H]$^+$.

Step 2: N-tert-butyl-1-(3,5-dichlorophenyl)-8-(1-((2,2-dimethyl-1,3-dioxolan-4-yl)methyl)-1H-pyrazol-4-yl)-7-methoxy-N-methyl-1,4-dihydrochromeno[4,3-c]pyrazole-3-carboxamide To a solution of 8-bromo-N-tert-butyl-1-(3,5-dichlorophenyl)-7-methoxy-N-methyl-1,4-dihydrochromeno[4,3-c]pyrazole-3-carboxamide (50 mg, 0.093 mmol) in dioxane/H$_2$O (5/1, 2 mL) were added 1-((2,2-dimethyl-1,3-dioxolan-4-yl)methyl)-4-(4,4,5,5-tetramethyl-1,3,2-dioxaborolan-2-yl)-1H-pyrazole (57 mg, 0.19 mmol), PdCl$_2$(dppf) (8 mg, 0.009 mmol) and Cs$_2$CO$_3$ (62 mg, 0.19 mmol) at RT under nitrogen. The reaction mixture was stirred at 90° C. for 2 h under MW conditions. The mixture was purified by preparative HPLC (mobile phase: acetonitrile/water, 10 mM) to afford N-tert-butyl-1-(3,5-dichlorophenyl)-8-(1-((2,2-dimethyl-1,3-dioxolan-4-yl)methyl)-1H-pyrazol-4-yl)-7-methoxy-N-methyl-1,4-dihydrochromeno[4,3-c]pyrazole-3-carboxamide (30 mg, 51%) as a white solid. LCMS (ESI) m/z=640 [M+H]$^+$.

Step 3: N-tert-butyl-1-(3,5-dichlorophenyl)-8-(1-(2,3-dihydroxypropyl)-1H-pyrazol-4-yl)-7-methoxy-N-methyl-1,4-dihydrochromeno[4,3-c]pyrazole-3-carboxamide To a solution of N-tert-butyl-1-(3,5-dichlorophenyl)-8-(1-((2,2-dimethyl-1,3-dioxolan-4-yl)methyl)-1H-pyrazol-4-yl)-7-methoxy-N-methyl-1,4-dihydrochromeno[4,3-c]pyrazole-3-carboxamide (30 mg, 0.05 mmol) in THF (3 mL) was added 1M HCl (aq., 0.6 mL) at 0° C. The solution was stirred at rt overnight Then the solution was diluted with CH$_2$Cl$_2$ (100 mL), washed with sat.NaHCO$_3$, dried over Na$_2$SO$_4$, and concentrated. The crude was purified by preparative HPLC (mobile phase: acetonitrile/water (10 mM) to afford N-tert-butyl-1-(3,5-dichlorophenyl)-8-(1-(2,3-dihydroxypropyl)-1H-pyrazol-4-yl)-7-methoxy-N-methyl-1,4-dihydrochromeno[4,3-c]pyrazole-3-carboxamide (20 mg, 67%) as a white solid. LCMS (ESI) m/z=600[M+H]$^+$. $^1$H NMR (400 MHz, CDCl$_3$) δ 7.71 (s, 1H), 7.55-7.53 (m, 3H), 7.51 (s, 1H), 7.07 (s, 1H), 6.68 (s, 1H), 5.44 (s, 2H), 4.27 (d, J=5.1 Hz, 2H), 4.11-4.08 (m, 1H), 3.90 (s, 3H), 3.68-3.59 (m, 2H), 3.26 (s, 3H), 1.52 (s, 9H). Chiral separation of Compound 190 gave Compound 191 and its stereoisomer Compound 192. Stereochemistry of both Compound 191 and Compound 192 are tentatively assigned.

The following compounds were prepared using procedures analogous to those disclosed in Scheme 17.

| Compound | Boronic Acid Starting Material | Amine Starting Material | LC-MS | NMR |
|---|---|---|---|---|
| 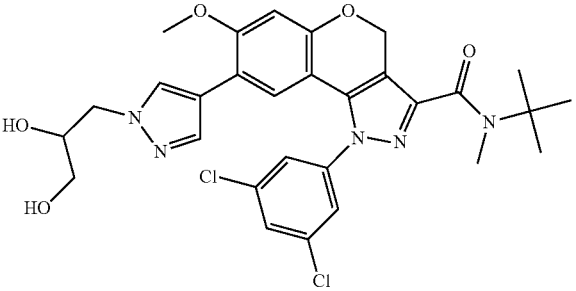<br>N-tert-butyl-1-(3,5-dichlorophenyl)-8-(1-(2,3-dihydroxypropyl)-1H-pyrazol-4-yl)-7-methoxy-N-methyl-1,4-dihydrochromeno[4,3-c]pyrazole-3-carboxamide<br>Compound 190 | |  | m/z: 600 [M + H]⁺ | ¹H NMR (400 MHz, CDCl₃) δ 7.71 (s, 1H), 7.55-7.53 (m, 3H), 7.51 (s, 1H), 7.07 (s, 1H), 6.68 (s, 1H), 5.44 (s, 2H), 4.27 (d, J = 5.1 Hz, 2H), 4.11-4.08 (m, 1H), 3.90 (s, 3H), 3.68-3.59 (m, 2H), 3.26 (s, 3H), 1.52 (s, 9H). |
| 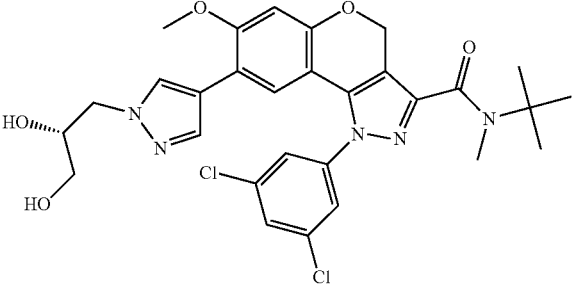<br>N-tert-butyl-1-(3,5-dichlorophenyl)-8-{1-[(2R)-2,3-dihydroxypropyl]-1H-pyrazol-4-yl}-7-methoxy-N-methyl-1H,4H-chromeno[4,3-c]pyrazole-3-carboxamide<br>Compound 191 | | 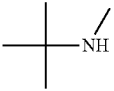 | m/z: 600 [M + H]⁺ | ¹H NMR (400 MHz, CDCl₃) δ 7.71 (s, 1H), 7.55-7.53 (m, 3H), 7.51 (s, 1H), 7.07 (s, 1H), 6.68 (s, 1H), 5.44 (s, 2H), 4.27 (d, J = 5.1 Hz, 2H), 4.11-4.08 (m, 1H), 3.90 (s, 3H), 3.68-3.59 (m, 2H), 3.26 (s, 3H), 1.52 (s, 9H). Stereochemistry is tentatively assigned. |
| 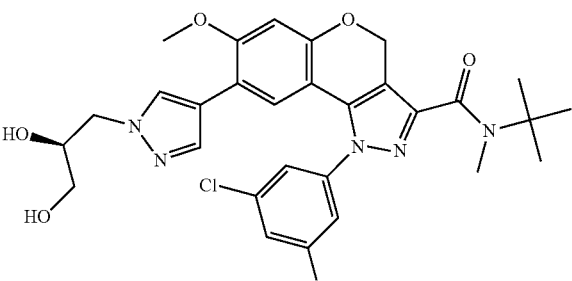<br>N-tert-butyl-1-(3,5-dichlorophenyl)-8-{1-[(2S)-2,3-dihydroxypropyl]-1H-pyrazol-4-yl}-7-methoxy-N-methyl-1H,4H-chromeno[4,3-c]pyrazole-3-carboxamide<br>Compound 192 | |  | m/z: 600 [M + H]⁺ | ¹H NMR (400 MHz, CDCl₃) δ 7.71 (s, 1H), 7.54 (d, J = 1.9 Hz, 3H), 7.51 (s, 1H), 7.07 (s, 1H), 6.68 (s, 1H), 5.44 (s, 2H), 4.27 (d, J = 5.1 Hz, 2H), 4.10 (s, 1H), 3.90 (s, 3H), 3.64 (dd, J = 8.9, 4.5 Hz, 2H), 3.26 (s, 3H), 1.52 (s, 9H). Stereochemistry is tentatively assigned. |

Example 19. N-tert-butyl-8-(1-hydroxypropan-2-yloxy)-7-methoxy-N-methyl-1-(thiophen-3-yl)-1,4-dihydrochromeno[4,3-c]pyrazole-3-carboxamide (Compound 193)

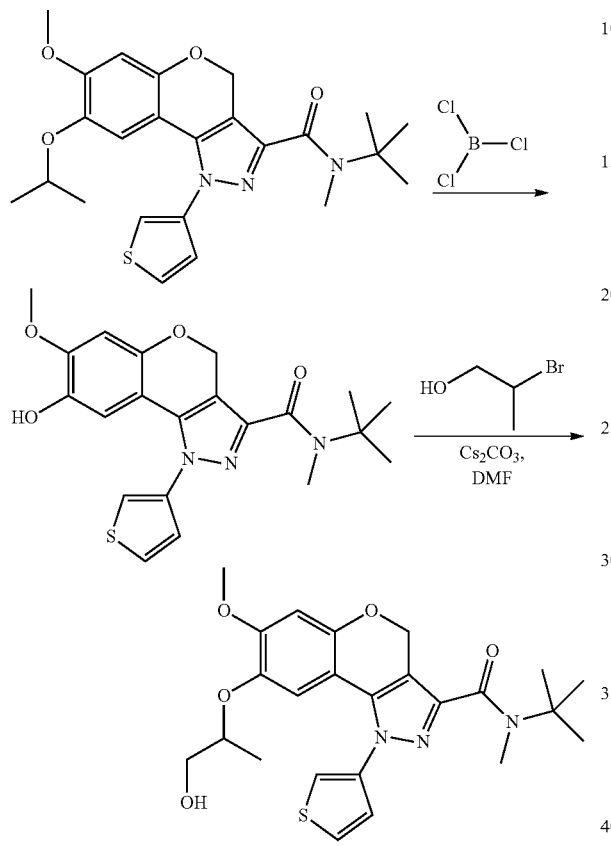

Step 1: N-tert-butyl-8-hydroxy-7-methoxy-N-methyl-1-(thiophen-3-yl)-1,4-dihydrochromeno[4,3-c]pyrazole-3-carboxamide At −10° C., BCl$_3$ was added to N-tert-butyl-8-isopropoxy-7-methoxy-N-methyl-1-(thiophen-3-yl)-1,4-dihydrochromeno[4,3-c]pyrazole-3-carboxamide (200 mg, 0.44 mmol) and stirred at −10° C. for 2 h. Then the resulting mixture was added to the sat.NaHCO$_3$ (20 ml) at 0° C., extracted with DCM (50 ml*3), dried and evaporated to get N-tert-butyl-8-hydroxy-7-methoxy-N-methyl-1-(thiophen-3-yl)-1,4-dihydrochromeno[4,3-c]pyrazole-3-carboxamide (220 mg, crude) as a white solid. LCMS m/z [M+H]$^+$ 414.

Step 2: N-tert-butyl-8-(1-hydroxypropan-2-yloxy)-7-methoxy-N-methyl-1-(thiophen-3-yl)-1,4-dihydrochromeno[4,3-c]pyrazole-3-carboxamide (Compound 193)

A mixture of N-tert-butyl-8-hydroxy-7-methoxy-N-methyl-1-(thiophen-3-yl)-1,4-dihydrochromeno[4,3-c]pyrazole-3-carboxamide (15 mg, 0.036 mmol), 2-bromopropan-1-ol (7.4 mg, 0.054 mmol) and Cs$_2$CO$_3$ (35 mg, 0.108 mmol) in DMF (1 ml) was stirred at RT for 5 h. Then the mixture was purified by preparative HPLC to get N-tert-butyl-8-(1-hydroxypropan-2-yloxy)-7-methoxy-N-methyl-1-(thiophen-3-yl)-1,4-dihydrochromeno[4,3-c]pyrazole-3-carboxamide (10 mg, 59%) as a white solid. LCMS m/z [M+H]$^+$ 472.0. $^1$H NMR (400 MHz, CDCl$_3$): 7.52-7.47 (m, 2H), 7.23-7.21 (m, 1H), 6.60 (s, 1H), 6.44 (s, 1H), 5.46-5.38 (m, 2H), 3.90-3.86 (m, 1H), 3.83 (s, 3H). 3.6 (t, 1H, J=6.0 Hz), 3.25 (s, 3H), 2.76 (t, 1H, J=6.4 Hz), 1.51 (s, 9H), 1.11 (d, 3H, J=6.4 Hz).

Example 20. N-tert-butyl-7-methoxy-N-methyl-1-(thiophen-3-yl)-8-(1H-1,2,3-triazol-4-yl)-1,4-dihydrochromeno[4,3-c]pyrazole-3-carboxamide (Compound 194)

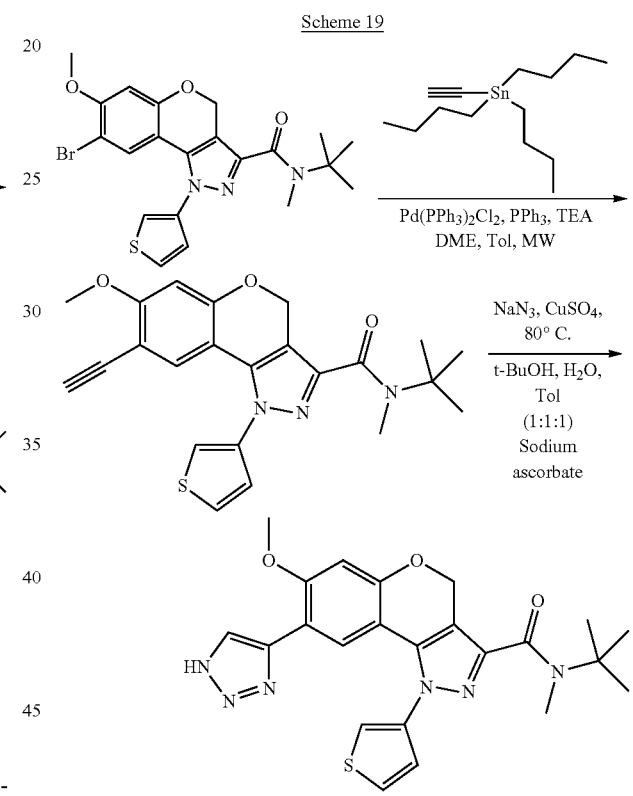

Step 1: N-tert-butyl-8-ethynyl-7-methoxy-N-methyl-1-(thiophen-3-yl)-1,4-dihydrochromeno[4,3-c]pyrazole-3-carboxamide A mixture of 8-bromo-N-tert-butyl-7-methoxy-N-methyl-1-(thiophen-3-yl)-1,4-dihydrochromeno[4,3-c]pyrazole-3-carboxamide (500 mg, 1.05 mmol), tributyl(ethynyl)stannane (1.65 g, 5.25 mmol), Pd(PPh$_3$)$_2$Cl$_2$ (147 mg, 0.21 mmol), PPh$_3$ (110 mg, 0.42 mmol), and TEA (318 mg, 3.15 mmol) in DME (10 ml) and toluene (5 ml) was heated at 140° C. by microwave for 5 h. Then the mixture was purified by column chromatography (silica gel: 200-300 mesh, PE:EtOAc=10:1) to get N-tert-butyl-8-ethynyl-7-methoxy-N-methyl-1-(thiophen-3-yl)-1,4-dihydrochromeno[4,3-c]pyrazole-3-carboxamide (390 mg, 88%) as a white solid. LCMS m/z [M+H]$^+$ 422.1.

Step 2: N-tert-butyl-7-methoxy-N-methyl-1-(thiophen-3-yl)-8-(1H-1,2,3-triazol-4-yl)-1,4-dihydrochromeno[4,3-c]pyrazole-3-carboxamide (Compound 194)

A mixture of N-tert-butyl-8-ethynyl-7-methoxy-N-methyl-1-(thiophen-3-yl)-1,4-dihydrochromeno[4,3-c]pyrazole-3-carboxamide (110 mg, 0.261 mmol), NaN$_3$ (85 mg, 1.306 mmol), sodium ascorbate (103 mg, 0.522 mmol) and CuSO$_4$ (42 mg, 0.261 mmol) in t-BuOH (3 ml), toluene (3 ml) and water (3 ml) was stirred at 80° C. under N$_2$ for 5 h. Then the mixture was filtered with celite and extracted with DCM (50 ml*3) and MeOH (5 ml*3) to afford the crude product. The residue was purified by Prep-TLC (silica gel: DCM:EA=10:1) to get N-tert-butyl-7-methoxy-N-methyl-1-(thiophen-3-yl)-8-(1H-1,2,3-triazol-4-yl)-1,4-dihydrochromeno[4,3-c]pyrazole-3-carboxamide (25 mg, 18%) as a white solid. LCMS m/z [M+H]+ 465.0. $^1$H NMR (400 MHz, CDCl$_3$): 7.65 (s, 1H), 7.56-7.55 (m, 2H), 7.25-7.23 (m, 2H), 6.69 (s, 1H), 5.55 (s, 2H), 3.976 (s, 3H), 3.281 (s, 3H), 1.515 (s, 9H).

Example 21. N-tert-butyl-1-(3,5-dichlorophenyl)-8-(2-fluoro-3-(hydroxymethyl)phenyl)-7-methoxy-N-methyl-1,4-dihydrochromeno[4,3-c]pyrazole-3-carboxamide (Compound 195)

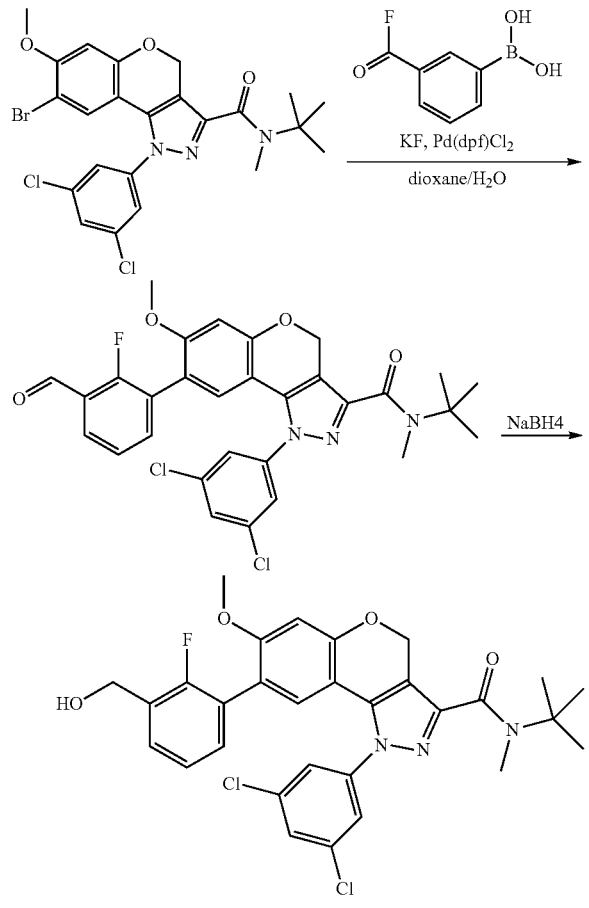

Scheme 20

Step 1: N-tert-butyl-1-(3,5-dichlorophenyl)-8-(2-fluoro-3-formylphenyl)-7-methoxy-N-methyl-1,4-dihydrochromeno[4,3-c]pyrazole-3-carboxamide To a solution of 8-bromo-N-tert-butyl-1-(3,5-dichlorophenyl)-7-methoxy-N-methyl-1,4-dihydrochromeno[4,3-c]pyrazole-3-carboxamide (50 mg, 0.093 mmol) in dioxane/H$_2$O (5/1, 2 mL) were added 2-fluoro-3-formylphenylboronic acid (35 mg, 0.186 mmol), KF (11 mg, 0.186 mmol), and Pd(dppf)Cl$_2$ (14 mg, 0.019 mmol) at RT under nitrogen. The reaction mixture was stirred at 90° C. for 2 h under MW conditions. The reaction mixture was directly purified by Combi-Flash (mobile phase: acetonitrile/water (10 mM NH$_4$HCO$_3$) to afford N-tert-butyl-1-(3,5-dichlorophenyl)-8-(2-fluoro-3-formylphenyl)-7-methoxy-N-methyl-1,4-dihydrochromeno[4,3-c]pyrazole-3-carboxamide (20 mg, 37%) as a white solid. LCMS m/z [M+H]$^+$ 582.

Step 2: N-tert-butyl-1-(3,5-dichlorophenyl)-8-(2-fluoro-3-(hydroxymethyl)phenyl)-7-methoxy-N-methyl-1,4-dihydrochromeno[4,3-c]pyrazole-3-carboxamide (Compound 195)

To a solution of N-tert-butyl-1-(3,5-dichlorophenyl)-8-(2-fluoro-3-formylphenyl)-7-methoxy-N-methyl-1,4-dihydrochromeno[4,3-c]pyrazole-3-carboxamide (20 mg, 0.034 mmol) in CH$_3$OH (2 mL) and THF (0.5 mL) was added NaBH$_4$ (2.6 mg, 0.069 mmol). The mixture was filtered, concentrated and purified by preparative HPLC (10 mM NH$_4$HCO$_3$) to give N-tert-butyl-1-(3,5-dichlorophenyl)-8-(2-fluoro-3-(hydroxymethyl)phenyl)-7-methoxy-N-methyl-1,4-dihydrochromeno[4,3-c]pyrazole-3-carboxamide (15 mg, 75%) as a white solid. LCMS m/z [M+H]$^+$ 584. $^1$H NMR (400 MHz, CDCl$_3$) δ 7.37 (d, J=1.8 Hz, 2H), 7.31-7.22 (m, 2H), 7.09-6.97 (m, 2H), 6.73 (s, 1H), 6.59 (s, 1H), 5.34 (s, 2H), 4.65 (s, 2H), 3.67 (s, 3H), 3.13 (s, 3H), 1.40 (s, 9H).

Example 22. N-(tert-butyl)-8-((1SR,2SR)-2-carbamoylcyclopropyl)-1-(3,5-dichlorophenyl)-7-methoxy-N-methyl-1,4-dihydrochromeno[4,3-c]pyrazole-3-carboxamide

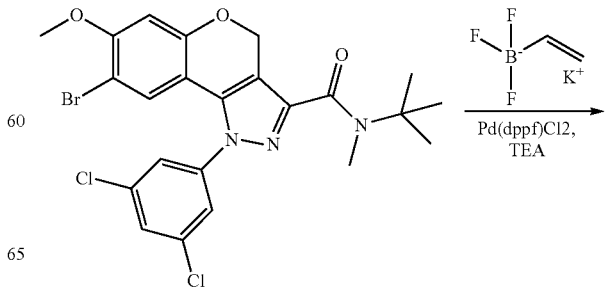

Scheme 21

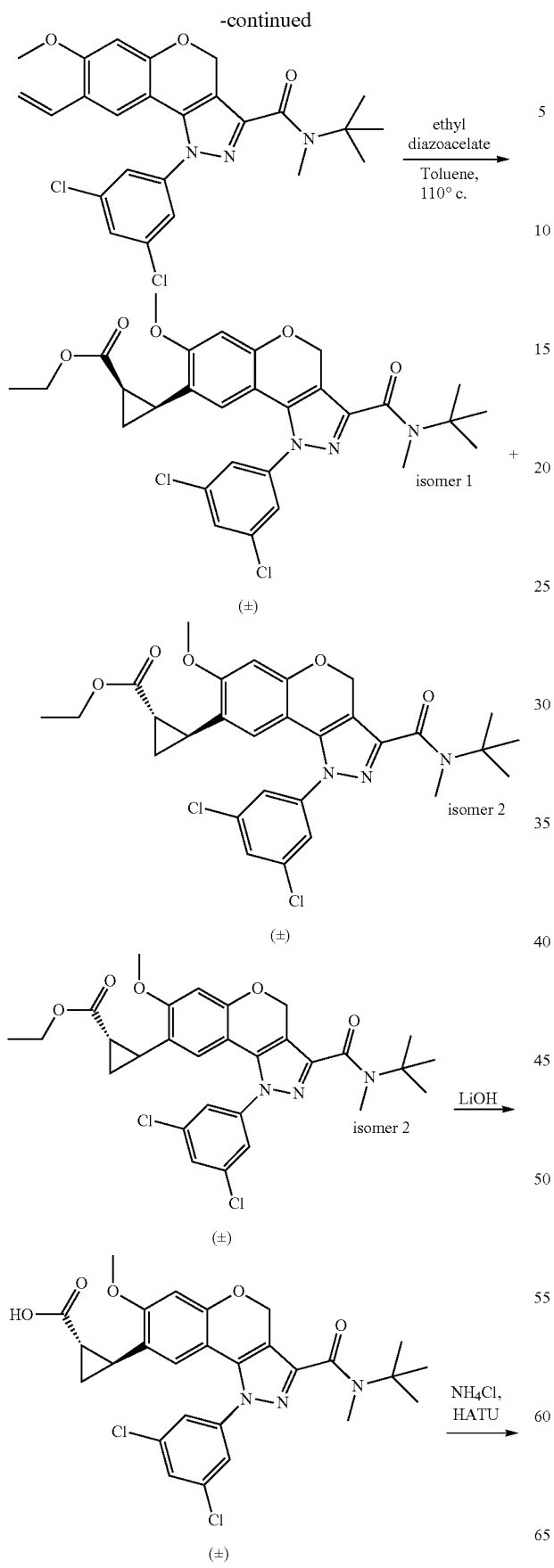

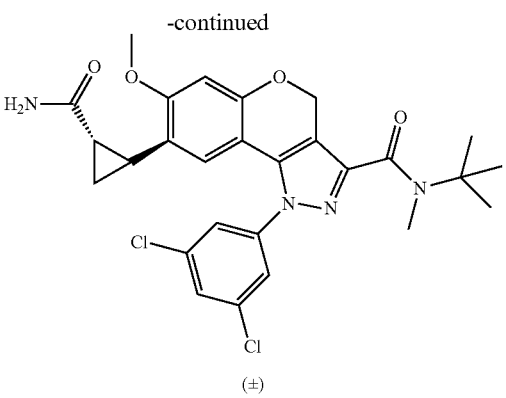

(±)

Step 1: N-(tert-butyl)-1-(3,5-dichlorophenyl)-7-methoxy-N-methyl-8-vinyl-1,4-dihydrochromeno[4,3-c]pyrazole-3-carboxamide A mixture of 8-bromo-N-tert-butyl-1-(3,5-dichlorophenyl)-7-methoxy-N-methyl-1,4-dihydrochromeno[4,3-c]pyrazole-3-carboxamide (100 mg, 0.186 mmol), potassium trifluoro(vinyl)borate (5 mg, 0.372 mmol), Pd(dppf)Cl$_2$'CH$_2$Cl$_2$ (0.1 eq.) and TEA (2 eq.) in 2 mL of EtOH (0.1 mol/L) was allowed to reflux for 3 hours under N$_2$. The reaction mixture was concentrated and purified by preparative TLC (DCM) to afford N-tert-butyl-1-(3,5-dichlorophenyl)-7-methoxy-N-methyl-8-vinyl-1,4-dihydrochromeno[4,3-c]pyrazole-3-carboxamide (85 mg, yield: 94.44%) as a white solid. LCMS: m/Z=487(M+H)+.

Step 2: (1RS,2SR)-ethyl 2-(3-(tert-butyl(methyl)carbamoyl)-1-(3,5-dichlorophenyl)-7-methoxy-1,4-dihydrochromeno[4,3-c]pyrazol-8-yl)cyclopropanecarboxylate (Compound 197) and (1SR,2SR)-ethyl 2-(3-(tert-butyl(methyl)carbamoyl)-1-(3,5-dichlorophenyl)-7-methoxy-1,4-dihydrochromeno[4,3-c]pyrazol-8-yl)cyclopropanecarboxylate (Compound 198)

A mixture of compound N-tert-butyl-1-(3,5-dichlorophenyl)-7-methoxy-N-methyl-8-vinyl-1,4-dihydrochromeno[4,3-c]pyrazole-3-carboxamide (85 mg, 0.175 mmol), ethyl diazoacetate (200 mg, 10 eq.) in 5 mL of toluene was sealed up and heated at 110° C. for 3 days. The reaction mixture was concentrated and purified by preparative HPLC to afford isomer 1 (10 mg, 10%) as a white solid and isomer 2 (25 mg, 25%) as a white solid.

Compound 197: LCMS: m/Z=572[M+H]+. $^1$H NMR (400 MHz, CDCl$_3$) δ 7.53-7.51 (m, 2H). 7.50-7.49 (m, 1H), 6.82 (s, 1H), 6.51 (s, 1H), 5.44-5.33 (m, 2H), 3.91-3.88 (m, 2H), 3.78 (s, 3H), 3.23 (s, 3H), 2.25-2.23 (m, 1H), 2.0-1.99 (m, 1H), 1.48 (s, 9H), 1.28-1.26 (m, 1H), 1.17-1.15 (m, 1H), 1.03-1.01 (m, 3H). Stereochemistry is tentatively assigned.

Compound 198: LCMS: m/Z=572 [M+H]+. $^1$H NMR (400 MHz, CDCl$_3$) δ 7.52-7.50 (m, 1H), 7.45-7.44 (m, 2H), 6.56 (s, 1H), 6.43 (s, 1H), 5.39-5.38 (m, 2H), 4.16-4.14 (m, 2H), 3.83 (s, 3H), 3.24-3.23 (m, 4H), 2.54-2.50 (m, 1H), 1.51 (s, 9H), 1.44-1.39 (m, 1H), 1.29-1.26 (m, 3H), 0.92-0.89 (m, 1H). Stereochemistry is tentatively assigned.

Step 3: (1SR,2SR)-2-(3-(tert-butyl(methyl)carbamoyl)-1-(3,5-dichlorophenyl)-7-methoxy-1,4-dihydrochromeno[4,3-c]pyrazol-8-yl)cyclopropanecarboxylic acid (Compound 204)

To a solution of (1SR,2SR)-ethyl 2-(3-(tert-butyl(methyl)carbamoyl)-1-(3,5-dichlorophenyl)-7-methoxy-1,4-dihydrochromeno[4,3-c]pyrazol-8-yl)cyclopropanecarboxylate (Compound 198) (20 mg, 0.035 mmol) in MeOH/H$_2$O (3:1) (4 mL) was added LiOH.H$_2$O (10 eq.). The reaction mixture was stirred at room temperature overnight. The solvent was concentrated and purified by Prep-TLC (DCM/MeOH=20:1) to afford 2-(3-(tert-butyl(methyl)carbamoyl)-1-(3,5-dichlorophenyl)-7-methoxy-1,4-dihydrochromeno[4,3-c]pyrazol-8-yl)cyclopropanecarboxylic acid (17 mg, yield: 89.5%) as a white solid. LCMS: m/z=544 [M+H]$^+$. $^1$H NMR (400 mHz, CDCl$_3$) δ 7.51-7.50 (m, 2H). 7.45-7.44 (m, 1H), 6.57 (s, 1H), 6.45 (s, 1H), 5.40-5.38 (m, 2H), 3.83 (s, 3H), 3.24 (s, 3H), 2.56-2.53 (m, 1H), 1.47 (s, 9H), 1.46-1.43 (m, 2H), 1.15-1.10 (m, 1H).

Step 4: N-(tert-butyl)-8-((1SR,2SR)-2-carbamoylcyclopropyl)-1-(3,5-dichlorophenyl)-7-methoxy-N-methyl-1,4-dihydrochromeno[4,3-c]pyrazole-3-carboxamide (Compound 201)

A mixture of compound 2-(3-(tert-butyl(methyl)carbamoyl)-1-(3,5-dichlorophenyl)-7-methoxy-1,4-dihydrochromeno[4,3-c]pyrazol-8-yl)cyclopropanecarboxylic acid (from Compound 204) (10 mg, 0.0184 mmol), NH4Cl (5 eq.), HATU (1.2 eq, 8.5 mg), DIPEA (3 eq.) in 3 mL of DMF was stirred at room temperature overnight. The reaction mixture was concentrated and purified by preparative HPLC to afford N-tert-butyl-8-(2-carbamoylcyclopropyl)-1-(3,5-dichlorophenyl)-7-methoxy-N-methyl-1,4-dihydrochromeno[4,3-c]pyrazole-3-carboxamide (8 mg, yield: 80.16%) as a white solid. LCMS: m/z=543 [M+H]+; $^1$H NMR (400 MHz, CDCl$_3$) δ 7.51-7.50 (m, 1H). 7.47-7.46 (m, 2H), 6.57 (s, 1H), 6.43 (s, 1H), 5.44 (bs, 1H), 5.35-5.31 (m, 3H), 3.23 (s, 3H), 3.02 (s, 3H), 2.54-2.50 (m, 1H), 1.46 (s, 9H), 1.45-1.40 (m, 1H), 1.34-1.30 (m, 1H), 0.89-0.84 (m, 1H).

The following compounds were prepared using procedures analogous to those disclosed in Scheme 21.

| Compound | | Amine Starting Material | LC-MS | NMR |
|---|---|---|---|---|
| 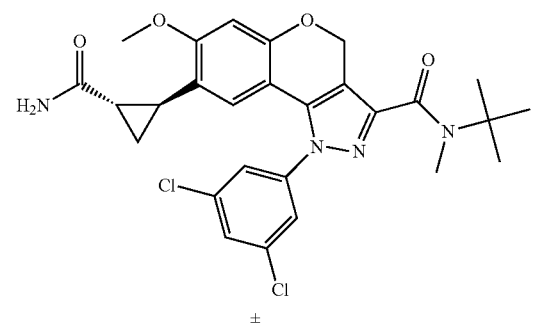 [SMILES: COc1cc2c(cc1[C@H]1C[C@@H]1C(N)=O)-c1c(c(C(=O)N(C)C(C)(C)C)nn1-c1cc(Cl)cc(Cl)c1)CO2] N-(tert-butyl)-8-((SR,2SR)-2-carbamoylcyclo-propyl)-1-(3,5-dichlorophenyl)-7-methoxy-N-methyl-1,4-dihydrochromeno[4,3-c]pyrazole-3-carboxamide Compound 200 | |  | m/z: 543 [M + H]$^+$ | $^1$H NMR (400 MHz, CDCl$_3$) δ 7.51-7.50 (m, 1H), 7.47-7.46 (m, 2H), 6.57 (s, 1H), 6.43 (s, 1H), 5.44 (bs, 1H), 5.35-5.31 (m, 3H), 3.23 (s, 3H), 3.02 (s, 3H), 2.54-2.50 (m, 1H), 1.46 (s, 9H), 1.45-1.40 (m, 1H), 1.34-1.30 (m, 1H), 0.89-0.84 (m, 1H). |
| 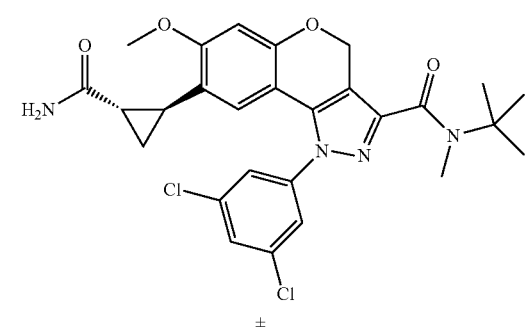 [SMILES: COc1cc2c(cc1[C@H]1C[C@@H]1C(N)=O)-c1c(c(C(=O)N(C)C(C)(C)C)nn1-c1cc(Cl)cc(Cl)c1)CO2] (1S,2SR)-2-(3-(tert-butyl(methyl)carb-amoyl)-1-(3,5-dichlorophenyl)-7-methoxy-1,4-dihydrochromeno[4,3-c]pyrazol-8-yl)cyclopropane-carboxylic acid Compound 203 | |  | m/z: 544 [M + H]$^+$ | $^1$H NMR (400 MHz, CDCl3) δ 7.51-7.50 (m, 2H), 7.45-7.44 (m, 1H), 6.57 (s, 1H), 6.45 (s, 1H), 5.40-5.38 (m, 2H), 3.83 (s, 3H), 3.24 (s, 3H), 2.56-2.53 (m, 1H), 1.47 (s, 9H), 1.46-1.43 (m, 2H), 1.15-1.10 (m, 1H). |

-continued

| Compound | Amine Starting Material | LC-MS | NMR |
|---|---|---|---|
| 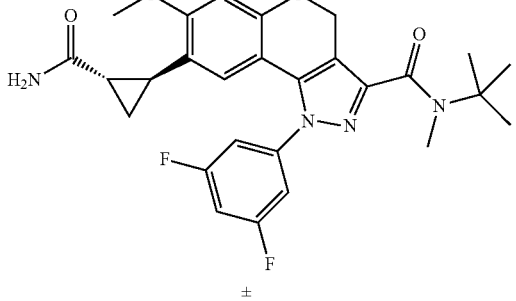<br>(1S,2SR)-2-(3-(tert-butyl(methyl)carb-amoyl)-1-(3,5-dichlorophenyl)-7-methoxy-1,4-dihydrochromeno[4,3-c]pyrazol-8-yl)cyclopropane-carboxylic acid<br>Compound 205 |  | m/z: 512 [M + H]⁺ | 1H NMR (400 MHz, Chloroform-d) δ 7.08 (dd, J = 7.0, 2.3 Hz, 2H), 6.98 (td, J = 8.9, 4.5 Hz, 1H), 6.54 (s, 1H), 6.44 (s, 1H), 5.39 (s, 2H), 3.80 (s, 3H), 3.24 (s, 3H), 2.67 (brs, 1H), 2.50-2.54 (m, 1H), 1.49-1.53 (m, 11H), 0.85-0.92 (m, 1H). |
| 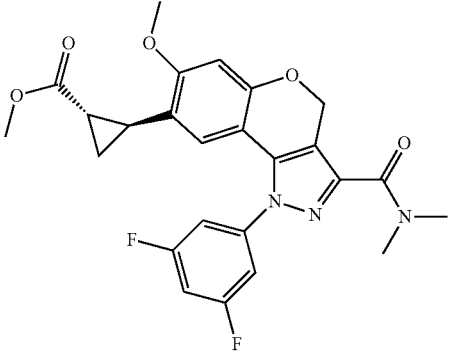<br>(1SR,2SR)-methyl 2-(3-(tert-butyl(methyl)carb-amoyl)-1-(3,5-difluorophenyl)-7-methoxy-1,4-dihydrochromeno[4,3-c]pyrazol-8-yl)cyclopropane carboxylate<br>Compound 206 |  | m/z: 526 [M + H]⁺ | 1H NMR (400 MHz, Chloroform-d) δ 7.10 (dd, J = 7.3, 2.3 Hz, 2H), 6.98 (tt, J = 8.7, 2.3 Hz, 1H), 6.56 (s, 1H), 6.44 (s, 1H), 5.39 (s, 2H), 3.82 (s, 3H), 3.70 (s, 3H), 3.25 (s, 3H), 2.51 (ddd, J = 9.2, 6.7, 4.3 Hz, 1H), 1.48 (s, 9H), 1.40 (dt, J = 9.3, 4.8 Hz, 1H), 0.83-0.87 (m, 2H). |
| 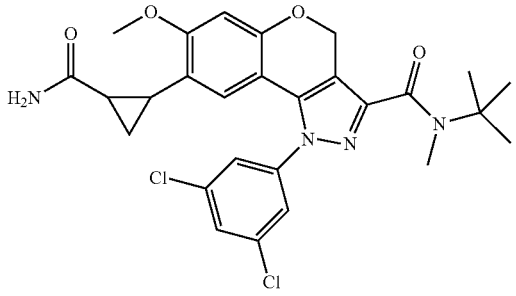<br>N-(tert-butyl)-8-((1SR,2SR)-2-carbamoylcyclo-propyl)-1-(3,5-difluorophenyl)-7-methoxy-N-methyl-1,4-dihydrochromeno[4,3-c]pyrazole-3-carboxamide<br>Compound 199 |  | m/z: 511 [M + H]⁺ | 1H NMR (400 MHz, Chloroform-d) δ 7.12 (dd, J = 7.3, 2.3 Hz, 2H), 6.99 (tt, J = 8.7, 2.3 Hz, 1H), 6.57 (s, 1H), 6.48 (s, 1H), 5.55 (s, 1H), 5.47-5.29 (m, 2H), 3.83 (s, 3H), 3.24 (s, 3H), 2.51 (ddd, J = 9.2, 6.7, 4.3 Hz, 1H), 1.51 (s, 9H), 1.43 (dt, J = 9.3, 4.8 Hz, 1H), 1.36-1.25 (m, 1H), 0.85 (ddd, J = 8.1, 6.7, 4.4 Hz, 1H). |

Example 23. N-tert-butyl-7-methoxy-N-methyl-1-(thiophen-3-yl)-8-(1H-1,2,4-triazol-3-yl)-1,4-dihydrochromeno[4,3-c]pyrazole-3-carboxamide (Compound 207)

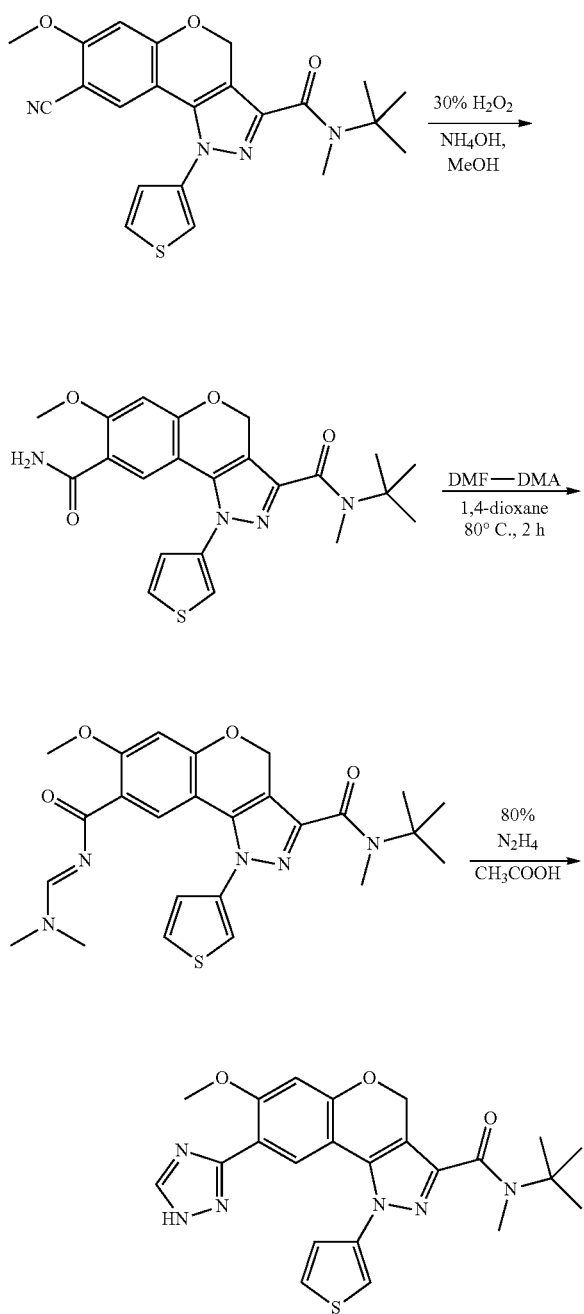

Step 1: N³-tert-butyl-7-methoxy-N³-methyl-1-(thiophen-3-yl)-1,4-dihydrochromeno[4,3-c]pyrazole-3,8-dicarboxamide A mixture of N-tert-butyl-8-cyano-7-methoxy-N-methyl-1-(thiophen-3-yl)-1,4-dihydrochromeno[4,3-c]pyrazole-3-carboxamide (200 mg, 0.47 mmol), 30% $H_2O_2$ (2 mL) and $NH_4OH$ (2 mL) in MeOH (10 mL) was heated at 50° C. overnight. After cooling to room temperature, the reaction was diluted with EtOAc (60 mL) and washed with water (10 mL×3), brine (20 mL), dried ($Na_2SO_4$), and evaporated to afford N3-tert-butyl-7-methoxy-N3-methyl-1-(thiophen-3-yl)-1,4-dihydrochromeno[4,3-c]pyrazole-3,8-dicarboxamide (151 mg, 72%) as a white solid which used directly without further purification. m/z=441.1 [M+H]⁺.

Step 2: (E)-N3-tert-butyl-N8-((dimethylamino)methylene)-7-methoxy-N3-methyl-1-(thiophen-3-yl)-1,4-dihydrochromeno[4,3-c]pyrazole-3,8-dicarboxamide A mixture of N3-tert-butyl-7-methoxy-N3-methyl-1-(thiophen-3-yl)-1,4-dihydrochromeno[4,3-c]pyrazole-3,8-dicarboxamide (30 mg, 0.068 mmol) and DMF-DMA (24 mg, 0.20 mmol) in 1,4-dioxane (3 mL) was heated at 80° C. for 2 hrs under $N_2$. After cooling to room temperature, then the reaction was concentrated to afford (E)-N³-tert-butyl-N⁸-((dimethylamino)methylene)-7-methoxy-N³-methyl-1-(thiophen-3-yl)-1,4-dihydrochromeno[4,3-c]pyrazole-3,8-dicarboxamide (35 mg, 100%) as a light-yellow oil which used directly without further purification. m/z=496 [M+H]⁺.

Step 3: N-tert-butyl-7-methoxy-N-methyl-1-(thiophen-3-yl)-8-(1H-1,2,4-triazol-3-yl)-1,4-dihydrochromeno[4,3-c]pyrazole-3-carboxamide (Compound 207)

To a solution of (E)-N³-tert-butyl-N⁸-((dimethylamino)methylene)-7-methoxy-N3-methyl-1-(thiophen-3-yl)-1,4-dihydrochromeno[4,3-c]pyrazole-3,8-dicarboxamide (10 mg, 0.02 mmol) in AcOH (1 mL) at 0° C., 80% $N_2H_4 \cdot H_2O$ (3 mg, 0.06 mmol) was added. Then the mixture was stirred at room temperature for 2 hrs. Then the reaction was diluted with EtOAc (60 mL) and washed with water (10 mL×3), $NaHCO_3$ (sat.) (10 mL×3), brine (20 mL), dried ($Na_2SO_4$), evaporated. The residue was purified by Pre-TLC (silica gel: PE:EA=1:1) to afford N-tert-butyl-7-methoxy-N-methyl-1-(thiophen-3-yl)-8-(1H-1,2,4-triazol-3-yl)-1,4-dihydrochromeno[4,3-c]pyrazole-3-carboxamide (5 mg, 48%) as a white solid. m/z=465.0 [M+H]. ¹H NMR (400 MHz, CDCl₃) δ ppm 11.46 (br, 1H), 7.88-7.85 (m, 2H), 7.55-7.54 (m, 2H), 7.26 (m, 1H), 6.72 (s, 1H), 5.56 (s, 2H), 4.03 (s, 3H), 3.29 (s, 3H), 2.86 (s, 3H), 1.51 (s, 9H).

The following compound was prepared using procedures analogous to those disclosed in Scheme 21.

| Compound | Hydrazinyl Starting material | Amine Starting material | LC/MS | NMR |
|---|---|---|---|---|
| N-tert-butyl-7-methoxy-N-methyl-8-(1-methyl-1H-1,2,4-triazol-5-yl)-1-(thiophen-3-yl)-1,4-dihydrochromeno[4,3-c]pyrazole-3-carboxamide Compound 208 | MeN$_2$H$_4$ | (t-butyl-methyl-amine) | m/z: 479 [M + H]$^+$ | $^1$H NMR (400 MHz, CDCl$_3$) δ ppm 7.87 (s, 1H), 7.49 (s, 1H), 7.44 (d, J = 5.2 Hz, 1H), 7.20 (d, J = 5.2 Hz, 1H), 6.92 (s, 1H), 6.68 (s, 1H), 5.55 (s, 2H), 3.82 (s, 3H), 3.68 (s, 3H), 3.27 (s, 3H), 1.51 (s, 9H). |

Example 24. EC$_{50}$ of Cyclic AMP Production in CHO FSHR Cells+EC$_{20}$ FSH (Assay A)

2500 Cho-FSHR-LUC-1-1-43 cells were plated per well in 5 µl of phenol red free DMEM/F12+1% FBS. Cells were plated in 384 well, solid white low volume plates (Greiner 784075) by Multidrop. Cells were assayed by adding 100 µl of 2×EC$_{20}$ FSH/IBMX in DMEM/F12+0.1% BSA) by Multidrop to 2 µl of test compound stamped in 384 well plates (compounds are diluted 1:50). The final FSH concentration was 0.265 pM, and the final IBMX concentration was 200 µM. The compound plate map was as follows: Column 1: 2 µl of DMSO; Column 2: 2 µl of DMSO; Columns 3-12 and 13-24: 2 µl of test compound, diluted 1:4 in 100% DMSO, or 2 µl of FSH, diluted 1:4 in DMEM/F12+0.1% BSA. The starting concentration for FSH was 50 nM (final concentration was 0.5 nM). Furthermore, Column 23 contained 2 µl of EC$_{100}$ FSH reference (100×) (diluted in DMEM/F12+0.1% BSA) at a final concentration of 0.5 nM, and Column 24 contained 2 µl of 1 mM AS707664/2 reference compound 2.5 µl of compound+EC$_{20}$ FSH mixture were transferred to cell plates (1:2 dilution into 5 µl of cell media) The plates were incubated at 37° C. for 1 h. 10 µl of mixed HTRF (CisBio #62AM4PEC) reagents were added per well and incubated at room temperature for 1 h. The plates were read on Envision using the cAMP HTRF—low volume 384 well protocol. The readout was the calculated fluorescence ratio (665 nm/620 nm). Values given in percent (%) indicate the percental effect (response) at a certain concentration of agonist relative to the maximum response of the FSH standard. The results are provided below.

Example 25. Rat Granulosa EC$_{50}$ FSH (Assay B)

The assay was performed pursuant to the teaching of Yanofsky et al. (2006) Allosteric activation of the follicle-stimulating hormone (FSH) receptor by selective, nonpeptide agonists (JBC 281(19): 13226-13233, which is incorporated by reference in the disclosure of the invention). The results are provided below.

The data is interpreted according to the following:

| Compound number | Assay A (nM) | Assay B (nM) |
|---|---|---|
| 1 | ++++ | +++ |
| 2 | ++++ | +++ |
| 3 | ++++ | +++ |
| 4 | +++ | + |
| 5 | +++ | ++ |
| 6 | ++++ | ++ |
| 7 | +++ | ++ |
| 8 | ++++ | ++ |
| 9 | ++++ | ++ |
| 10 | ++++ | +++ |
| 11 | ++++ | |
| 12 | ++++ | +++ |
| 13 | +++ | |
| 14 | ++++ | +++ |
| 15 | ++++ | |
| 16 | ++++ | ++ |
| 17 | ++++ | ++ |
| 18 | +++ | ++ |
| 19 | ++++ | ++ |
| 20 | ++++ | ++ |
| 21 | ++++ | +++ |
| 22 | ++++ | +++ |
| 23 | ++++ | +++ |
| 24 | ++++ | +++ |
| 25 | ++++ | +++ |
| 26 | +++ | ++ |
| 27 | +++ | + |
| 28 | ++++ | ++ |
| 29 | +++ | ++ |
| 30 | ++ | ++ |
| 31 | +++ | ++ |
| 32 | +++ | ++ |
| 33 | ++++ | +++ |
| 34 | ++++ | +++ |
| 35 | ++++ | |
| 36 | ++++ | +++ |
| 37 | +++ | + |
| 38 | +++ | ++ |
| 39 | +++ | ++ |
| 40 | ++++ | +++ |
| 41 | +++ | ++ |
| 42 | ++++ | +++ |
| 43 | ++++ | +++ |
| 44 | ++++ | +++ |
| 45 | ++++ | |
| 46 | +++ | ++ |
| 47 | +++ | |
| 48 | +++ | ++ |
| 49 | ++++ | +++ |
| 50 | ++++ | ++ |
| 51 | +++ | ++ |
| 52 | +++ | ++ |
| 53 | +++ | ++ |

| Compound number | Assay A (nM) | Assay B (nM) |
|---|---|---|
| 54 | ++++ | +++ |
| 55 | ++++ | +++ |
| 56 | +++ | ++ |
| 57 | +++ | ++ |
| 58 | +++ | + |
| 59 | +++ | + |
| 60 | ++++ | ++ |
| 61 | ++++ | +++ |
| 62 | ++++ | +++ |
| 63 | +++ | ++ |
| 64 | +++ | ++ |
| 65 | ++++ | +++ |
| 66 | ++++ | +++ |
| 67 | ++++ | ++ |
| 68 | ++++ | ++ |
| 69 | ++++ | +++ |
| 70 | ++++ | +++ |
| 71 | +++ | ++ |
| 72 | ++++ | +++ |
| 73 | ++++ | ++ |
| 74 | ++++ | +++ |
| 75 | +++ | +++ |
| 76 | +++ | + |
| 77 | ++++ | +++ |
| 78 | ++++ | +++ |
| 79 | +++ | ++ |
| 80 | ++++ | ++ |
| 81 | +++ | ++ |
| 82 | ++++ | + |
| 83 | ++++ | ++ |
| 84 | +++ | ++ |
| 85 | +++ | + |
| 86 | ++++ | ++ |
| 87 | +++ | ++ |
| 88 | +++ | ++ |
| 89 | ++++ | ++ |
| 90 | ++++ | ++ |
| 91 | ++++ | +++ |
| 92 | ++++ | +++ |
| 93 | ++++ | +++ |
| 94 | ++++ | ++++ |
| 95 | +++ | +++ |
| 96 | ++++ | ++++ |
| 97 | ++++ | ++++ |
| 98 | ++++ | ++ |
| 99 | ++++ | +++ |
| 100 | ++++ | +++ |
| 101 | ++++ | +++ |
| 102 | ++++ | +++ |
| 103 | +++ | + |
| 104 | +++ | + |
| 105 | ++++ | +++ |
| 106 | +++ | + |
| 107 | ++++ | ++ |
| 108 | ++++ | +++ |
| 109 | ++++ | +++ |
| 110 | ++++ | +++ |
| 111 | +++ | ++ |
| 112 | +++ | ++ |
| 113 | ++++ | +++ |
| 114 | +++ | ++ |
| 115 | ++++ | ++ |
| 116 | ++++ | +++ |
| 117 | ++++ | +++ |
| 118 | ++++ | +++ |
| 119 | ++++ | ++ |
| 120 | ++++ | +++ |
| 121 | +++ | + |
| 122 | +++ | ++ |
| 123 | ++++ | +++ |
| 124 | +++ | |
| 125 | ++++ | +++ |
| 126 | +++ | |
| 127 | +++ | ++ |
| 128 | +++ | |
| 129 | +++ | |
| 130 | +++ | ++ |
| 131 | +++ | +++ |
| 132 | +++ | ++ |
| 133 | ++++ | |
| 134 | +++ | + |
| 135 | ++++ | +++ |
| 136 | ++++ | +++ |
| 137 | ++++ | ++ |
| 138 | ++++ | ++ |
| 139 | ++++ | +++ |
| 140 | ++++ | ++ |
| 141 | ++++ | +++ |
| 142 | ++++ | +++ |
| 143 | +++ | |
| 144 | + | |
| 145 | ++++ | ++ |
| 146 | ++++ | ++ |
| 147 | ++++ | + |
| 148 | ++++ | +++ |
| 149 | ++++ | +++ |
| 150 | ++++ | +++ |
| 151 | ++++ | +++ |
| 152 | | |
| 153 | ++++ | +++ |
| 154 | ++++ | ++++ |
| 155 | ++++ | ++++ |
| 156 | ++++ | +++ |
| 157 | ++++ | ++++ |
| 158 | ++++ | +++ |
| 159 | ++++ | +++ |
| 160 | ++++ | +++ |
| 161 | ++++ | +++ |
| 162 | ++++ | ++ |
| 163 | ++++ | ++ |
| 164 | ++++ | ++++ |
| 165 | ++++ | +++ |
| 166 | ++++ | ++ |
| 167 | ++++ | +++ |
| 168 | ++++ | ++ |
| 169 | ++++ | ++ |
| 170 | ++++ | ++ |
| 171 | ++++ | ++++ |
| 172 | ++++ | +++ |
| 173 | ++++ | +++ |
| 174 | ++++ | +++ |
| 175 | ++++ | +++ |
| 176 | ++++ | +++ |
| 177 | ++++ | +++ |
| 178 | ++++ | ++++ |
| 179 | +++ | ++ |
| 180 | +++ | |
| 181 | ++++ | +++ |
| 182 | ++++ | ++++ |
| 183 | ++++ | +++ |
| 184 | ++++ | +++ |
| 185 | +++ | ++ |
| 186 | +++ | |
| 187 | ++++ | ++ |
| 188 | ++++ | ++ |
| 189 | +++ | ++ |
| 190 | +++ | + |
| 191 | +++ | ++ |
| 192 | ++ | |
| 193 | +++ | ++ |
| 194 | ++++ | + |
| 195 | +++ | +++ |
| 196 | ++++ | ++ |
| 197 | +++ | + |
| 199 | ++++ | ++ |
| 205 | +++ | |
| 206 | ++++ | ++ |

-continued

| Compound number | Assay A (nM) | Assay B (nM) |
|---|---|---|
| 207 | ++++ | ++ |
| 208 | +++ | + |

+ >500 nM;
++ 101-500 nM;
+++ 10-100 nM;
++++ <10 nM.

Example 26. Pharmaceutical Preparations (A) Injection vials: A solution of 100 g of an active ingredient according to the invention and 5 g of disodium hydrogen phosphate in 3 l of bidistilled water is adjusted to pH 6.5 using 2 N hydrochloric acid, sterile filtered, transferred into injection vials, is lyophilized under sterile conditions and is sealed under sterile conditions. Each injection vial contains 5 mg of active ingredient.

(B) Suppositories: A mixture of 20 g of an active ingredient according to the invention is melted with 100 g of soy lecithin and 1400 g of cocoa butter, is poured into moulds and is allowed to cool. Each suppository contains 20 mg of active ingredient.

(C) Solution: A solution is prepared from 1 g of an active ingredient according to the invention, 9.38 g of $NaH_2PO_4.2 H_2O$, 28.48 g of $Na_2HPO_4.12 H_2O$ and 0.1 g of benzalkonium chloride in 940 ml of bidistilled water. The pH is adjusted to 6.8, and the solution is made up to 1 l and sterilized by irradiation. This solution could be used in the form of eye drops.

(D) Ointment: 500 mg of an active ingredient according to the invention is mixed with 99.5 g of Vaseline under aseptic conditions.

(E) Tablets: A mixture of 1 kg of an active ingredient according to the invention, 4 kg of lactose, 1.2 kg of potato starch, 0.2 kg of talc and 0.1 kg of magnesium stearate is pressed to give tablets in a conventional manner in such a way that each tablet contains 10 mg of active ingredient.

(F) Coated tablets: Tablets are pressed analogously to Example E and subsequently are coated in a conventional manner with a coating of sucrose, potato starch, talc, tragacanth and dye.

(G) Capsules: 2 kg of an active ingredient according to the invention are introduced into hard gelatin capsules in a conventional manner in such a way that each capsule contains 20 mg of the active ingredient.

(H) Ampoules: A solution of 1 kg of an active ingredient according to the invention in 60 l of bidistilled water is sterile filtered, transferred into ampoules, is lyophilized under sterile conditions and is sealed under sterile conditions. Each ampoule contains 10 mg of active ingredient.

(I) Inhalation spray: 14 g of an active ingredient according to the invention are dissolved in 10 l of isotonic NaCl solution, and the solution is transferred into commercially available spray containers with a pump mechanism. The solution could be sprayed into the mouth or nose. One spray shot (about 0.1 ml) corresponds to a dose of about 0.14 mg.

While a number of embodiments of this invention are described herein, it is apparent that the basic examples may be altered to provide other embodiments that utilize the compounds and methods of this invention. Therefore, it will be appreciated that the scope of this invention is to be defined by the appended claims rather than by the specific embodiments that have been represented by way of example.

We claim:
1. A compound of formula I,

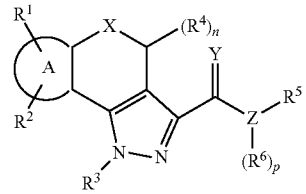

I or a pharmaceutically acceptable salt thereof, wherein:

X is O;

Y is O;

Z is N;

each R is independently hydrogen, $C_{1-6}$ aliphatic, aryl, a 3-8 membered saturated or partially unsaturated carbocyclic ring, a 3-7 membered heterocyclic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur, each of which is optionally substituted; or two R groups on the same atom are taken together with the atom to which they are attached to form an aryl ring, a 3-8 membered saturated or partially unsaturated carbocyclic ring, a 3-7 membered heterocyclic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur, each of which is optionally substituted;

Ring A is phenyl;

$R^1$ is —OR;

$R^2$ is aryl, a 3-8 membered saturated or partially unsaturated carbocyclic ring, or a 5-6 membered monocyclic heteroaryl ring having 1-4 heteroatoms independently selected from nitrogen, oxygen, or sulfur, each of which is optionally substituted;

$R^3$ is an optionally substituted phenyl;

each $R^4$ is independently —R, -halogen, -haloalkyl, —OR, —SR, —CN, —NO$_2$, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$;

$R^5$ is an optionally substituted $C_{1-6}$ aliphatic; and $R^6$ is an optionally substituted $C_{1-6}$ aliphatic;

or $R^5$, $R^6$, and Z together form an optionally substituted 3-8 membered heterocyclic ring having 1-4 heteroatoms independently selected from nitrogen, oxygen or sulfur;

n is 0; and p is 1.

2. The compound of claim 1, wherein $R^2$ is a 6-membered aryl ring, a 3-membered carbocyclic ring, or a 5-6 membered monocyclic heteroaryl ring having 1-4 nitrogen atoms, each of which is optionally substituted.

3. The compound of claim 2, wherein R² is
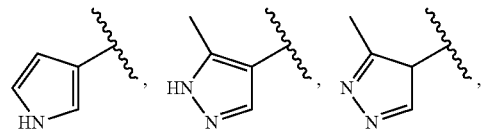
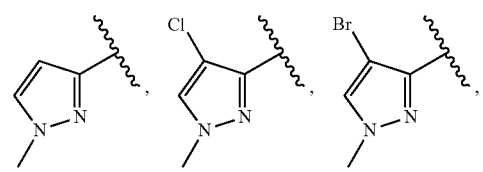
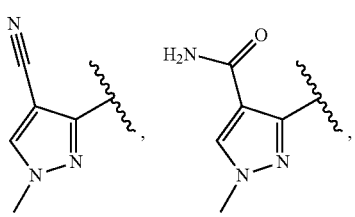
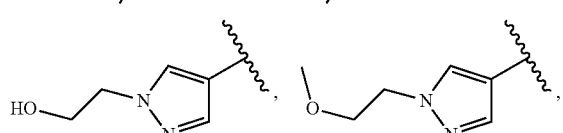
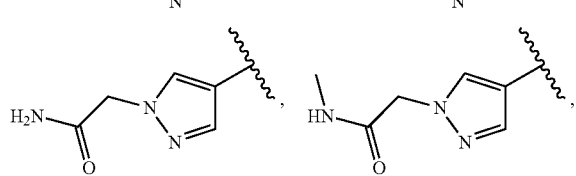
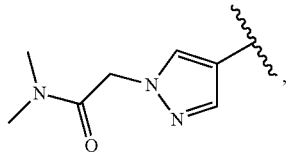
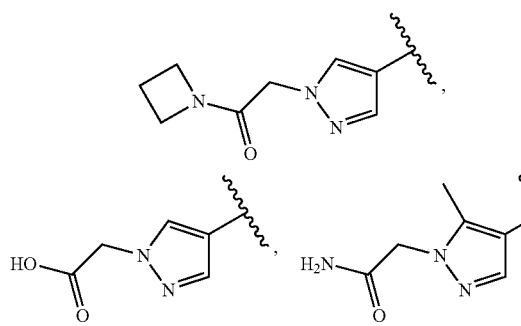
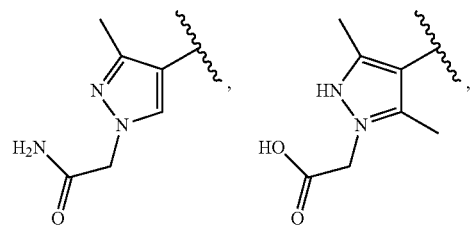
-continued
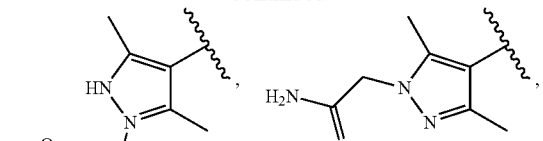
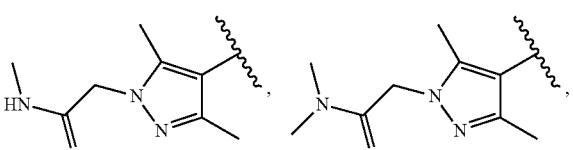
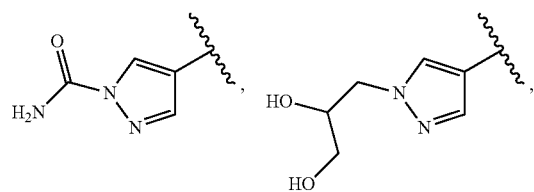
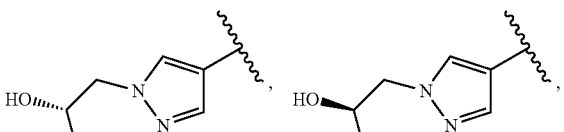
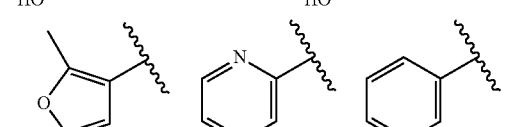
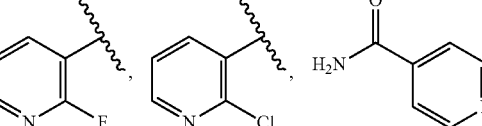
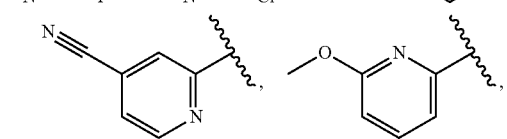
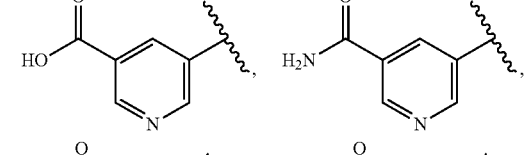
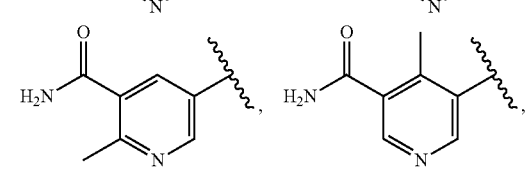

301
-continued
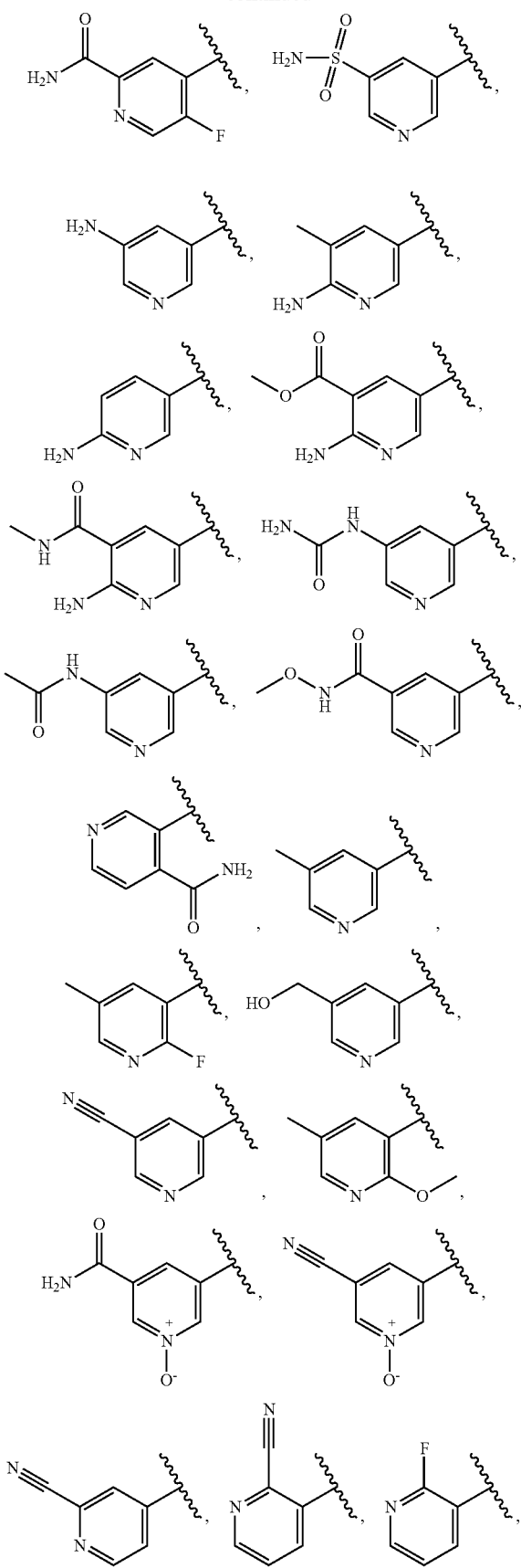
302
-continued
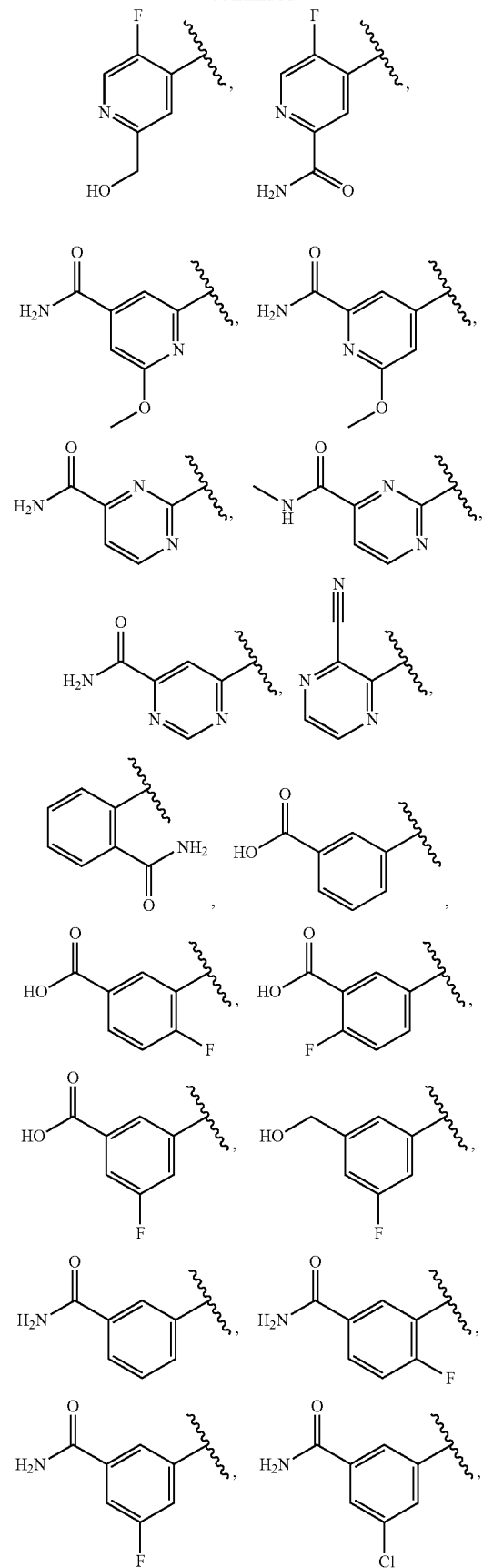

303
-continued
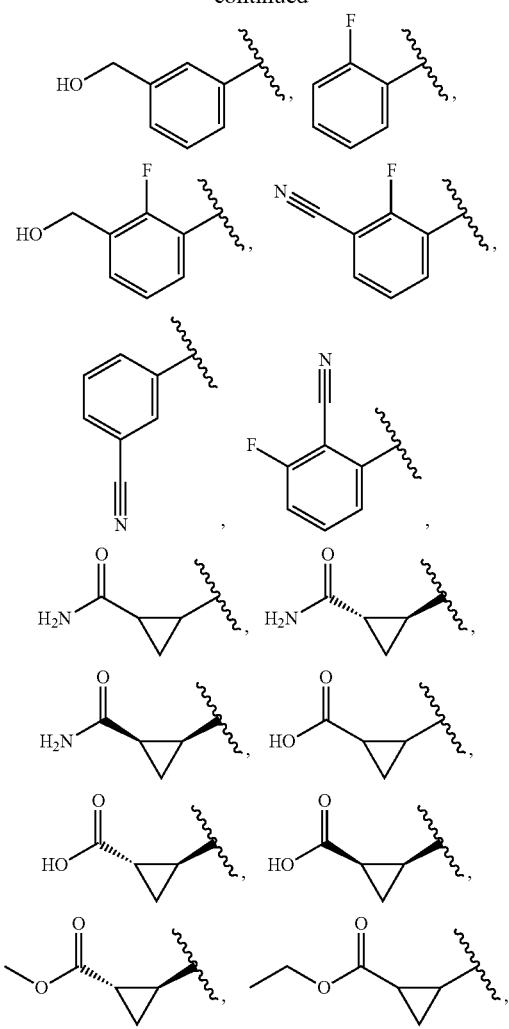
4. The compound of claim 1, wherein R³ is
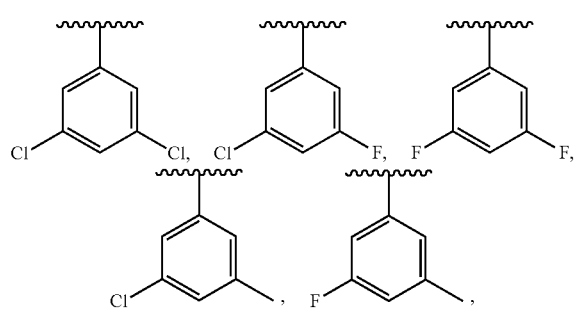
304
-continued
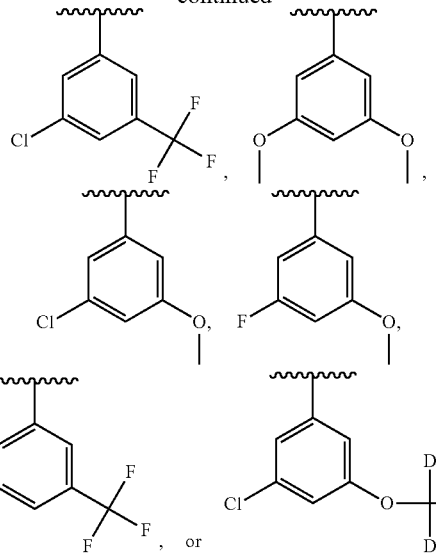
5. The compound of claim 1, wherein R⁵ is methyl, t-butyl,
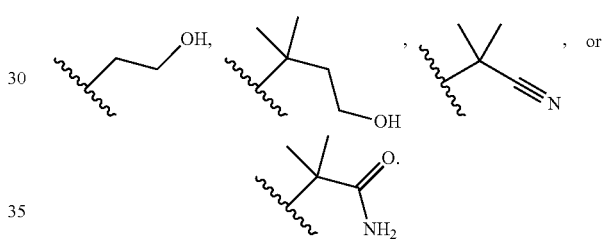
6. The compound of claim 1, wherein R⁶ is methyl, ethyl, or t-butyl.
7. The compound of claim 1, of formula I-e:
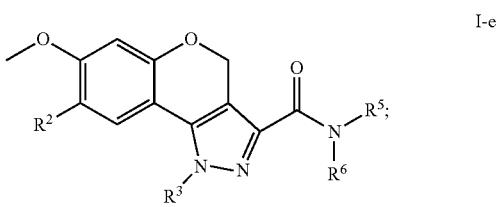
I-e
or a pharmaceutically acceptable salt thereof.
8. A compound selected from
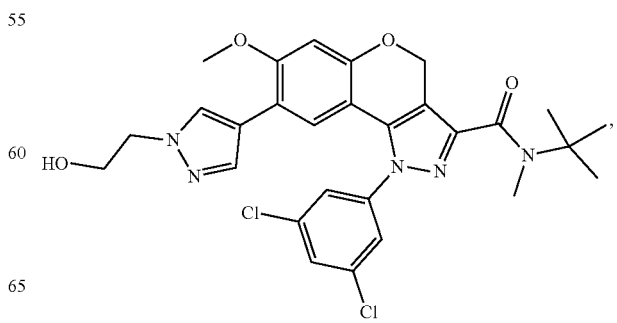

305
-continued
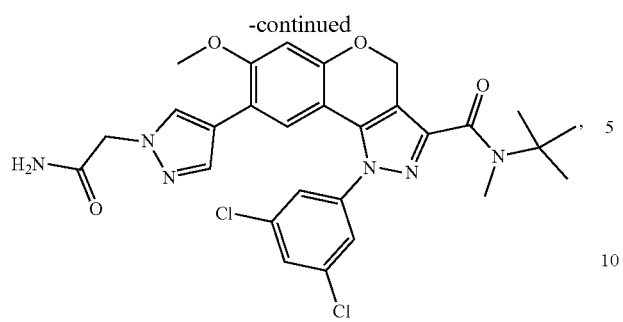
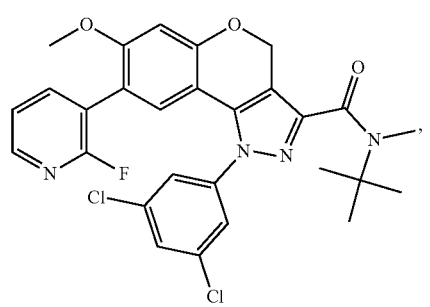
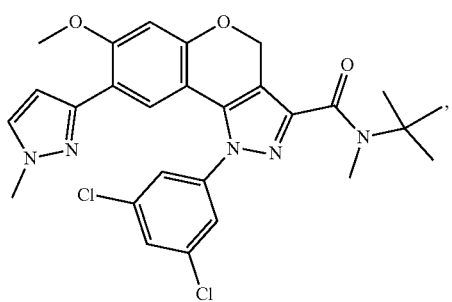
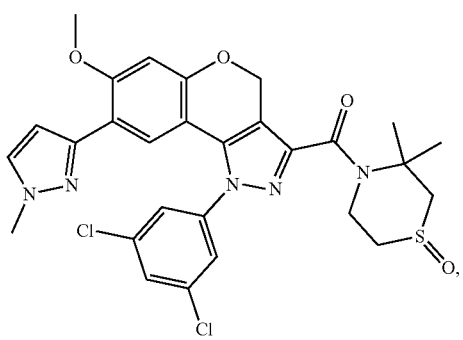
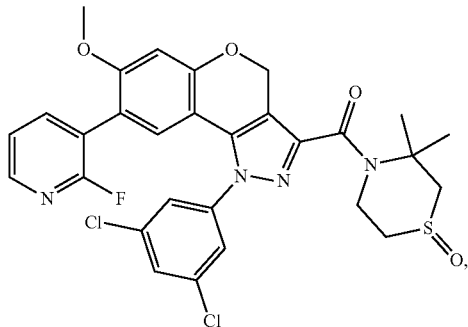
306
-continued
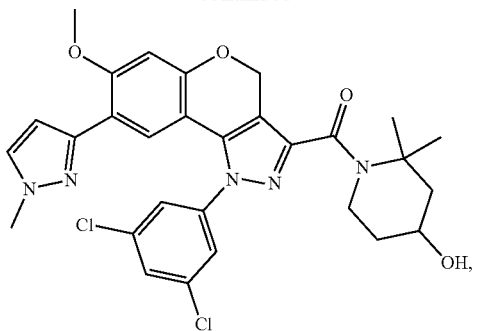
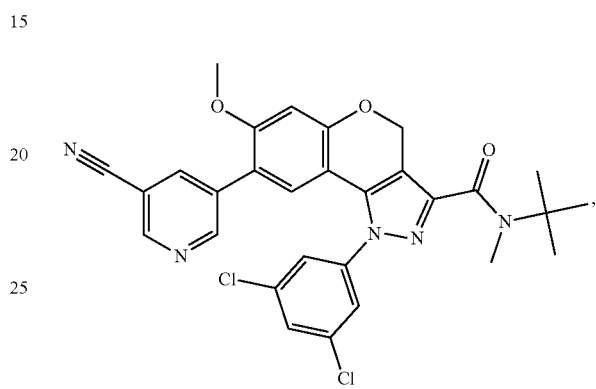
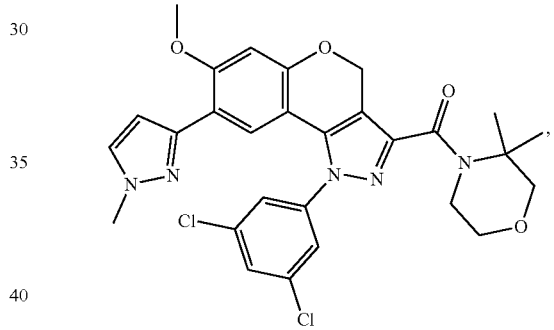
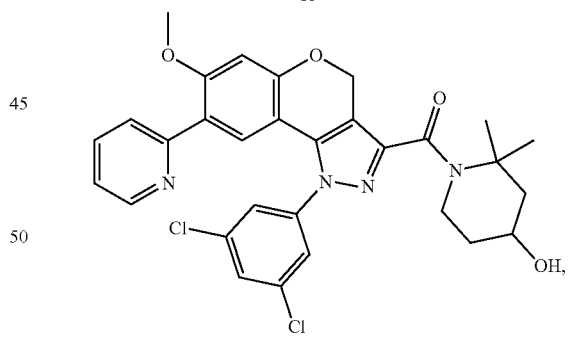
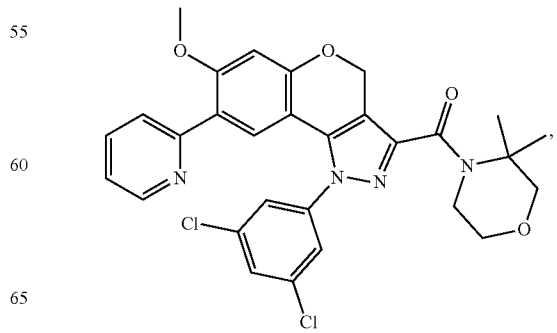

307
-continued
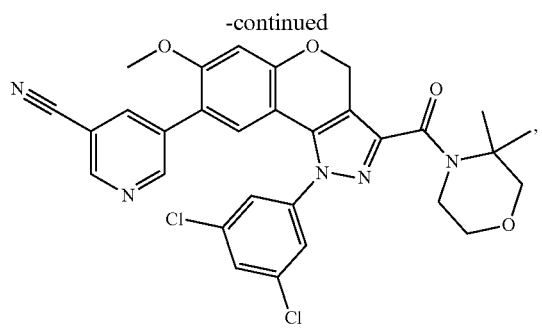
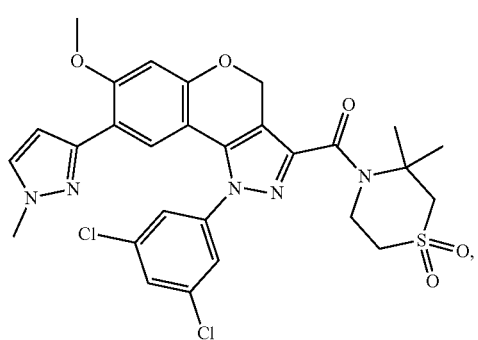
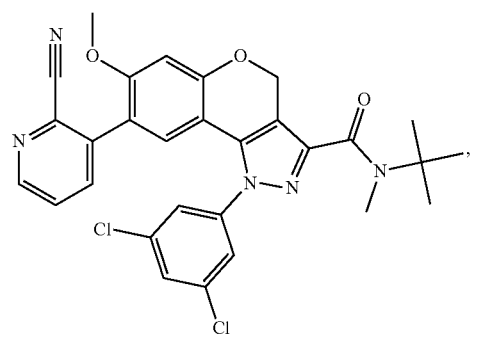
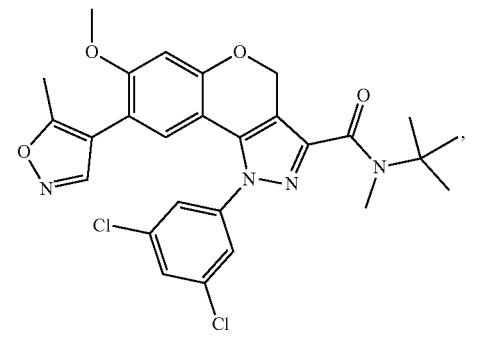
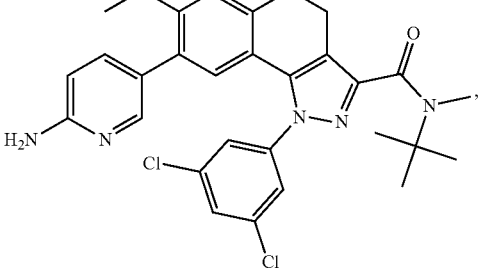
308
-continued
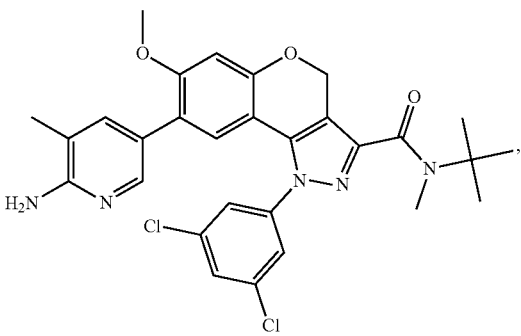
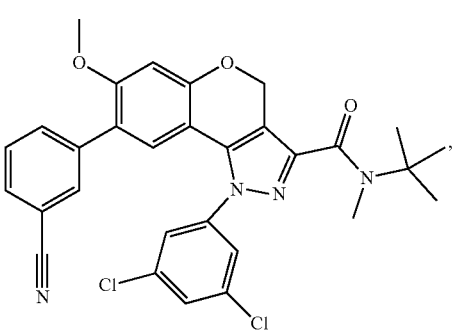
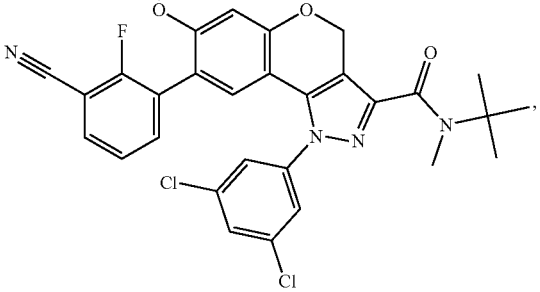
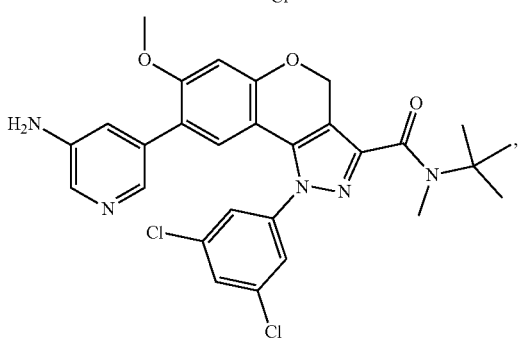
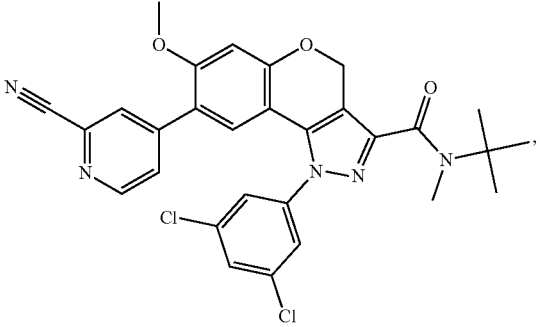

309
-continued
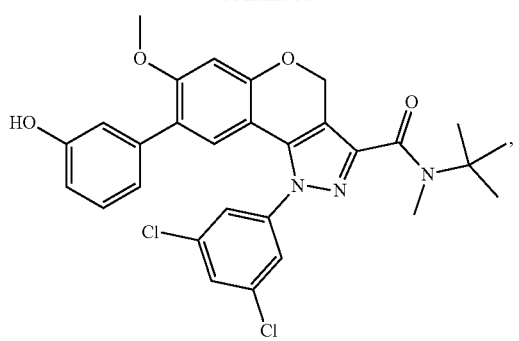
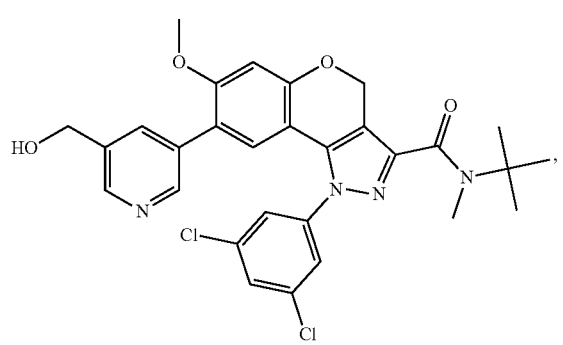
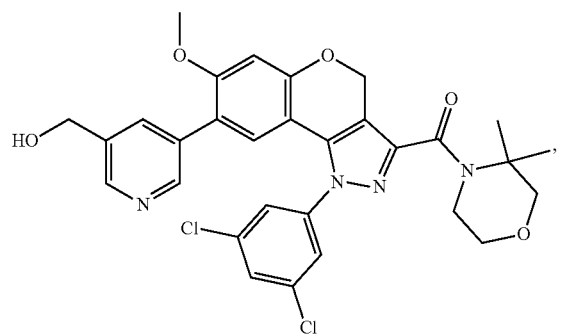
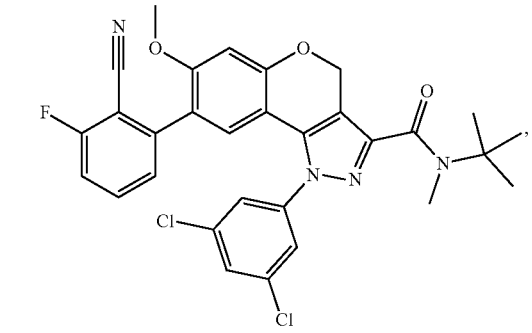
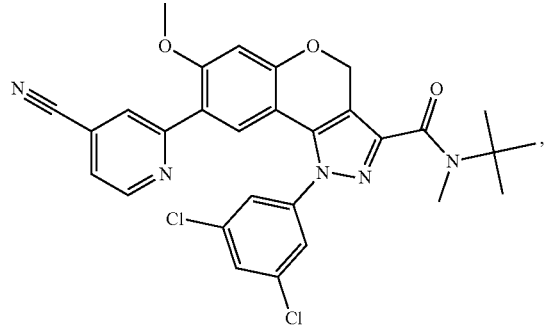
310
-continued
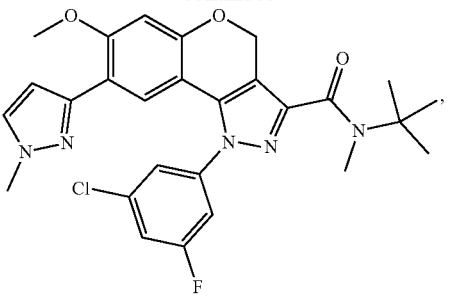
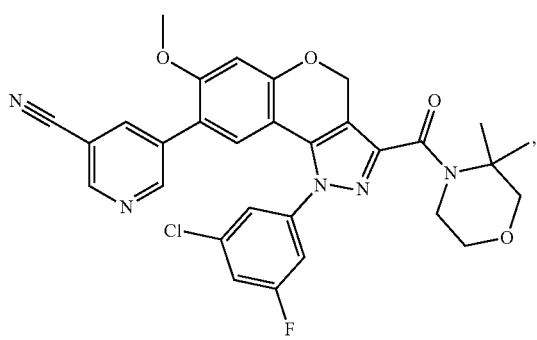
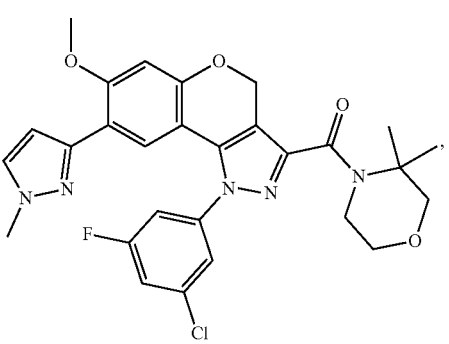
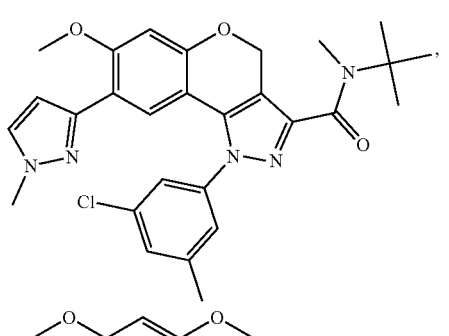
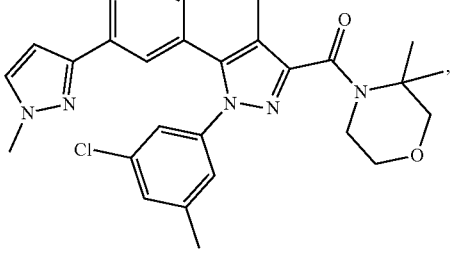

311
-continued
312
-continued
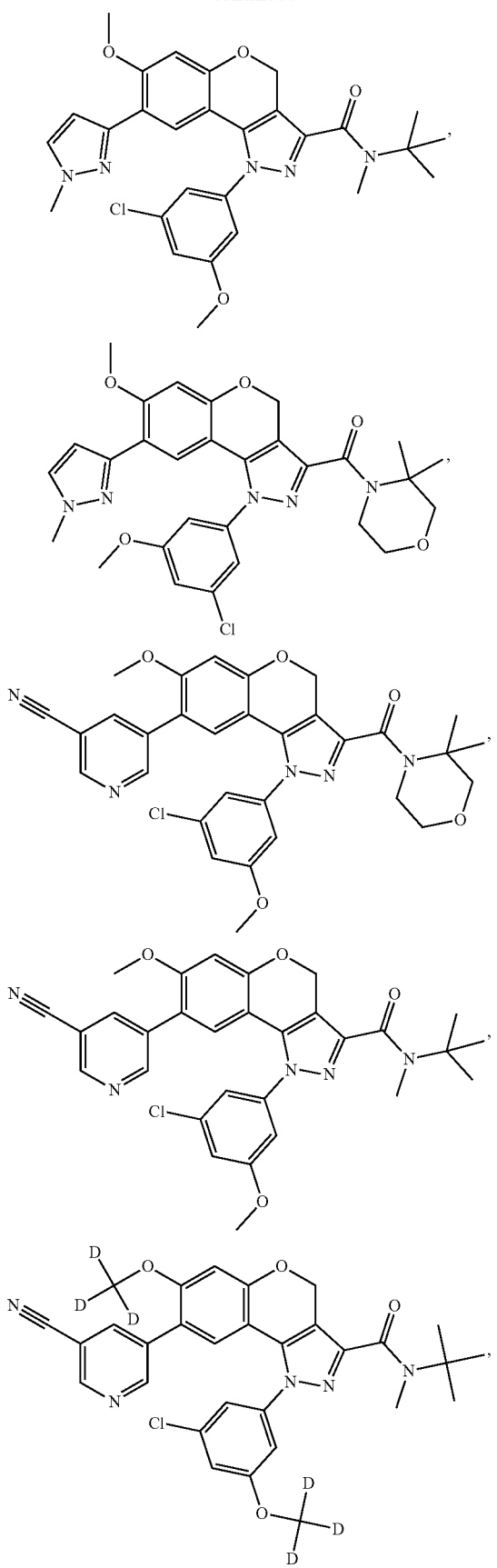
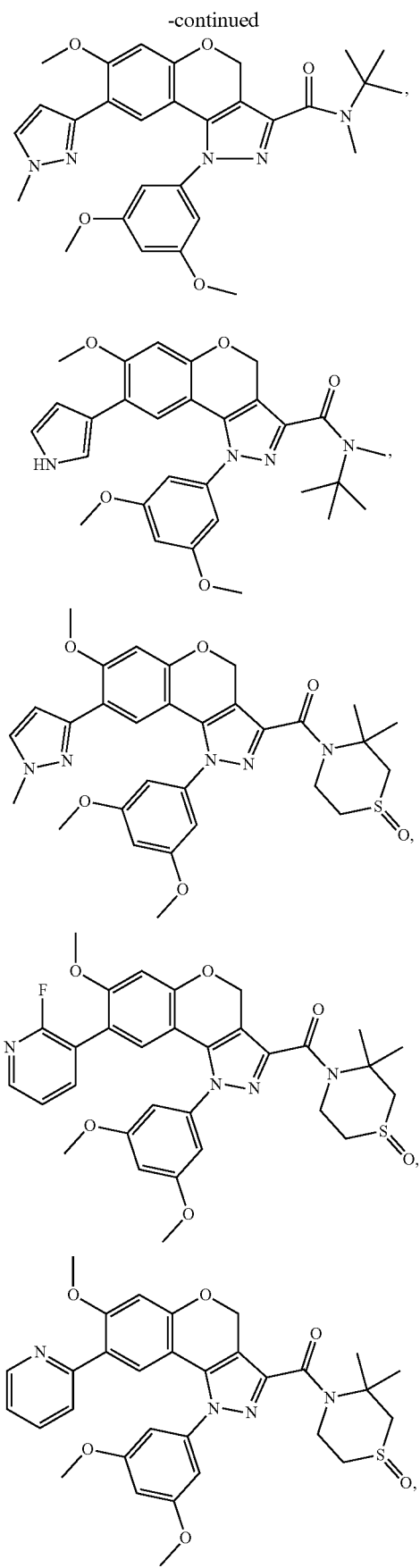

313
-continued
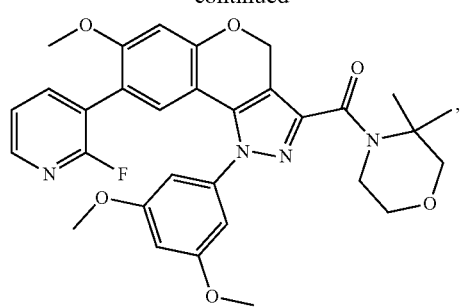
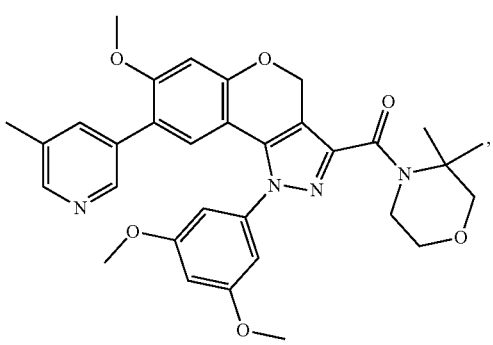
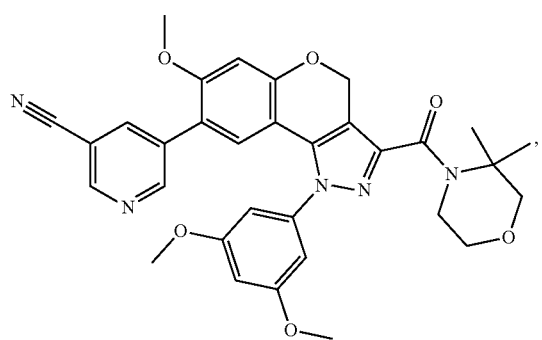
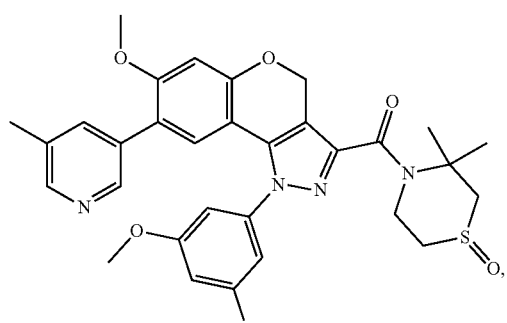
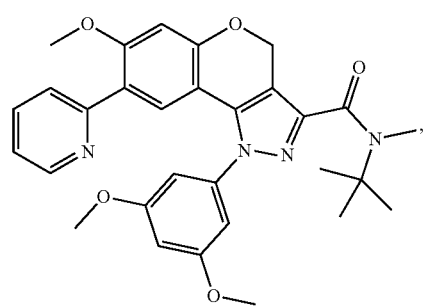
314
-continued
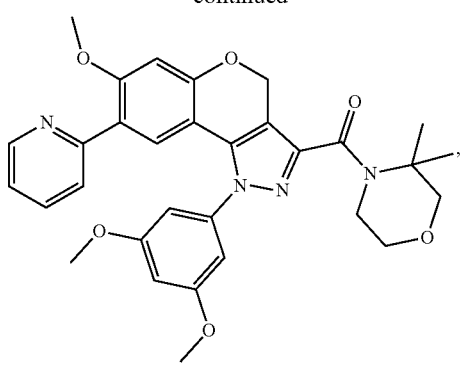
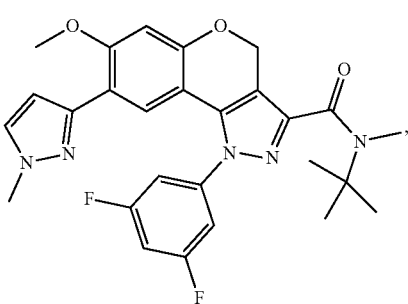
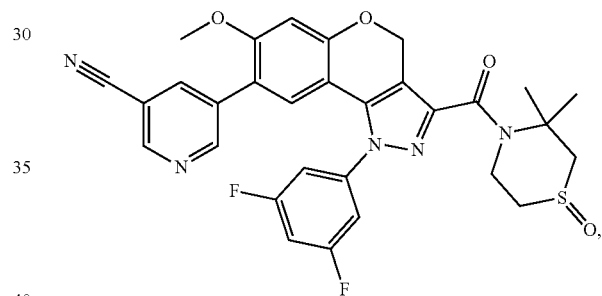
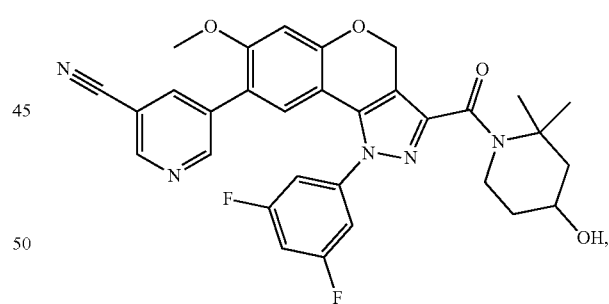
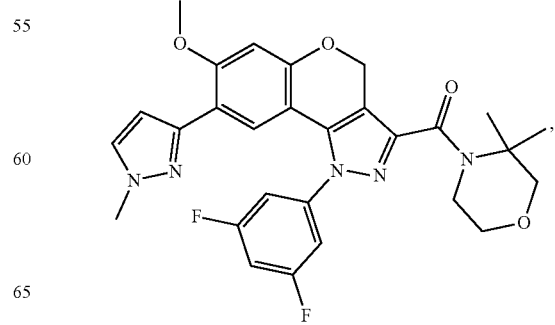

315
-continued
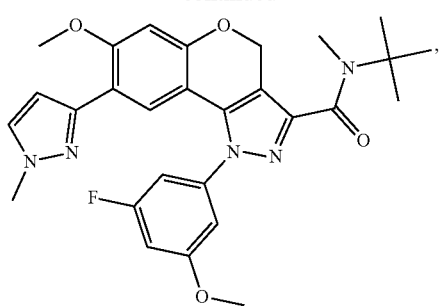
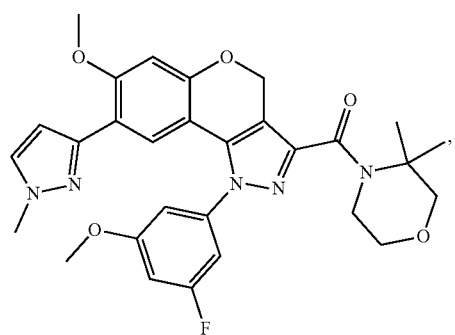
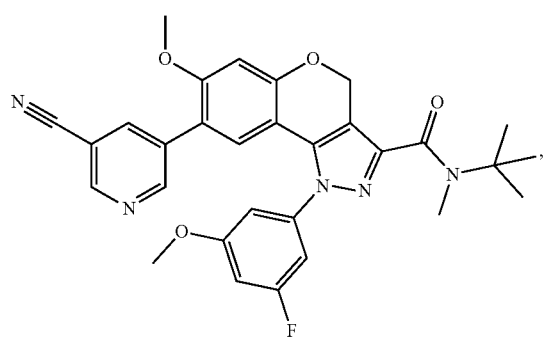
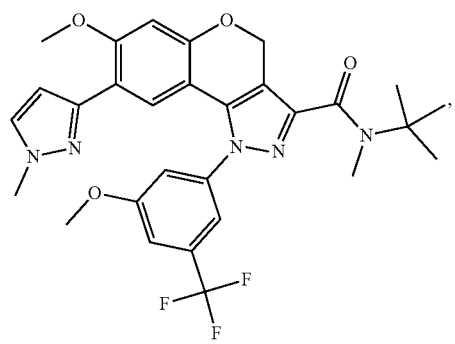
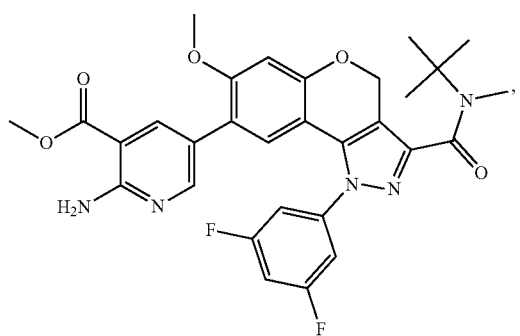
316
-continued
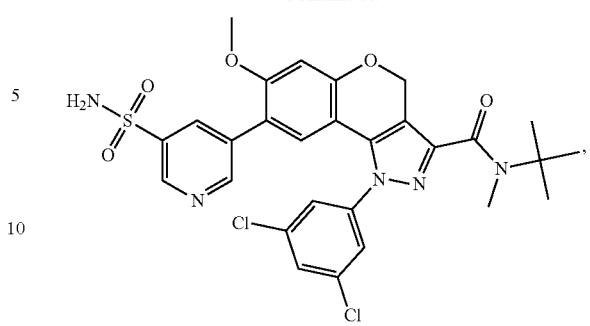
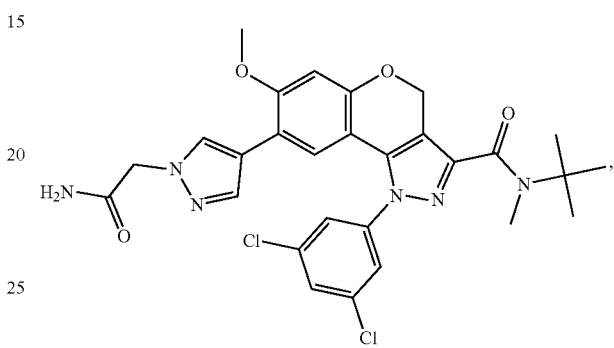
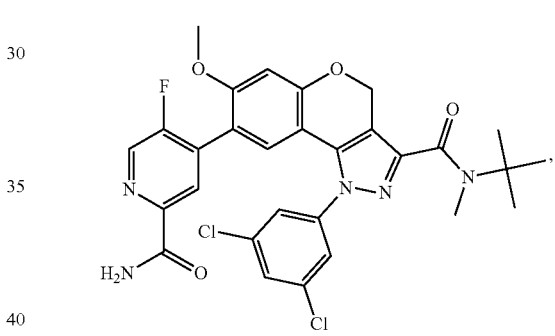
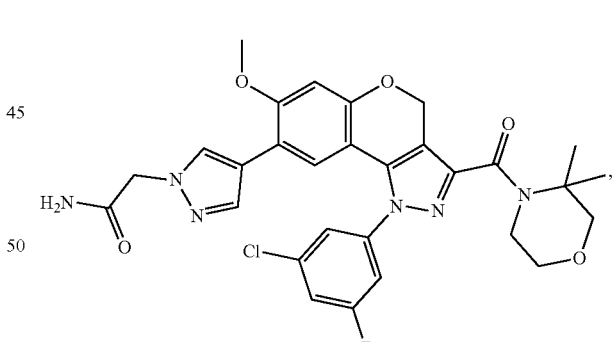
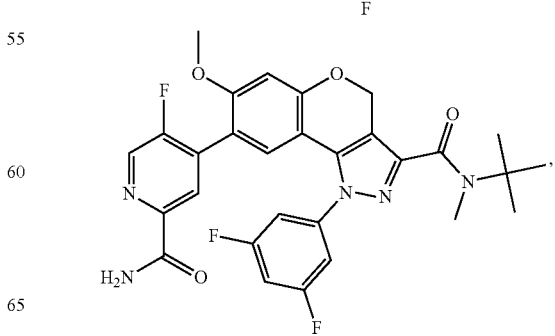

317
-continued
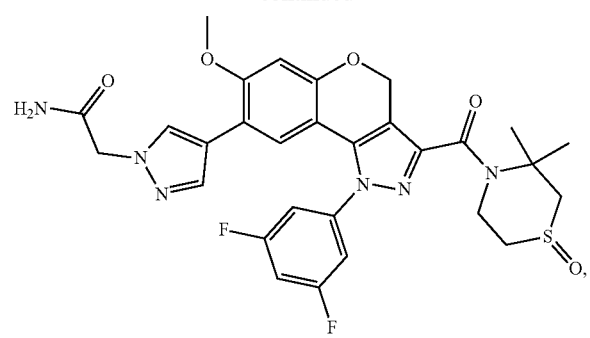
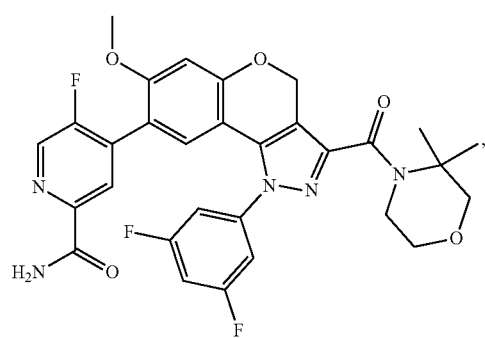
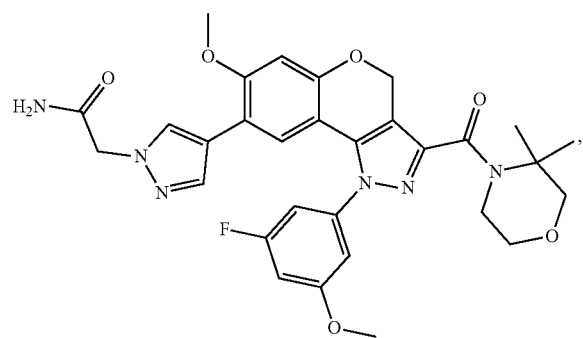
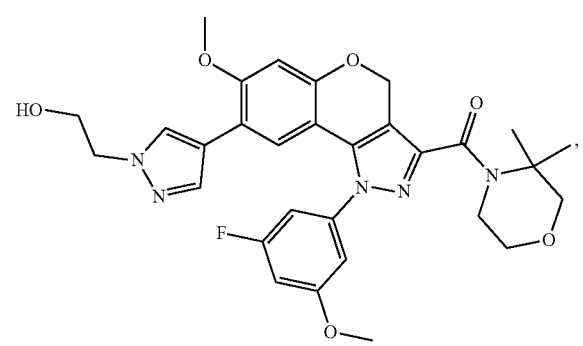
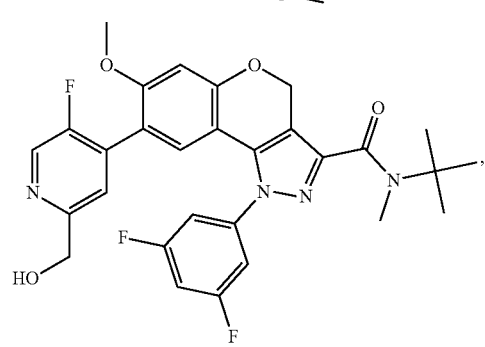
318
-continued
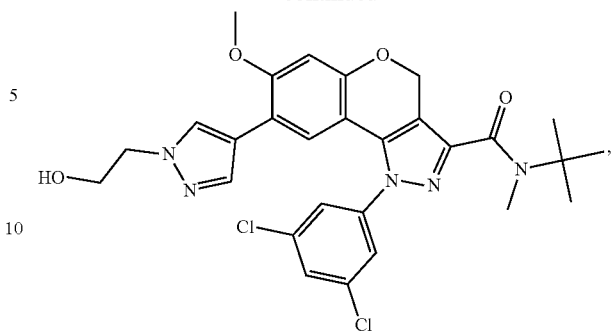
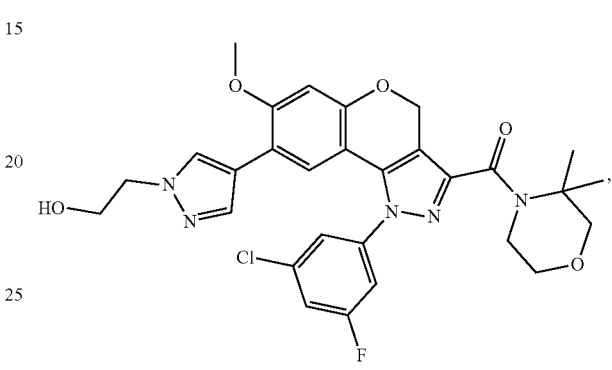
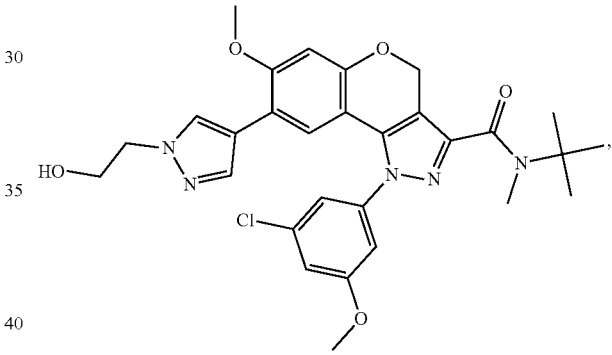
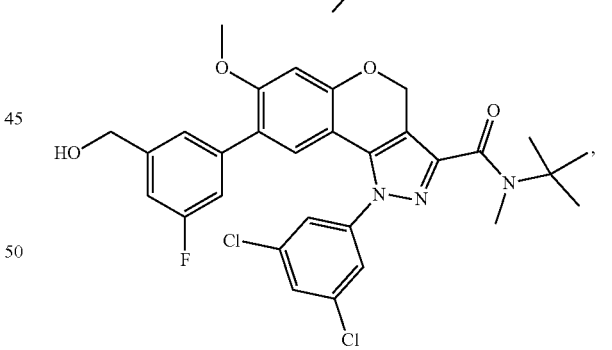
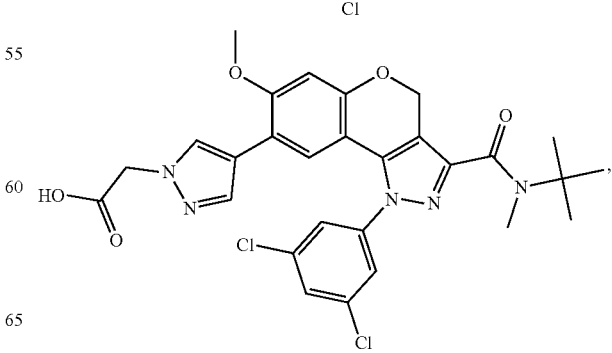

319
-continued
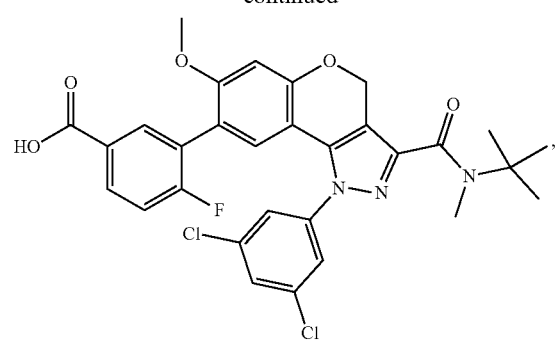
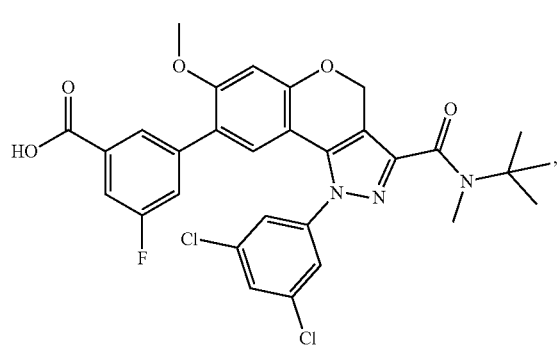
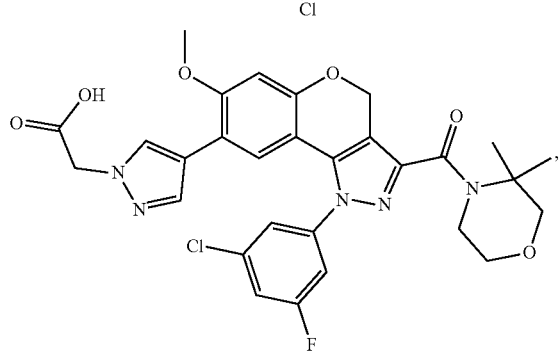
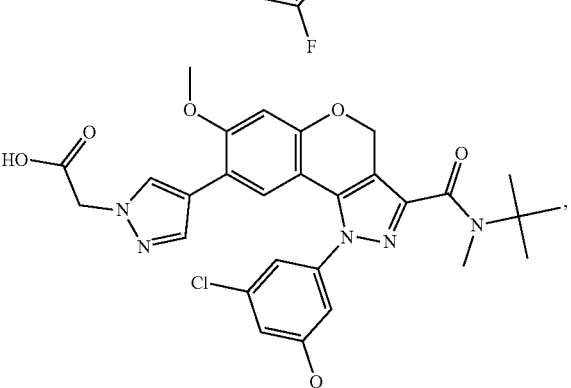
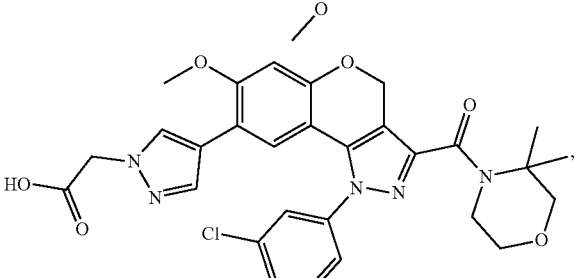
320
-continued
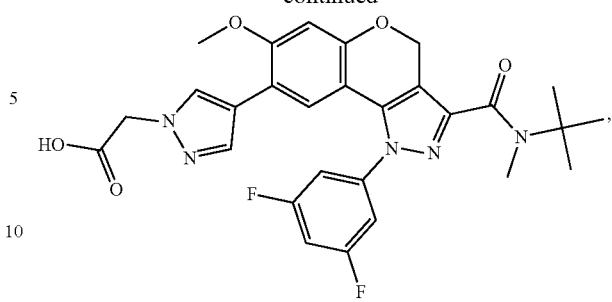
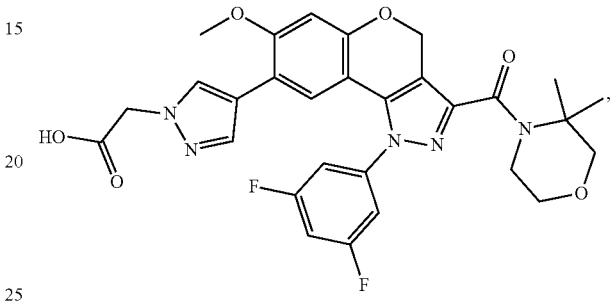
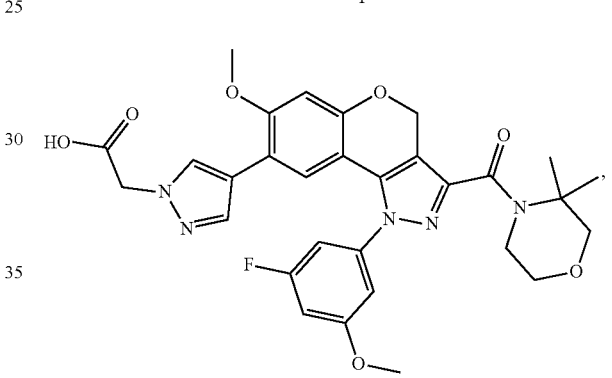

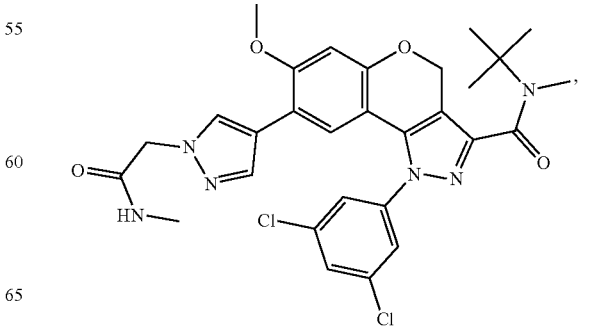

321
-continued
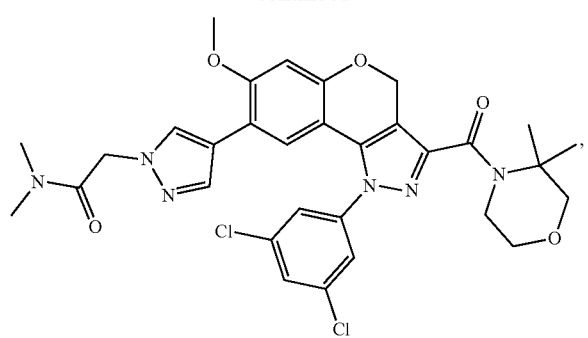
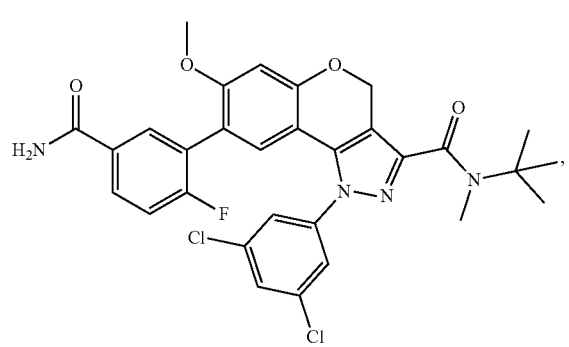
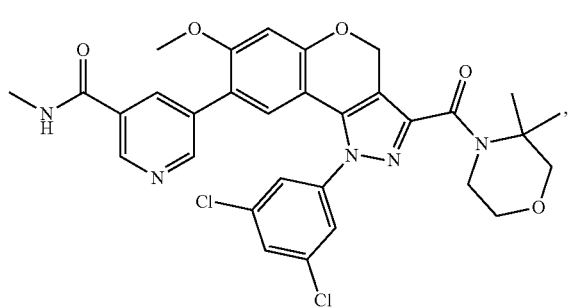
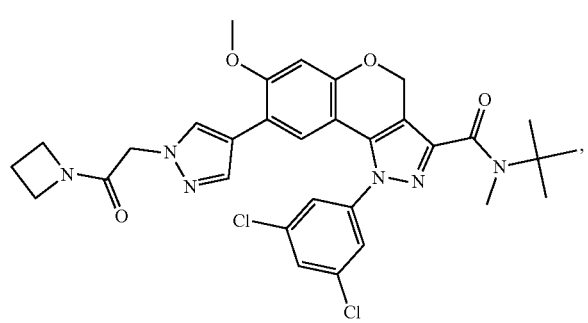
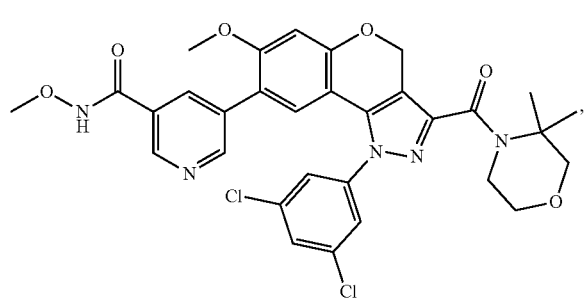
322
-continued
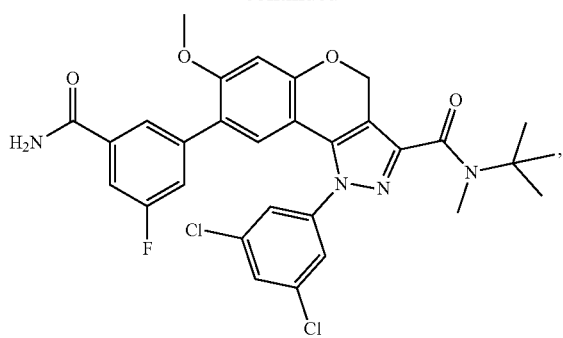
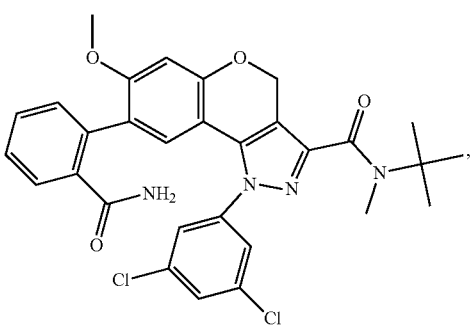
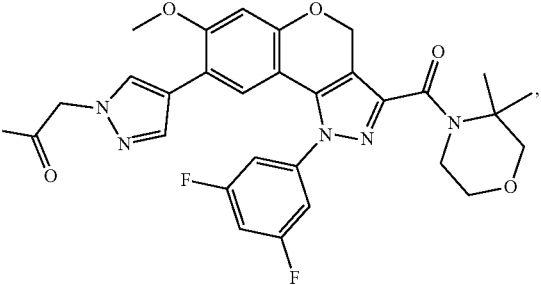
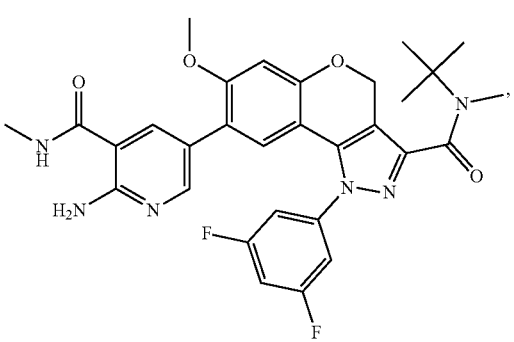
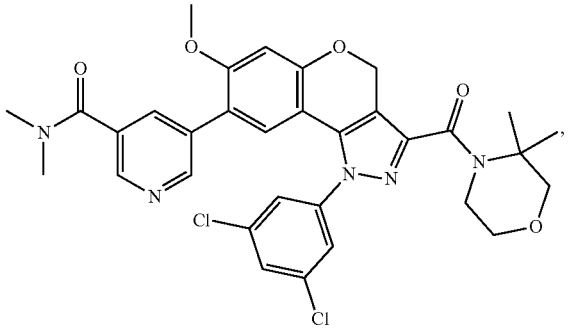

323
-continued
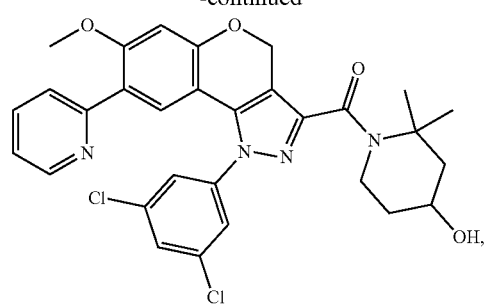
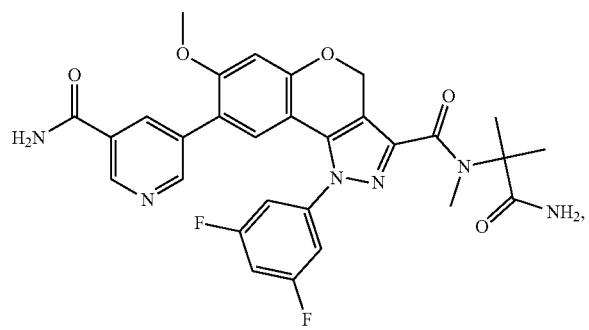
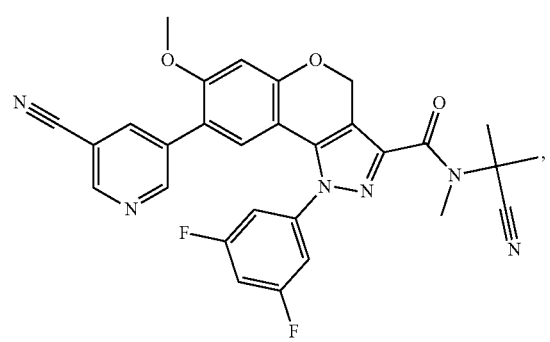
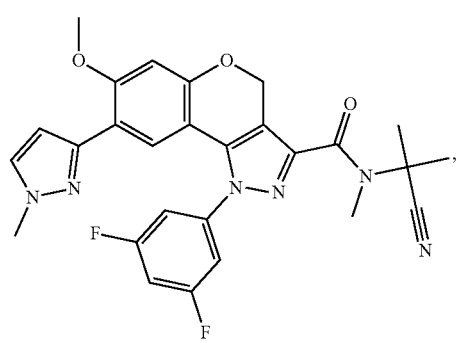
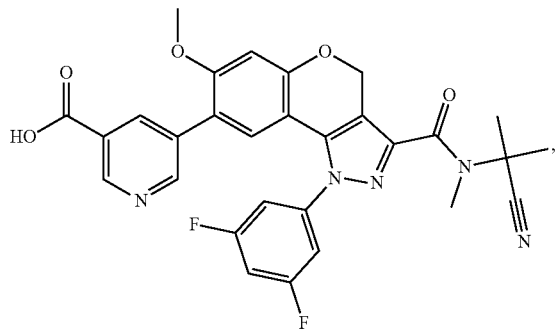
324
-continued
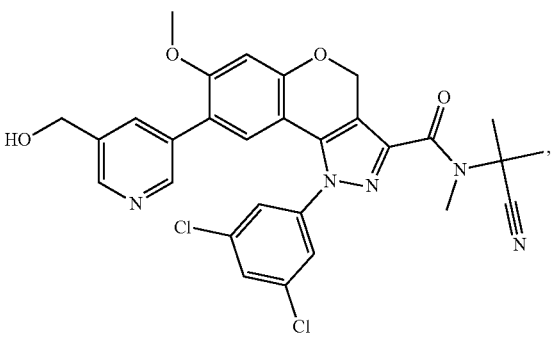
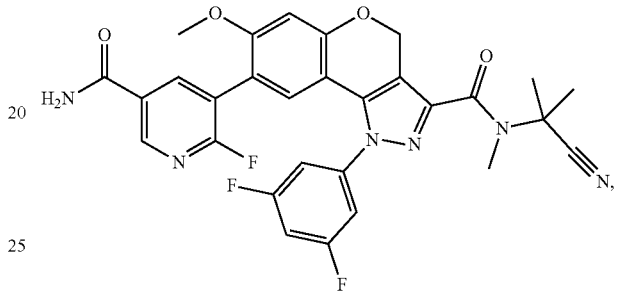
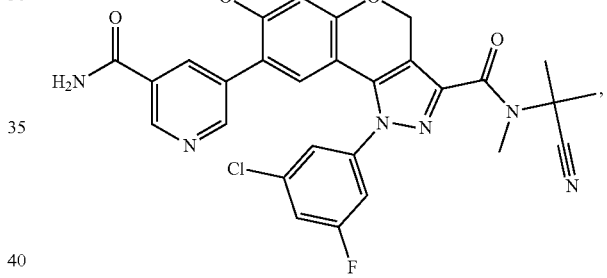
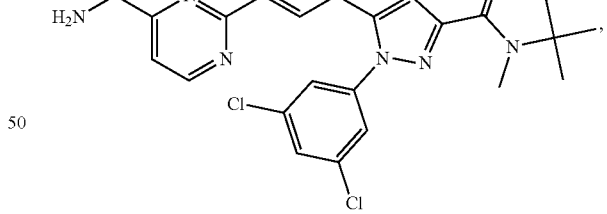
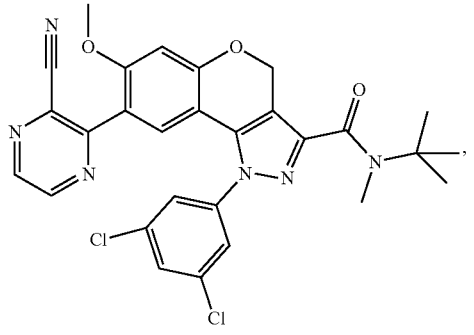

325
-continued
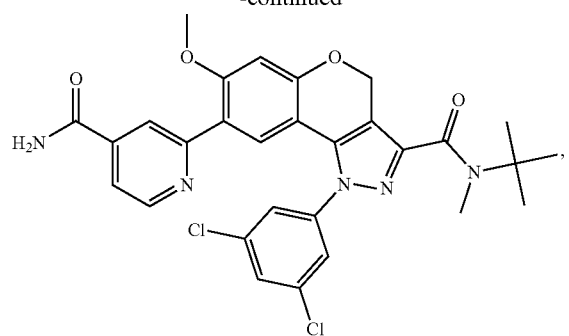
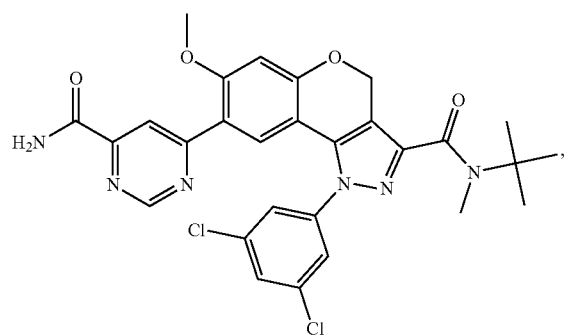
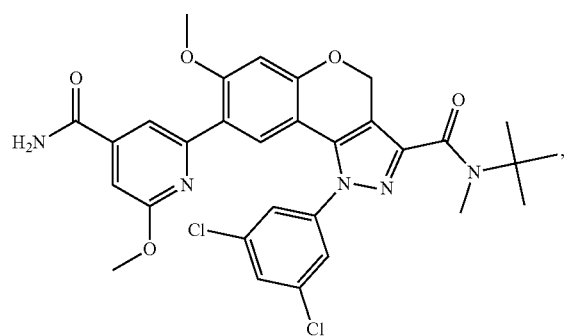
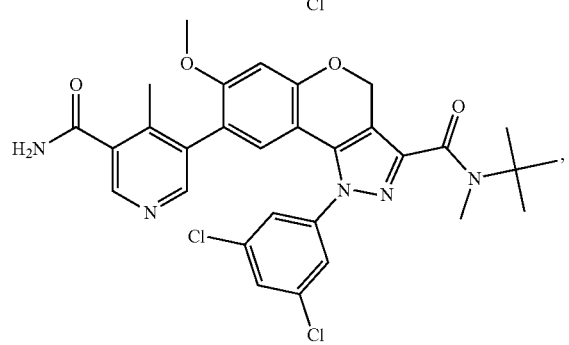
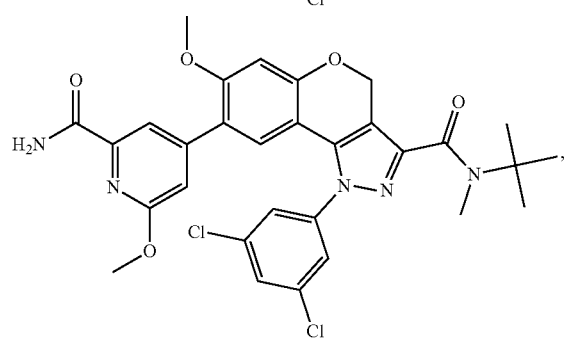
326
-continued
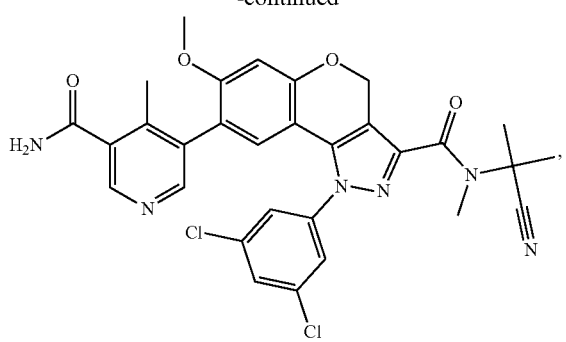
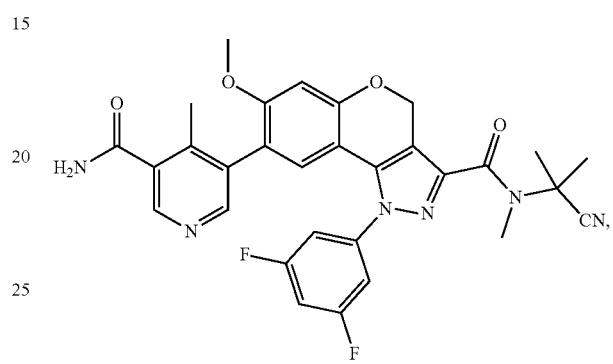
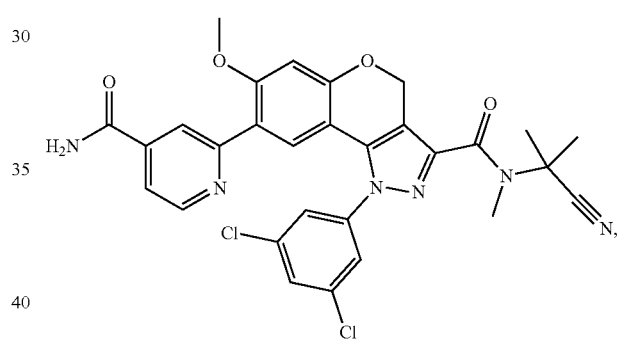
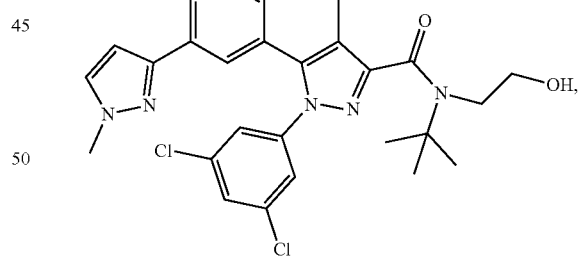
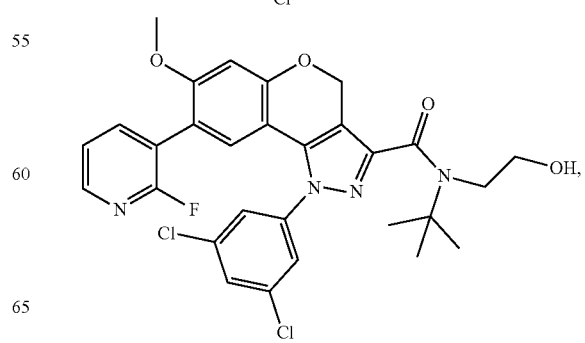

327
-continued
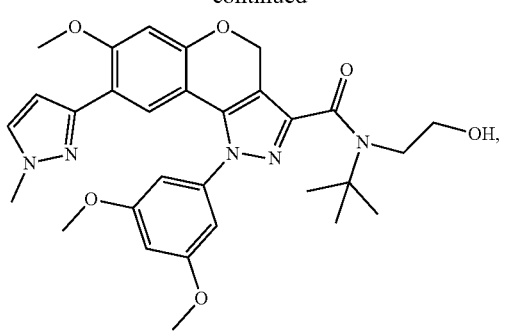
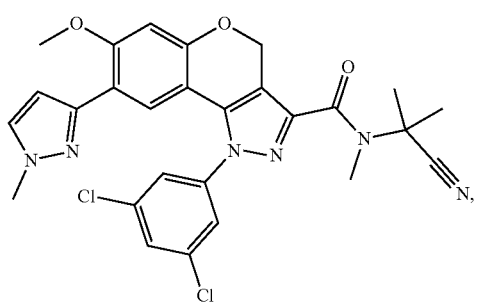
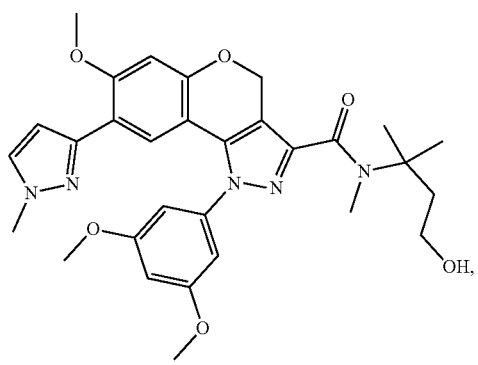
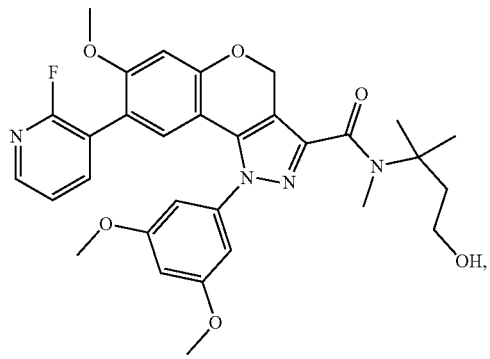
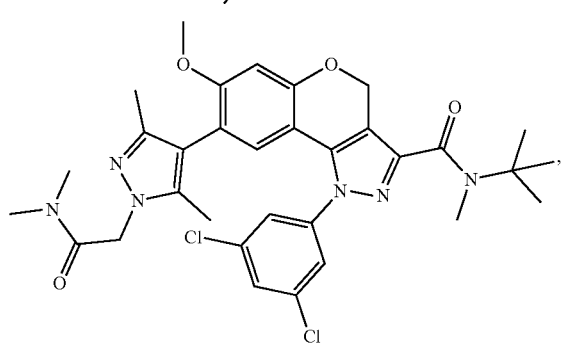
328
-continued
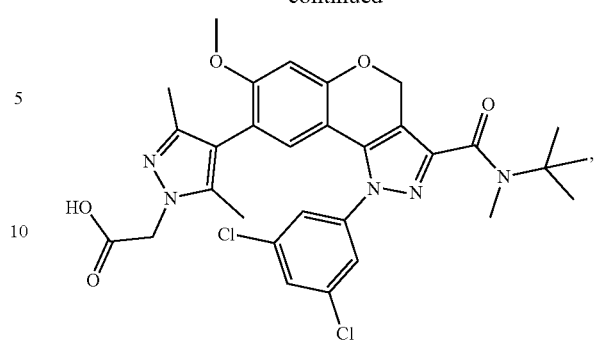
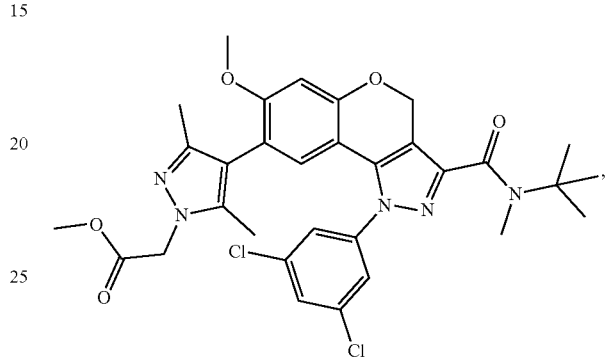
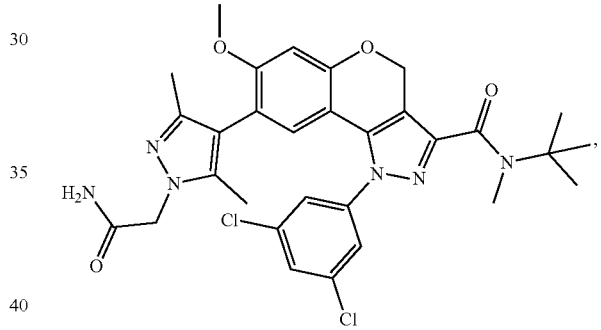
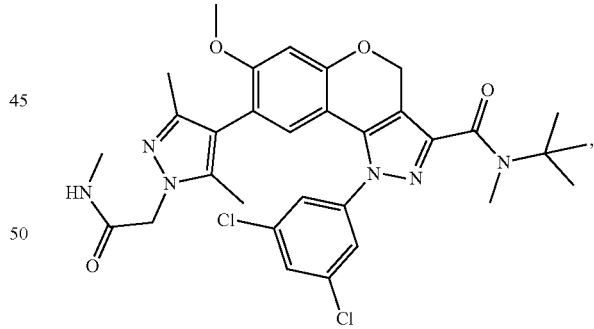
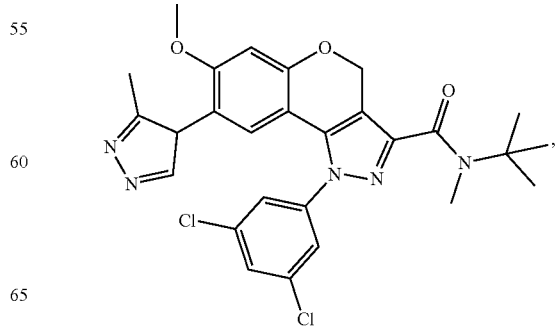

329
-continued
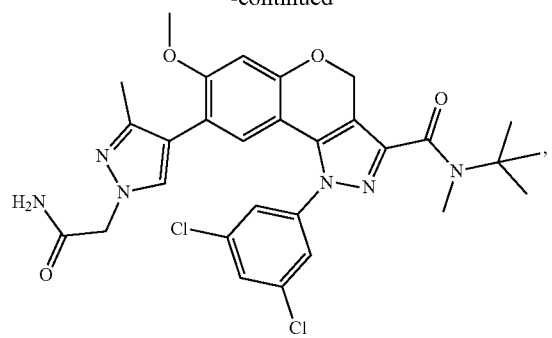
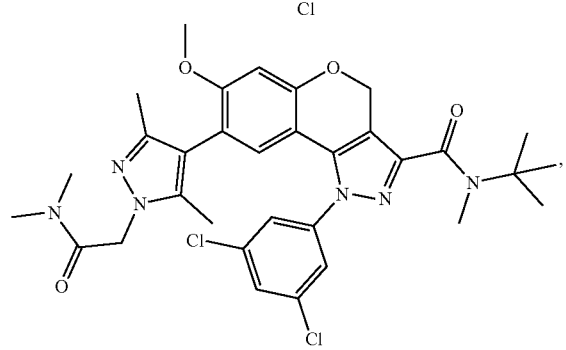
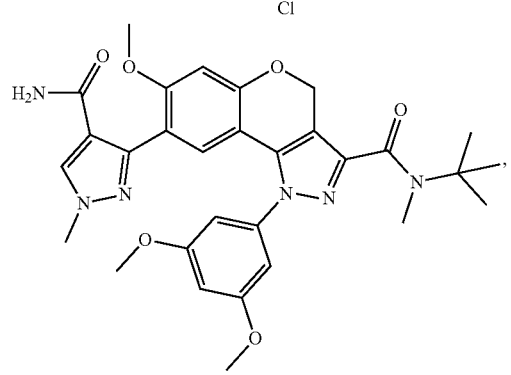
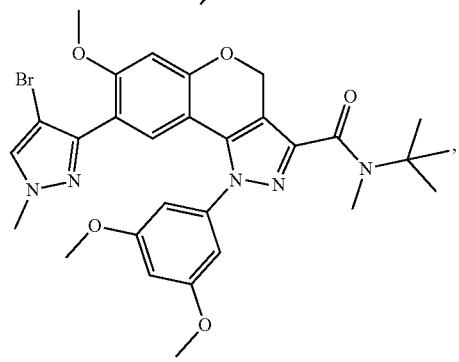
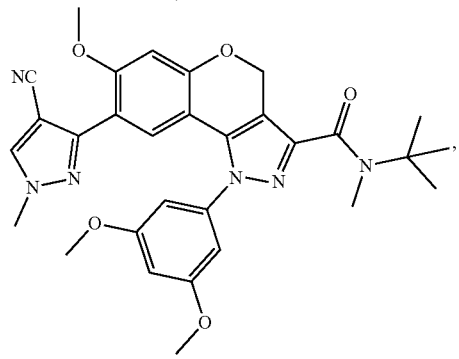
330
-continued
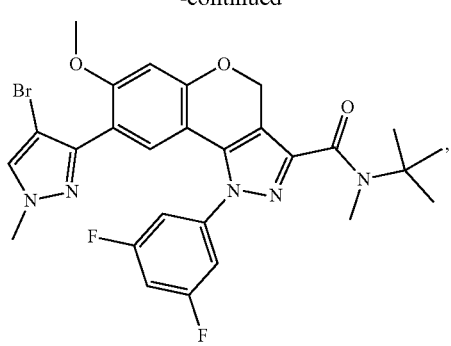
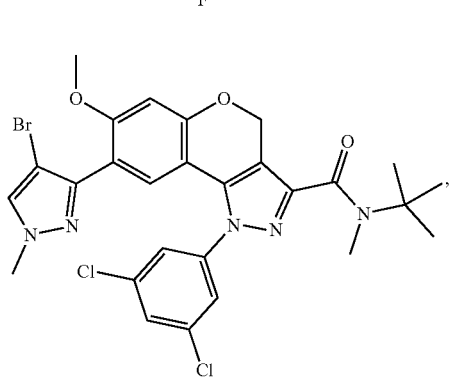
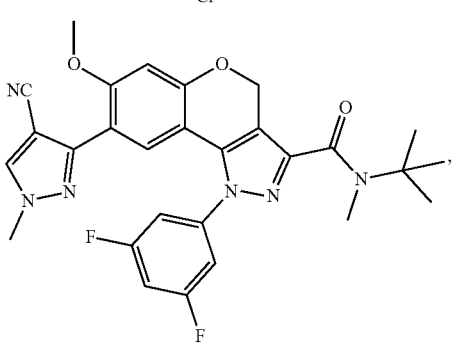
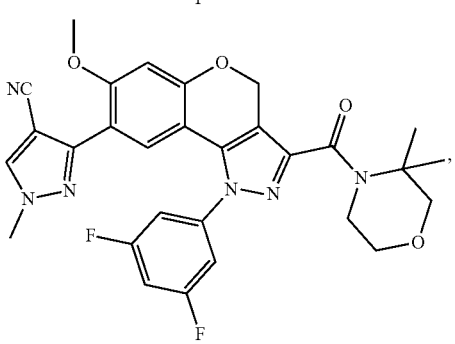
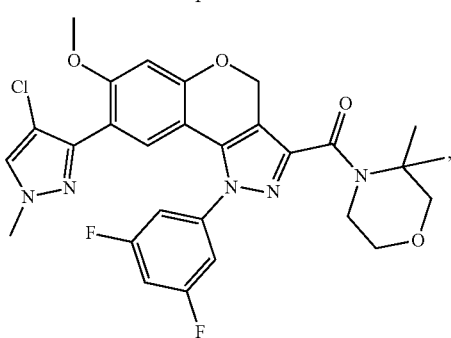

331
-continued
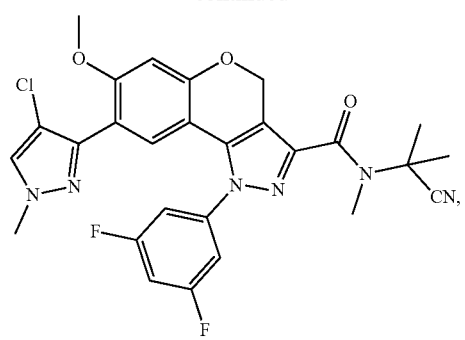
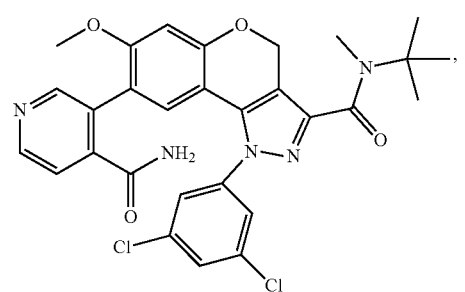
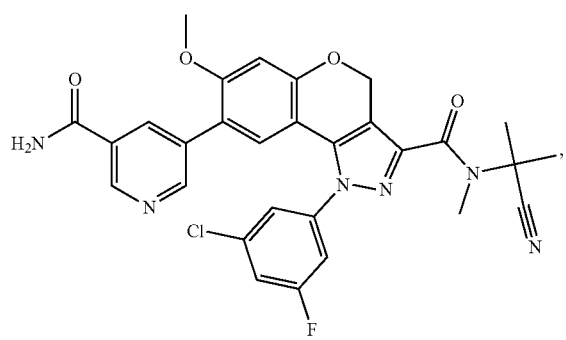
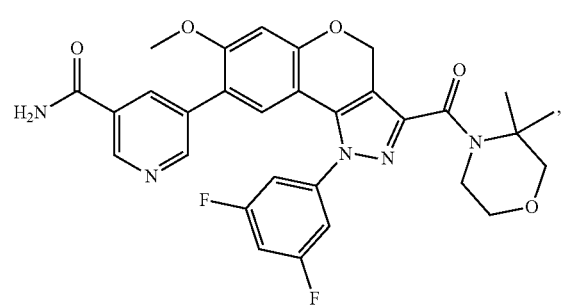
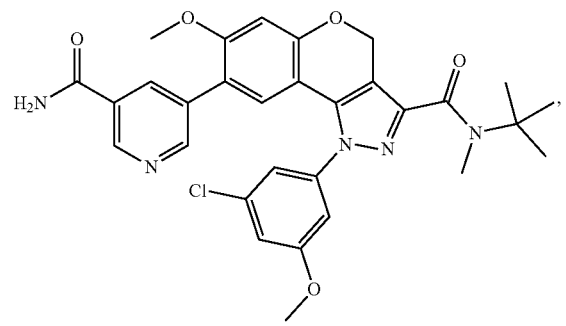
332
-continued
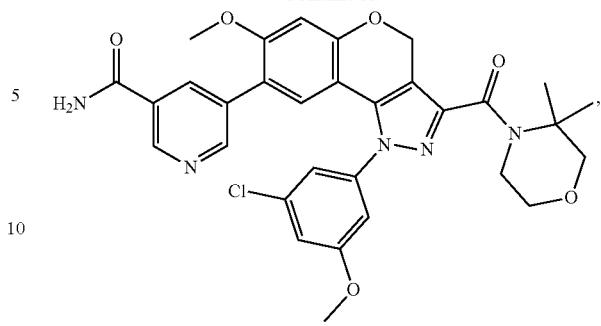
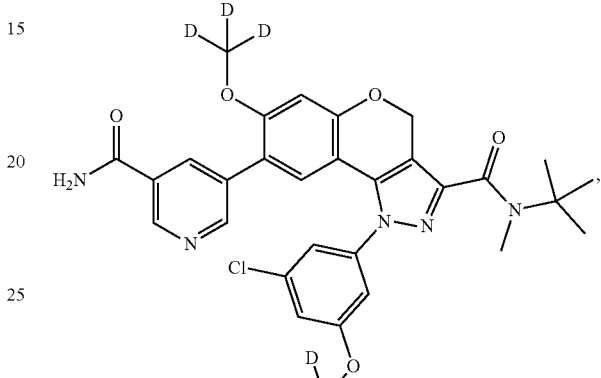
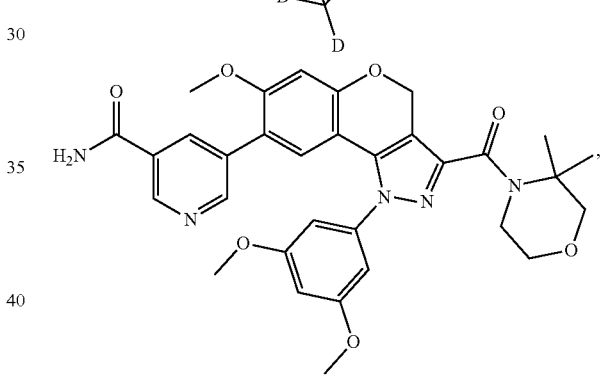
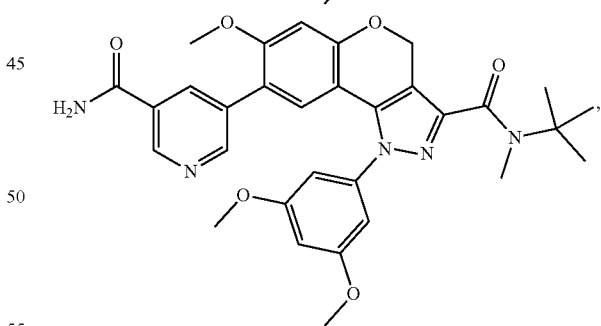
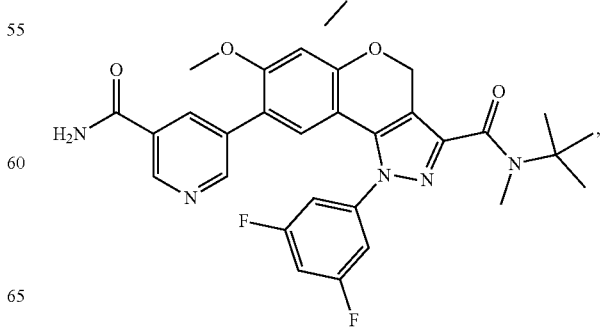

333
-continued
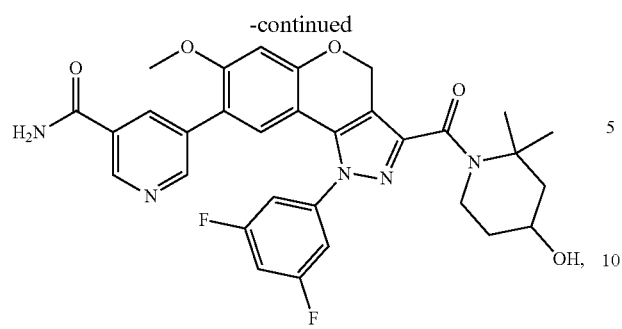
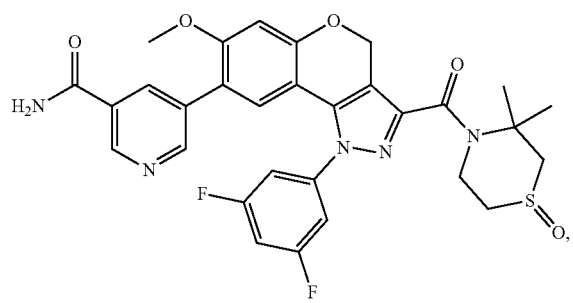
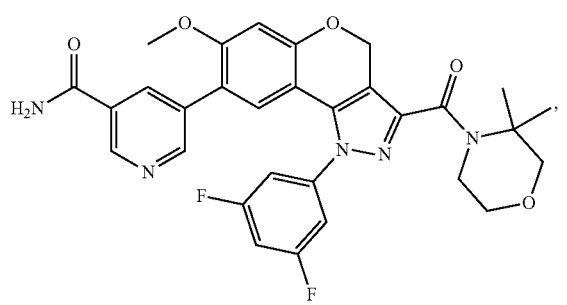
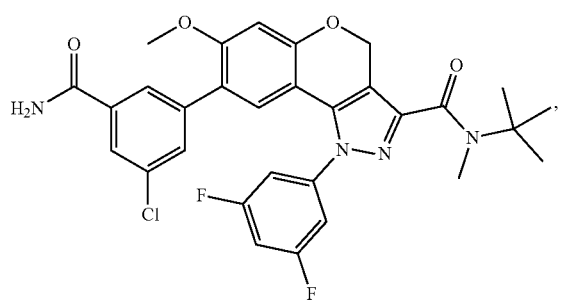
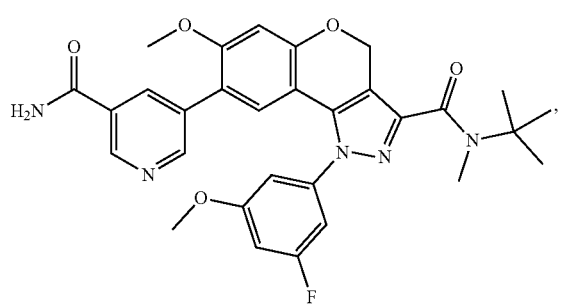
334
-continued
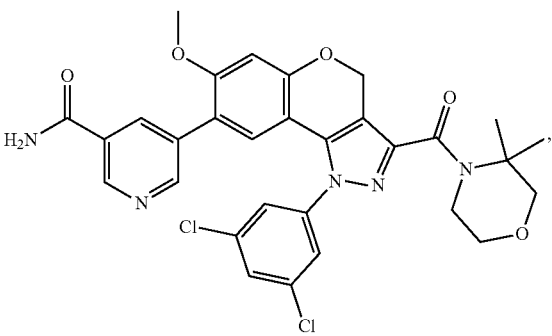
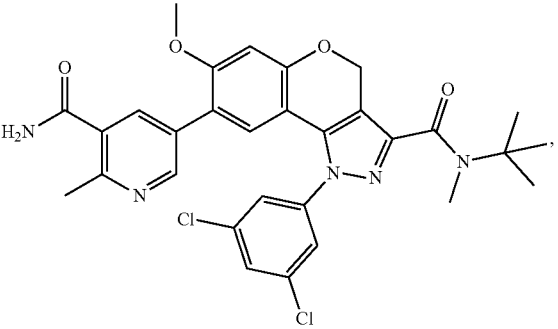
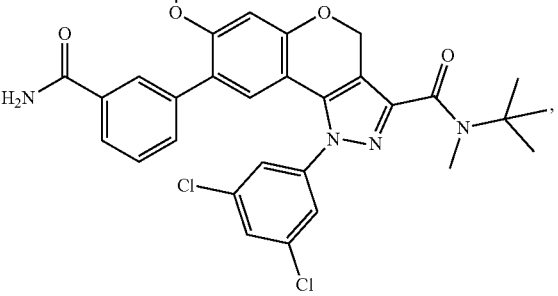
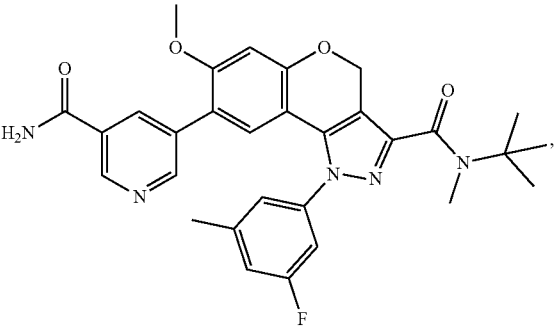
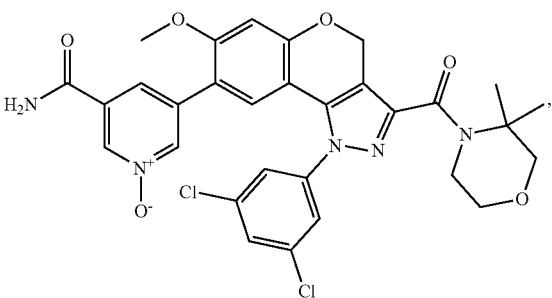

335
-continued
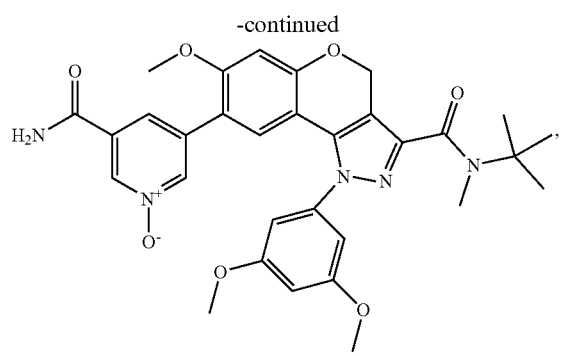
336
-continued
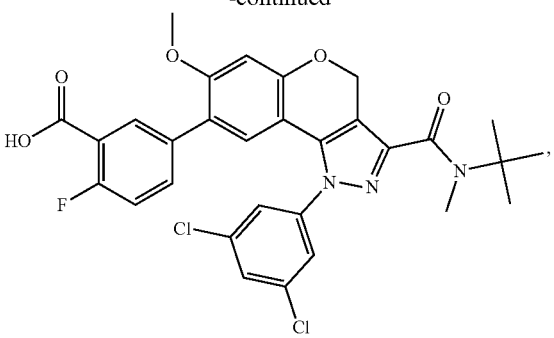

337
-continued
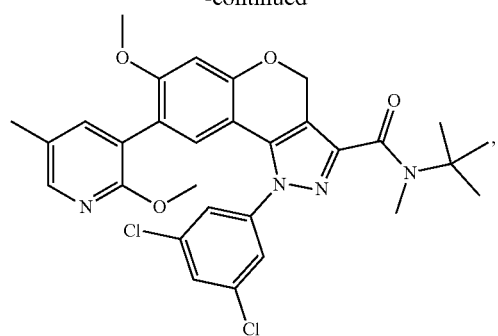
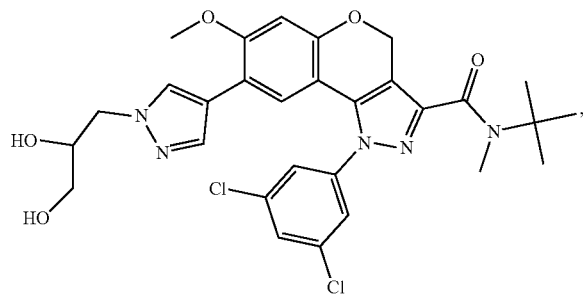
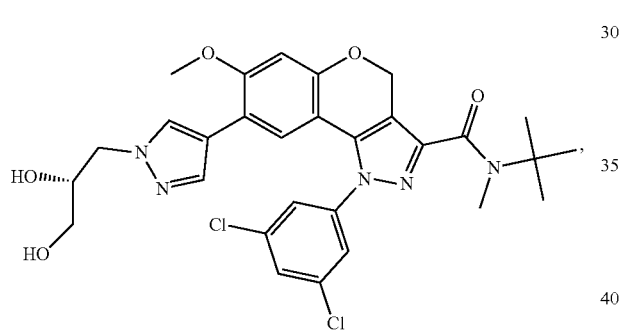
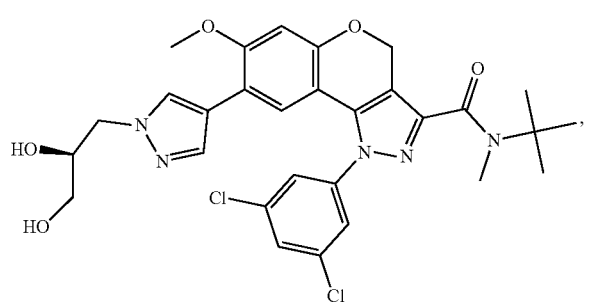
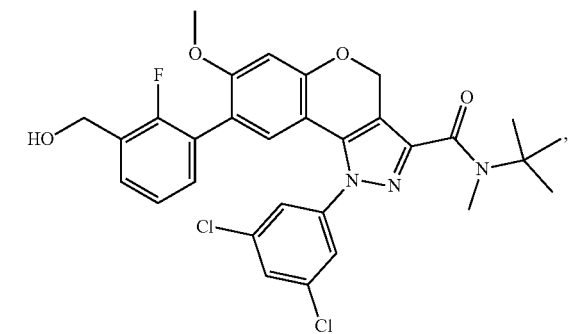
338
-continued
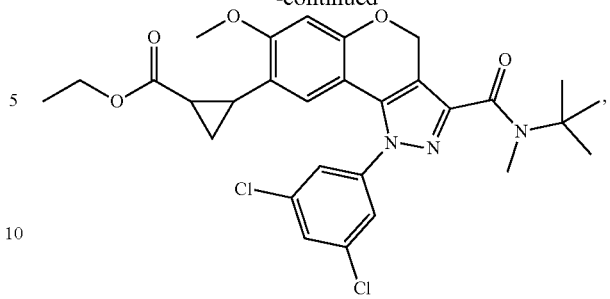
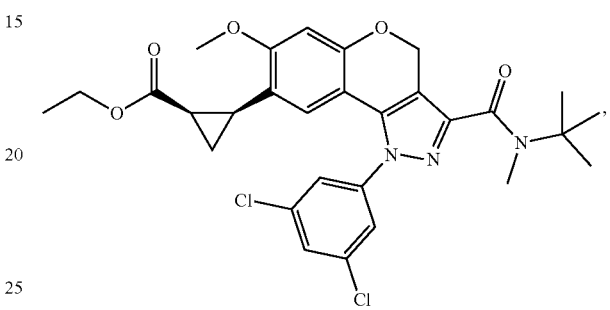
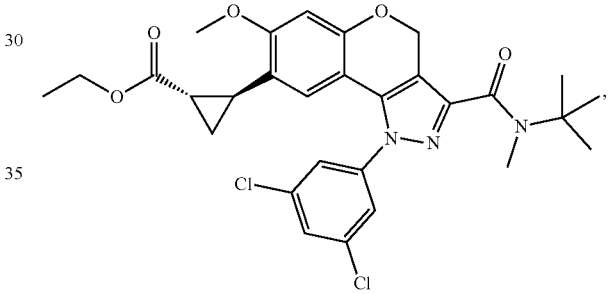
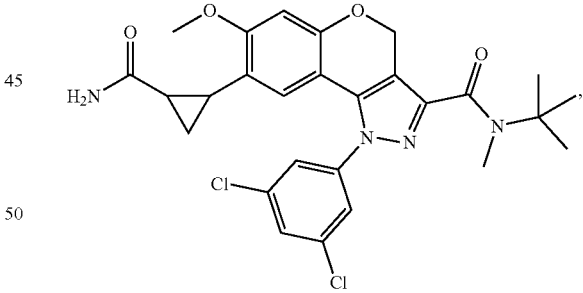
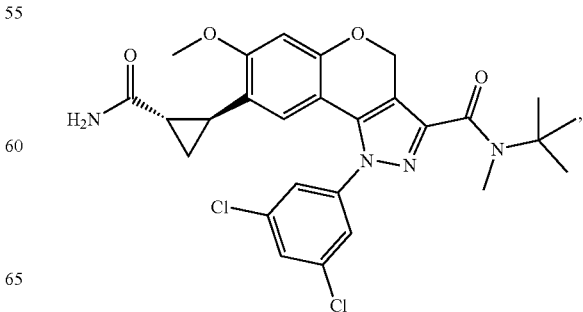

339
-continued
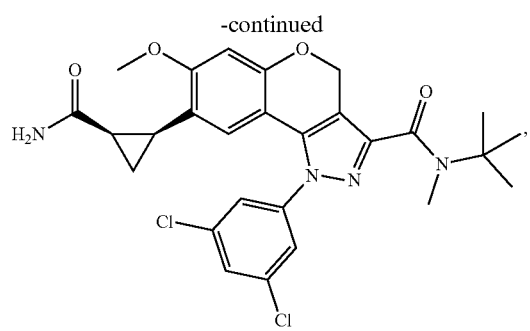
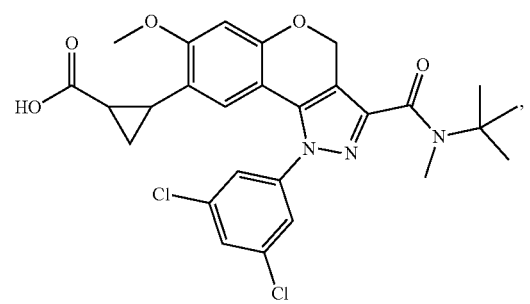
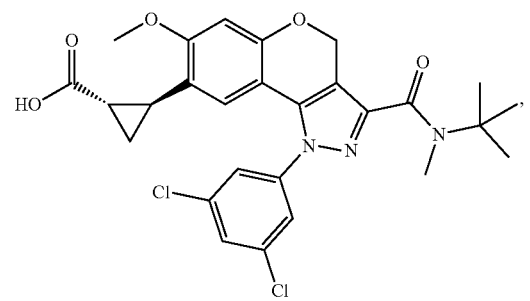
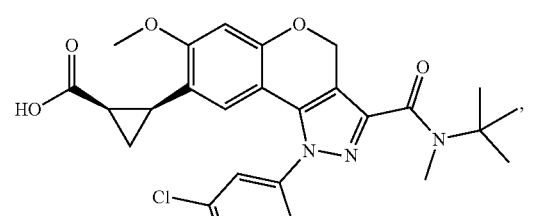
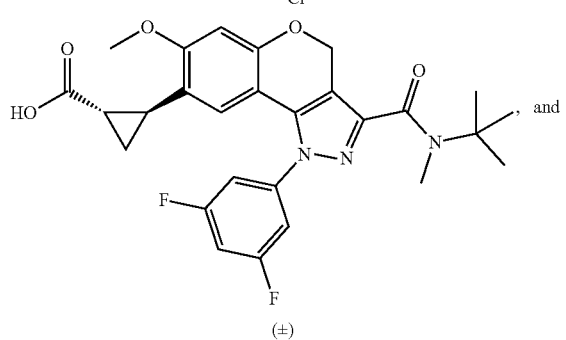
340
-continued
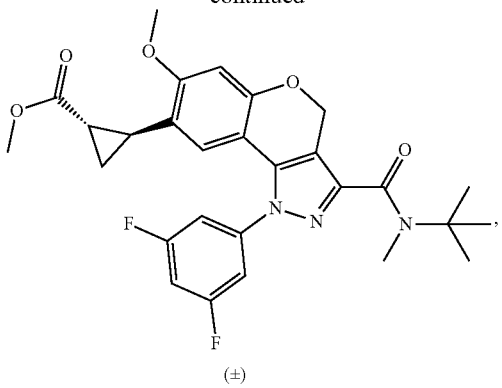
(±)
or a pharmaceutically acceptable salt thereof.
9. The compound of claim 1, wherein the compound is
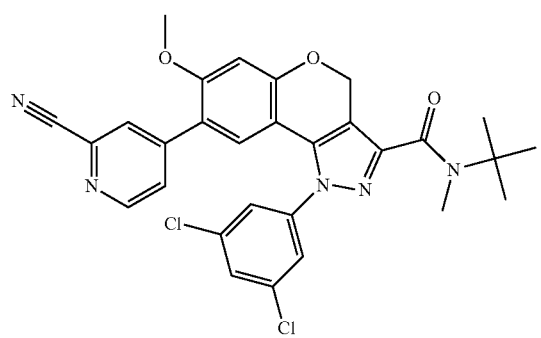 [SMILES: COc1cc2c(cc1-c1ccnc(C#N)c1)-c1c(c(C(=O)N(C)C(C)(C)C)nn1-c1cc(Cl)cc(Cl)c1)CO2]
or a pharmaceutically acceptable salt thereof.
10. The compound of claim 1, wherein the compound is
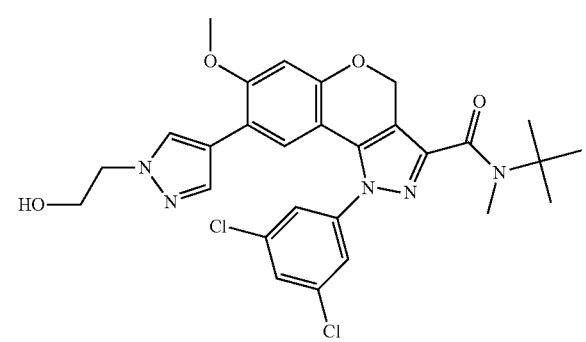 [SMILES: COc1cc2c(cc1-c1cnn(CCO)c1)-c1c(c(C(=O)N(C)C(C)(C)C)nn1-c1cc(Cl)cc(Cl)c1)CO2]
or a pharmaceutically acceptable salt thereof.

11. The compound of claim 1, wherein the compound is
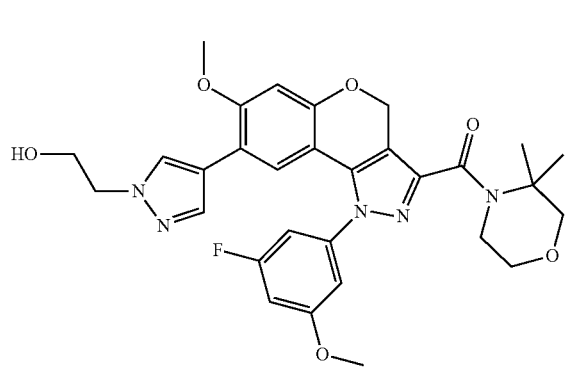 [SMILES: COc1cc(F)cc(-n2nc(C(=O)N3CCOCC3(C)C)c3c2-c2cc(-c4cnn(CCO)c4)c(OC)cc2OC3)c1]
or a pharmaceutically acceptable salt thereof.
12. The compound of claim 1, wherein the compound is
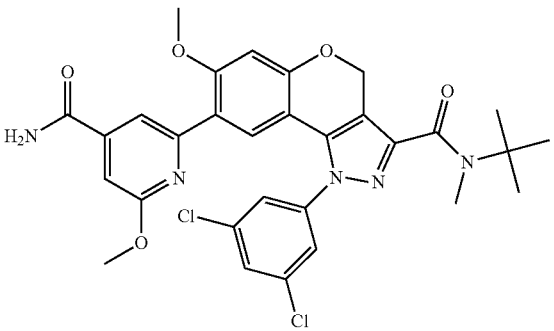
or a pharmaceutically acceptable salt thereof.
13. A pharmaceutical composition comprising a compound of claim 1, and a pharmaceutically acceptable adjuvant, carrier, or vehicle.
* * * * *

UNITED STATES PATENT AND TRADEMARK OFFICE
CERTIFICATE OF CORRECTION

PATENT NO. : 10,208,055 B2
APPLICATION NO. : 15/321249
DATED : February 19, 2019
INVENTOR(S) : Henry Yu et al.

Page 1 of 2

It is certified that error appears in the above-identified patent and that said Letters Patent is hereby corrected as shown below:

In the Claims

Claim 3, Column 303, Line 5:

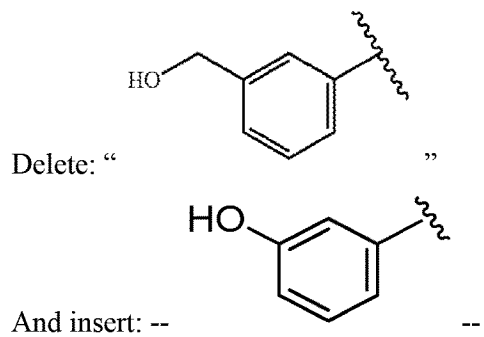

Delete: " " And insert: -- --

Claim 8, Column 315, Lines 40-50:

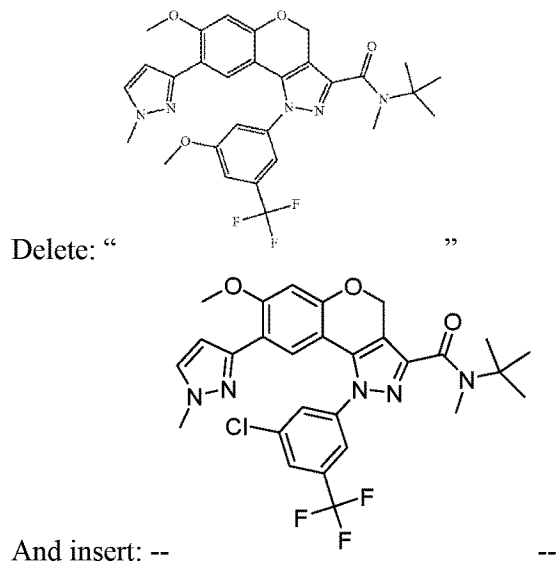

Delete: " " And insert: -- --

Signed and Sealed this
Eighteenth Day of June, 2019

Andrei Iancu
*Director of the United States Patent and Trademark Office*

CERTIFICATE OF CORRECTION (continued)
U.S. Pat. No. 10,208,055 B2

Claim 8, Column 324, Lines 15-25:

Delete: " 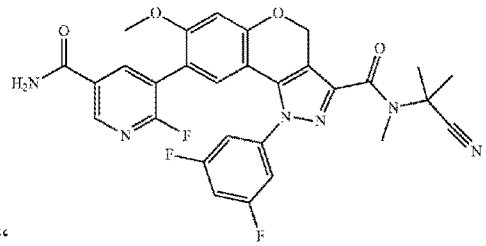 "

And insert: -- 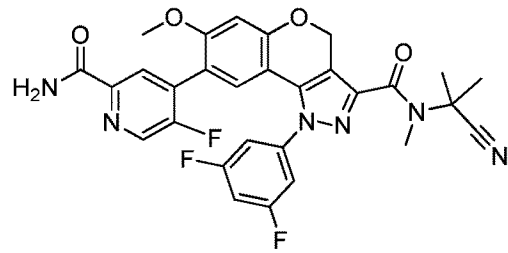 --